(12) United States Patent
Courtney et al.

(10) Patent No.: US 7,138,425 B2
(45) Date of Patent: Nov. 21, 2006

(54) PHTHALIMIDE CARBOXYLIC ACID DERIVATIVES

(75) Inventors: Stephen Martin Courtney, Oxfordshire (GB); Philip Andrew Hay, Oxfordshire (GB); David Ian Carter Scopes, Oxfordshire (GB)

(73) Assignee: Oxford Glycoscience (UK) Ltd., Abingdon (GB)

( * ) Notice: Subject to any disclaimer, the term of this patent is extended or adjusted under 35 U.S.C. 154(b) by 0 days.

(21) Appl. No.: 10/506,388

(22) PCT Filed: Mar. 6, 2003

(86) PCT No.: PCT/GB03/00926

§ 371 (c)(1),
(2), (4) Date: Apr. 14, 2005

(87) PCT Pub. No.: WO03/074516

PCT Pub. Date: Sep. 12, 2003

(65) Prior Publication Data

US 2005/0203153 A1    Sep. 15, 2005

(30) Foreign Application Priority Data

Mar. 6, 2002    (GB) ................ 0205256.1

(51) Int. Cl.
*A61K 31/4035* (2006.01)
*A61K 31/423* (2006.01)
*A61K 31/428* (2006.01)
*C07D 209/48* (2006.01)
*C07D 263/54* (2006.01)
*C07D 263/57* (2006.01)
*C07D 277/62* (2006.01)

(52) U.S. Cl. ............. 514/418; 514/367; 514/375; 548/456; 548/473; 548/202; 548/159; 548/235

(58) Field of Classification Search ........... 514/418, 514/367, 375; 548/473, 456, 159, 202, 235
See application file for complete search history.

(56) References Cited

FOREIGN PATENT DOCUMENTS

| JP | 63-073425 | 4/1988 |
|----|-----------|--------|
| JP | 01-247453 | 3/1989 |
| WO | WO 02/060373 A3 | 8/2002 |

OTHER PUBLICATIONS

Parish et al. Jul. 15, 1999, Cancer Resarch, 59, 3433-41, p. 3439. This publication is discloed in Applicatn's IDS.*
Bashkin, P., et al., "Basic fibroblast growth factor binds to subendothelial extracellular matrix and is released by heparitinase and heparin-like molecules," *Biochem.*, 1989, 28, 1737-1743.
Database Chemcats Online, *CAS*, Database Accession No. 1575853, 2001, XP002240053, order No. A0827/0038765, 1 page.
Database Chemcats Online, *CAS*, Database Accession No. 604372, 2001, XP002240054, order No. CHS 1040578, 1 page.
Database Chemcats Online, *CAS*, Database Accession No. 126220, 2001, XP002240055, order No. 2922-0873, 1 page.
Demir, M., et al., "Anticoagulant and antiprotease profiles of a novel natural heparinomimetic mannopentaose phosphate sulfate (PI-88)," *Clin. Appl. Thromb Hemost*, 2001, 7(2), 131-140.
Fang, J., et al., "Matrix metalloproteinase-2 is required for the switch to the angiogenic phenotype in a tumor model," *Proc. Natl. Acad. Sci. USA*, 2000, 97(8), 3884-3889.
Folkman, J., et al., "Control of angiogenesis by heparin and other sulfated polysaccharides," *Adv. Exp. Med. Biol.*, 1992, 313, 355-364.
Kondragnati, S., et al., "Selective suppression of matrix metalloproteinase-9 in human glioblastoma cells by antisense gene transfer impairs glioblastoma cell invasion," *Cancer Res.*, 2000, 60, 6851-6855.
Parish, C.R., et al., "Identification of sulfated oligosaccharide-based inhibitors of tumor growth and metastasis using novel *in vitro* assays for angiogenesis," *Cancer Res.*, 1999, 59, 3433-3441.

(Continued)

*Primary Examiner*—Kamal A. Saeed
*Assistant Examiner*—Yong Chu
(74) *Attorney, Agent, or Firm*—Woodcock Washburn LLP

(57) ABSTRACT

The present invention relates to phthalimide carboxylic acid derivatives of formula (I), methods for their preparation, pharmaceutical compositions containing them and their use in medicine, specifically in the treatment of cancer. (I), wherein X is O or S; $R^1$ is a phthalimide carboxylic acid group of formula (II). R is hydrogen, $C^1$–$C^6$ alkyl, aryl or $C^1$–$C^3$ alkylaryl and $R^2$, $R^3$ and $R^4$ represent various substituents

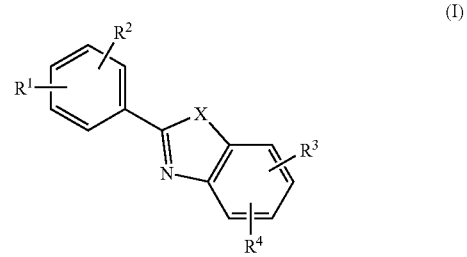

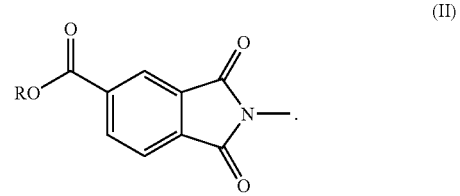

16 Claims, No Drawings

OTHER PUBLICATIONS

Parish, C.R., et al., "Treatment of central nervous system inflammation with inhibitors of basement membrane degradation," *Immunol. & Cell Biol.*, 1998, 76, 104-113.

Takuji, H., et al., "Thermoplastic polyester resin composition," *Patent Abstracts of Japan* 1989, esp@cenet database, 1 page.

Tyle, P., "Iontophoretic devices for drug delivery," *Pharmaceutical Res.*, 1986, 3(6), 318-326.

Vlodavsky, I., et al., "Inhibition of tumor metastasis by heparanase inhibiting species of heparin," *Invasion Metastasis*, 1994-95, 14, 290-302.

Vlodavsky, I., et al., "Mammalian heparanase: gene cloning, expression and function in tumor progression and metastasis," *Nature Medicine*, 1999, 5(7), 793-802.

* cited by examiner

PHTHALIMIDE CARBOXYLIC ACID DERIVATIVES

The present invention relates to novel compounds useful as inhibitors of heparanase. The invention also relates to methods for their synthesis, pharmaceutical compositions comprising the novel compounds and their use in medicine, in particular for the treatment of cancer.

Heparanases are enzymes that can degrade heparan sulfate, heparin and heparan sulfate proteoglycans and hence function as important carbohydrate degrading enzymes.

The extracellular matrix (ECM), which is comprised largely of carbohydrates, is the structural surround for cells in a multicellular organism and acts as a key modulator and mediator of their physiology, differentiation, organisation and repair. It also acts as the principal barrier to tumour growth and metastasis. Hence, tumour cells secrete a number of degradative enzymes, including heparanases, in order to breakdown the ECM so that there is ample space to traverse. Degradation of the ECM is also required to provide avenues for new blood vessel formation (angiogenesis). Tumours promote abnormal angiogenesis in order to supply the increased nutrient requirements of rapidly growing tumors.

Studies have demonstrated that inhibiting even just one ECM degrading enzyme appears to provide significant benefit in treating cancer. For example, inhibitors of certain proteases have been studied in preclinical and clinical trials as anticancer agents (Fang J et al., (2000) Proc. Natl. Acad. Sci. USA, April 11, 97(8), 3884–9 & Kondraganti S et al., (2000) Cancer Res, December 15, 60(24), 6851–5).

Accordingly, there is a good correlation between raised levels of carbohydrate processing enzymes secreted by tumour cells, such as heparanases, and their metastatic potential (e.g. Vlodavsky et al. (1994) Invasion Metastasis 14:290–302; (1999) Nature Medicine 5:793–802). Furthermore, the carbohydrate fragments generated by heparanase glycosidase action may also promote the cancer phenotype since many of these fragments are growth-stimulatory. For example, heparanase activity can release heparan sulfate fragments which can increase the potency of a variety of cell growth factors as well as stimulate cell growth when it itself is bound to appropriate cell surface receptors (e.g. Folkman and Shing (1992) Adv. Exp. Med. Biol. 313:355–64). Likewise, heparanase activity results in the release of certain growth factors that can stimulate angiogenesis and hence promote tumour growth (Bashkin et al. (1989) Biochemistry 28:1737–43).

Thus, inhibitors of ECM carbohydrate degradation may be potent anticancer agents. For example, sulfated oligosaccharide heparanase inhibitors block tumour metastasis in some animal models (Vlodavsky et al., (1994) Invasion Metastasis 14:290–302; Parish et al., (1999) Cancer Res. 59:3433–41). Interestingly, heparinomimetic compounds are being developed as anticoagulant and antiproliferative agents for the control of thrombotic and proliferative disorders (Demir et al., Clin Appl Thromb Hemost 2001 April; 7(2):131–40). Thus, heparanase inhibitors may be beneficial for use in cardiovascular diseases, including blood clotting conditions, e.g. thromboembolic disease, arterial thrombosis and restenosis, as agents that prevent the degradation of heparin.

WO01/35967 discloses the use of heparanase inhibitors for the treatment or prevention of congestive heart failure e.g. primary cardiomyopathy. Associated conditions treated or prevented with such inhibitors include peripheral odemas, pulmonary and hepatic congestion, dyspnoea, hydrothorax, sepsis and ascites. Renal disorders, e.g. renal disease associated with diabetes or nocturia can also be treated.

Inflammatory conditions, including autoimmune disorders, e.g. Multiple Sclerosis may also benefit from treatment with heparanase inhibitors (Parish et al., 1998, Immunol. Cell Biol. 76(1), 104–113).

Japanese patent application No: 63-073425 (publication no. 01-247453) discloses (benzothiazol-2-yl)phenyl substituted phthalamides as light stabilizers for use in thermoplastic polyester resins, including the compound 2-[4-(5-carboxy-1,3-dihydro-1,3-dioxo-2H-isoindol-2-yl)phenyl]-6-benzothiazolecarboxylic acid.

The present invention provides a novel class of compounds, which can be used as inhibitors of heparanase. Thus, these compounds provide the opportunity for establishing new treatments for cancer, angiogenesis, inflammatory conditions and cardiovascular diseases.

The invention provides a compound of formula (I) or a pharmaceutically acceptable salt or prodrug thereof:

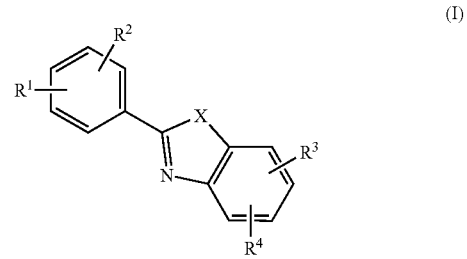

wherein
X is O or S;
$R^1$ is a phthalimide carboxylic acid group of formula (II):

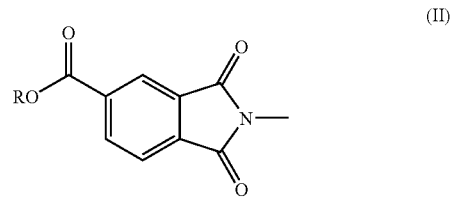

R is hydrogen, $C_1$–$C_6$ alkyl, aryl or $C_1$–$C_3$ alkylaryl;
$R^2$ is hydrogen, halogen, $C_1$–$C_6$ alkyl, $OR^5$, a 5-membered heteroaryl ring or $NR^5R^5$ wherein the $R^5$ substituents together with the nitrogen to which they are attached may form a 5- or 6-membered ring which may contain an additional heteroatom selected from O, S and $NR^{10}$;
$R^3$ and $R^4$ are independently hydrogen, halogen, $C_1$–$C_6$ alkyl optionally substituted by hydroxy or $C_1$–$C_3$ alkoxy, $CF_3$, $OCF_3$, $OR^{10}$, $COR^6$, $NHCOR^7$, $NHSO_2R^9$, CN, $S(O)_pR^9$, phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^6$, CN, CHO, $OCHF_2$, $NR^7R^8$, $NHCOR^7$, $NHSO_2R^9$, $S(O)_pR^9$ and methylenedioxy; or a 5- to 10-membered heteroaryl ring which is optionally substituted by $C_1$–$C_6$ alkyl; or $R^3$ and $R^4$ together may form a fused phenyl ring or a —O—$(CH_2)_x$—O— group, wherein x is 1 or 2;
$R^5$ is independently hydrogen, $C_3$–$C_6$ alkenyl, $C_3$–$C_6$ alkynyl, or $C_1$–$C_6$ alkyl optionally substituted by hydroxy, $C_1$–$C_3$ alkoxy, $NR^7R^8$, phenyl or a 5- or 6-membered heteroaryl ring, wherein phenyl is optionally substituted by one or more substituents selected from halogen, $CF_3$, $OCF_3$, CHO, $OR^{10}$, $COR^{10}$, $R^{10}$, CN and methylenedioxo and the heteroaryl ring is optionally substituted by $C_1$–$C_6$ alkyl;

$R^6$ is $C_1$–$C_6$ alkyl, $OR^5$, $NR^7R^8$ or phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^{10}$, CN, CHO, $OCHF_2$, $NR^7R^8$, $NHCOR^7$, $NHSO_2R^9$, $S(O)_pR^9$ and methylenedioxo;

$R^7$ and $R^8$ are independently hydrogen, phenyl, a 5- to 10-membered heterocyclic ring, $C_1$–$C_6$ alkoxy, or $C_1$–$C_6$ alkyl optionally substituted by phenyl or a 5- to 10-membered heterocyclic ring, wherein in each case, the phenyl is optionally substituted by one or more substituents selected from halogen, $CF_3$, $OCF_3$, CHO, $OR^{10}$, $COR^{10}$, $R^{10}$, CN and methylenedioxo and the heterocyclic ring is optionally substituted by $C_1$–$C_6$ alkyl;

or $R^7$ and $R^8$ together with the nitrogen to which they are attached may form a 5- or 6-membered heterocyclic ring which is optionally substituted by $CONR^{10}R^{10}$ and may optionally contain an additional heteroatom selected from O, S and $NR^{11}$;

$R^9$ is $C_1$–$C_6$ alkyl or phenyl optionally substituted by one or more substituents selected from halogen, $CF_3$, $OCF_3$, CHO, $OR^{10}$, $COR^{10}$, $R^{10}$, CN and methylenedioxo;

$R^{10}$ is hydrogen, $C_3$–$C_6$ alkenyl, $C_3$–$C_6$ alkynyl, or $C_1$–$C_6$ alkyl optionally substituted by hydroxy or $C_1$–$C_3$ alkoxy;

$R^{11}$ is hydrogen, phenyl or $C_1$–$C_3$ alkyl optionally substituted by phenyl, wherein in each case the phenyl is optionally substituted by one or more substituents selected from halogen, $CF_3$, $OCF_3$, CHO, $OR^{10}$, $COR^{10}$, $R^{10}$, CN and methylenedioxo; and p is 0, 1 or 2;

provided that the compound is not 2-[4-(5-carboxy-1,3-dihydro-1,3-dioxo-2H-isoindol-2-yl)phenyl]-benzothiazole-carboxylic acid.

The compounds of the invention preferably have a molecular weight of less than 800, more preferably less than 600.

The term "alkyl" as used herein whether on its own or as part of a larger group e.g. "alkoxy", includes both straight and branched chain radicals. The term alkyl also includes those radicals wherein one or more hydrogen atoms are replaced by fluorine. Alkenyl and alkynyl should be interpreted accordingly.

The term "heteroaryl" as used herein includes a mono- or bicyclic aromatic ring containing up to three heteroatoms selected from oxygen, nitrogen and sulfur. Suitable ring systems include, for example, thiophene, benzofuran e.g. 2-benzofuran, benzothiophene, benzoxazole e.g. 2-benzoxazole, benzothiazole e.g. 2-benzothiazole, quinoline, isoquinoline, pyridine, pyrimidine, pyrazine, oxadiazole, imidazole, tetrazole, thiazole and furan.

The term "heterocyclic ring" as used herein includes both unsaturated and saturated mono- or bicyclic cyclic ring systems. The ring may contain up to 3 heteroatoms selected from oxygen, nitrogen and sulfur. Suitable ring systems include, for example, furan, thiophene, pyrrole, imidazole, oxadiazole, oxazole, thiazole, pyrazole, benzofuran, benzoxazole, benzothiazole, quinoline, isoquinoline, tetrazole, piperidine, piperizine and morpholine.

X is preferably O.

R is preferably hydrogen or $C_1$–$C_3$ alkyl. More preferably R is hydrogen.

$R^2$ is preferably hydrogen, $OR^5$ or $NR^5R^5$. More preferably R is $OR^5$ or $NR^5R^5$. Yet more preferably $R^2$ is —$OCH_3$ or —NH—$(CH_2)_2$—$CH_3$.

$R^3$ is preferably hydrogen or halogen.

$R^4$ is preferably hydrogen, halogen, $C_1$–$C_6$ alkyl optionally substituted by hydroxy or $C_1$–$C_3$ alkoxy, $CF_3$, $OCF_3$, $OR^{10}$, $COR^6$, phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^6$, CN, CHO, $OCHF_2$ and $NR^7R^8$; or a 5- to 10-membered heteroaryl ring which is optionally substituted by $C_1$–$C_6$ alkyl; or $R^3$ and $R^4$ together may form a fused phenyl ring.

$R^4$ is more preferably $COR^6$, phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^6$, CN, CHO, $OCHF_2$ and $NR^7R^8$; or a 5- to 10-membered heteroaryl ring which is optionally substituted by $C_1$–$C_6$ alkyl. Yet more preferably, $R^4$ is phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^6$, CN, CHO, $OCHF_2$ and $NR^7R^8$; or a 5- to 10-membered heteroaryl ring which is optionally substituted by $C_1$–$C_6$ alkyl.

$R^5$ is preferably hydrogen, $C_3$–$C_6$ alkenyl, $C_3$–$C_6$ alkynyl, or $C_1$–$C_6$ alkyl optionally substituted by one of the following substituents, hydroxy, $C_1$–$C_3$ alkoxy or a 5- or 6-membered heteroaryl ring, wherein the heteroaryl ring is optionally substituted by $C_1$–$C_6$ alkyl.

$R^6$ is preferably $C_1$–$C_6$ alkyl, $OR^5$ or $NR^7R^8$. $R^6$ is more preferably $OR^5$ or $NR^7R^8$.

$R^7$ and $R^8$ are preferably independently hydrogen, or $C_1$–$C_6$ alkyl optionally substituted by phenyl or a 5- to 10-membered heterocyclic ring, wherein the phenyl is optionally substituted by one or more substituents selected from halogen, $CF_3$, $OCF_3$, CHO, $OR^{10}$, $COR^{10}$, $R^{10}$, CN and methylenedioxo and the heterocyclic ring is optionally substituted by $C_1$–$C_6$ alkyl; or $R^7$ and $R^8$ together with the nitrogen to which they are attached may form a 5- or 6-membered heterocyclic ring which is optionally substituted by $CONH_2$ and may optionally contain an additional heteroatom selected from O, S and $NR^{11}$.

$R^9$ is preferably $C_1$–$C_6$ alkyl.

$R^{10}$ is preferably $C_1$–$C_6$ alkyl optionally substituted by hydroxy or $C_1$–$C_3$ alkoxy. More preferably $R^{10}$ is —$CH_3$.

Preferably $R^1$ is meta to the benzoxazole or benzothiazole group.

Preferably $R^2$ is ortho or para to the benzoxazole or benzothiazole group.

Preferably $R^3$ or $R^4$ is located at position 5 or 6 on the benzoxazole or benzothiazole group.

When R is aryl or alkylaryl, suitable aryl groups include, for example, phenyl.

When $R^2$ is a 5-membered heteroaryl ring, the heteroaryl ring may be, for example, thiophene.

When $R^2$ is $NR^5R^5$ and the $R^5$ substituents, together with the nitrogen to which they are attached, form a 5- or 6-membered ring, the ring may be, for example, morpholine.

When $R^3$ or $R^4$ is a 5- to 10-membered heteroaryl ring, suitable ring systems include, for example, thiophene, benzofuran e.g. 2-benzofuran, benzothiophene, benzoxazole e.g. 2-benzoxazole, benzothiazole e.g. 2-benzothiazole, quinoline, isoquinoline, pyridine, pyrimidine, pyrazine, oxadiazole, imidazole, tetrazole and furan. Preferred ring systems include thiophene, furan, benzothiophene and benzofuran.

When $R^5$ is alkyl optionally substituted by a 5- or 6-membered heteroaryl ring, suitable heteroaryl groups include, for example, furan, thiophene, imidazole, oxadiazole, thiazole, tetrazole, pyridine, pyrimidine and pyrazine.

When $R^7$ or $R^8$ is a 5- to 10-membered heterocyclic ring, or alkyl optionally substituted by a 5- to 10-membered heterocyclic ring, suitable ring systems include, for example, furan, tetrahydrofuran, thiophene, pyrrole, imidazole, oxadiazole, oxazole, thiazole, pyrazole, benzofuran, benzoxazole, benzothiazole, quinoline, isoquinoline, and tetrazole. Preferred ring systems include furan, tetrahydrofuran and thiophene.

When $R^7$ and $R^8$ together with the nitrogen to which they are attached form a 5- or 6-membered heterocyclic ring, the ring is preferably saturated and may be, for example, piperazine, piperidine, or morpholine. More preferably, the saturated ring is piperazine.

As described herein, for all aspects of the invention, reference to compounds of formula (I) encompasses the pharmaceutically acceptable salts and prodrugs thereof.

A specific group of compounds that may be mentioned include compounds of formula (I)a

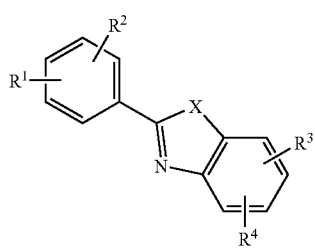

(I)a wherein

X is O or S;

$R^1$ is a phthalimide carboxylic acid group of formula (II):

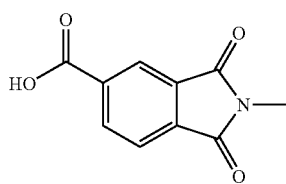

(II)

$R^2$ is hydrogen, halogen, $C_1$–$C_6$ alkyl, $OR^5$ or $NR^5R^5$ wherein the $R^5$ substituents together with the nitrogen to which they are attached may form a 5- or 6-membered ring which may contain an additional heteroatom selected from oxygen, nitrogen and sulfur;

$R^3$ and $R^4$ are independently hydrogen, halogen, $C_1$–$C_6$ alkyl optionally substituted by hydroxy or $C_1$–$C_3$ alkoxy, $CF_3$, $OCF_3$, $OR^{10}$, $COR^6$, $NHCOR^7$, $NHSO_2R^9$, $CN$, $S(O)_p$ $R^9$, phenyl optionally substituted by one or more substituents selected from halogen, $C_{1-6}$ alkyl, $CF_3$, $OCF_3$, $OR^5$, $COR^6$, $CN$, $NHCOR^7$ and methylenedioxo, or a 5- to 10-membered mono- or bicyclic heteroaromatic ring containing up to three heteroatoms selected from oxygen, nitrogen and sulfur which heteroaromatic ring may be substituted by $C_1$–$C_6$ alkyl; or $R^3$ and $R^4$ together may form a fused phenyl ring;

$R^5$ is independently hydrogen, $C_3$–$C_6$ alkenyl, $C_3$–$C_6$ alkynyl, or $C_1$–$C_6$ alkyl optionally substituted by hydroxy, $C_1$–$C_3$ alkoxy, $NR^7R^8$, phenyl optionally substituted by one or more substituents selected from halogen, $C_1$–$C_6$ alkyl, $CF_3$, $OCF_3$, $CN$, or a 5- or 6-membered heteroaromatic group optionally substituted by $C_1$–$C_6$ alkyl;

$R^6$ is $C_1$–$C_6$ alkyl, $OR^5$ or $NR^7R^8$, or phenyl optionally substituted by one or more substituents selected from halogen, $C_1$–$C_6$ alkyl, $CF_3$, $OCF_3$, $OR^5$, $COR^6$, $CN$, and $NHCOR^7$;

$R^7$ and $R^8$ are independently $C_1$–$C_6$ alkyl, $C_1$–$C_6$ alkoxy, phenyl optionally substituted by one or more substituents selected from halogen, $CF_3$, $OCF_3$, $OR^5$, and $CN$, or a 5- to 10-membered mono or bicyclic heteroaromatic ring containing up to three heteroatoms selected from oxygen, nitrogen and sulfur which heteroaromatic ring may be substituted by $C_1$–$C_6$ alkyl; or $R^7$ and $R^8$ together with the nitrogen to which they are attached may form a 5- or 6-membered ring which may contain an additional heteroatom selected from oxygen, nitrogen and sulfur;

$R^9$ is $C_1$–$C_6$ alkyl, or phenyl optionally substituted by one or more substituents selected from halogen, $CF_3$, $OCF_3$, $OR^5$, and $CN$;

$R^{10}$ is hydrogen, $C_3$–$C_6$ alkenyl, $C_3$–$C_6$ alkynyl, or $C_1$–$C_6$ alkyl optionally substituted by hydroxy or $C_1$–$C_3$ alkoxy; and p is 0, 1 or 2;

provided that the compound is not 2-[4-(5-carboxy-1,3-dihydro-1,3-dioxo-2H-isoindol-2-yl)phenyl]-6-benzothiazolecarboxylic acid.

Specific compounds of formula (I) that may be mentioned include those provided in the examples. A preferred list of specific compounds of the invention include:

2-[3-(Naphth[2,3-d]oxazol-2-yl)phenyl]-2,3-dihydro-1,3-dioxo-1H-isoindole-5-carboxylic acid;

2-[3-(5-Chlorobenzoxazol-2-yl)phenyl]-2,3-dihydro-1,3-dioxo-1H-isoindole-5-carboxylic acid;

2-[2-Methoxy-5-(5-phenylbenzoxazol-2-yl)phenyl]-1,3-dioxo-2,3-dihydro-1H-isoindole-5-carboxylic acid;

2-[2-Methoxy-5-[5-(benzofuran-2-yl)benzoxazol-2-yl]phenyl]-1,3-dioxo-2,3-dihydro-1H-isoindole-5-carboxylic acid;

2-[2-Methoxy-5-[5-(3,4-methylenedioxyphenyl)benzoxazol-2-yl]phenyl]-1,3-dioxo-2,3-dihydro-1H-isoindole-5-carboxylic acid;

2-[2-Methoxy-5-[5-(4-chlorophenyl)benzoxazol-2-yl]phenyl]-1,3-dioxo-2,3-dihydro-1H-isoindole-5-carboxylic acid;

2-[2-Methoxy-5-[5-(3,4-dichloro)phenylbenzoxazol-2-yl]phenyl]-1,3-dioxo-2,3-dihydro-1H-isoindole-5-carboxylic acid;

2-[2-Methoxy-5-[5-(3-chloro-4-fluoro)phenylbenzoxazol-2-yl]phenyl]-1,3-dioxo-2,3-dihydro-1H-isoindole-5-carboxylic acid;

2-[2-Methoxy-5-[5-(4-methyl)phenylbenzoxazol-2-yl]phenyl]-1,3-dioxo-2,3-dihydro-1H-isoindole-5-carboxylic acid;

2-[2-Methoxy-5-[5-(4-methoxy)phenylbenzoxazol-2-yl]phenyl]-1,3-dioxo-2,3-dihydro-1H-isoindole-5-carboxylic acid;

2-[2-Methoxy-5-[5-(3-fluoro)phenylbenzoxazol-2-yl]phenyl]-1,3-dioxo-2,3-dihydro-1H-isoindole-5-carboxylic acid;

2-[2-Methoxy-5-[5-(3-chloro)phenylbenzoxazol-2-yl]phenyl]-1,3-dioxo-2,3-dihydro-1H-isoindole-5-carboxylic acid;

2-[2-Methoxy-5-[5-(4-fluoro)phenylbenzoxazol-2-yl]phenyl]-1,3-dioxo-2,3-dihydro-1H-isoindole-5-carboxylic acid;

2-[2-Methoxy-5-[5-(2,4-difluoro)phenylbenzoxazol-2-yl]phenyl]-1,3-dioxo-2,3-dihydro-1H-isoindole-5-carboxylic acid;

2-[2-Methoxy-5-[5-(3,5-difluoro)phenylbenzoxazol-2-yl]phenyl]-1,3-dioxo-2,3-dihydro-1H-isoindole-5-carboxylic acid;

2-[2-Methoxy-5-[5-(4-trifluoromethoxy)phenylbenzoxazol-2-yl]phenyl]-1,3-dioxo-2,3-dihydro-1H-isoindole-5-carboxylic acid;

2-[4-Methoxy-5-[5-(3,4-methylenedioxyphenyl)benzoxazol-2-yl]phenyl]-1,3-dioxo-2,3-dihydro-1H-isoindole-5-carboxylic acid;

2-[4-Propylamino-5-[5-(4-chlorophenyl)benzoxazol-2-yl]phenyl]-1,3-dioxo-2,3-dihydro-1H-isoindole-5-carboxylic acid;

2-[2-Methoxy-5-[5-(2-benzothiophenyl)benzoxazol-2-yl]phenyl]-1,3-dioxo-2,3-dihydro-1H-isoindole-5-carboxylic acid;

2-[3-(5-Bromo-7-fluorobenzoxazol-2-yl)-4-propylaminophenyl]-1,3-dioxo-2,3-dihydro-1H-isoindole-5-carboxylic acid;

2-[4-Propylamino-3-[5-(2-benzofuranyl)benzoxazol-2-yl]phenyl]-1,3-dioxo-2,3-dihydro-1H-isoindole-5-carboxylic acid;

2-[4-Propylamino-5-[5-(2-benzothiophenyl)benzoxazol-2-yl]phenyl]-1,3-dioxo-2,3-dihydro-1H-isoindole-5-carboxylic acid;

2-[4-Propylamino-5-[5-(4-fluorophenyl)benzoxazol-2-yl]phenyl]-1,3-dioxo-2,3-dihydro-1H-isoindole-5-carboxylic acid;

2-[3-(6-Fluorobenzoxazol-2-yl)-4-propylaminophenyl]-1,3-dioxo-2,3-dihydro-1H-isoindole-5-carboxylic acid;

2-[3-(6-Methylbenzoxazol-2-yl)-4-propylaminophenyl]-1,3-dioxo-2,3-dihydro-1H-isoindole-5-carboxylic acid;

2-[4-Propylamino-5-[5-(4-trifluoromethoxy)phenylbenzoxazol-2-yl]phenyl]-1,3-dioxo-2,3-dihydro-1H-isoindole-5-carboxylic acid;

2-[2-Methoxy-5-[5-(4-N,N-dimethylaminophenyl)benzoxazol-2-yl]phenyl]-1,3-dioxo-2,3-dihydro-1H-isoindole-5-carboxylic acid; and 2-[4-Methoxy-5-[5-(3,5-difluorophenyl)benzoxazol-2-yl]phenyl]-1,3-dioxo-2,3-dihydro-1H-isoindole-5-carboxylic acid.

A more highly preferred list of specific compounds of the invention include:

2-[2-Methoxy-5-[5-(benzofuran-2-yl)benzoxazol-2-yl]phenyl]-1,3-dioxo-2,3-dihydro-1H-isoindole-5-carboxylic acid;

2-[4-Methoxy-5-[5-(3,4-methylenedioxyphenyl)benzoxazol-2-yl]phenyl]-1,3-dioxo-2,3-dihydro-1H-isoindole-5-carboxylic acid;

2-[4-Propylamino-5-[5-(4-chlorophenyl)benzoxazol-2-yl]phenyl]-1,3-dioxo-2,3-dihydro-1H-isoindole-5-carboxylic acid;

2-[2-Methoxy-5-[5-(2-benzothiophenyl)benzoxazol-2-yl]phenyl]-1,3-dioxo-2,3-dihydro-1H-isoindole-5-carboxylic acid;

2-[3-(5-Bromo-7-fluorobenzoxazol-2-yl)-4-propylaminophenyl]-1,3-dioxo-2,3-dihydro-1H-isoindole-5-carboxylic acid;

2-[4-Propylamino-3-[5-(2-benzofuranyl)benzoxazol-2-yl]phenyl]-1,3-dioxo-2,3-dihydro-1H-isoindole-5-carboxylic acid;

2-[4-Propylamino-5-[5-(2-benzothiophenyl)benzoxazol-2-yl]phenyl]-1,3-dioxo-2,3-dihydro-1H-isoindole-5-carboxylic acid;

2-[3-(6-Fluorobenzoxazol-2-yl)-4-propylaminophenyl]-1,3-dioxo-2,3-dihydro-1H-isoindole-5-carboxylic acid;

2-[3-(6-Methylbenzoxazol-2-yl)-4-propylaminophenyl]-1,3-dioxo-2,3-dihydro-1H-isoindole-5-carboxylic acid;

2-[4-Propylamino-5-[5-(4-trifluoromethoxy)phenylbenzoxazol-2-yl]phenyl]-1,3-dioxo-2,3-dihydro-1H-isoindole-5-carboxylic acid;

2-[4-Propylamino-5-[5-(4-fluorophenyl)benzoxazol-2-yl]phenyl]-1,3-dioxo-2,3-dihydro-1H-isoindole-5-carboxylic acid;

2-[2-Methoxy-5-[5-(4-N,N-dimethylaminophenyl)benzoxazol-2-yl]phenyl]-1,3-dioxo-2,3-dihydro-1H-isoindole-5-carboxylic acid; and 2-[4-Methoxy-5-[5-(3,5-difluorophenyl)benzoxazol-2-yl]phenyl]-1,3-dioxo-2,3-dihydro-1H-isoindole-5-carboxylic acid.

Suitable pharmaceutically acceptable salts of the compounds include those derived from inorganic and organic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such organic bases are well known in the art and may include amino acids such as arginine and lysine, mono-, di-, or tri-hydroxyalkylamines such as mono-, di-, or tri-ethanolamine or choline, mono-, di-, and tri-alkylamines, such as methylamine, dimethylamine, and trimethylamine, guanidine, N-methylglucosamine, N-methylpiperazine, morpholine, ethylenediamine, N-benzylphenethylamine, tris(hydroxymethyl)aminomethane, meglumine and the like.

Salts may be prepared in a conventional manner using methods well known in the art, for example by treatment of a solution of the compound of formula (I) with a solution of the base, for example, potassium or sodium hydroxide, or potassium or sodium hydrogen carbonate.

The invention also includes prodrugs of the aforementioned compounds. A prodrug is commonly described as an inactive or protected derivative of an active ingredient or a drug, which is converted to the active ingredient or drug in the body. Examples of prodrugs include pharmaceutically acceptable esters, including $C_1$–$C_6$ alkyl esters and pharmaceutically acceptable amides, including secondary $C_1$–$C_3$ alkylamides.

The compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

In addition, the invention extends to active derivatives of the aforementioned compounds.

Certain of the compounds of formula (I) may exist in the form of optical isomers, e.g. diastereoisomers and mixtures of isomers in all ratios, e.g. racemic mixtures. The invention includes all such forms, in particular the pure isomeric forms (R or S). The different isomeric forms may be separated or resolved one from the other by conventional methods, or any given isomer may be obtained by conventional synthetic methods or by stereospecific or asymmetric syntheses. Where a compound contains an alkene moiety, the alkene can be presented as a cis or trans isomer or a mixture thereof. When an isomeric form of a compound of the invention is provided substantially free of other isomers, it will preferably contain less than 5% w/w, more preferably less than 2% w/w and especially less than 1% w/w of the other isomers.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5%, e.g. 10 to 59% of a compound of formula (I).

The compounds of formula (I) can be prepared by art-recognized procedures from known or commercially available starting materials. If the starting materials are unavailable from a commercial source, their synthesis is described herein, or they can be prepared by procedures known in the art.

The invention also provides a process for preparing a compound of formula (I), comprising: treating a compound of formula (III):

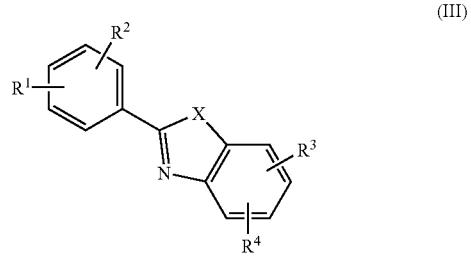

wherein $R^1$ is $NH_2$ or a protected derivative thereof and X, $R^2$, $R^3$ and $R^4$ are as defined for formula (I), with a compound of formula (IV):

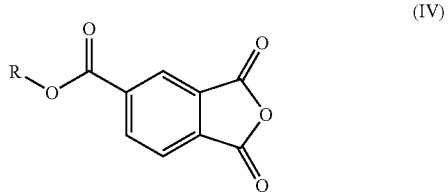

wherein R is as defined for formula (I) e.g. H, $CH_3$, $C_2H_5$, or $CH_2Ph$, by heating in a suitable acidic medium, for example, in a solution of acetic acid or other suitable organic acid.

Alternatively, compounds of formula (I) may be prepared by heating a compound of formula (III) wherein $R^1$ is $NH_2$ and a compound of formula (IV) with an organic base, for example triethylamine in a suitable solvent, for example, dimethylformamide, followed by heating in a suitable acidic medium, for example, acetic acid.

The compounds where R is $C_1$–$C_6$ alkyl, aryl or $C_1$–$C_3$ alkylaryl may be converted to the compounds of formula (I) where R is H using methods well known to those skilled in the art, for example, by hydrolysis with sodium hydroxide in water, or by hydrogenation (where R=$CH_2Ph$) with palladium on charcoal catalyst/hydrogen. Certain basic conditions may cause phthalimide ring cleavage and re-cyclisation can then be carried out using the acidic conditions described above.

A compound of formula (III) wherein $R^1$ is $NH_2$ may be prepared from a corresponding compound of formula (III), wherein $R^1$ is $NO_2$ and X, $R^2$, $R^3$ and $R^4$ are as defined for formula (I), by methods well known to those skilled in the art, for example, by hydrogenation with palladium on charcoal catalyst. The compounds of formula (III) wherein $R^1$ is $NO_2$, may be prepared by treatment of a compound of formula (V):

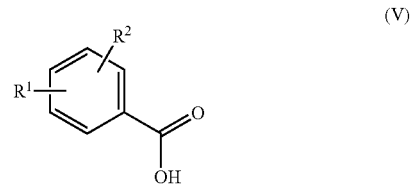

wherein $R^1$ is $NO_2$ and $R^2$ is as defined for formula (I), with a compound of formula (VI):

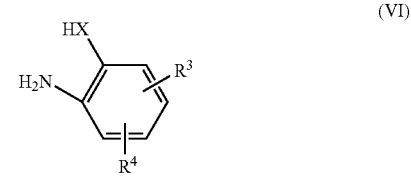

wherein X, $R^3$ and $R^4$ are as defined for formula (I) by,
(i) heating in a condensation/cyclisation reaction using, for example, polyphosphoric acid or
(ii) by firstly coupling a compound of formula (VI) to a compound of formula (V) via either an ester/thioester or amide formation reaction, using methods well known to those of skill in the art, followed by direct heating or heating with an acidic media with a suitable solvent to effect cyclisation, for example, p-toluenesulfonic acid in toluene. Alternatively this may be achieved via oxidative cyclisation of a Schiff base, derived from the condensation of the 2-aminophenol or 2-aminothiophenol and aldehydes, using various oxidants such as $PhI(OAc)_2$, $Pb(OAc)_4$ or DDQ.

Compounds of formulae (V) and (VI) may be available through the usual commercial sources. They and derivatives thereof may also be prepared by methods well known to those skilled in the art.

The compounds of formula (III) where $R^3$ or $R^4$ is a halogen, may be converted to other compounds of formula (III) where $R^3$ or $R^4$ is phenyl or a 5- to 10-membered heteroaryl ring, either of which is optionally substituted as defined in formula (I). Thus, the compounds of formula (III) where $R^3$ or $R^4$ is halogen, may be further modified by a coupling reaction with compounds of formula (VII) using an appropriate catalyst for example tetrakis (triphenylphosphine) palladium:

wherein $R^{12}$ is phenyl or a 5- to 10-membered heteroaryl ring, either of which is optionally substituted as defined in formula (I). Likewise a similar palladium coupling reaction with halo aromatic compounds may be used with corresponding compounds of formula (III), wherein $R^1$ is $NO_2$, $R^2$ is $OR^5$ or $NR^5R^5$ and $R^3$ or $R^4$ is independently $B(OH)_2$.

Furthermore, compounds of formula (III) where $R^2$ is halogen may be converted to other compounds of formula (III) where $R^2$ is a 5-membered heteroaryl ring by reaction with an alcohol or amine via a nucleophilic aromatic substitution or by a coupling reaction with compounds of formula (VII) wherein $R^{12}$ is a 5-membered heteroaryl ring, by the method described above.

During the synthesis of the compounds of formula (I), labile functional groups in the intermediate compounds, e.g. hydroxy, carboxy and amino groups, may be protected. The protecting groups may be removed at any stage in the synthesis of the compounds of formula (I) or may be present on the final compound of formula (I). A comprehensive discussion of the ways in which various labile functional groups groups may be protected and methods for cleaving the resulting protected derivatives is given in, for example, Protective Groups in Organic Chemistry, T. W. Greene and P. G. M. Wuts, (1991) Wiley-Interscience, New York, 2nd edition.

Further details for the preparation of compounds of formula (I) are found in the examples.

Any novel intermediate compounds as described herein also fall within the scope of the present invention.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I).

As mentioned above the compounds of the invention find use in therapy. Thus according to a further aspect the present invention provides a compound of formula (I), but without the proviso, for use in medicine.

The compounds of the invention may be administered in conventional dosage forms prepared by combining one of the aforementioned compounds ("active ingredient") with standard pharmaceutical carriers or diluents according to conventional procedures well known in the art. These procedures may involve mixing, granulating and compressing or dissolving the ingredients as appropriate to the desired preparation.

According to a further aspect the present invention provides a pharmaceutical composition comprising a compound of formula (I) but without the proviso, or a pharmaceutically acceptable salt or prodrug thereof, and a pharmaceutically acceptable carrier, excipient and/or diluent.

The compounds or pharmaceutical compositions may be administered to a subject by any of the routes conventionally used for drug administration, for example they may be adapted for oral (including buccal, sublingual), topical (including transdermal), nasal (including inhalation), rectal, vaginal or parenteral (including subcutaneous, intramuscular, intravenous or intradermal) administration to e.g. mammals including humans. The most suitable route for administration in any given case will depend on the particular compound or pharmaceutical composition, the subject, and the nature and severity of the disease and the physical condition of the subject. Such compositions may be prepared by any method known in the art of pharmacy, for example by bringing into association the active ingredient with the carrier(s) excipient(s) or diluent(s). Such carriers may be present as from about 1% up to about 98% of the formulation. More usually they will form up to about 80% of the formulation.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams. Such applications include those to the eye or other external tissues, for example the mouth and skin and the compositions are preferably applied as a topical ointment or cream. When formulated in an ointment, the active ingredient may be employed, for example, a paraffinic or a water-miscible ointment base. Alternatively, the active ingredient may be formulated in a cream with an oil-in-water cream base or a water-in-oil base. The composition may also contain compatible conventional carriers, such as cream or ointment bases and ethanol or oleyl alcohol for lotions.

Pharmaceutical compositions adapted for topical administration to the eye include eye drops wherein the active ingredient is dissolved or suspended in a suitable carrier, especially an aqueous solvent Pharmaceutical compositions adapted for topical administration in the mouth include lozenges, pastilles and mouth washes.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318, (1986).

Pharmaceutical compositions adapted for nasal administration wherein the carrier is a solid include a coarse powder having a particle size, for example, in the range 20 to 500 microns, which is administered by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for rectal administration may be presented as suppositories or enemas. Suppositories will contain conventional suppository bases, e.g. cocoa-butter or other glyceride.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

For parenteral administration, fluid unit dosage forms are prepared utilizing the active ingredient and a sterile vehicle, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum The dry lyophilized powder is then sealed in the vial and an accompanying vial of water for injection may be supplied to reconstitute the liquid prior to use. Parenteral suspensions are prepared in substantially the same manner except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

The pharmaceutical compositions according to the invention are preferably adapted for oral administration.

It should be understood that in addition to the ingredients particularly mentioned above, the compositions may also include other agents conventional in the art having regard to the type of formulation in question, for example those suitable for oral administration may include flavouring agents. They may also contain therapeutically active agents in addition to the compounds of the invention.

The compositions may contain from 0.1% by weight, preferably from 10–60% by weight, of the active ingredient, depending on the method of administration.

Pharmaceutical compositions may be presented in unit dose forms containing a predetermined amount of active ingredient per dose. Such a unit may contain for example 0.1 mg/kg to 750 mg/kg, more preferably 0.1 mg/kg to 10 mg/kg depending on the condition being treated, the route of administration and the age, weight and condition of the subject. Preferred unit dosage compositions are those containing a daily dose or sub-dose, as herein above recited, or an appropriate fraction thereof, of an active ingredient It will be recognized by one of skill in the art that the optimal quantity and spacing of individual dosages of the compounds of the invention will be determined by the nature and extent of the condition being treated, the form, route and site of administration, and the particular subject being treated, and that such optimums can be determined by conventional techniques. It will also be appreciated by one of skill in the art that the optimal course of treatment, i.e. the number of doses of the aforementioned compounds given per day for a defined number of days, can be ascertained by those skilled in the art using conventional course of treatment determination tests.

No toxicological effects are indicated when the aforementioned compounds of formula (I) are administered in the above mentioned dosage range.

The compounds of the invention or pharmaceutical compositions can be administered simultaneously, separately or sequentially with one or more other therapeutic agents.

By the term "treatment" is meant either prophylactic or therapeutic i.e. curative therapy.

The compounds of the present invention are useful in that they are capable of inhibiting the enzyme heparanase. Thus, the compounds of the invention can be used in the treatment of cancers, preferably for the treatment of metastatic tumour cells. Examples of such types of cells include, melanoma, mesothelioma, lymphoma, leukaemia, fibrosarcoma, rhabdomyosarcoma and mastocytoma. Types of cancer include, cancer of the colorectum, prostate, lung (e.g. small cell lung and non-small cell lung), breast, pancreas, kidney, liver, stomach (e.g. gastric, intestine, colon), bladder, skin, uterus, cervix or ovaries.

The compounds of the present invention can also be used in combination with one or more additional treatments or therapeutic compounds for cancer. Examples of such treatments include, surgery and radiation therapy. Examples of therapeutic compounds include, but are not limited to, cyclophosphamide (Cytoxan™); methotrexate (Methotrexate™); 5-fluorouracil (5-FU); paclitaxel (Taxol™); docetaxel (Taxotere™); vincristine (Oncovin™); vinblastine (Velban™); vinorelbine (Navelbine™); doxorubicin (Adriamycin™); tamoxifen (Nolvadex™); toremifene (Fareston™); megestrol acetate (Megace™); anastrozole (Arimidex™); goserelin (Zoladex™); anti-HER2 monoclonal antibody (Herceptin™); capecitabine (Xeloda™) and raloxifene hydrochloride (Evista™).

The compounds of the present invention can also be used in the treatment of angiogenesis and angiogenesis related disorders which include angiogenesis associated with the growth of solid tumours and retinopathy.

The compounds of the present invention can also be used in combination with one or more additional treatments or therapeutic compounds for angiogenesis. Examples of such other therapeutic compounds include but are not limited to recombinant platelet-derived growth factor-BB (Regranex™).

The compounds of the present invention can also be used in the treatment of inflammatory conditions, including autoimmune disorders, such as but not limited to, rheumatoid arthritis, inflammatory bowel disease, wound healing and Multiple Sclerosis.

The compounds of the present invention can also be used in the treatment of cardiovascular diseases such as but not limited to blood clotting conditions, for example thromboembolic disease, arterial thrombosis and restenosis.

The compounds of the invention can also be used in the treatment of associated conditions, such as, peripheral odemas, pulmonary and hepatic congestion, dyspnoea, hydrothorax, sepsis and ascites.

The compounds of the invention can also be used in the treatment of renal disorders, e.g. renal disease associated with diabetes or nocturia.

In additional aspects, therefore, the present invention provides:

(i) the use of a compound of formula (I), but without the proviso, as an inhibitor of the enzyme heparanase.
(ii) the use of a compound of formula (I), but without the proviso, in the manufacture of a medicament for the treatment of cancer, preferably the treatment of metastatic tumour cells. Examples of such types of cells include melanoma, mesothelioma, lymphoma, leukaemia, fibrosarcoma, rhabdomyosarcoma and mastocytoma. Types of cancer include but are not limited to, cancer of the colorectum, prostate, lung (e.g. small cell lung and non-small cell lung), breast, pancreas, kidney, liver, stomach (e.g. gastric, intestine, colon), bladder, skin, uterus, cervix or ovaries.
(iii) the use of a compound of formula (I), but without the proviso, in the manufacture of a medicament for the treatment of angiogenesis and angiogenesis related disorders which include angiogenesis associated with the growth of solid tumours and retinopathy.
(iv) the use of a compound of formula (I), but without the proviso, in the manufacture of a medicament for the treatment of inflammatory conditions, including autoimmune conditions, such as but not limited to rheumatoid arthritis, inflammatory bowel disease, wound healing and Multiple Sclerosis.
(v) the use of a compound of formula (I), but without the proviso, in the manufacture of a medicament for the treatment of cardiovascular diseases, such as but not limited to, blood clotting conditions, for example, thromoembolic disease, arterial thrombosis and restenosis.
(vi) the use of a compound of formula (I), but without the proviso, in the manufacture of a medicament for the treatment of conditions, such as, peripheral odemas, pulmonary and hepatic congestion, dyspnoea, hydrothorax, sepsis and ascites.
(vii) the use of a compound of formula (I), but without the proviso, in the manufacture of a medicament for the treatment of renal disorders, e.g. renal disease associated with diabetes or nocturia.
(viii) a method for the treatment of cancer, preferably the treatment of metastatic tumour cells which comprises the step of administering to a patient an effective amount of a compound of formula (I), but without the proviso.
(ix) a method for the treatment of angiogenesis and angiogenesis related disorders, which include angiogenesis associated with the growth of solid tumours and retinopathy, which comprises the step of administering to a patient an effective amount of a compound of formula (I), but without the proviso.
(x) a method for the treatment of inflammatory diseases, including autoimmune disorders, such as but not limited to rheumatoid arthritis, inflammatory bowel disease, wound healing and Multiple Sclerosis, which comprises the step of administering to a patient an effective amount of a compound of formula (I), but without the proviso.
(xi) a method for the treatment of cardiovascular diseases, such as but not limited to blood clotting conditions, for example thromboembolic disease, arterial thrombosis and restenosis which comprises the step of administering to a patient an effective amount of a compound of formula (I), but without the proviso.
(xii) a method for the treatment of conditions, such as but not limited to, peripheral odemas, pulmonary and hepatic congestion, dyspnoea, hydrothorax, sepsis and ascites which comprises the step of administering to a patient an effective amount of a compound of formula (I), but without the proviso.
(xiii) a method for the treatment of renal disorders, such as but not limited to, renal disease associated with diabetes or nocturia which comprises the step of administering to a patient an effective amount of a compound of formula (I), but without the proviso.

All publications, including, but not limited to, patents and patent applications cited in this specification, are herein incorporated by reference as if each individual publication were specifically and individually indicated to be incorporated by reference herein as though fully set forth.

The invention will now be described by reference to the following examples which are merely illustrative and are not to be construed as a limitation of the scope of the present invention.

EXAMPLES

Example 1

2-[3-(Benzoxazol-2-yl)phenyl]-2,3-dihydro-1,3-dioxo-1H-isoindole-5-carboxylic acid a) 2-(3-Aminophenyl)benzoxazole 3-Aminobenzoic acid (500 mg, 3.65 mmol) and 2-aminophenol (398 mg, 3.65 mmol) were mixed with polyphosphoric acid (5 ml). The reaction was heated to 200° C. for 4 h. The reaction mixture was slowly poured into ice water (100 ml) and the resulting mixture basified with solid sodium hydroxide. At pH5–6 the precipitate was filtered, washed with water and dried to give the subtitle compound, 625 mg (82%). $^1$H NMR (CDCl$_3$) δ 7.78(m, 1H), 7.65(d, J=7.5 Hz, 1H) 7.59(m, 2H), 7.36(m, 3H), 6.86(dd, J=2.2, 7.9 Hz, 1H). MS 211 m/z (M+H)$^+$.

b) 2-[3-(Benzoxazol-2-yl)phenyl]-2,3-dihydro-1,3-dioxo-1H-isoindole-5-carboxylic acid

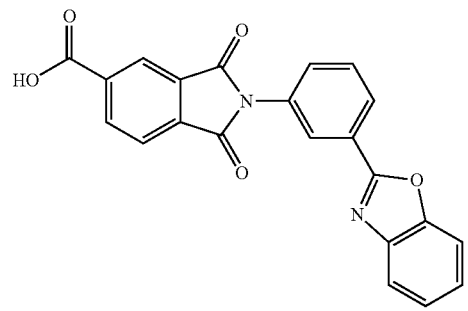

2-(3-Aminophenyl)benzoxazole (500 mg, 2.4 mmol) and 1,2,4-benzenetricarboxylic anhydride (546 mg, 2.4 mmol) in acetic acid (25 ml) were heated to reflux overnight. On cooling the precipitate was filtered, washed with acetic acid and dried to give the title compound 710 mg (71%). $^1$H NMR (CDCl$_3$) δ 8.44(dd, J=1.5, 7.9 Hz, 1H), 8.36(d, J=4.5 Hz, 2H) 8.28(dt, J=1.5, 7.2 Hz, 1H), 8.12(d, J=7.9 Hz, 1H), 7.86–7.39(m, 4H), 7.45(m, 2H). MS 383 m/z (M−H)$^-$.

Example 2

2-[3-(Naphth[2,3-d]oxazol-2-yl)phenyl]-2,3-dihydro-1,3-dioxo-1H-isoindole-5-carboxylic acid a) 2-(3-Aminophenyl)naphth[2,3-d]oxazole Prepared by the method of Example 1a), from 3-amino-2-naphthol (579 mg, 3.6 mmol) and 3-aminobenzoic acid (500 mg, 3.6 mmol) the subtitle compound was obtained, 58 mg (6%). $^1$H NMR (CDCl$_3$) δ 8.12(s, 1H), 7.90(m, 3H), 7.65(dt, J=1.5, 7.5 Hz, 1H), 7.60(t, J=2.3 Hz, 1H), 7.42(m, 2H), 7.27(t, J=7.9 Hz), 6.82(dd, J=2.3, 7.9 Hz). MS 261 m/z (M+H)$^+$.

b) 2-[3-(Naphth[2,3-d]oxazol-2-yl)phenyl]-2,3-dihydro-1,3-dioxo-1H-isoindole-5-carboxylic acid Prepared by the method of Example 1b), from 2-(3-aminophenyl)naphth[2,3-d]oxazole (36 mg, 0.14 mmol) and 1,2,4-benzenetricarboxylic anhydride (30 mg, 0.16 mmol) the title compound was obtained, 30 mg (44%). $^1$H NMR (DMSO) δ 8.45(m, 2H), 8.38(d, 3H), 8.30(s, 1H), 8.12(m, 3H), 7.82(m, 2H), 7.55(m, 2H). MS 433 m/z (M−H)$^-$.

Example 3

2-[3-(6-Methylbenzoxazol-2-yl)phenyl]-2,3-dihydro-1,3-dioxo-1H-isoindole-5-carboxylic acid a) 2-(3-Aminophenyl)-6-methylbenzoxazole Prepared by the method of Example 1a), from 2-amino-5-methylphenol (448 mg, 3.6 mmol) and 3-aminobenzoic acid (500 mg, 3.6 mmol) the subtitle compound was obtained, 97 mg (12%). $^1$H NMR (CDCl$_3$) δ 7.55(d, J=8.2 Hz, 2H), 7.49(t, J=1.9 Hz, 1H), 7.30(s, 1H), 7.22(t, J=7.5 Hz, 1H), 7.08(dd, J=1.1, 8.2 Hz, 1H), 6.76(dd, J=2.3, 7.9 Hz, 1H), 2.43(s, 3H). MS 225 m/z (M+H)$^+$.

b) 2-[3-(6-Methylbenzoxazol-2-yl)phenyl]-2,3-dihydro-1,3-dioxo-1H-isoindole-5-carboxylic acid

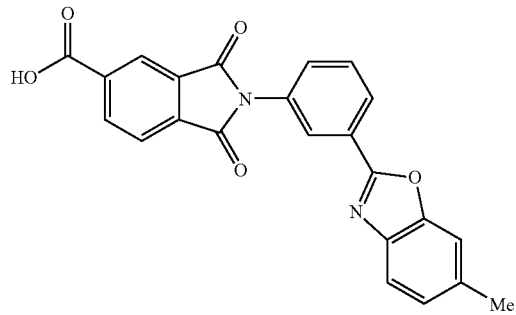

Prepared by the method of Example 1b), from 2-(3-aminophenyl)-6-methylbenzoxazole (32 mg, 0.14 mmol) and 1,2,4-benzenetricarboxylic anhydride (30 mg, 0.16 mmol) the title compound was obtained, 42 mg (72%). $^1$H NMR (DMSO) δ 8.45(dd, 1H), 8.34(bd, 2H), 8.25(dt, 1H), 8.13(d, 1H), 7.75(m, 3H), 7.63(s, 1H), 7.26(d, 1H), 2.50(s, 3H). MS 397 m/z (M−H)$^-$.

Example 4

2-[3-(5-Chlorobenzoxazol-2-yl)phenyl]-2,3-dihydro-1,3-dioxo-1H-isoindole-5-carboxylic acid a) 2-(3-Aminophenyl)-5-chlorobenzoxazole Prepared by the method of Example 1a), from 2-amino-4-chlorophenol (522 mg, 3.6 mmol) and 3-aminobenzoic acid (500 mg, 3.6 mmol) the subtitle compound was obtained, 114 mg (13%). $^1$H NMR (CDCl$_3$) δ 7.81(bs, 1H), 7.69–7.60(m, 3H), 7.49(t, J=7.1 Hz), 7.41–7.27(m, 2H), 6.96(dd, J=2.6, 7.9 Hz, 1H). MS 245, 247 m/z (M+H)$^+$.

b) 2-[3-(5-Chlorobenzoxazol-2-yl)phenyl]-2,3-dihydro-1,3-dioxo-1H-isoindole-5-carboxylic acid

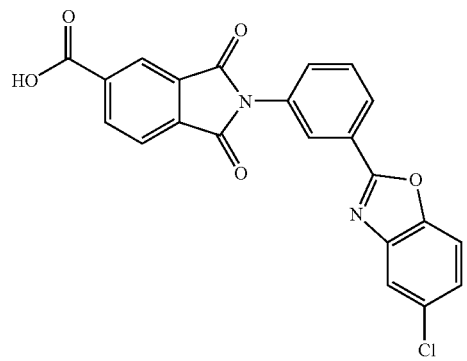

Prepared by the method of Example 1b), from 2-(3-aminophenyl)-5-chlorobenzoxazole (34 mg, 0.14 mmol) and 1,2,4-benzenetricarboxylic anhydride (30 mg, 0.16 mmol) the title compound was obtained, 38 mg (64%). $^1$H NMR (DMSO) δ 8.48(dd, 1H), 8.39(bd, 2H), 8.30(dt, 1H), 8.16(d, 1H), 8.00(d, 1H), 7.88(m, 4H), 7.54(dd, 1H). MS 417 m/z (M−H)$^-$.

Example 5

2-[3-(5-Phenylbenzoxazol-2-yl)phenyl]-2,3-dihydro-1,3-dioxo-1H-isoindole-5-carboxylic acid a) 2-(3-Aminophenyl)-5-phenylbenzoxazole Prepared by the method of Example 1a), from 2-amino-4-phenylphenol (674 mg, 3.6 mmol) and 3-aminobenzoic acid (500 mg, 3.6 mmol) the subtitle compound was obtained, 84 mg (8%). $^1$H NMR (CDCl$_3$) δ 7.97(bs, 1H), 7.70–7.57(m, 5H), 7.49(t, 1H), 7.45–7.35(m, 2H), 6.96(d, J=7.9 Hz, 1H). MS 287 m/z (M+H)$^+$.

b) 2-[3-(5-Phenylbenzoxazol-2-yl)phenyl]-2,3-dihydro-1,3-dioxo-1H-isoindole-5-carboxylic acid

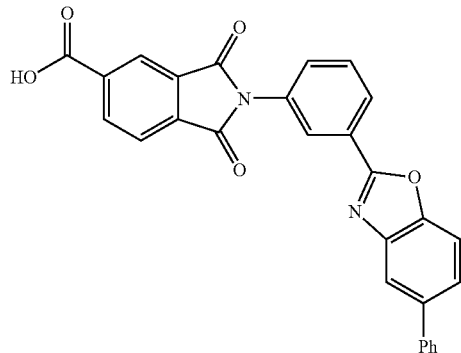

Prepared by the method of Example 1b), from 2-(3-aminophenyl)-5-phenylbenzoxazole (40 mg, 0.14 mmol) and 1,2,4-benzenetricarboxylic anhydride (30 mg, 0.16 mmol) the title compound was obtained, 45 mg (70%). $^1$H NMR (DMSO) δ 8.45(dd, 1H), 8.38(d, 2H), 8.30(dt, 1H), 8.12(m, 2H), 7.9(d, 1H), 7.78(m, 5H), 7.51(t, 2H), 7.40(t, 1H). MS 459 m/z (M−H)$^−$.

Example 6

2-[2-Methoxy-5-(naphth[2,3-d]oxazol-2-yl)phenyl]-2,3-dihydro-1,3-dioxo-1H-isoindole-5-carboxylic acid a) 2-(3-Amino-4-methoxyphenyl)-naphth[2,3-d]oxazole Prepared by the method of Example 1a), from 3-amino-2-naphthol (476 mg, 2.9 mmol) and 4-methoxy-3-aminobenzoic acid (500 mg, 2.9 mmol) the subtitle compound was obtained, 120 mg (14%). $^1$H NMR (CDCl$_3$) δ 8.06(s, 1H), 7.92–7.83(m, 3H), 7.67(dd, J=1.9, 8.2 Hz, 1H), 7.60(d, J=1.9 Hz, 1H), 7.38(m, 2H), 6.85(d, J=8.3 Hz, 1H), 3.88(s, 3H). MS 291 m/z (M+H)$^+$.

b) 2-[2-Methoxy-5-(naphth[2,3-d]oxazol-2-yl)phenyl]-2,3-dihydro-1,3-dioxo-1H-isoindole-5-carboxylic acid

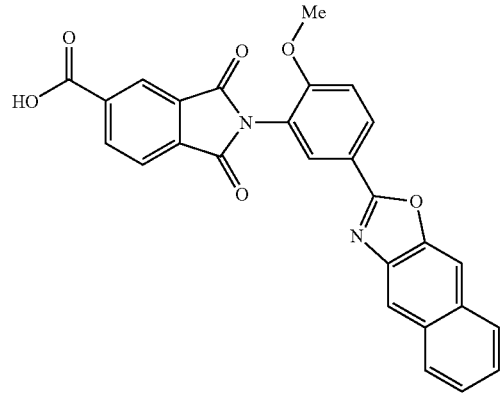

Prepared by the method of Example 1b), from 2-(3-amino-4-methoxyphenyl)naphth[2,3-d]oxazole (67 mg, 0.23 mmol) and 1,2,4-benzenetricarboxylic anhydride (50 mg, 0.26 mmol) the title compound was obtained, 40 mg (37%). $^1$H NMR (DMSO) δ 8.34(m, 4H), 8.24(d, 1H), 8.15(s, 1H), 8.01(m, 3H), 8.43(m, 3H), 3.81(s, 3H). MS 463 m/z (M−H)$^−$.

Example 7

2-[2-Methoxy-5-(6-methylbenzoxazol-2-yl)phenyl]-2,3-dihydro-1,3-dioxo-1H-isoindole-5-carboxylic acid a) 2-(3-Amino-4-methoxyphenyl)-6-methylbenzoxazole Prepared by the method of Example 1a), from 2-amino-5-methylphenol (368 mg, 2.9 mmol) and 4-methoxy-3-aminobenzoic acid (500 mg, 2.9 mmol) the subtitle compound was obtained, 75 mg (10%). $^1$H NMR (CDCl$_3$) δ 7.69–7.58(m, 4H), 7.35(bs, 1H), 6.92(d, J=7.9 Hz), 3.85(s, 3H), 2.51(s, 3H). MS 255 m/z (M+H)$^+$.

b) 2-[2-Methoxy-5-(6-methylbenzoxazol-2-yl)phenyl]-2,3-dihydro-1,3-dioxo-1H-isoindole-5-carboxylic acid

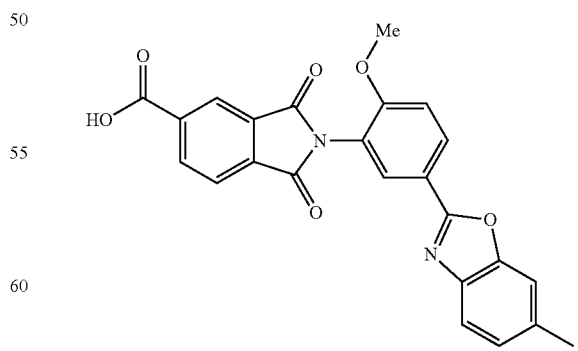

Prepared by the method of Example 1b), from 2-(3-amino-4-methoxyphenyl)-6-methylbenzoxazole (58 mg, 0.23 mmol) and 1,2,4-benzenetricarboxylic anhydride (50 mg, 0.26 mmol) the title compound was obtained, 54 mg (55%). ¹H NMR (DMSO) δ 8.31(dd, 1H) 8.16(m, 3H), 7.97(d, 1H), 7.50(d, 1H), 7.43(s, 1H), 7.32(d, 1H), 7.08(d, 1H), 3.73(s, 3H), 2.33(s, 3H). MS 427 m/z (M−H)⁻.

Example 8

2-[2-Methoxy-5-(5-chlorobenzoxazolyl)phenyl]-2,3-dihydro-1,3-dioxo-1H-isoindole-5-carboxylic acid a) 2-(3-Amino-4-methoxyphenyl)-5-chlorobenzoxazole Prepared by the method of Example 1a), from 4-chloro-2-aminophenol (429 mg, 2.9 mmol) and 4-methoxy-3-aminobenzoic acid (500 mg, 2.9 mmol) the subtitle compound was obtained, 111 mg (10%). ¹H NMR (CDCl₃) δ 7.70(d, J=1.9 Hz, 1H), 7.65(dd, J=1.9, 8.3 Hz, 1H), 7.59(d, J=1.9 Hz, 1H), 7.46(d, J=8.3 Hz, 1H), 7.28(dd, J=1.9, 8.3 Hz, 1H), 6.90(d, J=8.3 Hz, 1H), 3.96(s, 3H). MS 275 m/z (M+H)⁺.

b) 2-[2-Methoxy-5-(5-chlorobenzoxazolyl)phenyl]-2,3-dihydro-1,3-dioxo-1H-isoindole-5-carboxylic acid

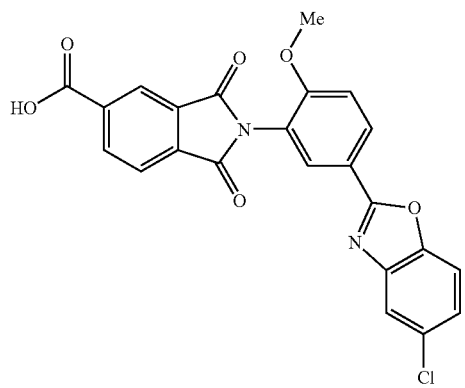

Prepared by the method of Example 1b), from 2-(3-amino-4-methoxyphenyl)-5-chlorobenzoxazole (63 mg, 0.23 mmol) and 1,2,4-benzenetricarboxylic anhydride (50 mg, 0.26 mmol) the title compound was obtained, 62 mg (60%). ¹H NMR (DMSO) δ 8.45(dd, 1H), 8.33(m, 3H), 8.12(d, 1H), 7.89(d, 1H), 7.80(d, 1H), 7.47(m, 2H), 3.89(s, 3H). MS 447 m/z (M−H)⁻.

Example 9

2-[2-Methoxy-5-(5-phenylbenzoxazol-2-yl)phenyl]-1,3-dioxo-2,3-dihydro-1H-isoindole-5-carboxylic acid a) 2-(3-Amino-4-methoxyphenyl)-5-phenylbenzoxazole Prepared by the method of Example 1a), from 2-amino-4-phenylphenol (554 mg, 2.9 mmol) and 4-methoxy-3-aminobenzoic acid (500 mg, 2.9 mmol) the subtitle compound was obtained, 111 mg (10%). ¹H NMR (CDCl₃) δ 7.84(s, 1H), 7.72–7.38(m, 9H), 6.93(d, J=8.3 Hz, 1H), 3.96(s, 3H). MS 316 m/z (M+H)⁺.

b) 2-[2-Methoxy-5-(5-phenylbenzoxazol-2-yl)phenyl]-1,3-dioxo-2,3-dihydro-1H-isoindole-5-carboxylic acid

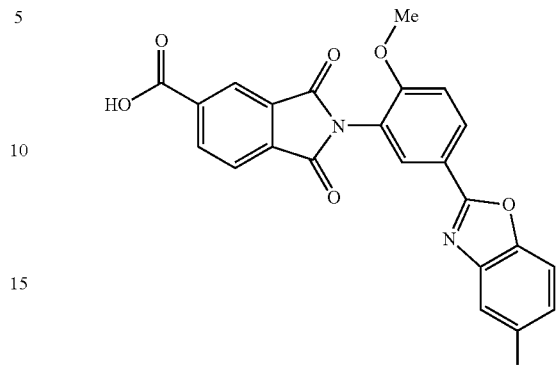

Prepared by the method described in Example 1b), from 2-(3-amino-4-methoxyphenyl)-5-phenylbenzoxazole (73 mg, 0.23 mmol) and 1,2,4-benzenetricarboxylic anhydride (50 mg, 0.26 mmol) the title compound was obtained, 50 mg (44%). ¹H NMR (DMSO) δ 8.46(dd, 1H), 8.35(m, 3H), 8.13(d, 1H), 8.03(d, 1H), 7.84(d, 1H), 7.73(m, 3H), 7.49(m, 3H), 7.39(t, 1H), 3.90(s, 3H). MS 489 m/z (M−H)⁻.

Example 10

2-[2-Methoxy-5-(benzoxazol-2-yl)phenyl]-2,3-dihydro-1,3-dioxo-1H-isoindole-5-carboxylic acid a) 2-(3-Amino-4-methoxyphenyl)-benzoxazole Prepared by the method of Example 1a), from 2-aminophenol (326 mg, 2.9 mmol) and 4-methoxy-3-aminobenzoic acid (500 mg, 2.9 mmol) the subtitle compound was obtained, 97 mg (13%). ¹H NMR (CDCl₃) δ 7.66–7.45(m, 4H), 7.24(m, 2H), 6.82(d, J=8.3 Hz, 1H), 3.86(s, 3H). MS 241 m/z (M+H)⁺.

b) 2-[2-Methoxy-5-(benzoxazol-2-yl)phenyl]-2,3-dihydro-1,3-dioxo-1H-isoindole-5-carboxylic acid

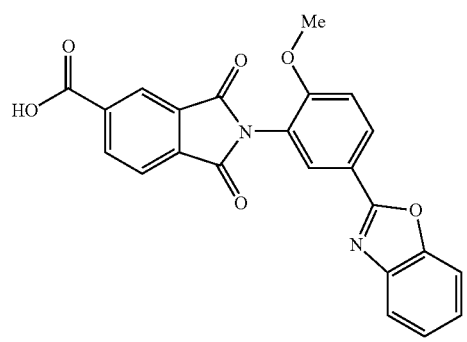

Prepared by the method of Example 1b), from 2-(3-amino-4-methoxyphenyl)benzoxazole (55 mg, 0.23 mmol) and 1,2,4-benzenetricarboxylic anhydride (50 mg, 0.26 mmol) the title compound was obtained, 64 mg (67%). ¹H NMR (DMSO) δ 8.45(dd, 1H), 8.32(m, 3H), 8.12(d, 1H), 7.78(m, 2H), 7.49(d, 1H), 7.41(m, 2H), 3.88(s, 3H). MS 413 m/z (M−H)⁻.

Example 11

2-[2-Chloro-(5-chlorobenzoxazol-2-yl)phenyl]-2,3-dihydro-1,3-dioxo-1H-isoindole-5-carboxylic acid a) 2-(3-Amino-6-chlorophenyl)-5-chlorobenzoxazole Prepared by the method of Example 1a), from 4-chloro-2-aminophenol (861 mg, 6.0 mmol) and 4-chloro-3-aminobenzoic acid (1 g, 6.0 mmol) the subtitle compound was obtained, 1.57 g (97%). $^1$H NMR (CDCl$_3$) δ 7.73(d, J=2.3 Hz, 1H), 7.65(d, J=1.9 Hz, 1H), 7.55(dd, J=2.3 Hz, 1H), 7.49(d, 1H), 7.33(dd, 1H). MS 279, 281 m/z (M+H)$^+$.

b) 2-[2-Chloro-(5-chlorobenzoxazol-2-yl)phenyl]-2,3-dihydro-1,3-dioxo-1H-isoindole-5-carboxylic acid

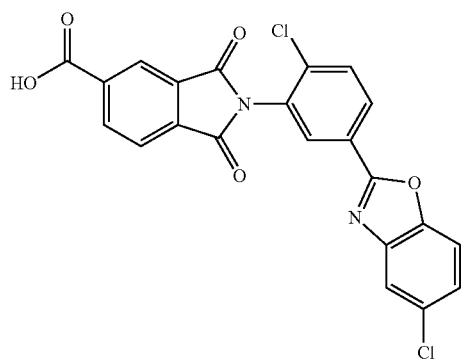

Prepared by the method of Example 1b), from 2-(3-amino-6-chlorophenyl)-5-chlorobenzoxazole (327 mg, 1.2 mmol) and 1,2,4-benzenetricarboxylic anhydride (250 mg, 1.3 mmol) the title compound was obtained, 180 mg (31%). $^1$H NMR (DMSO) δ 8.33(d, 1H), 8.25(dd, 1H), 8.16(bs, 1H), 8.12(dd, 1H), 7.95(d, 1H), 7.77(d, 1H), 7.74(d, 1H), 7.63(d, 1H). MS 451, 452 m/z (M–H)$^-$.

Example 12

2-[4-Chloro-(5-phenylbenzoxazol-2-yl)phenyl]-2,3-dihydro-1,3-dioxo-1H-isoindole-5-carboxylic acid a) 2-(2-Chloro-5-aminophenyl)benzoxazole Prepared by the method of Example 1a), from 2-aminophenol (318 mg, 2.9 mmol) and 4-chloro-3-aminobenzoic acid (500 mg, 2.9 mmol) the subtitle compound was obtained, 583 mg (82%). $^1$H NMR (CDCl$_3$) δ 7.81(t, 1H), 7.59(t, 1H), 7.44(d, 1H), 7.36(d, 1H), 7.29(d, 1H), 6.74(dd, 2H). MS 245 m/z (M+H)$^+$.

b) 2-[4-Chloro-(5-phenylbenzoxazol-2-yl)phenyl]-2,3-dihydro-1,3-dioxo-1H-isoindole-5-carboxylic acid

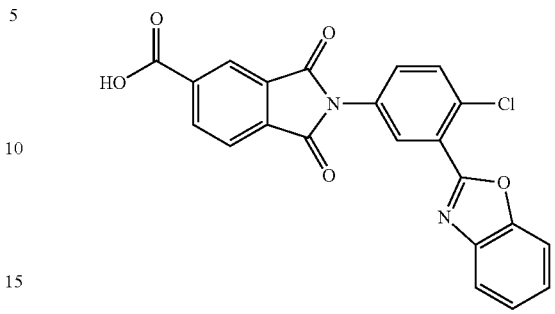

Prepared by the method of Example 1b), from 2-(2-chloro-5-aminophenyl)benzoxazole (250 mg, 1.0 mmol) and 1,2,4-benzenetricarboxylic anhydride (196 mg, 1.0 mmol) the title compound was obtained, 350 mg (82%). $^1$H NMR (DMSO) δ 8.50(dd, 1H), 8.42(m, 2H), 8.18(d, 1H), 7.96(m, 3H), 7.83(dd, 1H), 7.56(m, 2H). MS 417 m/z (M–H)$^-$.

Example 13

2-[2-Methyl-5-(5-phenylbenzoxazol-2-yl)phenyl]-2,3-dihydro-1,3-dioxo-1H-isoindole-5-carboxylic acid a) 2-(3-Amino-4-methylphenyl)-4-phenylbenzoxazole Prepared by the method of Example 1a), from 2-amino-4-phenylphenol (1.23 g, 7.0 mmol) and 3-amino-4-methylbenzoic acid (1.00 g, 7.0 mmol) the subtitle compound was obtained, 814 mg (41%). $^1$H NMR (DMSO) δ 8.01(d, 1H), 7.82(d, 1H), 7.73(m, 2H), 7.67(dd, 1H), 7.49(m, 3H), 7.40(d, 1H), 7.34(dd, 1H), 7.15(d, 1H), 2.50(s, 3H). MS 301 m/z (M+H)$^+$.

b) 2-[2-Methyl-5-(5-phenylbenzoxazol-2-yl)phenyl]-2,3-dihydro-1,3-dioxo-1H-isoindole-5-carboxylic acid

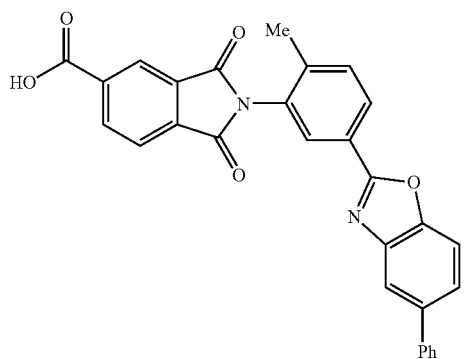

Prepared by the method of Example 1b), from 2-(3-amino-4-methylphenyl)-4-phenylbenzoxazole (167 mg, 0.9 mmol) and 1,2,4-benzenetricarboxylic anhydride (250 mg, 0.9 mmol) the title compound was obtained, 340 mg (82%). $^1$H NMR (DMSO) δ 8.45(dd, 1H), 8.34(d, 2H), 8.26(dd, 1H), 8.13(d, 1H), 8.05(d, 1H), 7.85(d, 1H), 7.73(m, 4H), 7.50(t, 1H), 7.39(t, 1H), 2.28(s, 3H). MS 473 m/z (M−H)⁻.

Example 14

2-[2-Methyl-5-(benzoxazol-2-yl)phenyl]-2,3-dihydro-1,3-dioxo-1H-isoindole-5-carboxylic acid a) 2-(3-Amino-4-methylphenyl)benzoxazole Prepared by the method of Example 1a), from 2-aminophenol (720 mg, 7.0 mmol) and 3-amino-4-methylbenzoic acid (1.00 g, 7.0 mmol) the subtitle compound was obtained, 942 mg (57%). ¹H NMR (DMSO) δ 7.67(m, 2H), 7.42(s, 1H), 7.31(m, 2H), 7.24(d, 1H), 7.07(d, 1H), 2.43(s, 3H). MS 225 m/z (M+H)⁺.

b) 2-[2-Methyl-5-(benzoxazol-2-yl)phenyl]-2,3-dihydro-1,3-dioxo-1H-isoindole-5-carboxylic acid

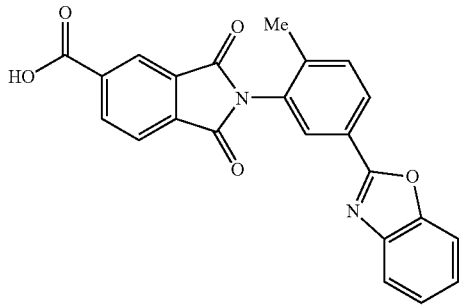

Prepared by the method of Example 1b), from 2-(3-amino-4-methylphenyl)benzoxazole (250 mg, 1.1 mmol) and 1,2,4-benzenetricarboxylic anhydride (214 mg, 1.1 mmol) the title compound was obtained. 375 mg (84%). ¹H NMR (DMSO) δ 8.45(dd, 1H), 8.33(d, 2H), 8.23(dd, 1H), 8.12(d, 1H), 7.79(m, 2H), 7.68(d, 1H), 7.44(m, 2H). MS 397 m/z (M−H)⁻.

Example 15

2-[2-Methoxy-5-[5-(benzofuran-2-yl)benzoxazol-2-yl]phenyl]-1,3-dioxo-2,3-dihydro-1H-isoindole-5-carboxylic acid a) 4-Methoxy-3-nitro-benzoyl chloride Oxalyl chloride (15.8 ml, 180 mmol) was added dropwise with stirring to a solution of 4-methoxy-3-nitrobenzoic acid (7.00 g, 36.00 mmol) in THF containing 10 μL DMF. After 1 h the solvent was removed under reduced pressure. The product was used directly in the next step.

b) N-(2-Hydroxy-5-bromophenyl)-3-nitro-4-methoxybenzamide

A solution of 4-methoxy-3-nitro-benzoyl chloride (7.12 g, 33.0 mmol) in THF (50 ml) was added dropwise with stirring to a solution of 4-bromo-2-aminophenol (6.20 g, 33.0 mmol) in THF (50 ml) containing triethylamine (6.82 ml, 66.0 mmol). After addition was complete the reaction was stirred at room temperature overnight. The reaction mixture was concentrated to approximately half the original volume and the precipitate collected by filtration. The solid was washed with methanol and ether and dried under vacuum to give the subtitle compound as a brown solid (5.24 g, 42%). ¹H NMR (DMSO) δ 8.58(d, 1H), 8.36(dd, 1H), 7.55(d, 1H), 6.96(m, 2H), 6.68(dd, 1H), 4.05(s, 3H).

c) 2-(3-Nitro-4-methoxyphenyl)-5-bromobenzoxazole

A suspension of N-(2-hydroxy-5-bromophenyl)-3-nitro-4-methoxybenzamide (5.24 g, 14.2 mmol) and toluenesulfonic acid monohydrate (5.36 g, 31.2 mmol) in toluene (100 ml) was heated to reflux overnight. The cooled reaction mixture was washed with saturated sodium hydrogen carbonate solution (care foaming) and the organic layer separated. The aqueous layer was extracted with ethyl acetate (2×50 ml) and the combined organic layers dried over sodium sulfate and the solvent removed under reduced pressure. The residue was triturated with ether, filtered and dried under vacuum to give the subtitle compound as a pale pink solid (4.51 g, 93%). ¹H NMR (DMSO) δ 8.61(d, 1H), 8.42(dd, 1H), 8.05(d, 1H), 7.79(d, 1H), 7.61(m, 2H), 4.05(s, 3H). MS m/z 349.0 (M+H)⁺.

d) 2-(3-Nitro-4-methoxyphenyl)-5-(benzofuran-2-yl)benzoxazole 2-(3-Nitromethoxyphenyl)-5-bromobenzoxazole (200 mg, 0.57 mmol) was suspended in degassed ethylene glycol dimethyl ether (DME, 10 ml). Tetrakis (triphenylphosphine) palladium (0) (33 mg, 0.03 mmol), 2M sodium carbonate (0.5 ml) and benzofuran-2-boronic acid (137 mg, 0.85 mmol) were added and the reaction was further degassed. The reaction was heated to reflux for 16 h. The cooled reaction mixture was diluted with water (10 ml) and extracted with dichloromethane (2×10 ml). The combined organic extracts were dried over sodium sulfate, filtered and the solvent removed under reduced pressure. The residue was triturated with methanol (5 ml) and filtered. The solid was dried under vacuum to give the subtitle compound (50 mg, 15%). ¹H NMR (DMSO) δ 8.63(d, 1H), 8.44(dd, 1H), 8.29(d, 1H), 8.01(dd, 1H), 7.92(d, 1H), 7.69–7.59(m, 3H), 7.54(s, 1H), 7.36–7.25(m, 2H), 4.04(s, 3H).

e) 2-(3-Amino-4-methoxyphenyl)-5-(benzofuran-2-yl)benzoxazole

A suspension of 2-(3-nitro-4-methoxyphenyl)-5-(benzofuran-2-yl)benzoxazole (50 mg, 0.13 mmol) in dioxane (10 ml) was placed under an atmosphere of argon. Palladium on carbon (10%) (10 mg) was added and the reaction purged with hydrogen and stirred at room temperature for 36 h. The reaction was filtered through a bed of celite and the filtrate concentrated to give the subtitle compound (40 mg, 86%). MS m/z 357.1 (M+H)⁺.

f) 2-[2-Methoxy-5-[(5-benzofuran-2-yl)benzoxazol-2-yl]phenyl]-1,3-dioxo-2,3-dihydro-1H-isoindole-5-carboxylic acid

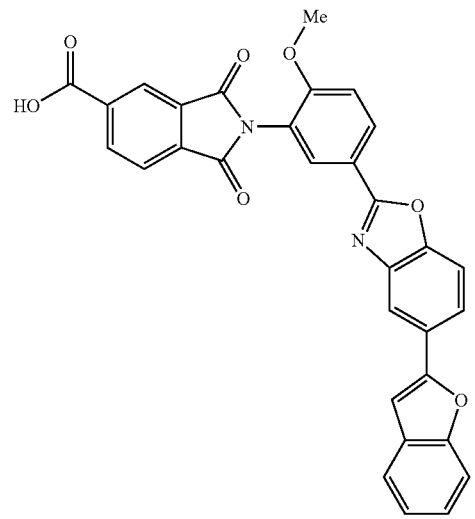

2-(3-Amino-4-methoxyphenyl-5-(benzofuran-2-yl)benzoxazole (40 mg, 0.11 mmol) and 1,2,4-benzenetricarboxylic anhydride (23 mg, 0.12 mmol) in acetic acid (5 ml) were heated to reflux overnight. On cooling the precipitate was filtered, washed with acetic acid and dried under vacuum to give the title compound (30 mg, 51%). $^1$H NMR (DMSO) δ 8.45(dd, 1H), 8.38–8.35(m, 3H), 8.29(d, 1H), 8.13(dd, 1H), 8.00(dd, 1H), 7.90(d, 1H), 7.67(m, 2H), 7.55(s, 1H), 7.50(d, 1H), 7.36–7.25(m, 2H), 3.89(s, 3H). MS m/z 528.6 (M+H)$^+$.

Example 16

2-[2-Methoxy-5-[5-(3-acetyl)phenylbenzoxazol-2yl]phenyl]-1,3-dioxo-2,3-dihydro-1H-isoindole-5-carboxylic acid a) 2-(3-Nitro-4-methoxyphenyl)-5-(3-acetylphenyl)benzoxazole Prepared by the method of Example 15d), from 2-(3-nitro-4-methoxyphenyl)-5-bromobenzoxazole (200 mg, 0.57 mmol) and 3-acetylphenylboronic acid (139 mg, 0.85 mmol) the subtitle compound was obtained (89 mg, 26%). $^1$H NMR (DMSO) δ 8.75(d, 1H), 8.46(dd, 1H), 8.23(t, 1H), 7.98–7.96(m, 2H), 7.69–7.56(m, 3H), 7.27(d, 1H), 4.08(s, 3H), 2.68(s, 3H).

b) 2-(3-Amino-4-methoxyphenyl)-5-(3-acetylphenyl)benzoxazole

Prepared by the method of Example 15e), from 2-(3-nitro-4-methoxyphenyl)-5-(3-acetylphenyl)-benzoxazole (89 mg, 0.23 mmol) the subtitle compound was obtained (80 mg, 97%). MS m/z 359.1 (M+H)$^+$.

c) 2-[2-Methoxy-5-[5-(3-acetyl)phenylbenzoxazol-2-yl]phenyl]-1,3-dioxo-2,3-dihydro-1H-isoindole-5-carboxylic acid

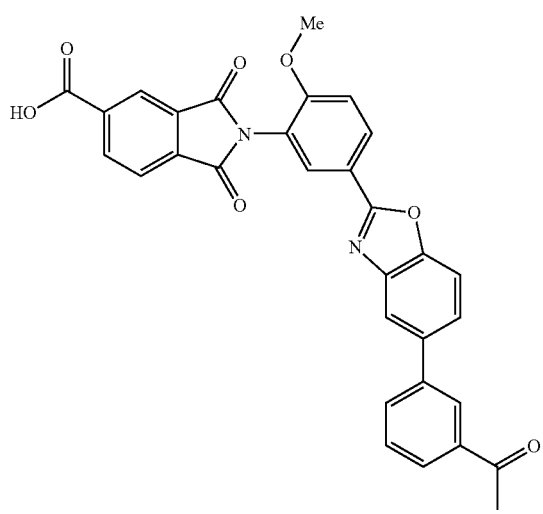

Prepared by the method of Example 15f), from 2-(3-amino-4-methoxyphenyl-5-(3-acetylphenyl)benzoxazole (80 mg, 0.22 mmol) and 1,2,4-benzenetricarboxylic anhydride (47 mg, 0.25 mmol) the title compound was obtained (84 mg, 71%). $^1$H NMR (DMSO) δ 8.45(dd, 1H), 8.39–8.33 (m, 3H), 8.26(s, 1H), 8.26(t, 1H), 8.14–8.11(m, 2H), 8.01(d, 1H), 7.96(d, 1H), 7.88(d, 1H), 7.78(dd, 1H), 7.65(t, 1H), 7.50(d, 1H). MS m/z 533.0 (M+H)$^+$.

Example 17

2-[2-Methoxy-5-[5-(3,4-methylenedioxyphenyl)benzoxazol-2-yl]phenyl]-1,3-dioxo-2,3-dihydro-1H-isoindole-5-carboxylic acid a) 2-(3-Nitro-4-methoxyphenyl)-5-[3,4-(methylenedioxy)phenyl]benzoxazole Prepared by the method of Example 15d), from 2-(3-nitro-4-methoxyphenyl)-5-bromobenzoxazole (200 mg, 0.57 mmol) and 3,4-methylenedioxyboronic acid (141 mg, 0.85 mmol) the subtitle compound was obtained (127 mg, 38%). $^1$H NMR (DMSO) δ 8.63(d, 1H), 8.45(dd, 1H), 7.99(d, 1H), 7.82(d, 1H), 7.82(dd, 1H), 7.62(d, 1H), 7.33(d, 1H), 7.21(dd, 1H), 7.02(d, 1H), 6.08(s, 2H), 4.05(s, 3H).

b) 2-(3-Amino-4-methoxyphenyl)-5-[3,4-(methylenedioxy)phenyl]benzoxazole

Prepared by the method of Example 15e), from 2-(3-nitro-4-methoxyphenyl)-5-[3,4-(methylenedioxy)phenyl]benzoxazole (135 mg, 0.35 mmol) the subtitle compound was obtained (120 mg, 95%) MS m/z 361.1 (M+H)$^+$.

c) 2-[2-Methoxy-5-[5-(3,4-methylenedioxyphenyl)benzoxazol-2-yl]phenyl]-1,3-dioxo-2,3-dihydro-1H-isoindole-5-carboxylic acid

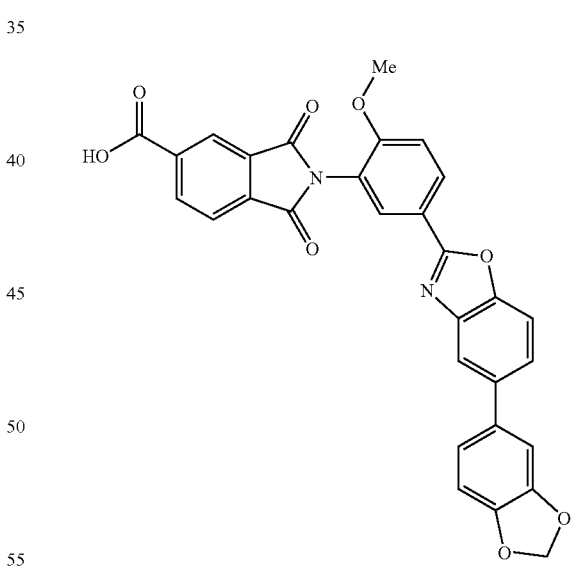

Prepared by the method of Example 15f), from 2-(3-amino-4-methoxyphenyl-5-[3,4-(methylenedioxy)phenyl]benzoxazole (120 mg, 0.33 mmol) and 1,2,4-benzenetricarboxylic anhydride (70 mg, 0.36 mmol) the title compound was obtained (82 mg, 46%). $^1$H NMR (DMSO) δ 8.45(dd, 1H), 8.37–8.32(m, 3H), 8.12(d, 1H), 7.96(d, 1H), 7.79(d, 1H), 7.63(dd, 1H), 7.49(d, 1H), 7.33(d, 1H), 7.20(dd, 1H), 7.02(d, 1H), 6.06(2H, s), 3.88(s, 3H). MS m/z 535.0 (M+H)$^+$.

Example 18

2-[2-Methoxy-5-[5-(4-chlorophenyl)benzoxazol-2-yl]phenyl]-1,3-dioxo-2,3-dihydro-1H-isoindole-5-carboxylic acid a) 2-(3-Nitro-4-methoxyphenyl)-5-(4-chlorophenyl)benzoxazole Prepared by the method of Example 15d), from 2-(3-nitro-4-methoxyphenyl)-5-bromobenzoxazole (200 mg, 0.57 mmol) and 4-chlorophenylboronic acid (134 mg, 0.85 mmol) the subtitle compound was obtained (148 mg, 68%). $^1$H NMR (CDCl$_3$) δ 8.74(s, 1H), 8.45(dd, 1H), 7.90(d, 1H), 7.64(d, 1H), 7.55(d, 3H), 7.44(d, 2H), 7.26(d, 1H), 4.07(s, 3H).

b) 2-(3-Amino-4-methoxyphenyl)-5-(4-chlorophenyl)benzoxazole

Prepared by the method of Example 15e), from 2-(3-nitro-4-methoxyphenyl)-5-(4-chlorophenyl)benzoxazole (134 mg, 0.35 mmol) the subtitle compound was obtained (104 mg, 85%). MS m/z 351.1 (M+H)$^+$.

c) 2-[2-Methoxy-5-[5-(4-chlorophenyl)benzoxazol-2-yl]phenyl]-1,3-dioxo-2,3-dihydro-1H-isoindole-5-carboxylic acid

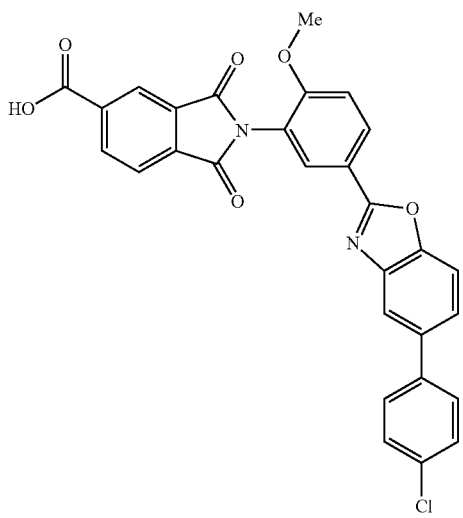

Prepared by the method of Example 15f), from 2-(3-amino-4-methoxyphenyl)-5-(4-chlorophenyl)benzoxazole (104 mg, 0.30 mmol) and 1,2,4-benzenetricarboxylic anhydride (58 mg, 0.33 mmol) the title compound was obtained (67 mg, 43%). $^1$H NMR (DMSO) δ 8.45(dd, 1H), 8.38–8.33(m, 3H), 8.12(d, 1H), 8.05(d, 1H), 7.86(d, 1H), 7.77(d, 1H), 7.70(dd, 1H), 7.55–7.48(m, 3H), 3.89(s, 3H). MS m/z 525.1 (M+H)$^+$.

Example 19

2-[2-Methoxy-5-[5-(3,4-dimethoxy)phenylbenzoxazol-2-yl]phenyl]-1,3-dioxo-2,3-dihydro-1H-isoindole-5-carboxylic acid a) 2-(3-Nitro-4-methoxyphenyl)-5-(3,4-dimethoxyphenyl)benzoxazole Prepared by the method of Example 15d), from 2-(3-nitro-4-methoxyphenyl)-5-bromobenzoxazole (200 mg, 0.57 mmol) and 3,4-dimethoxyphenylboronic acid (157 mg, 0.85 mmol) the subtitle compound was obtained (180 mg, 78%). $^1$H NMR (CDCl$_3$) δ 8.74(d, 1H), 8.44(dd, 1H), 7.91(d, 1H), 7.62(d, 1H), 7.57(dd, 1H), 7.25(d, 1H), 7.19–7.14(m, 2H), 6.98(d, 1H), 4.07(s, 3H), 3.97(s, 3H), 3.94(s, 3H).

b) 2-(3-Amino-4-methoxyphenyl)-5-(3,4-dimethoxyphenyl)benzoxazole

Prepared by the method of Example 15e), from 2-(3-nitro-4-methoxyphenyl)-5-(3,4-dimethoxyphenyl)benzoxazole (157 mg, 0.39 mmol) the subtitle compound was obtained (137 mg, 93%). MS m/z 377.1 (M+H)$^+$.

c) 2-[2-Methoxy-5-[5-(3,4-dimethoxy)phenylbenzoxazol-2-yl]phenyl]-1,3-dioxo-2,3-dihydro-1H-isoindole-5-carboxylic acid

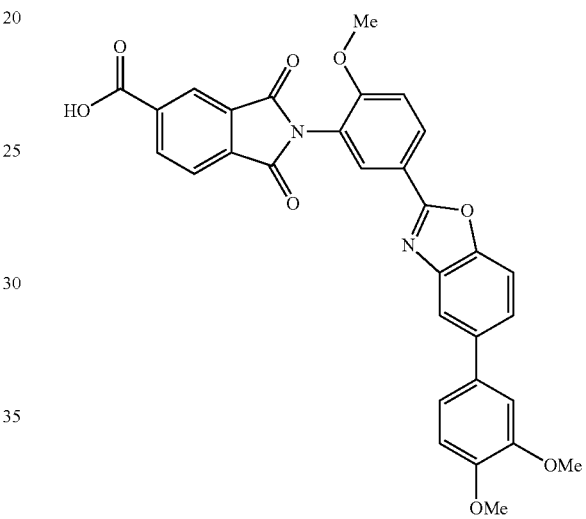

Prepared by the method of Example 15f), from 2-(3-amino-4-methoxyphenyl)-5-(3,4-dimethoxyphenyl)benzoxazole (137 mg, 0.36 mmol) and 1,2,4-benzenetricarboxylic anhydride (69 mg, 0.39 mmol) the title compound was obtained (101 mg, 51%). $^1$H NMR (DMSO) δ 8.45(dd, 1H), 8.37–8.32(m, 3H), 8.13(d, 1H), 8.02(d, 1H), 7.80(d, 1H), 7.68(dd, 1H), 7.50(d, 1H), 7.30–7.24(m, 3H), 7.05(d, 1H), 3.88(s, 3H), 3.87(s, 3H), 3.80(s, 3H). MS m/z 551.2 (M+H)$^+$.

Example 20

2-[2-Methoxy-5-[5-(2-methoxy)phenylbenzoxazol-2-yl]phenyl]-1,3-dioxo-2,3-dihydro-1H-isoindole-5-carboxylic acid a) 2-(3-Nitro-4-methoxyphenyl)-5-(2-methoxyphenyl)benzoxazole Prepared by the method of Example 15d), from 2-(3-nitro-4-methoxyphenyl)-5-bromobenzoxazole (200 mg, 0.57 mmol) and 2-methoxyphenylboronic acid (130 mg, 0.85 mmol) the subtitle compound was obtained (163 mg, 76%). $^1$H NMR (CDCl$_3$) δ 8.75(d, 1H), 8.45(dd, 1H), 7.93(d, 1H), 7.61(d, 1H), 7.54(dd, 1H), 7.39–7.34(m, 2H), 7.25(d, 1H), 7.09–7.01(m, 2H), 4.07(s, 3H), 3.83(s, 3H).

b) 2-(3-Amino-4-methoxyphenyl)-5-(2-methoxyphenyl)benzoxazole

Prepared by the method of Example 15e), from 2-(3-nitro-4-methoxyphenyl-5-(2-methoxyphenyl)benzoxazole (130 mg, 0.35 mmol) the subtitle compound was obtained (120 mg, 99%). MS m/z 347.1 (M+H)+.

c) 2-[2-Methoxy-5-[5-(2-methoxy)phenylbenzoxazol-2-yl]phenyl]-1,3-dioxo-2,3-dihydro-1H-isoindole-5-carboxylic acid

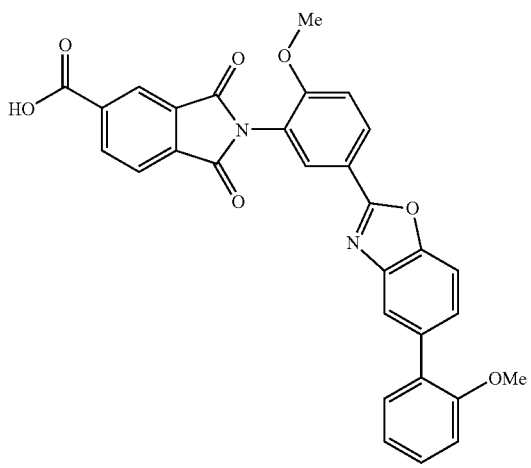

Prepared by the method of Example 15f), from 2-(3-amino-4-methoxyphenyl)-5-(2-methoxyphenyl)benzoxazole (346 mg, 0.40 mmol) and 1,2,4-benzenetricarboxylic anhydride (77 mg, 0.44 mmol) the title compound was obtained (61 mg, 29%). $^1$H NMR (DMSO) δ 8.45(dd, 1H), 8.38–8.33(m, 3H), 8.13(d, 1H), 7.82(d, 1H), 7.78(d, 1H), 7.49(d, 2H), 7.36(m, 2H), 7.14(d, 1H), 7.06(t, 1H), 3.89(s, 3H), 3.79(s, 3H). MS m/z 521.2 (M+H)+.

Example 21

2-[2-Methoxy-5-[5-(3,4-dichloro)phenylbenzoxazol-2-yl]phenyl]-1,3-dioxo-2,3-dihydro-1H-isoindole-5-carboxylic acid a) 2-(3-Nitro-4-methoxyphenyl)-5-(3,4-dichlorophenyl)benzoxazole Prepared by the method of Example 15d), from 2-(3-nitro-4-methoxyphenyl)-5-bromobenzoxazole (200 mg, 0.57 mmol) and 3,4-dichlorophenylboronic acid (176 mg, 0.85 mmol) the subtitle compound was obtained (176 mg, 74%). $^1$H NMR (CDCl$_3$) δ 8.74(d, 1H), 8.44(dd, 1H), 7.89(d, 1H), 7.70(d, 1H), 7.65(d, 1H), 7.54(d, 2H), 7.44(dd, 1H), 7.26(d, 1H), 4.08(s, 3H).

b) 2-(3-Amino-4-methoxyphenyl)-5-(3,4-dichlorophenyl)benzoxazole

Prepared by the method of Example 15e), from 2-(3-nitro-4-methoxyphenyl)-5-(3,4-dichlorophenyl)benzoxazole (164 mg, 0.39 mmol) the subtitle compound was obtained (114 mg, 76%). MS m/z 385.0 (M+H)+.

c) 2-[2-Methoxy-5-[5-(3,4-dichloro)phenylbenzoxazol-2-yl]phenyl]-1,3-dioxo-2,3-dihydro-1H-isoindole-5-carboxylic acid

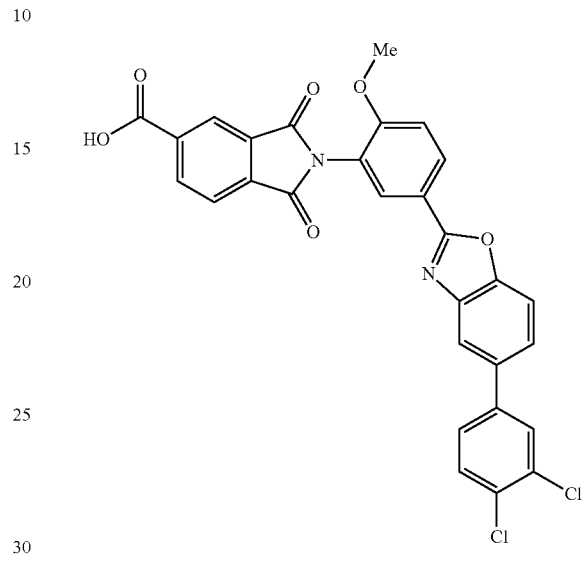

Prepared by the method of Example 15f), from 2-(3-amino-4-methoxyphenyl)-5-(3,4-dichlorophenyl)benzoxazole (114 mg, 0.30 mmol) and 1,2,4-benzenetricarboxylic anhydride (58 mg, 0.33 mmol) the title compound was obtained (88 mg, 53%). $^1$H NMR (DMSO) δ 8.45(dd, 1H), 8.38–8.33(m, 3H), 8.13–8.10(m, 2H), 8.03(d, 1H), 7.76(d, 1H), 7.77–7.75(m, 3H), 7.49(d, 1H), 3.89(s, 3H). MS m/z 559.1 (M+H)+.

Example 22

2-[2-Methoxy-5-[5-(3-chloro-4-fluoro)phenylbenzoxazol-2-yl]phenyl]-1,3-dioxo-2,3-dihydro-1H-isoindole-5-carboxylic acid a) 2-(3-Nitro-4-methoxyphenyl)-5-(3-chloro-4-fluorophenyl)benzoxazole Prepared by the method of Example 15d), from 2-(3-nitro-4-methoxyphenyl)-5-bromobenzoxazole (200 mg, 0.57 mmol) and 3-chloro-4-fluorophenylboronic acid (150 mg, 0.85 mmol) the subtitle compound was obtained (163 mg, 72%). $^1$H NMR (CDCl$_3$) δ 8.74(d, 1H), 8.45(dd, 1H), 7.87(d, 1H), 7.64(m, 2H), 7.52(dd, 1H), 7.49–7.44(m, 1H), 7.28–7.21(m, 2H), 4.08(s, 3H).

b) 2-(3-Amino-4-methoxyphenyl)-5-(3-chloro-4-fluorophenyl)benzoxazole

Prepared by the method of Example 15e), from 2-(3-nitro-4-methoxyphenyl)-5-(3-chloro-4-fluorophenyl)benzoxazole (150 mg, 0.38 mmol) the subtitle compound was obtained (107 mg, 76%). MS m/z 369.1 (M+H)+.

c) 2-[2-Methoxy-5-[5-(3-chloro-4-fluoro)phenylbenzoxazol-2-yl]phenyl]-1,3-dioxo-2,3-dihydro-1H-isoindole-5-carboxylic acid

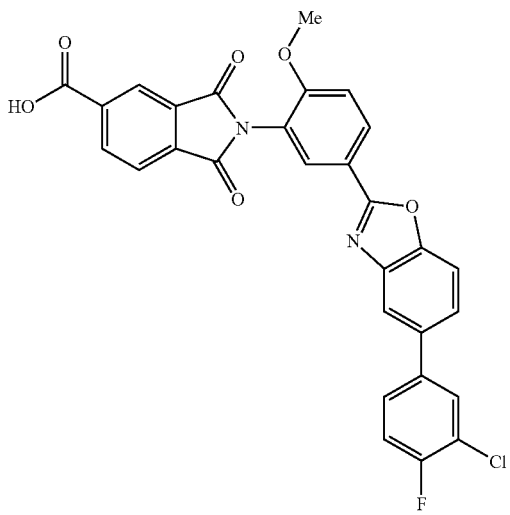

Prepared by the method of Example 15f), from 2-(3-amino-4-methoxyphenyl)-5-(4-fluoro-3-chlorophenyl)benzoxazole (107 mg, 0.29 mmol) and 1,2,4-benzenetricarboxylic anhydride (56 mg, 0.31 mmol) the title compound was obtained (101 mg, 64%). $^1$H NMR (DMSO) δ 8.45(dd, 1H), 8.38–8.33(m, 3H), 8.12(d, 1H), 8.09(d, 1H), 7.98(dd, 1H), 7.85(d, 1H), 7.79–7.71(m, 2H), 7.55(d, 1H), 7.49(d, 1H). MS m/z 543.1 (M+H)$^+$.

Example 23

2-[2-Methoxy-5-[5-(4-trifluoromethyl)phenylbenzoxazol-2-yl]phenyl]-1,3-dioxo-2,3-dihydro-1H-isoindole-5-carboxylic acid a) 2-(3-Nitro-4-methoxyphenyl)-5-(4-trifluoromethylphenyl)benzoxazole Prepared by the method of Example 15d), from 2-(3-nitro-4-methoxyphenyl)-5-bromobenzoxazole (200 mg, 0.57 mmol) and 4-trifluoromethylphenylboronic acid (161 mg, 0.85 mmol) the subtitle compound was obtained (204 mg, 58%). $^1$H NMR (DMSO) δ 8.64(d, 1H), 8.46(dd, 1H), 8.16(d, 1H), 7.97(d, 2H), 7.92(d, 1H), 7.85–7.78(m, 3H), 7.63(d, 1H), 4.05(s, 3H).

b) 2-(3-Amino-4-methoxyphenyl)-5-(3-trifluoromethylphenyl)benzoxazole

Prepared by the method of Example 15e), from 2-(3-nitro-4-methoxyphenyl)-5-(3-trifluoromethylphenyl)benzoxazole (113 mg, 0.27 mmol) the subtitle compound was obtained (107 mg, 99%). MS m/z 415.1 (M+H)$^+$.

c) 2-[2-Methoxy-5-[5-(4-trifluoromethyl)phenylbenzoxazol-2-yl]phenyl]-1,3-dioxo-2,3-dihydro-1H-isoindole-5-carboxylic acid

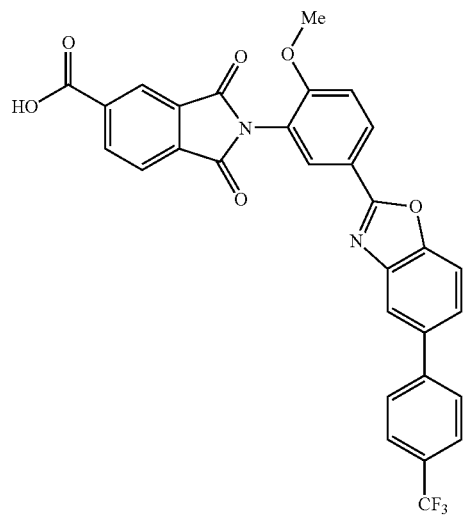

Prepared by the method of Example 15f), from 2-(3-amino-4-methoxyphenyl)-5-(4-trifluorophenyl)benzoxazole (107 mg, 0.28 mmol) and 1,2,4-benzenetricarboxylic anhydride (53 mg, 0.30 mmol) the title compound was obtained (107 mg, 69%). $^1$H NMR (DMSO) δ 8.45(dd, 1H), 8.38–8.34(m, 3H), 8.14–8.10(m, 2H), 7.98(d, 2H), 7.89(d, 1H), 7.84(d, 2H), 7.77(dd, 1H), 7.50(d, 1H), 3.89(s, 3H). MS m/z 559.1 (M+H)$^+$.

Example 24

2-[2-Methoxy-5-[5-[4-(1-hydroxyethyl)]phenylbenzoxazol-2-yl]phenyl]-1,3-dioxo-2,3-dihydro-1H-isoindole-5-carboxylic acid a) 2-(3-Nitro-4-methoxyphenyl)-5-(4-acetylphenyl)benzoxazole Prepared by the method of Example 15d), from 2-(3-nitro-4-methoxyphenyl)-5-bromobenzoxazole (200 mg, 0.57 mmol) and 4-acetylphenylboronic acid (139 mg, 0.85 mmol) the subtitle compound was obtained (119 mg, 36%). $^1$H NMR (DMSO) δ 8.64(d, 1H), 8.46(dd, 1H), 8.16(d, 1H), 8.06(d, 2H), 7.93–7.90(m, 3H), 7.81(dd, 1H), 7.63(d, 1H), 4.05(s, 3H), 2.63(s, 3H).

b) 2-(3-Amino-4-methoxyphenyl)-5-[4-(ethyl-2-hydroxy)phenyl]benzoxazole

Prepared by the method of Example 15e), from 2-(3-nitro-methoxyphenyl)-5-(3-acetylphenyl)benzoxazole (51 mg, 0.13 mmol) the subtitle compound was obtained (43 mg, 99%). MS m/z 389.1 (M+H)$^+$.

c) 2-[2-Methoxy-5-[5-[4-(1-hydroxyethyl)]phenylbenzoxazol-2-yl]phenyl]-1,3-dioxo-2,3-dihydro-1H-isoindole-5-carboxylic acid

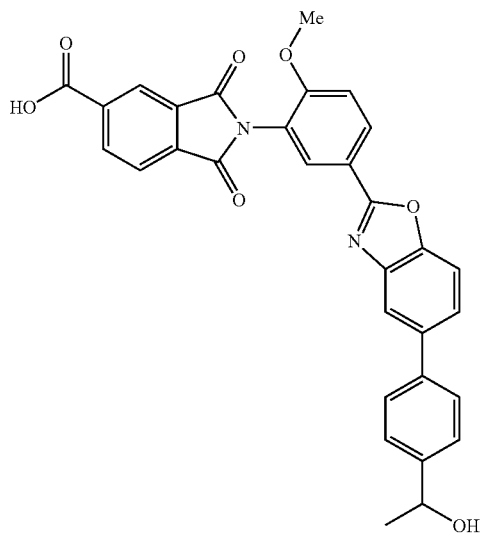

Prepared by the method of Example 15f), from 2-(3-amino-4-methoxyphenyl-5-[4-(ethyl-2-hydroxy)phenyl]benzoxazole (43 mg, 0.12 mmol) and 1,2,4-benzenetricarboxylic anhydride (25 mg, 0.13 mmol) the title compound was obtained (6 mg, 9%). $^1$H NMR (DMSO) δ 8.45(dd, 1H), 8.38–8.33(m, 3H), 8.12(d, 1H), 8.02(d, 1H), 7.84(d, 1H), 7.74–7.67(m, 3H), 7.49(m, 3H), 5.84(q, 1H), 3.89(s, 3H), 1.51(d, 3H). MS m/z 517.1 (M+H)$^+$.

Example 25

2-[2-Methoxy-5-[5-(4-methyl)phenylbenzoxazol-2-yl]phenyl]-1,3-dioxo-2,3-dihydro-1H-isoindole-5-carboxylic acid Prepared by the method of Example 15d), from 2-(3-nitro-4-methoxyphenyl)-5-bromobenzoxazole (200 mg, 0.57 mmol) and 4-methylphenylboronic acid (116 mg, 0.85 mmol) the subtitle compound was obtained (201 mg, 66%). $^1$H NMR (DMSO) δ 8.68(d, 1H), 8.51(dd, 1H), 8.07(d, 1H), 7.90(d, 1H), 7.74–7.67(m, 3H), 7.36–7.33(d, 2H), 4.10(s, 3H), 2.41(s, 3H).

b) 2-(3-Amino-4-methoxyphenyl)-5-(4-methylphenyl)benzoxazole

Prepared by the method of Example 15e), from 2-(3-nitro-4-methoxyphenyl)-5-(4-methylphenyl)benzoxazole (82 mg, 0.23 mmol) the subtitle compound was obtained (59 mg, 99%). MS m/z 361.1 (M+H)$^+$.

c) 2-[2-Methoxy-5-[5-(4-methyl)phenylbenzoxazol-2-yl]phenyl]-1,3-dioxo-2,3-dihydro-1H-isoindole-5-carboxylic acid

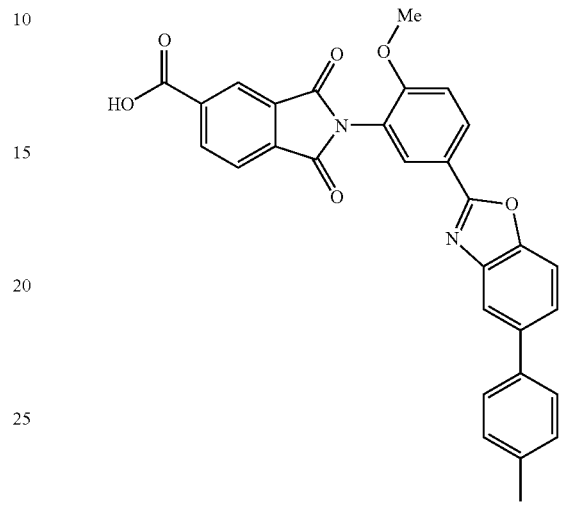

Prepared by the method of Example 15f), from 2-(3-amino-4-methoxyphenyl-5-(4-methylphenyl)benzoxazole (59 mg, 0.18 mmol) and 1,2,4-benzenetricarboxylic anhydride (38 mg, 0.20 mmol) the title compound was obtained (69 mg, 50%). $^1$H NMR (DMSO) δ 8.45(d, 1H), 8.38–8.32(m, 3H), 8.12(d, 1H), 7.99(d, 1H), 7.82(d, 1H), 7.69–7.61(m, 3H), 7.49(d, 1H), 7.29(d, 2H), 3.89(s, 3H), 2.36(s, 3H). MS m/z 505.1 (M+H)$^+$.

Example 26

2-[2-Methoxy-5-[5-[(5-methyl)thiophen-2-yl]benzoxazol-2-yl]phenyl]-1,3-dioxo-2,3-dihydro-1H-isoindole-5-carboxylic acid a) 2-(3-Nitro-4-methoxyphenyl)-5-[(5-methyl)thiophen-2-yl]benzoxazole Prepared by the method of Example 15d), from 2-(3-nitro-4-methoxyphenyl)-5-bromobenzoxazole (200 mg, 0.57 mmol) and 2-(5-methyl)thiopheneboronic acid (121 mg, 0.85 mmol) the subtitle compound was obtained (301 mg, 96%). $^1$H NMR (DMSO) δ 8.62(d, 1H), 8.43(dd, 1H), 7.97(d, 1H), 7.80(d, 1H), 7.63(m, 2H), 7.38(d, 1H), 6.84(dd, 1H), 4.05(s, 3H), 2.50(s, 3H).

b) 2-(3-Amino-4-methoxyphenyl)-5-[(5-methyl)thiophen-2yl]benzoxazole

Prepared by the method of Example 15e), from 2-(3-nitro-4-methoxyphenyl)-5-[(5-methyl)thiophen-2-yl]benzoxazole (75 mg, 0.20 mmol) the subtitle compound was obtained (64 mg, 99%). MS m/z 367.1 (M+H)$^+$.

c) 2-[2-Methoxy-5-[5-[(5-methyl)thiophen-2-yl]benzoxazol-2-yl]phenyl]-1,3-dioxo-2,3-dihydro-1H-isoindole-5-carboxylic acid

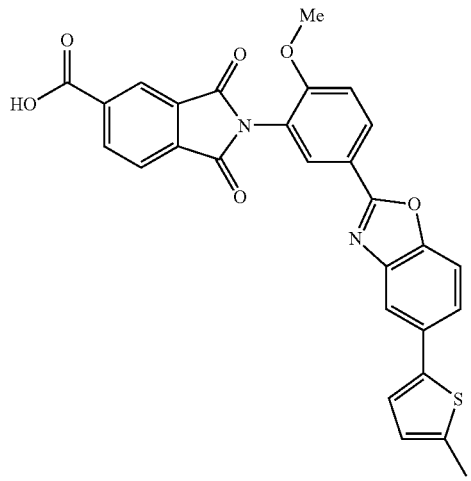

Prepared by the method of Example 15f), from 2-(3-amino-4-methoxyphenyl-5-[(5-methyl)thiophen-2-yl]benzoxazole (64 mg, 0.19 mmol) and 1,2,4-benzenetricarboxylic anhydride (40 mg, 0.20 mmol) the title compound was obtained (62 mg, 64%). $^1$H NMR (DMSO) δ 8.45(dd, 1H), 8.36–8.30(m, 3H), 8.11(d, 1H), 7.94(d, 1H), 7.77(d, 1H), 7.61(dd, 1H), 7.49(d, 1H), 7.36(d, 1H), 6.84(dd, 1H), 3.89(s, 3H), 2.50(s, 3H). MS m/z 511.1 (M+H)$^+$.

Example 27

2-[2-Methoxy-5-[5-(4-methoxy)phenylbenzoxazol-2-yl]phenyl]-1,3-dioxo-2,3-dihydro-1H-isoindole-5-carboxylic acid a) 2-(3-Nitro-4-methoxyphenyl)-5-(4-methoxyphenyl)benzoxazole Prepared by the method of Example 15d), from 2-(3-nitro-4-methoxyphenyl)-5-bromobenzoxazole (200 mg, 0.57 mmol) and 4-methoxyphenylboronic acid (129 mg, 0.85 mmol) the subtitle compound was obtained (193 mg, 60%). $^1$H NMR (DMSO) δ 8.63(d, 1H), 8.45(dd, 1H), 7.99(d, 1H), 7.83(d, 1H), 7.67(d, 3H), 7.62(d, 1H), 7.05(d, 2H), 4.05(s, 3H), 3.81(s, 3H).

b) 2-(3-Amino-4-methoxyphenyl)-5-(4-methoxyphenyl)benzoxazole

Prepared by the method of Example 15e), from 2-(3-nitro-4-methoxyphenyl)-5-(4-methoxyphenyl)benzoxazole (102 mg, 0.27 mmol) the subtitle compound was obtained (103 mg, 99%). MS m/z 377.1 (M+H)$^+$.

c) 2-[2-Methoxy-5-[5-(4-methoxy)phenylbenzoxazol-2-yl]phenyl]-1,3-dioxo-2,3-dihydro-1H-isoindole-5-carboxylic acid

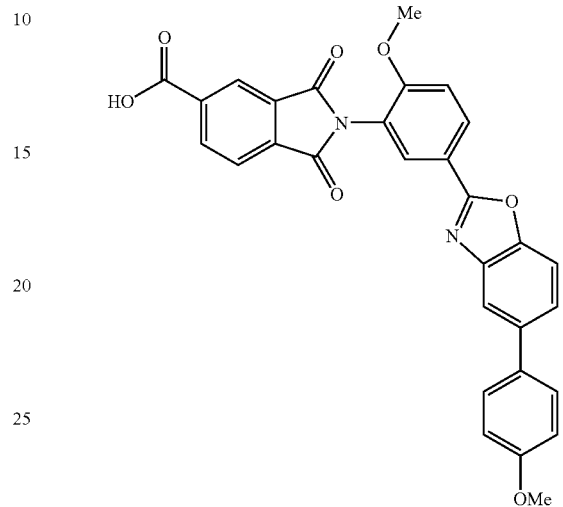

Prepared by the method of Example 15f), from 2-(3-amino-4-methoxyphenyl)-5-(4-methoxyphenyl)benzoxazole (103 mg, 0.30 mmol) and 1,2,4-benzenetricarboxylic anhydride (63 mg, 0.20 mmol) the title compound was obtained (91 mg, 58%). $^1$H NMR (DMSO) δ 8.45(dd, 1H), 8.38–8.32(m, 3H), 8.12(d, 1H), 7.96(d, 1H), 7.80(d, 1H), 7.69–7.63(m, 3H), 7.49(d, 1H), 7.65(d, 2H), 3.89(s, 3H), 3.81(s, 3H). MS m/z 521.1 (M+H)$^+$.

Example 28

2-[2-Methoxy-5-[5-(3-cyano)phenylbenzoxazol-2-yl]phenyl]-1,3-dioxo-2,3-dihydro-1H-isoindole-5-carboxylic acid a) 2-(3-Nitro-4-methoxyphenyl)-5-(3-cyanophenyl)benzoxazole Prepared by the method of Example 15d), from 2-(3-nitro-4-methoxyphenyl)-5-bromobenzoxazole (200 mg, 0.57 mmol) and 3-cyanophenylboronic acid (126 mg, 0.86 mmol) the subtitle compound was obtained (65 mg, 31%). $^1$H NMR (DMSO) δ 8.75(d, 1H), 8.57(dd, 1H), 8.35(t, 1H), 8.29(d, 1H), 8.21(dt, 1H), 8.00(d, 1H), 7.97(dt, 1H), 7.93(d, 1H), 7.80(t, 1H), 7.74(d, 1H), 4.17(s, 3H).

b) 2-(3-Amino-4-methoxyphenyl)-5-(3-cyanophenyl)benzoxazole

Prepared by the method of Example 15e), from 2-(3-nitro-4-methoxyphenyl)-5-(3-cyanophenyl)benzoxazole (50 mg, 0.14 mmol) the subtitle compound was obtained (33 mg, 71%). The product was used directly in the next step without purification.

c) 2-[2-Methoxy-5-[5-(3-cyano)phenylbenzoxazol-2-yl]phenyl]-1,3-dioxo-2,3-dihydro-1H-isoindole-5-carboxylic acid

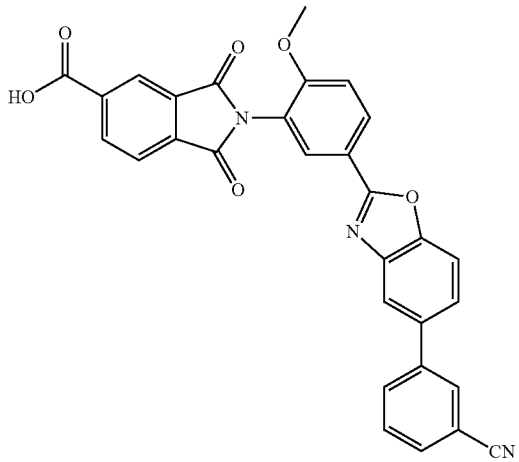

Prepared by the method of Example 15f), from 2-(3-amino-4-methoxyphenyl)-5-(3-cyanophenyl)benzoxazole (31 mg, 0.09 mmol) and 1,2,4-benzenetricarboxylic anhydride (17 mg, 0.09 mmol) the title compound was obtained, (14 mg, 30%). $^1$H NMR (DMSO) δ 8.47(dd, 1H), 8.38(d, 1H), 8.35(q, 2H), 8.25(t, 1H), 8.17(d, 1H), 8.13(d, 1H), 8.11(dt, 1H), 7.90(d, 1H), 7.85(d, 1H), 7.80(dd, 1H), 7.70(t, 1H), 7.50(d, 1H), 3.90(s, 3H). MS 516 m/z (M+H)$^+$.

Example 29

2-[2-Methoxy-5-[5-(3-methyl)phenylbenzoxazol-2-yl]phenyl]-1,3-dioxo-2,3-dihydro-1H-isoindole-5-carboxylic acid a) 2-(3-Nitro-4-methoxyphenyl)-5-(3-methylphenyl)benzoxazole Prepared by the method of Example 15d), from 2-(3-nitro-4-methoxyphenyl)-5-bromobenzoxazole (200 mg, 0.57 mmol) and 3-methylphenylboronic acid (117 mg, 0.86 mmol) the subtitle compound was obtained, (69 mg, 33%). $^1$H NMR (DMSO) δ 8.64(d, 1H), 847(dd, 1H), 8.14(d, 1H), 7.86(d, 1H), 7.72(dd, 1H), 7.64(d, 1H), 7.55(m, 2H), 7.39(t, 1H), 7.22(d, 1H), 4.07(s, 1H), 2.40(s, 3H).

b) 2-(3-Amino-4-methoxyphenyl)-5-(3-methylphenyl)benzoxazole

Prepared by the method of Example 15e), from 2-(3-nitro-4-methoxyphenyl)-5-(3-methylphenyl)benzoxazole (61 mg, 0.17 mmol) the subtitle compound was obtained, (47 mg, 84%). The product was used directly in the next step without purification.

c) 2-[2-Methoxy-5-[5-(3-methyl)phenylbenzoxazol-2-yl]phenyl]-1,3-dioxo-2,3-dihydro-1H-isoindole-5-carboxylic acid

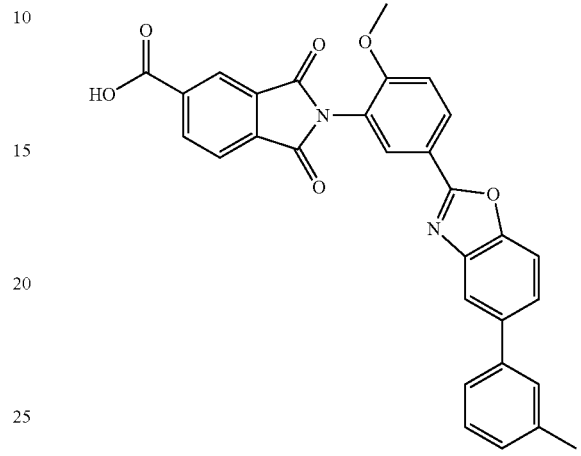

Prepared by the method of Example 15f), from 2-(3-amino-4-methoxyphenyl)-5-(3-methylphenyl)benzoxazole (44 mg, 0.13 mmol) and 1,2,4-benzenetricarboxylic anhydride (25 mg, 0.13 mmol) the title compound was obtained, (31 mg, 46%). $^1$H NMR (DMSO) δ 8.46(dd, 1H), 8.38(d, 1H), 8.34(q, 2H), 8.13(d, 1H), 8.02(d, 1H), 7.84(d, 1H), 7.68(dd, 1H), 7.52(m, 3H), 7.48(t, 1H), 7.20(d, 1H), 3.89(s, 3H), 2.40(s, 3H). MS 505 m/z (M+H)$^+$.

Example 30

2-[2-Methoxy-5-[5-(3-methoxy)phenylbenzoxazol-2-yl]phenyl]-1,3-dioxo-2,3-dihydro-1H-isoindole-5-carboxylic acid a) 2-(3-Nitro-4-methoxyphenyl)-5-(3-methoxyphenyl)benzoxazole Prepared by the method of Example 15d), from 2-(3-nitro-4-methoxyphenyl)-5-bromobenzoxazole (200 mg, 0.57 mmol) and 3-methoxyphenylboronic acid (131 mg, 0.86 mmol) the subtitle compound was obtained, (98 mg, 45%). $^1$H NMR (DMSO) δ 8.71(d, 1H), 8.52(dd, 1H), 8.35(t, 1H), 8.17(d, 1H), 7.93(d, 1H), 7.82(dd, 1H), 7.69(d, 1H), 7.48(t, 1H), 7.36(m, 2H), 7.03(dd, 1H), 4.12(s, 3H), 3.90(s, 3H).

b) 2-(3-Amino-4-methoxyphenyl)-5-(3-methoxyphenyl)benzoxazole

Prepared by the method of Example 15e), from 2-(3-nitro-4-methoxyphenyl)-5-(3-methoxyphenyl)benzoxazole (87 mg, 0.23 mmol) the subtitle compound was obtained, (66 mg, 82%). The product was used directly in the next step without purification.

c) 2-[2-Methoxy-5-[5-(3-methoxy)phenylbenzoxazol-2-yl]phenyl]-1,3-dioxo-2,3-dihydro-1H-isoindole-5-carboxylic acid c) 2-[2-Methoxy-5-[5-(3-fluoro)phenylbenzoxazol-2-yl]phenyl]-1,3-dioxo-2,3-dihydro-1H-isoindole-5-carboxylic acid

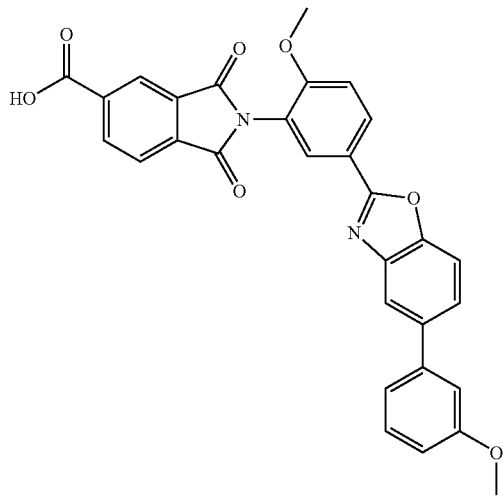

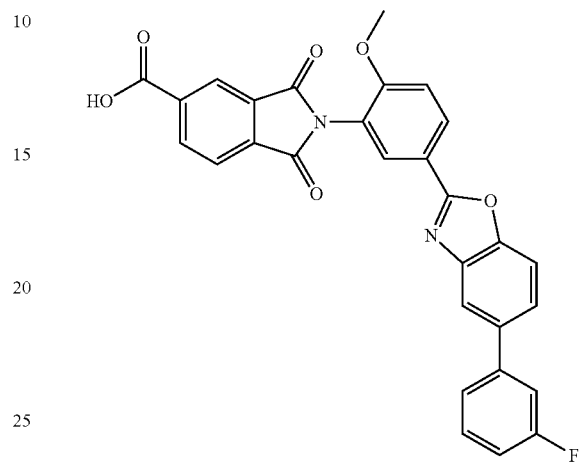

Prepared by the method of Example 15f), from 2-(3-amino-4-methoxyphenyl)-5-(3-methoxyphenyl)benzoxazole (62 mg, 0.18 mmol) and 1,2,4-benzenetricarboxylic anhydride (35 mg, 0.18 mmol) the title compound was obtained, (47 mg, 50%). $^1$H NMR (DMSO) δ 8.35(dd, 1H), 8.28(d, 1H), 8.22(q, 2H), 8.02(d, 1H), 7.93(d, 1H), 7.72(d, 1H), 7.60(dd, 1H), 7.40(d, 1H), 7.30(t, H), 7.17(m, 2H), 6.85(dd, 1H), 3.79(s, 3H), 3.75(s, 3). MS 521 m/z $(M+H)^+$.

Prepared by the method of Example 15f), from 2-(3-amino-4-methoxyphenyl)-5-(3-fluorophenyl)benzoxazole (67 mg, 0.20 mmol) and 1,2,4-benzenetricarboxylic anhydride (38 mg, 0.20 mmol) the title compound was obtained, (65 mg, 64%). $^1$H NMR (DMSO) δ 8.33(dd, 1H), 8.28(d, 1H), 8.22(q, 2H), 8.02(d, 1H), 7.98(d, 1H), 7.74(d, 1H), 7.64(dd, 1H), 7.45(m, 3H), 7.38(d, 1H), 7.10(dt, 1H), 3.77(s, 3H). MS 509 m/z $(M+H)^+$.

Example 31

2-[2-Methoxy-5-[5-(3-fluoro)phenylbenzoxazol-2-yl]phenyl]-1,3-dioxo-2,3-dihydro-1H-isoindole-5-carboxylic acid a) 2-(3-Nitro-4-methoxyphenyl)-5-(3-fluorophenyl)benzoxazole Prepared by the method of Example 15d), from 2-(3-nitro-4-methoxyphenyl)-5-bromobenzoxazole (200 mg, 0.57 mmol) and 3-fluorophenylboronic acid (120 mg, 0.86 mmol) the subtitle compound was obtained, (103 mg, 49%). $^1$H NMR (DMSO) δ 8.59(d, 1H), 8.40(dd, 1H), 8.08(d, 1H), 7.82(d, 1H), 7.72(dd, 1H), 7.52(m, 4H), 7.17(dt, 1H), 4.02(s, 3H).

b) 2-(3-Amino-4-methoxyphenyl)-5-(3-fluorophenyl)benzoxazole

Prepared by the method of Example 15e), from 2-(3-nitro-4-methoxyphenyl)-5-(3-fluorophenyl)benzoxazole (94 mg, 0.26mmol) the subtitle compound was obtained, (73 mg, 85%). The product was used directly in the next step without purification.

Example 32

2-[2-Methoxy-5-[5-(3-chloro)phenylbenzoxazol-2-yl]phenyl]-1,3-dioxo-2,3-dihydro-1H-isoindole-5-carboxylic acid a) 2-(3-Nitro-4-methoxyphenyl)-5-(3-chlorophenyl)benzoxazole Prepared by the method of Example 15d), from 2-(3-nitro-4-methoxyphenyl)-5-bromobenzoxazole (200 mg, 0.57 mmol) and 3-chlorophenylboronic acid (134 mg, 0.86 mmol) the subtitle compound was obtained, (72 mg, 33%). $^1$H NMR (DMSO) δ 8.71(d, 1H), 8.53(dd, 1H), 8.19(d, 1H), 7.95(d, 1H), 7.88(t, 1H), 7.83(dd, 1H), 7.79(d, 1H), 7.70(d, 1H), 7.58(t, 1H), 7.52(d, 1H), 4.12(s, 3H).

b) 2-(3-Amino-4-methoxyphenyl)-5-(3-chlorophenyl)benzoxazole

Prepared by the method of Example 15e), from 2-(3-nitro-4-methoxyphenyl)-5-(3-chlorophenyl)benzoxazole (62 mg, 0.16 mmol) the subtitle compound was obtained, (44 mg, 77%). The product was used directly in the next step without purification.

c) 2-[2-Methoxy-5-[5-(3-chloro)phenylbenzoxazol-2-yl]phenyl]-1,3-dioxo-2,3-dihydro-1H-isoindole-5-carboxylic acid

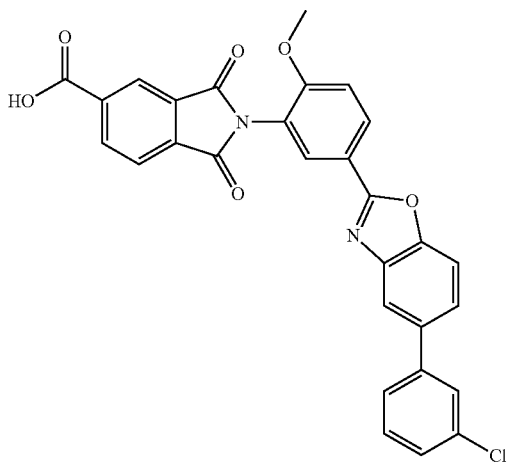

Prepared by the method of Example 15f), from 2-(3-amino-4-methoxyphenyl)-5-(3-chlorophenyl)benzoxazole (42 mg, 0.12 mmol) and 1,2,4-benzenetricarboxylic anhydride (23 mg, 0.12 mmol) the title compound was obtained, (33 mg, 53%). $^1$H NMR (DMSO) δ 8.48(dd, 1H), 8.42(d, 1H), 8.37(q, 2H), 8.16(d, 1H), 8.13(d, 1H), 7.89(d, 1H), 7.84(t, 1H), 7.75(m, 2H), 7.52(m, 3H), 3.91(s, 3H). MS 525 m/z (M+H)$^+$.

Example 33

2-[2-Methoxy-5-[5-(4-fluoro)phenylbenzoxazol-2-yl]phenyl]-1,3-dioxo-2,3-dihydro-1H-isoindole-5-carboxylic acid a) 2-(3-Nitro-4-methoxyphenyl)-5-(4-fluorophenyl)benzoxazole Prepared by the method of Example 15d), from 2-(3-nitro-4-methoxyphenyl)-5-bromobenzoxazole (200 mg, 0.57 mmol) and 4-fluorophenylboronic acid (120 mg, 0.86 mmol) the subtitle compound was obtained, (135 mg, 65%). $^1$H NMR (DMSO) δ 8.64(d, 1H), 8.45(dd, 1H), 8.05(d, 1H), 7.87(d, 2H), 7.78(dd, 1H), 7.72(dd, 1H), 7.62(d, 2H), 7.33(t, 1H), 4.08(s, 3H).

b) 2-(3-Amino-4-methoxyphenyl)-5-(4-fluorophenyl)benzoxazole

Prepared by the method of Example 15e), from 2-(3-nitro-4-methoxyphenyl)-5-(4-fluorophenyl)benzoxazole (122 mg, 0.33 mmol) the subtitle compound was obtained, (66 mg, 59%). The product was used directly in the next step without purification.

c) 2-[2-Methoxy-5-[5-(4-fluoro)phenylbenzoxazol-2-yl]phenyl]-1,3-dioxo-2,3-dihydro-1H-isoindole-5-carboxylic acid

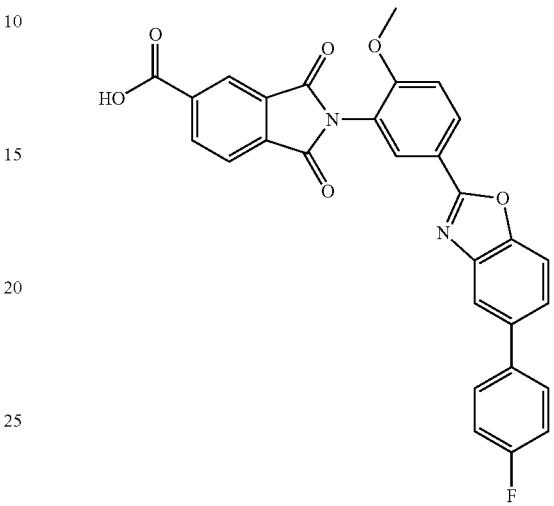

Prepared by the method of Example 15f), from 2-(3-amino-4-methoxyphenyl)-5-(4-fluorophenyl)benzoxazole (55 mg, 0.16 mmol) and 1,2,4-benzenetricarboxylic anhydride (31 mg, 0.16 mmol) the title compound was obtained, (41 mg, 49%). $^1$H NMR (DMSO) δ 8.45(dd, 1H), 8.38(d, 1H), 8.34(q, 2H), 8.12(d, 1H), 8.02(d, 1H), 7.84(d, 2H), 7.78(dd, 1H), 7.68(dd, 1H), 7.49(d, 2H), 7.32(t, 1H), 3.88(s, 3H). MS 509 m/z (M+H)$^+$.

Example 34

2-[2-Methoxy-5-[5-(2,4-difluoro)phenylbenzoxazol-2-yl]phenyl]-1,3-dioxo-2,3-dihydro-1H-isoindole-5-carboxylic acid a) 2-(3-Nitro-4-methoxyphenyl)-5-(2,4-difluorophenyl)benzoxazole Prepared by the method of Example 15d), from 2-(3-nitro-4-methoxyphenyl)-5-bromobenzoxazole (200 mg, 0.57 mmol) and 2,4-difluorophenylboronic acid (136 mg, 0.86 mmol) the subtitle compound was obtained, (57 mg, 26%). $^1$H NMR (DMSO) δ 8.71(d, 1H), 8.53(dd, 1H), 8.01(s, 1H), 7.97(d, 1H), 7.70(m, 3H), 7.48(dt, 1H), 7.30(dt, 1H), 4.12(s, 3H). MS 383 m/z (M+H)$^+$.

b) 2-(3-Amino-4-methoxyphenyl)-5-(2,4-difluorophenyl)benzoxazole

Prepared by the method of Example 15e), from 2-(3-nitro-4-methoxyphenyl)-5-(2,4-difluorophenyl)benzoxazole (50 mg, 0.15 mmol) the subtitle compound was obtained, (50 mg, 95%). The product was used directly in the next step without purification.

c) 2-[2-Methoxy-5-[5-(2,4-difluoro)phenylbenzoxazol-2-yl]phenyl]-1,3-dioxo-2,3-dihydro-1H-isoindole-5-carboxylic acid

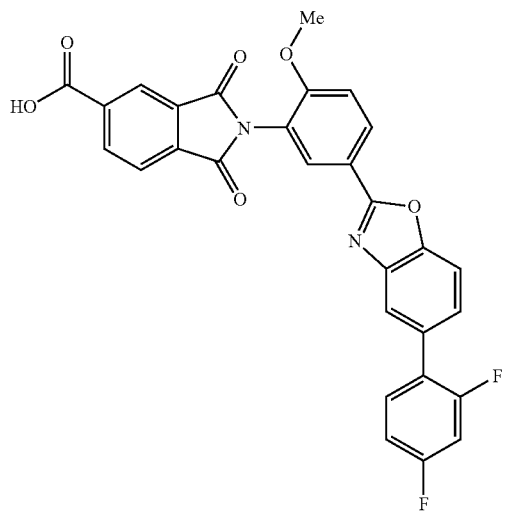

Prepared by the method of Example 15f), from 2-(3-amino-4-methoxyphenyl)-5-(2,4-difluorophenyl)benzoxazole (50 mg, 0.14 mmol) and 1,2,4-benzenetricarboxylic anhydride (27 mg, 0.16 mmol) the title compound was obtained, (25 mg, 33%). $^1$H NMR (DMSO) δ 8.45(dd, 1H), 8.38(d, 1H), 8.35(q, 2H), 8.12(d, 1H), 7.91(s, 1H), 7.87(d, 1H), 7.67(dt, 1H), 7.57(dt, 1H), 7.50(d, 1H), 7.41(m, 1H), 7.23(dt, 1H), 3.89(s, 3H). MS 527 m/z (M+H)$^+$.

Example 35

2-[2-Methoxy-5-[5-(3,5-difluoro)phenylbenzoxazol-2-yl]phenyl]-1,3-dioxo-2,3-dihydro-1H-isoindole-5-carboxylic acid a) 2-(3-Nitro-4-methoxyphenyl)-5-(3,5-difluorophenyl)benzoxazole Prepared by the method of Example 15d), from 2-(3-nitro-4-methoxyphenyl)-5-bromobenzoxazole (200 mg, 0.57 mmol) and 3,5-difluorophenylboronic acid (136 mg, 0.86 mmol) the subtitle compound was obtained, (120 mg, 64%). $^1$H NMR (DMSO) δ 8.70(d, 1H), 8.52(dd, 1H), 8.26(d, 1H), 7.96(d, 1H), 7.88(dd, 1H), 7.69(d, 1H), 7.61(dd, 2H), 7.33(tt, 1H), 4.12(s, 3H). MS 383 m/z (M+H)$^+$.

b) 2-(3-Amino-4-methoxyphenyl)-5-(3,5-difluorophenyl)benzoxazole

Prepared by the method of Example 15e), from 2-(3-nitro-4-methoxyphenyl)-5-(3,5-difluorophenyl)benzoxazole (120 mg, 0.31 mmol) the subtitle compound was obtained, (90 mg, 82%). The product was used directly in the next step without purification.

c) 2-[2-Methoxy-5-[5-(3,5-difluoro)phenylbenzoxazol-2-yl]phenyl]-1,3-dioxo-2,3-dihydro-1H-isoindole-5-carboxylic acid

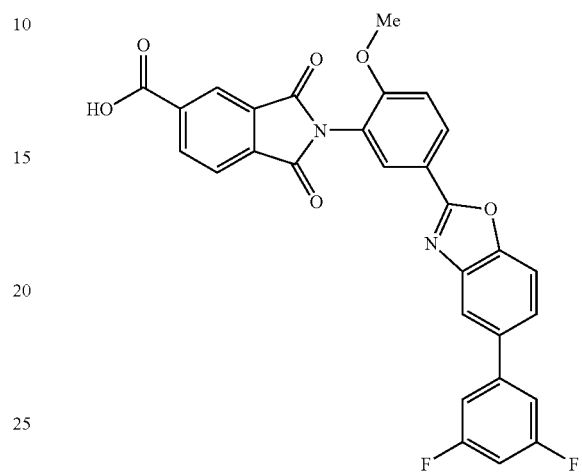

Prepared by the method of Example 15f), from 2-(3-amino-4-methoxyphenyl)-5-(3,5-difluorophenyl)benzoxazole (90 mg, 0.26 mmol) and 1,2,4-benzenetricarboxylic anhydride (49 mg, 0.28 mmol) the title compound was obtained, (58 mg, 43%). $^1$H NMR (DMSO) δ 8.60(dd, 1H), 8.52(d, 1H), 8.49(d, 2H), 8.31(d, 1H), 8.26(d, 1H), 8.01(d, 1H), 7.93(dd, 1H), 7.69(dd, 2H), 7.64(d, 1H), 7.40(tt, 1H), 4.04(s, 3H). MS 527 m/z (M+H)$^+$.

Example 36

2-[2-Methoxy-5-[5-(4-trifluoromethoxy)phenylbenzoxazol-2-yl]phenyl]-1,3-dioxo-2,3-dihydro-1H-isoindole-5-carboxylic acid a) 2-(3-Nitro-4-methoxyphenyl)-5-(4-trifluoromethoxyphenyl)benzoxazole Prepared by the method of Example 15d), from 2-(3-nitro-4-methoxyphenyl)-5-bromobenzoxazole (200 mg, 0.57 mmol) and 4-trifluoromethoxyphenylboronic acid (177 mg, 0.86 mmol) the subtitle compound was obtained, (119 mg, 48%). $^1$H NMR (DMSO) δ 8.70(s, 1H), 8.52(d, 1H), 8.16(s, 1H), 7.93(d, 3H), 7.81(d, 2H), 7.68(d, 1H), 7.55(d, 1H), 4.12(s, 3H). MS 431 m/z (M+H)$^+$.

b) 2-(3-Amino-4-methoxyphenyl)-5-(4-trifluoromethoxyphenyl)benzoxazole

Prepared by the method of Example 15e), from 2-(3-nitro-4-methoxyphenyl)-5-(4-trifluoromethoxyphenyl)benzoxazole (127 mg, 0.30 mmol) the subtitle compound was obtained, (90 mg, 76%). The product was used directly in the next step without purification.

c) 2-[2-Methoxy-5-[5-(4-trifluoromethoxy)phenylbenzoxazol-2-yl]phenyl]-1,3-dioxo-2,3-dihydro-1H-isoindole-5-carboxylic acid

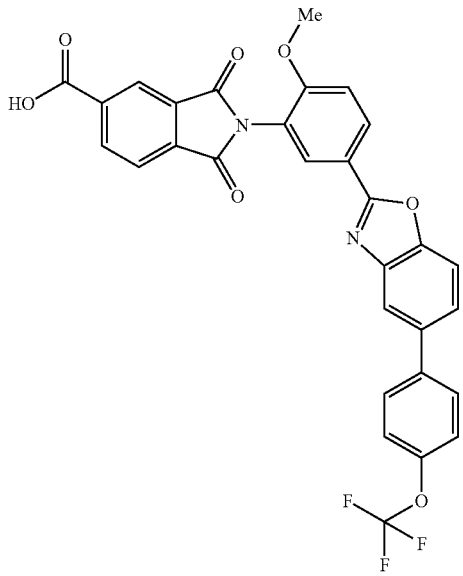

Prepared by the method of Example 15f), from 2-(3-amino-4-methoxyphenyl)-5-(4-trifluoromethoxyphenyl)benzoxazole (90 mg, 0.23 mmol) and 1,2,4-benzenetricarboxylic anhydride (43 mg, 0.25 mmol) the title compound was obtained, (52 mg, 40%). $^1$H NMR (DMSO) δ 8.32(dd, 1H), 8.25(d, 1H), 8.22(q, 2H), 7.99(d, 1H), 7.95(d, 1H), 7.76(s, 1H), 7.73(s, 2H), 7.59(dd, 1H), 7.36(dd, 3H), 3.77(s, 3H). MS 575 m/z (M+H)$^+$.

Example 37

2-[2-Methoxy-5-[5-(4-trifluoromethoxy)phenylbenzoxazol-2-yl]phenyl]-1,3-dioxo-2,3-dihydro-1H-isoindole-5-carboxylic acid a) 2-(3-Nitro-4-methoxyphenyl)-5-(3-trifluoromethylphenyl)benzoxazole Prepared by the method of Example 15d), from 2-(3-nitro-4-methoxyphenyl)-5-bromobenzoxazole (200 mg, 0.57 mmol) and 3-trifluoromethylphenylboronic acid (163 mg, 0.86 mmol) the subtitle compound was obtained, (120 mg, 51%). $^1$H NMR (DMSO) δ 8.70(s, 1H), 8.52(d, 1H), 8.24(s, 1H), 8.11(s, 1H), 7.97(d, 1H), 7.86(d, 1H), 7.81(s, 2H), 7.68(d, 1H), 4.11(s, 3H). MS 415 m/z (M+H)$^+$.

b) 2-(3-Amino-4-methoxyphenyl)-5-(3-trifluoromethylphenyl)benzoxazole

Prepared by the method of Example 15e), from 2-(3-nitro-4-methoxyphenyl)-5-(3-trifluoromethylphenyl)benzoxazole (120 mg, 0.29 mmol) the subtitle compound was obtained, (110 mg, 99%). The product was used directly in the next step without purification.

c) 2-[2-Methoxy-5-[5-(4-trifluoromethoxy)phenylbenzoxazol-2-yl]phenyl]-1,3-dioxo-2,3-dihydro-1H-isoindole-5-carboxylic acid

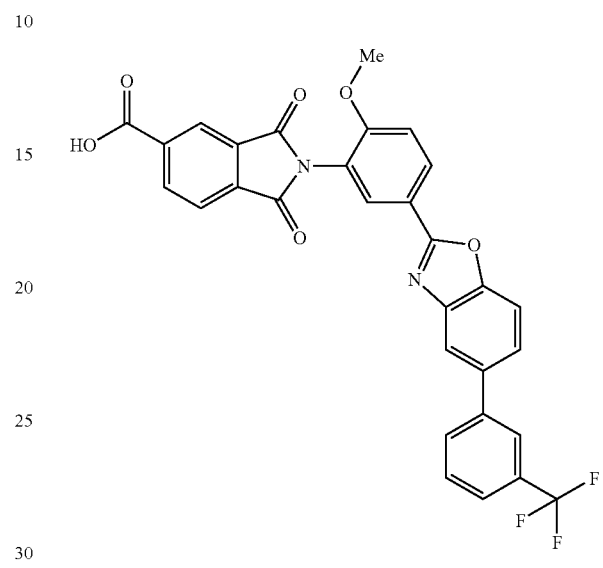

Prepared by the method of Example 15f), from 2-(3-amino-4-methoxyphenyl)-5-(3-trifluoromethylphenyl)benzoxazole (110 mg, 0.29 mmol) and 1,2,4-benzenetricarboxylic anhydride (55 mg, 0.31 mmol) the title compound was obtained, (78 mg, 49%). $^1$H NMR (DMSO) δ 8.45(dd, 1H), 8.38(d, 1H), 8.34(q, 2H), 8.15(d, 1H), 8.12(d, 1H), 8.05(s, 2H), 7.88(d, 1H), 7.75(s, 2H), 7.50(d, 1H), 3.89(s, 3H). MS 575 m/z (M+H)$^+$.

Example 38

2-[2-Methoxy-5-[5-(2,4-dichloro)phenylbenzoxazol-2-yl]phenyl]-1,3-dioxo-2,3-dihydro-1H-isoindole-5-carboxylic acid a) 2-(3-Nitro-4-methoxyphenyl)-5-(2,4-dichlorophenyl)benzoxazole Prepared by the method of Example 15d), from 2-(3-nitro-4-methoxyphenyl)-5-bromobenzoxazole (200 mg, 0.57 mmol) and 2,4-dichlorophenylboronic acid (164 mg, 0.86 mmol) the subtitle compound was obtained, (148 mg, 62%). $^1$H NMR (DMSO) δ 8.69(s, 1H), 8.51(d, 1H), 7.93(d, 1H), 7.84(s, 1H), 7.60(m, 3H), 4.12(s, 3H). MS 415 m/z (M+H)$^+$.

b) 2-(3-Amino-4-methoxyphenyl)-5-(2,4-dichlorophenyl)benzoxazole

Prepared by the method of Example 15e), from 2-(3-nitro-4-methoxyphenyl)-5-(2,4-dichlorophenyl)benzoxazole (148 mg, 0.36 mmol) the subtitle compound was obtained, (110 mg, 80%). The product was used directly in the next step without purification.

c) 2-[2-Methoxy-5-[5-(2,4-dichloro)phenylbenzoxazol-2-yl]phenyl]-1,3-dioxo-2,3-dihydro-1H-isoindole-5-carboxylic acid

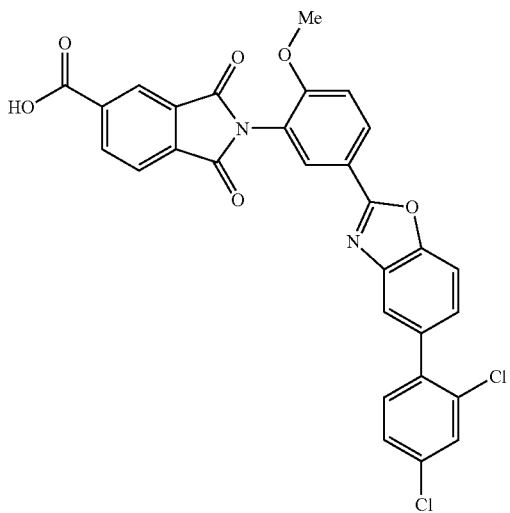

Prepared by the method of Example 15f), from 2-(3-amino-4-methoxyphenyl)-5-(2,4-dichlorophenyl)benzoxazole (110 mg, 0.29 mmol) and 1,2,4-benzenetricarboxylic anhydride (55 mg, 0.31 mmol) the title compound was obtained, (62 mg, 39%). $^1$H NMR (DMSO) δ 8.36(dd, 1H), 8.29(d, 1H), 8.26(q, 2H), 8.03(d, 1H), 7.77(d, 1H), 7.74(d, 1H), 7.69(s, 1H), 7.45(s, 2H), 7.41(d, 1H), 7.36(dd, 1H), 3.80(s, 3H). MS 575 m/z (M+H)$^+$.

Example 39

2-[2-Propargyloxy-5-(5-phenylbenzoxazol-2-yl)phenyl]-1,3-dioxo-2,3-dihydro-1H-isoindole-5-carboxylic acid a) 2-(3-Nitro-4-propargyloxy)-5-phenylbenzoxazole Potassium carbonate (330 mg, 2.4 mmol) was added in one portion to a stirred solution of 2-(3-nitro-4-fluoro)-5-phenylbenzoxazole (400 mg, 1.2 mmol) and propargyl alcohol (0.07 ml, 1.2 mmol) in DMF (4 ml) at room temperature under argon. The resulting mixture was heated at 85° C. for 16 h. After being allowed to cool to room temperature the mixture was poured into water (5 ml) and 10% aqueous hydrochloric acid was added until pH 3. Then, the aqueous mixture was extracted with EtOAc (3×5 ml) and the combined organic extracts were washed with 10% aqueous hydrochloric acid (10 ml), brine (5 ml), dried (Na$_2$SO$_4$) and evaporated under reduced pressure to give the subtitle compound (408 mg, 92%) as a brown solid which was sufficiently pure (by TLC and $^1$H NMR spectroscopy) to be used in the next step, R$_F$(3:1 Petrol-EtOAc) 0.41; $^1$H NMR (DMSO) δ 8.69(1H, d, J=2.5 Hz, Ar), 8.52(1H, dd, J=2.5, 9.0 Hz, Ar), 8.10(1H, d, J=1.5 Hz, Ar), 7.92(1H, d, J=8.5 Hz, Ar), 7.79–7.69(4H, m, Ar), 7.54(2H, t, J=7.0 Hz, Ar), 7.43(1H, t, J=7.0 Hz, Ar), 5.21(2H, d, J=2.5 Hz, CH$_2$), 3.85(1H, t, J=2.5 Hz, CH).

b) 2-(3-Amino-4-propargyloxy)-5-phenylbenzoxazole

Tin(II) chloride dihydrate (148 mg, 0.7 mmol) was added in one portion to a stirred suspension of 2-(3-nitro-4-propargyloxy)-5-phenylbenzoxazole (100 mg, 0.3 mmol), powdered zinc (43 mg, 0.7 mmol) and 37% aqueous hydrochloric acid (0.2 ml, 4.9 mmol) in AcOH (1.5 ml) at room temperature. After 2 h, 6 M aqueous sodium hydroxide solution was added until pH 10 was obtained and the mixture was extracted with EtOAc (3×3 ml), dried (Na$_2$SO$_4$) and evaporated under reduced pressure to give the crude subtitle compound (62 mg, 67%) as a pale yellow solid which was sufficiently pure (by TLC and $^1$H NMR spectroscopy) to be used in the next step, R$_F$(3:1 Petrol-EtOAc) 0.36; $^1$H NMR (CDCl$_3$) δ 7.84(1H, d, J=1.0 Hz, Ar), 7.60–7.52(4H, m, Ar), 7.49–7.44(2H, m, Ar), 7.39(2H, brt, J=7.0 Hz, Ar), 7.28(1H, tt (appearing as a t), J=7.5 Hz, Ar), 6.93(1H, d, J=8.0 Hz, Ar), 4.73(2H, d, J=2.5 Hz, CH$_2$), 3.93(2H, brs, NH$_2$), 2.49(1H, t, J=2.5 Hz, CH).

c) 2-[2-Propargyloxy-5-(5-phenylbenzoxazol-2-yl)phenyl]-1,3-dioxo-2,3-dihydro-1H-isoindole-5-carboxylic acid

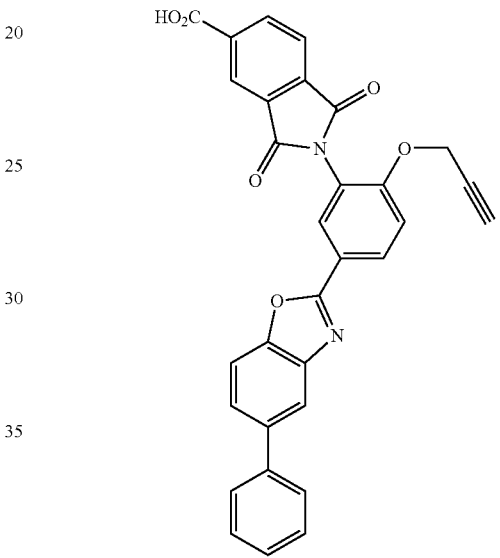

Prepared by the method of Example 15f), from 2-(3-amino-4-propargyloxy)-5-phenylbenzoxazole (62 mg, 0.2 mmol) and 1,2,4-benzene tricarboxylic anhydride (35 mg, 0.2 mmol) in AcOH (1 ml) gave the title compound (27 mg, 29%) as a brown solid, $^1$H NMR (DMSO) δ 13.87(1H, brs, CO$_2$H), 8.52–8.40(4H, m, Ar), 8.18(1H, d, J=8.0 Hz, Ar), 8.10(1H, d, J=1.5 Hz, Ar), 7.91(1H, d, J=8.5 Hz, Ar), 7.81–7.74(3H, m, Ar), 7.62–7.52(3H, m, Ar), 7.44(1H, brt, J=7.0 Hz, Ar), 5.04(2H, d, J=2.0 Hz, CH$_2$), 3.72(1H, t, J=2.0 Hz, CH).

Example 40

2-[2-Ethoxy-5-(5-phenylbenzoxazol-2-yl)phenyl]-1,3-dioxo-2,3-dihydro-1H-isoindole-5-carboxylic acid a) 2-(3-Nitro-4-ethoxyphenyl)-5-phenylbenzoxazole Sodium ethoxide (41 mg, 0.6 mmol) was added portionwise to a stirred suspension of 2-(3-nitro-4-fluoro)-5-phenylbenzoxazole (200 mg, 0.6 mmol) in EtOH (2 ml) at 0° C. under argon. When gas evolution had visibly ceased the mixture was allowed to warm to room temperature and then heated at 85° C. for 1 h. After being allowed to cool to room temperature the mixture was carefully diluted with water (5 ml) and extracted with EtOAc (3×5 ml). The combined organic extracts were washed with brine (5 ml), dried (Na$_2$SO$_4$) and evaporated under reduced pressure to give the crude subtitle compound (207 mg, 96%) as a pale brown solid which was sufficiently pure (by TLC and $^1$H NMR spectroscopy) to be used in the next step, R$_F$(3:1 Petrol-EtOAc) 0.37; $^1$H NMR (DMSO) δ 8.65(1H, d, J=2.0 Hz, Ar), 8.45(1H, dd, J=2.5, 9.0 Hz, Ar), 8.08(1H, d, J=1.5 Hz, Ar), 7.90(1H, d, J=8.5 Hz, Ar), 7.79–7.74(3H, m, Ar), 7.63(1H, d, J=9.0 Hz, Ar), 7.54(2H, t, J=7.0 Hz, Ar), 7.43(1H, t, J=7.0 Hz, Ar), 4.38(2H, q, J=7.0 Hz, CH$_2$), 1.43(1H, t, J=7.0 Hz, CH$_3$).

b) 2-(3-Amino-4-ethoxyphenyl)-5-phenylbenzoxazole

Prepared by the method of Example 15e), from palladium (10 mol %) on carbon (10 mg, 0.1 mmol) and 2-(3-nitro-4-ethoxyphenyl)-5-phenylbenzoxazole (100 mg, 0.3 mmol) in dioxane (1 ml) which gave the crude subtitle compound (51 mg, 56%) as a white solid which was sufficiently pure (by TLC and $^1$H NMR spectroscopy) to be used in the next step, R$_F$(2:1 Petrol-EtOAc) 0.50; $^1$H NMR (CDCl$_3$) δ 7.92(1H, d, J=1.0, Ar), 7.68–7.60(4H, m, Ar), 7.57–7.51(2H, m, Ar), 7.47(2H, brt, J=7.0 Hz, Ar), 7.36(1H, tt, J=1.0, 6.5 Hz, Ar), 6.89(1H, d, J=8.5 Hz, Ar), 4.16(2H, q, J=7.0 Hz, CH$_2$), 3.98(2H, brs, NH$_2$), 1.49(1H, t, J=2.5 Hz, CH$_3$).

c) 2-[2-Ethoxy-5-(5-phenylbenzoxazol-2-yl)phenyl]-1,3-dioxo-2,3-dihydro-1H-isoindole-5-carboxylic acid

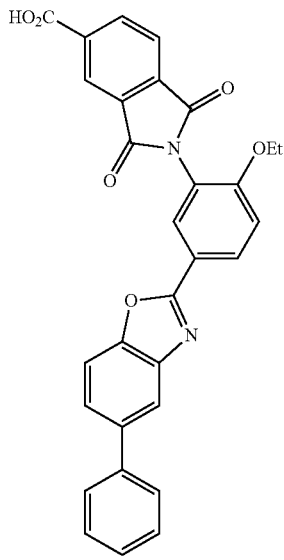

Prepared by the method of Example 15f), from 2-(3-amino-4-ethoxy)-5-phenylbenzoxazole (43 mg, 0.1 mmol) and 1,2,4-benzene tricarboxylic anhydride (25 mg, 0.1 mmol) in AcOH (1 ml) gave the title compound (27 mg, 41%) as a white solid, $^1$H NMR δ (DMSO) 13.88(1H, brs, CO$_2$H), 8.49(1H, d, J=8.0 Hz, Ar), 8.40–8.36(3H, m, Ar), 8.07(1H, s, Ar), 7.90(1H, d, J=8.5 Hz, Ar), 7.79–7.72(3H, m, Ar), 7.54(3H, brt, J=7.0 Hz, Ar), 7.45–7.40(1H, m, Ar), 4.25(2H, q, J=6.5 Hz, CH$_2$), 1.26(3H, t, J=6.5 Hz, CH$_3$).

Example 41

2-[2-(2-Methoxyethylamino)-5-(5-phenylbenzoxazol-2-yl)phenyl]-1,3-dioxo-2,3-dihydro-1H-isoindole-5-carboxylic acid a) 2-[3-Nitro-4-(2-methoxyethylamino)]-5-phenylbenzoxazole 2-Methoxyethylamine (2.0 ml, 23.9 mmol) was added dropwise to 2-(3-nitro-4-fluoro)-5-phenylbenzoxazole (200 mg, 0.6 mmol) with stirring at room temperature under argon. The resulting suspension was stirred at room temperature for 15 min. EtOAc (10 ml) was then added and the mixture was washed with 10% aqueous hydrochloric acid (10 ml), brine (10 ml), dried (Na$_2$SO$_4$) and evaporated under reduced pressure to give the crude subtitle compound (235 mg, 100%) as an orange solid which was sufficiently pure (by TLC and $^1$H NMR spectroscopy) to be used in the next step, R$_F$(2:1 Petrol-EtOAc) 0.18; $^1$H NMR (CDCl$_3$) δ 9.01 (1H, d, J=2.5 Hz, Ar), 8.49(1H, brt, J=~4.5 Hz, NH), 8.24(1H, dd, J=2.0, 9.0 Hz, Ar), 7.85(1H, d, J=1.0 Hz, Ar), 7.58–7.48(4H, m, Ar), 7.43–7.38(2H, m, Ar), 7.32–7.27(1H, m, Ar), 6.95(1H, d, J=9.0 Hz, Ar), 3.65(2H, t, J=5.5 Hz, CH$_2$O), 3.52(2H, td (appearing as a q), J=5.5 Hz, CH$_2$N), 3.39(3H, s, OMe).

b) 2-[3-Amino-4-(2-methoxyethylamino)]-5-phenylbenzoxazole

Prepared by the method of Example 15e), from palladium (10 mol %) on carbon (10 mg, 0.1 mmol) and 2-[3-nitro-4-(2-methoxyethylamino)]-5-phenylbenzoxazole (100 mg, 0.3 mmol) in dioxane (1 ml) which gave the crude subtitle compound (75 mg, 81%) as a white solid which was sufficiently pure (by TLC and $^1$H NMR spectroscopy) to be used in the next step, $^1$H NMR (CDCl$_3$) δ 7.89(1H, d, J=1.0 Hz, Ar), 7.77(1H, dd, J=2.0, 8.5 Hz, Ar), 7.65–7.62(3H, m, Ar), 7.58–7.51(2H, m, Ar), 7.46(2H, brt, J=7.0 Hz, Ar), 7.36(1H, brt, J=7.0 Hz, Ar), 7.36(1H, tt (appearing as a brt), J=7.0 Hz, Ar), 6.73(1H, d, J=8.5 Hz, Ar), 3.70(2H, t, J=5.5 Hz, CH$_2$O), 3.43(3H, s, OMe), 3.39(2H, t, J=5.5 Hz, CH$_2$N).

c) 2-[2-(2-Methoxyethylamino)-5-(5-phenylbenzoxazol-2-yl)phenyl]-1,3-dioxo-2,3-dihydro-1H-isoindole-5-carboxylic acid

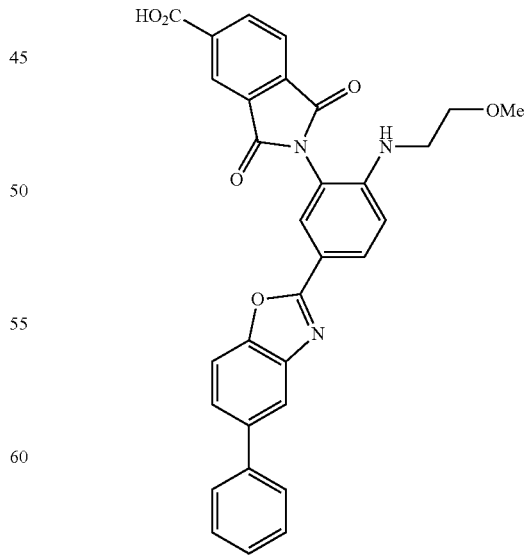

Prepared by the method of Example 15f), from 2-[3-amino-4-(2-methoxyethylamino)]-5-phenylbenzoxazole (54 mg, 0.2 mmol) and 1,2,4-benzene tricarboxylic anhydride (29 mg, 0.2 mmol) in AcOH (1 ml) gave the title compound (10 mg, 12%) as a pale brown solid, $^1$H NMR (DMSO) δ 13.40(1H, brs, CO$_2$H), 8.52(1H, s, Ar), 8.29–8.20(4H, m, Ar), 8.11(1H, s, Ar), 7.98–7.91(2H, m, Ar), 7.81–7.74 (3H, m, Ar), 7.55(2H, brt, J=7.0 Hz, Ar), 7.44(1H, brt, J=7.5 Hz, Ar), 4.31–4.24(2H, m, CH$_2$O), 3.61 (2H, t, J=5.0 Hz, CH$_2$N), 3.11(3H, s, OMe).

Example 42

2-[4-Methoxy-5-(5-phenylbenzoxazol-2-yl)phenyl]-1,3-dioxo-2,3-dihydro-1H-isoindole-5-carboxylic acid a) 2-Fluoro-5-nitrobenzoyl chloride Prepared by the method of Example 15a), from 2-fluoro-5-nitrobenzoyl chloride (5 g, 0.03 mol) the subtitle compound was obtained. The product was used directly in the next step without purification.

b) N-(2-Hydroxy-5-bromophenyl)-2-fluoro-5-nitrobenzamide

Prepared by the method of Example 15b), from 2-amino-4-phenylphenol (5.55 g, 0.03 mol) and 2-fluoro-5-nitrobenzoyl chloride (7.0 g, 0.035 mol) the subtitle compound was obtained (11.0 g, 100%).

c) 2-(3-Nitro-6-fluorophenyl)-5-phenylbenzoxazole

Prepared by the method of Example 15c), from N-(2-hydroxy-5-bromophenyl)-2-fluoro-5-nitrobenzamide (11.0 g, 0.03 mol) and p-toluenesulfonic acid monohydrate (11.88 g, 0.06 mol) the subtitle compound was obtained (6 g, 58%). $^1$H NMR (DMSO) δ 8.98(dd, 1H), 8.54(m, 1H), 8.19(d, 1H), 7.97(d, 1H), 7.81(m, 4H), 7.52(t, 2H), 7.42(d, 1H).

d) 2-(3-Nitro-6-methoxyphenyl)-5-phenylbenzoxazole

Prepared by the method of Example 40a), from 2-(3-nitro-6-fluorophenyl)-5-phenylbenzoxazole (500 mg, 1.5 mmol) and sodium methoxide (161 mg, 3.0 mmol) the subtitle compound was obtained (450 mg, 87%). $^1$H NMR (DMSO) δ 8.88(d, 1H), 8.48(dd, 1H), 8.12(d, 1H), 7.89(d, 1H), 7.75(m, 3H), 7.53(d, 1H), 7.50(t, 2H), 7.40(d, 1H), 4.11(s, 3H).

e) 2-(3-Amino-6-methoxyphenyl)-5-phenylbenzoxazole

Prepared by the method of Example 15e), from palladium (10 mol %) on carbon and 2-(3-nitro-6-methoxyphenyl)-5-phenylbenzoxazole (450 mg, 1.3 mmol) the subtitle compound was obtained (420 mg, 99%). The product was used directly in the next step without purification.

f) 2-[4-Methoxy-5-(5-phenylbenzoxazol-2-yl)phenyl]-1,3-dioxo-2,3-dihydro-1H-isoindole-5-carboxylic acid

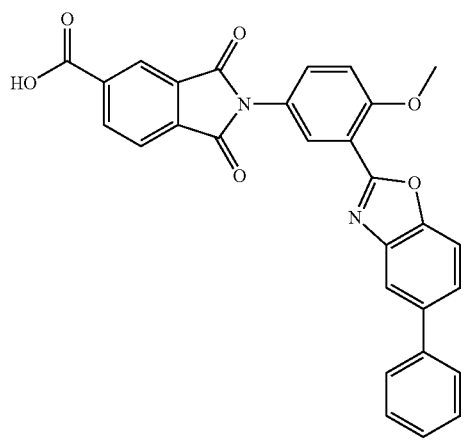

Prepared by the method of Example 15f), from 2-(3-amino-6-methoxyphenyl)-5-phenylbenzoxazole (420 mg, 1.42 mmol) and 1,2,4-benzenetricarboxylic anhydride (273 mg, 1.42 mmol) the title compound was obtained, (460 mg, 66%). $^1$H NMR (DMSO) δ 13.85(s, 1H), 8.51(dd, 1H), 8.41(s, 1H), 8.29(d, 1H), 8.16(m, 2H), 7.95(d, 1H), 7.81(m, 4H), 7.58(m, 2H), 7.54(d, 1H), 7.48(d, 1H), 4.12(s, 3H). MS 491 m/z (M+H)$^+$.

Example 43

2-[4-Ethoxy-3-(5-phenylbenzoxazol-2-yl)phenyl]-1,3-dioxo-2,3-dihydro-1H-isoindole-5-carboxylic acid a) 2-(5-Nitro-2-ethoxyphenyl)-5-phenylbenzoxazole Prepared by the method of Example 40a), from 2-(5-nitro-2-fluorophenyl)-5-phenylbenzoxazole (200 mg, 0.60 mmol) and sodium ethoxide (41 mg, 0.61 mmol) the subtitle compound was obtained (197 mg, 91%). $^1$H NMR (DMSO) δ 8.92(d, 1H), 8.51(dd, 1H), 8.18(s, 1H), 7.95(d, 1H), 7.83(d, 2H), 7.56(t, 3H), 7.47(t, 3H), 4.50(q, 2H), 1.57(t, 3H).

b) 2-(5-Amino-2-ethoxyphenyl)-5-phenylbenzoxazole

Prepared by the method of Example 15e), from 2-(5-nitro-2-ethoxyphenyl)-5-phenylbenzoxazole (197 mg, 0.55 mmol) the subtitle compound was obtained (157 mg, 87%). MS 331 m/z (M+H)$^+$.

c) 2-[4-Ethoxy-3-(5-phenylbenzoxazol-2-yl)phenyl]-1,3-dioxo-2,3-dihydro-1H-isoindole-5-carboxylic acid

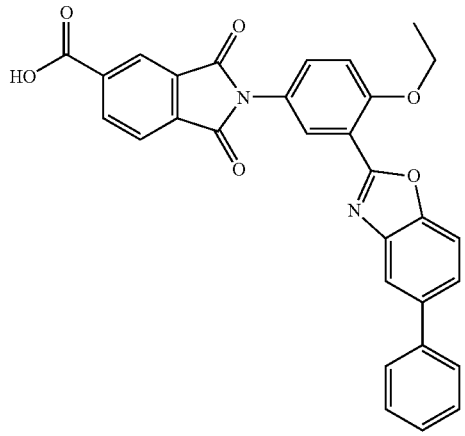

Prepared by the method of Example 1b), from 2-(5-amino-2-ethoxyphenyl)-5-phenylbenzoxazole (157 mg, 0.44 mmol) and 1,2,4-benzenetricarboxylic anhydride (84 mg, 0.44 mmol) the title compound was obtained (133 mg, 60%). $^1$H NMR (DMSO) δ 8.50(dd, 1H), 8.40(s, 1H), 8.25(d, 1H), 8.17(m, 2H), 7.93(d, 1H), 7.80(m, 4H), 7.50(m, 4H), 4.41(q, 2H), 1.52(t, 3H). MS 505 m/z (M+H)$^+$.

Example 44

2-[4-(2-Methoxyethoxy)-3-(5-phenylbenzoxazol-2-yl)phenyl]-1,3-dioxo-2,3-dihydro-1H-isoindole-5-carboxylic acid a) 2-(5-Nitro-2-(2-methoxyethoxy)phenyl)-5-phenylbenzoxazole Sodium hydride (30 mg, 1.2 mmol) was added portionwise to a stirred suspension of 2-(2-fluoro-5-nitrophenyl)-5-phenylbenzoxazole (200 mg, 0.6 mmol) in methoxyethanol (2 ml) at 0° C. When gas evolution had visibly ceased the mixture was allowed to warm to room temperature and then heated at 55° C. for 3 h. After being allowed to cool to room temperature the mixture was diluted with water (5 ml) and extracted with EtOAc (3×5 ml). The combined organic extracts were washed with brine (5 ml), dried ($Na_2SO_4$) and evaporated under reduced pressure to give the subtitle compound (186 mg, 79%). $^1$H NMR (DMSO) δ 8.90(d, 1H), 8.45(dd, 1H), 8.10(d, 1H), 7.85(d, 1H), 7.77(m, 3H), 7.52 (m, 3H), 7.41(t, 1H), 4.50(t, 2H), 4.84(t, 2H), 3.40(s, 3H).

b) 2-(5-Amino-2-(2-methoxyethoxy)phenyl)-5-phenylbenzoxazole

Prepared by the method of Example 15e), from 2-(5-nitro-2-(2-methoxyethoxy)phenyl)-5-phenylbenzoxazole (186 mg, 0.48 mmol) the subtitle compound was obtained (171 mg, 99%). MS 361 m/z (M+H)$^+$.

c) 2-[4-(2-Methoxyethoxy)-3-(5-phenylbenzoxazol-2-yl)phenyl]-1,3-dioxo-2,3-dihydro-1H-isoindole-5-carboxylic acid

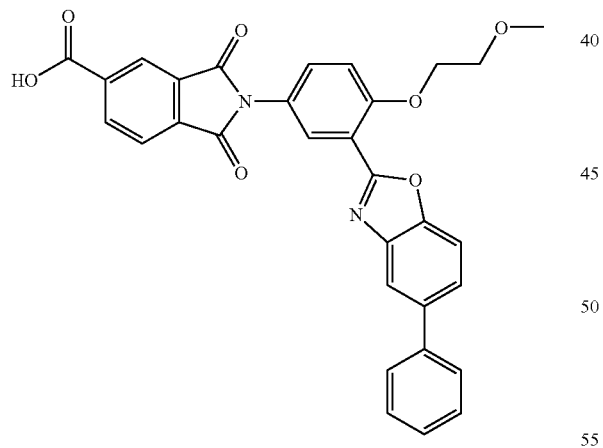

Prepared by the method of Example 1b), from 2-(5-amino-2-(2-methoxyethoxy)phenyl)-5-phenylbenzoxazole (171 mg, 0.47 mmol) and 1,2,4-benzenetricarboxylic anhydride (90 mg, 0.47 mmol) the title compound was obtained (141 mg, 56%). $^1$H NMR (DMSO) δ 8.57(dd, 1H), 8.46(s, 1H), 8.34(d, 1H), 8.24(d, 1H), 8.19(d, 1H), 7.97(d, 1H), 7.85(m, 4H), 7.63(t, 3H), 7.53(t, 1H), 4.51(t, 2H), 3.95(t, 2H), 3.52(s, 3H). MS 535 m/z (M+H)$^+$.

Example 45

2-[4-Butoxy-3-(5-phenylbenzoxazol-2-yl)phenyl]-1,3-dioxo-2,3-dihydro-1H-isoindole-5-carboxylic acid a) 2-(5-Nitro-2-butoxyphenyl)-5-phenylbenzoxazole Prepared by the method of Example 44a), from 2-(2-fluoro-5-nitrophenyl)-5-phenylbenzoxazole (200 mg, 0.6 mmol) in butanol (2 ml) the subtitle compound was obtained (195 mg, 87%). $^1$H NMR (DMSO) δ 8.87(d, 1H), 8.45(dd, 1H), 8.08(d, 1H), 7.85(d, 1H), 7.70(m, 3H), 7.51(t, 3H), 7.40(t, 1H), 4.35(t, 2H), 1.83(q, 2H), 1.57(m, 2H), 1.01(t, 3H).

b) 2-(5-Amino-2-butoxyphenyl)-5-phenylbenzoxazole

Prepared by the method of Example 15e), from 2-(5-nitro-2-butoxyphenyl)-5-phenylbenzoxazole (195 mg, 0.50 mmol) the subtitle compound was obtained (174 mg, 97%). MS 359 m/z (M+H)$^+$.

c) 2-[4-Butoxy-3-(5-phenylbenzoxazol-2-yl)phenyl]-1,3-dioxo-2,3-dihydro-1H-isoindole-5-carboxylic acid

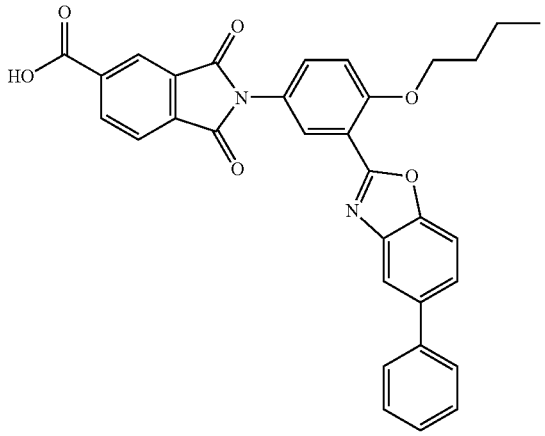

Prepared by the method of Example 1b), from 2-(5-amino-2-butoxyphenyl)-5-phenylbenzoxazole (174 mg, 0.49 mmol) and 1,2,4-benzenetricarboxylic anhydride (94 mg, 0.49 mmol) the title compound was obtained (146 mg, 56%). $^1$H NMR (DMSO) δ 8.44(dd, 1H), 8.32(s, 1H), 8.18(d, 1H), 8.12(d, 1H), 8.05(d, 1H), 7.82(d, 1H), 7.71(m, 4H), 7.48(m, 3H), 7.39(t, 1H), 4.25(t, 2H), 1.83(m, 2H), 1.58(m, 2H), 1.00(t, 3H). MS 533 m/z (M+H)$^+$.

Example 46

2-[4-Isopropoxy-3-(5-phenylbenzoxazol-2-yl)phenyl]-1,3-dioxo-2,3-dihydro-1H-isoindole-5-carboxylic acid a) 2-(5-Nitro-2-isopropoxyphenyl)-5-phenylbenzoxazole Prepared by the method of Example 44a), from 2-(2-fluoro-5-nitrophenyl)-5-phenylbenzoxazole (200 mg, 0.6 mmol) and isopropanol (2 ml) the subtitle compound was obtained (204 mg, 84%). $^1$H NMR (DMSO) δ 8.85(d, 1H), 8.44(dd, 1H), 8.12(d, 1H), 7.90(d, 1H), 7.76(m, 3H), 7.54 (m, 3H), 7.40(t, 1H), 4.35(m, 1H), 1.45(d, 6H).

b) 2-(5-Amino-2-isopropoxyphenyl)-5-phenylbenzoxazole

Prepared by the method of Example 15e), from 2-(5-nitro-2-isopropylphenyl)-5-phenylbenzoxazole (204 mg, 0.54 mmol) the subtitle compound was obtained (188 mg, 100%). MS 345 m/z (M+H)+.

c) 2-[4-Isopropoxy-3-(5-phenylbenzoxazol-2-yl)phenyl]-1,3-dioxo-2,3-dihydro-1H-isoindole-5-carboxylic acid

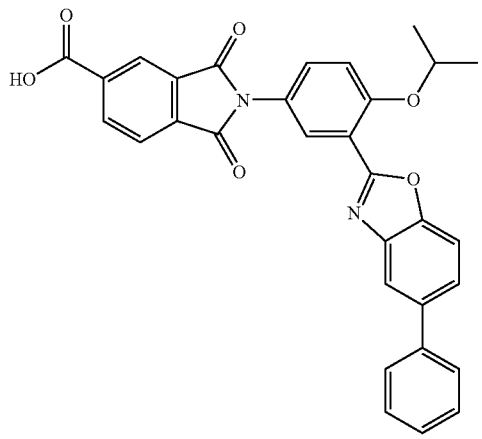

Prepared by the method of Example 1b), from 2-(5-amino-2-isopropylphenyl)-5-phenylbenzoxazole (188 mg, 0.55 mmol) and 1,2,4-benzenetricarboxylic anhydride (106 mg, 0.55 mmol) the title compound was obtained (102 mg, 36%). $^1$H NMR (DMSO) δ 8.42(dd, 1H), 8.32(s, 1H), 8.18(d, 1H), 8.09(m, 2H), 7.85(d, 1H), 7.71(m, 3H), 7.50(m, 3H), 7.39(t, 1H), 4.87(m, 1H), 1.41(d, 6H). MS 519 m/z (M+H)+.

Example 47

2-[4-Allyloxy-3-(5-phenylbenzoxazol-2-yl)phenyl]-1,3-dioxo-2,3-dihydro-1H-isoindole-5-carboxylic acid a) 2-(5-Nitro-2-allyloxyphenyl)-5-phenylbenzoxazole Prepared by the method of Example 44a), from 2-(2-fluoro-5-nitrophenyl)-5-phenylbenzoxazole (200 mg, 0.6 mmol) and allyl alcohol (4 ml) the subtitle compound was obtained (216 mg, 97%). $^1$H NMR (DMSO) δ 8.83(d, 1H), 8.38(dd, 1H), 8.06(d, 1H), 7.82(d, 1H), 7.69(m, 3H), 7.44(t, 3H), 7.33(t, 1H), 6.08(m, 1H), 5.60(dd, 1H), 5.30(dd, 1H), 4.90(m, 2H).

b) 2-(5-Amino-2-allyloxyphenyl)-5-phenylbenzoxazole

Powdered zinc (377 mg, 5.8 mmol) was added to a solution of 2-(5-nitro-2-allyloxyphenyl)-5-phenylbenzoxazole (216 mg, 0.58 mmol) in acetic acid (2 ml). After 2 h the reaction mixture was filtered through celite and the filtrate concentrated. The residue was dissolved in ethyl acetate (10 ml) and washed with saturated sodium hydrogen carbonate solution (2×25 ml). The organic layer was dried over sodium sulfate and concentrated to give the subtitle compound (342 mg, 100%). The product was used directly in the next step without purification.

c) 2-[4-Allyloxy-3-(5-phenylbenzoxazol-2-yl)phenyl]-1,3-dioxo-2,3-dihydro-1H-isoindole-5-carboxylic acid

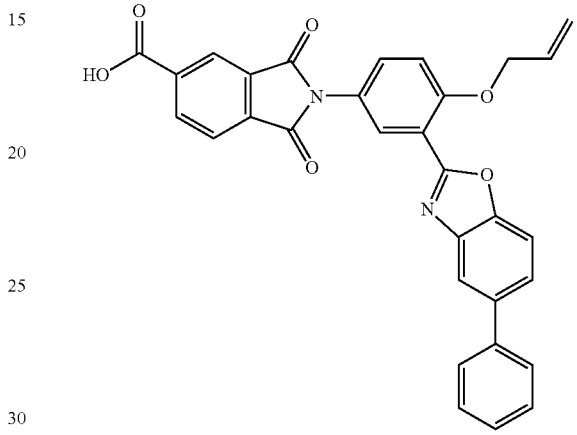

Prepared by the method of Example 1b), from 2-(5-amino-2-allyloxyphenyl)-5-phenylbenzoxazole (190 mg, 0.55 mmol) and 1,2,4-benzenetricarboxylic anhydride (106 mg, 0.55 mmol) the title compound was obtained (102 mg, 36%). $^1$H NMR (DMSO) δ 8.57(m, 1H), 8.35(dd, 1H), 8.37(s, 1H), 8.13(d, 1H), 7.94(m, 3H), 7.77(d, 1H), 7.63(m, 3H), 7.35(m, 4H), 6.04(m, 1H), 5.49(dd, 1H), 5.33(dd, 1H), 4.77(d, 2H). MS 517 m/z (M+H)+.

Example 48

2-[4-Hydroxy-3-(5-phenylbenzoxazol-2-yl)phenyl]-1,3-dioxo-2,3-dihydro-1H-isoindole-5-carboxylic acid a) 2-(5-Nitro-2-(3-furanylmethoxy)phenyl)-5-phenylbenzoxazole Prepared by the method of Example 44a), from 2-(2-fluoro-5-nitrophenyl)-5-phenylbenzoxazole (400 mg, 1.2 mmol) in 3-furanmethanol (2 ml) the subtitle compound was obtained (392 mg, 79%). The product was used directly in the next step without purification.

b) 2-(5-Amino-2-(3-furanylmethoxy)phenyl)-5-phenylbenzoxazole

Prepared by the method of Example 47b), from 2-(5-nitro-2-(3-furanylmethoxy)phenyl)-5-phenylbenzoxazole (392 mg, 0.95 mmol) and zinc (622 mg, 9.5 mmol) the subtitle compound was obtained (382 mg, 93%). The product was used directly in the next step without purification.

c) 2-[4-Hydroxy-3-(5-phenylbenzoxazol-2-yl)phenyl]-1,3-dioxo-2,3-dihydro-1H-isoindole-5-carboxylic acid c) 2-[4-Propoxy-5-(5-phenylbenzoxazol-2-yl)phenyl]-1,3-dioxo-2,3-dihydro-1H-isoindole-5-carboxylic acid

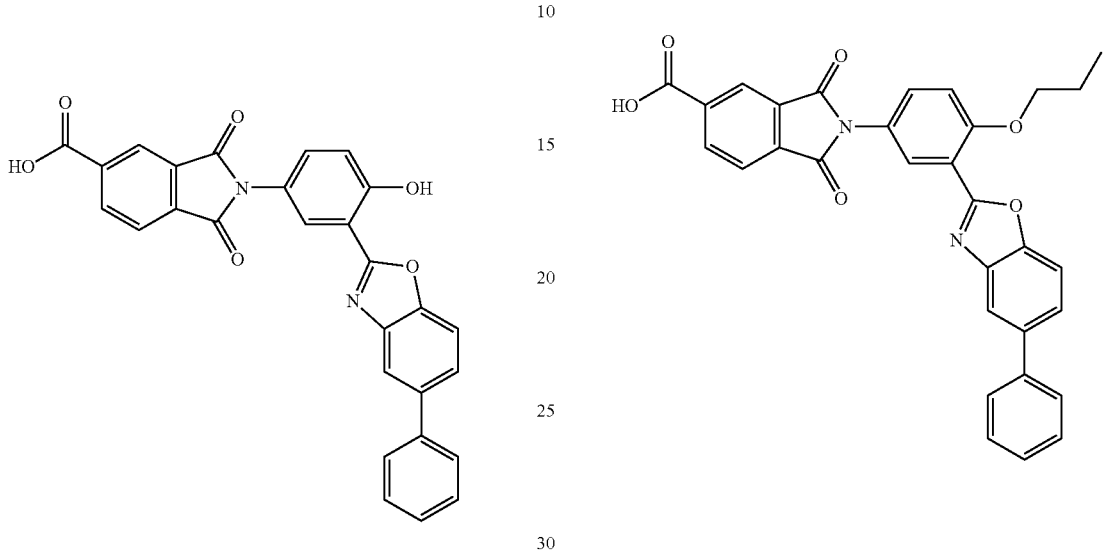

Prepared by the method of Example 1b), from 2-(5-amino-2-(3-furanylmethoxy)phenyl)-5-phenylbenzoxazole (144 mg, 0.28 mmol) and 1,2,4-benzenetricarboxylic anhydride (73 mg, 0.38 mmol) the title compound was obtained (100 mg, 55%). $^1$H NMR (DMSO) δ 8.48(dd, 1H), 8.39(s, 1H), 8.25(d, 1H), 8.21(d, 1H), 8.17(d, 1H), 8.00(d, 1H), 7.82(m, 3H), 7.70(dd, 1H), 7.57(t, 2H), 7.46(t, 1H), 7.38(d, 1H). MS 477 m/z (M+H)$^+$.

Example 49

2-[4-Propoxy-5-(5-phenylbenzoxazol-2-yl)phenyl]-1,3-dioxo-2,3-dihydro-1H-isoindole-5-carboxylic acid a) 2-(5-Nitro-2-propoxyphenyl)-5-phenylbenzoxazole Prepared by the method of Example 44a), from 2-(2-fluoro-5-nitrophenyl)-5-phenylbenzoxazole (400 mg, 1.2 mmol) in propanol (2 ml) the subtitle compound was obtained (325 mg, 73%). MS 375 m/z (M+H)$^+$.

b) 2-(5-Amino-2-propoxyphenyl)-5-phenylbenzoxazole

Prepared by the method of Example 15e), from 2-(5-nitro-2-propoxyphenyl)-5-phenylbenzoxazole (325 mg, 0.89 mmol) the subtitle compound was obtained (264 mg, 88%). MS 345 m/z (M+H)$^+$.

Prepared by the method of Example 1b), from 2-(5-nitro-2-propoxyphenyl)-5-phenylbenzoxazole (125 mg, 0.36 mmol) and 1,2,4-benzenetricarboxylic anhydride (68 mg, 0.36 mmol) the title compound was obtained (37 mg, 21%). $^1$H NMR (DMSO) δ 8.47(d, 1H), 8.38(s, 1H), 8.25(d, 1H), 8.13(m, 2H), 7.89(d, 1H), 7.76(m, 4H), 7.49(m, 4H), 4.27(t, 2H), 1.92(m, 2H), 1.15(t, 3H). MS 519 m/z (M+H)$^+$.

Example 50

2-[2-(3-Furanylmethoxy)-5-(5-phenylbenzoxazol-2-yl)phenyl]-1,3-dioxo-2,3-dihydro-1H-isoindole-5-carboxylic acid a) 2-(3-Nitro-4-(3-furanylmethoxy)-5-phenylbenzoxazole Prepared by the method of Example 44a), from 2-(3-nitro-4-fluorophenyl)-5-phenylbenzoxazole (0.70 g, 3.0 mmol) and 3-furanmethanol (3.0 ml) the subtitle compound was obtained (0.78 g, 90%). $^1$H NMR (DMSO) δ 8.63(d, 1H), 8.44(dd, 1H), 8.06(d, 1H), 7.87(m, 2H), 7.76–7.71(m, 5H), 7.50(m, 2H), 7.39(t, 1H), 6.60(d, 1H), 5.32(s, 2H).

b) 2-(3-Amino-4-(3-furanylmethoxy)-5-phenylbenzoxazole

Prepared by the method of Example 40b), from 2-(3-nitro-4-(3-furanylmethoxy)-5-phenylbenzoxazole (0.78 g, 1.9 mmol) the subtitle compound was obtained (0.40 g, 56%). $^1$H NMR (DMSO) δ 7.94(d, 1H), 7.70–7.46(m, 10H), 7.38(t, 1H), 7.01(d, 1H), 6.55(s, 1H), 5.08(s, 2H).

c) 2-[2-(3-Furanylmethoxy)-5-(5-phenylbenzoxazol-2-yl)phenyl]-1,3-dioxo-2,3-dihydro-1H-isoindole-5-carboxylic acid c) 2-[2-(2-Methoxyethoxy)-5-(5-phenylbenzoxazol-2-yl)phenyl]-1,3-dioxo-2,3-dihydro-1H-isoindole-5-carboxylic acid

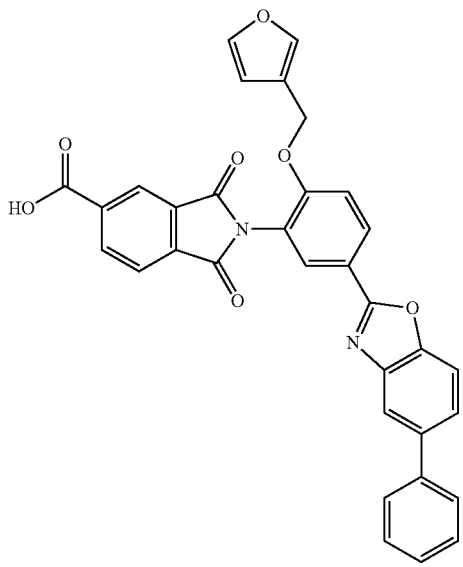

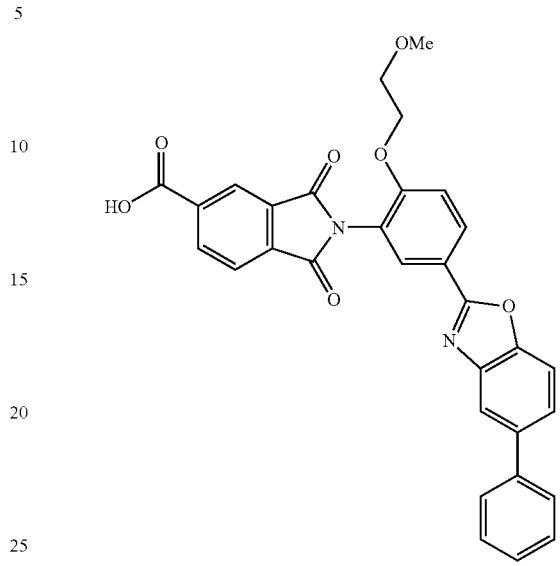

Prepared by the method of Example 15f), from 2-(3-amino-4-(3-furanylmethoxy)-5-phenylbenzoxazole (200 mg, 0.52 mmol) and 1,2,4-benzenetricarboxylic anhydride (10 mg, 0.52 mmol) the title compound was obtained (149 mg, 51%). $^1$H NMR (DMSO) δ 8.45(dd, 1H), 8.34(m, 3H), 8.13(d, 1H), 8.03(d, 1H), 7.84(d, 1H), 7.75–7.69(m, 4H), 7.58(m, 2H), 7.49(m, 2H), 7.39(t, 2H), 6.41(d, 1H), 5.18(s, 2H). MS 555.4 m/z (M–H)$^-$.

Prepared by the method of Example 15f), from 2-(3-amino-4-(2-methoxyethoxy)-5-phenylbenzoxazole (48 mg, 0.13 mmol) and 1,2,4-benzenetricarboxylic anhydride (25 mg, 0.13 mmol) the title compound was obtained (30 mg, 42%). $^1$H NMR (CDCl$_3$) δ 8.68(s, 1H), 8.56(d, 1H), 8.36–8.30(m, 2H), 8.12–8.06(m, 2H), 7.68–7.62(m, 4H), 7.49(m, 2H), 7.39(t, 1H), 7.24(m, 1H), 4.28(t, 2H), 3.70(t, 2H), 3.31(s, 3H). MS 533.1 m/z (M–H)$^-$.

Example 51

2-[2-(2-Methoxyethoxy)-5-(5-phenylbenzoxazol-2-yl)phenyl]-1,3-dioxo-2,3-dihydro-1H-isoindole-5-carboxylic acid a) 2-(3-Nitro-4-(2-methoxyethoxy)-5-phenylbenzoxazole Prepared by the method of Example 44a), from methoxyethanol (2.0 ml) and 2-(3-nitro-4-fluorophenyl)-5-phenylbenzoxazole (0.20 g, 3.0 mmol) the subtitle compound was obtained (0.23 g, 99%). $^1$H NMR (CDCl$_3$) δ 8.61(d, 1H), 8.41(dd, 1H), 8.05(d, 1H), 7.86(d, 1H), 7.75–7.70(m, 3H), 7.62(d, 1H), 7.50(m, 2H), 7.39(t, 1H), 4.42(t, 2H), 3.72(t, 2H), 3.33(s, 3H).

b) 2-(3-Amino-4-(2-methoxyethoxy)-5-phenylbenzoxazole

Prepared by the method of Example 40b), from 2-[3-nitro-4-(2-methoxyethoxy)]-5-phenylbenzoxazole (0.10 g, (1.9 mmol) the subtitle compound was obtained (0.60 g, 65%). $^1$H NMR (CDCl$_3$) δ 7.93(d, 1H), 7.67–7.53(m, 6H), 7.48(m, 2H), 7.37(t, 1H), 6.93(d, 1H), 4.26(t, 2H), 3.82(t, 2H), 3.48(s, 3H).

Example 52

2-[5-(5-Phenylbenzoxazol-2-yl)-2-(3-tetrahydrofuranylmethoxy)phenyl]-1,3-dioxo-2,3-dihydro-1H-isoindole-5-carboxylic acid a) 2-(3-Nitro-4-(3-tetrahydrofuranylmethoxy)-5-phenylbenzoxazole Prepared by the method of Example 44a), from 2-(3-nitro-4-fluoro)-5-phenylbenzoxazole (200 mg, 0.6 mmol) and tetrahydro-3-furanmethanol (1.221 g, 11.69 mmol) the subtitle compound was obtained (220 mg, 88%). $^1$H NMR (DMSO) δ 8.61(d, 1H), 8.41(dd, 1H), 8.04(d, 1H), 7.85(d, 1H), 7.27(m, 3H), 7.60(d, 1H), 7.50(m, 2H), 7.40(t, 1H), 4.23(m, 2H), 3.79(m, 2H), 3.67(m, 1H), 3.57(m, 1H), 2.70 (m, 1H), 2.03(m, 1H), 1.70(m, 1H).

b) 2-(3-Amino-4-(3-tetrahydrofuranylmethoxy)-5-phenylbenzoxazole

Prepared by the method of Example 47b), from 2-(3-nitro-4-(3-tetrahydrofuranylmethoxy)-5-phenylbenzoxazole (150 mg, 0.36 mmol) and powdered zinc (235 mg, 3.6 mmol) the subtitle compound was obtained (115 mg, 83%). $^1$H NMR (DMSO) δ 7.98(d, 1H), 7.79(d, 1H), 7.73(m, 2H), 7.65(dd, 1H), 7.54–7.36(m, 5H), 7.02(d, 1H), 4.01(m, 2H), 3.88–3.76(m, 2H), 3.68(m, 1H), 3.59(m, 1H), 2.71(m, 1H), 2.07(m, 1H), 1.70(m, 1H).

c) 2-[5-(5-Phenylbenzoxazol-2-yl)-2-(3-tetrahydrofuranyl-methoxy)phenyl]-1,3-dioxo-2,3-dihydro-1H-isoindole-5-carboxylic acid

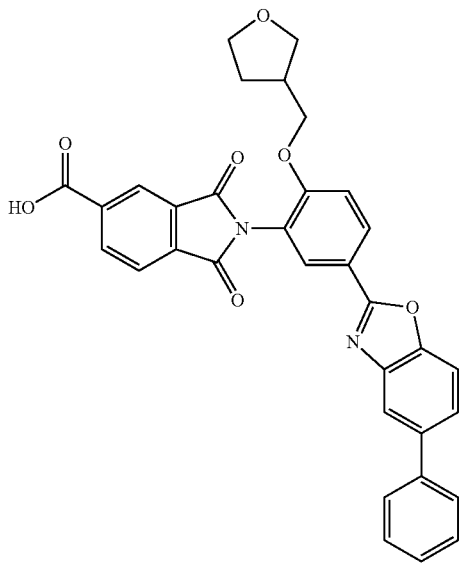

Prepared by the method of Example 15f), from 2-(3-amino-4-(3-tetrahydrofuranylmethoxy)-5-phenylbenzoxazole (50 mg, 0.13 mmol) and 1,2,4-benzenetricarboxylic anhydride (25 mg, 0.13 mmol) the title compound was obtained (20 mg, 28%). $^1$H NMR (DMSO) δ 8.46(dd, 1H), 8.35(m, 3H), 8.14(dd, 1H), 8.03(d, 1H), 7.85(d, 1H), 7.72 (m, 3H), 7.50(m, 3H), 7.39(t, 1H), 4.10(m, 2H), 3.56(m, 3H), 3.52(m, 2H), 1.85(m, 1H), 1.54(m, 1H). MS 559.0 m/z (M−H)⁻.

Example 53

2-[5-(5-Phenylbenzoxazol-2-yl)-2-(3-thiophenyl-methoxy)phenyl]-1,3-dioxo-2,3-dihydro-1H-isoindole-5-carboxylic acid a) 2-(3-Nitro-4-(3-thiophenylmethoxy)-5-phenylbenzoxazole Prepared by the method of Example 44a), from 2-(3-nitro-4-fluorophenyl)-5-phenylbenzoxazole (200 mg, 0.6 mmol) and 3-thiophenemethanol (1.36 g, 12 mmol) the subtitle compound was obtained (202 mg, 79%). $^1$H NMR (DMSO) δ 8.64(d, 1H), 8.43(dd, 1H), 8.05(d, 1H), 7.86(d, 1H), 7.73(m, 4H), 7.62(m, 2H), 7.49(m, 2H), 7.39(t, 1H), 7.21 (dd, 1H), 5.44(s, 2H).

b) 2-(3-Amino-4-(3-thiophenylmethoxy)-5-phenylbenzoxazole

Prepared by the method of Example 47b), from 2-(3-nitro-4-thiophen-3-ylmethoxyphenyl)-5-phenylbenzoxazole (150 mg, 0.35 mmol) the subtitle compound was obtained (84 mg, 60%). $^1$H NMR (DMSO) δ 7.99(s, 1H), 7.81–7.32 (m, 11H), 7.24(d, 1H), 7.09(d, 1H), 5.22(s, 2H).

c) 2-[5-(5-Phenylbenzoxazol-2-yl)-2-(3-thiophenyl-methoxy)phenyl]-1,3-dioxo-2,3-dihydro-1H-isoindole-5-carboxylic acid

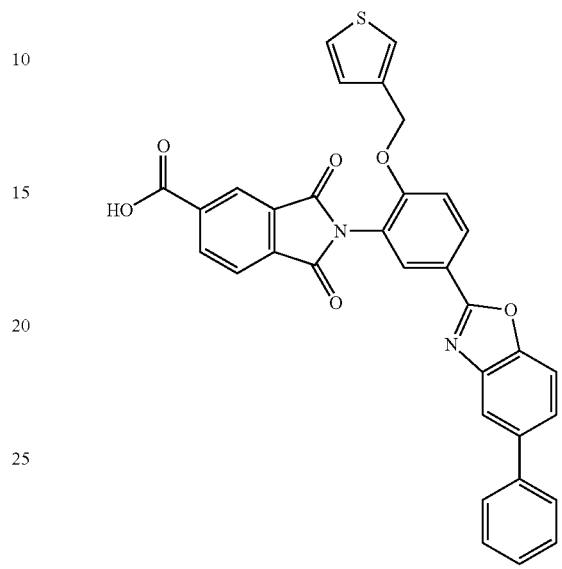

Prepared by the method of Example 15f), from 2-(3-amino-4-(3-thiophenylmethoxy)-5-phenylbenzoxazole (50 mg, 0.13 mmol) and 1,2,4-benzenetricarboxylic anhydride (25 mg, 0.13 mmol) the title compound was obtained (34 mg, 47%). $^1$H NMR (DMSO) δ 8.45(dd, 1H), 8.34(m, 3H), 8.14(d, 1H), 8.03(d, 1H), 7.84(d, 1H), 7.73(m, 3H), 7.56–7.47(m, 5H), 7.39(t, 1H), 7.04(dd, 1H), 5.31(s, 2H). MS 570.9 m/z (M−H)⁻.

Example 54

2-[2-(4-Morpholinyl)-5-(5-phenylbenzoxazol-2-yl)phenyl]-1,3-dioxo-2,3-dihydro-1H-isoindole-5-carboxylic acid, acetic acid salt a) 2-(3-Nitro-4-morpholinyl)-5-phenylbenzoxazole Morpholine (2.0 ml) was added dropwise to a solution of 2-(3-nitro-4-fluorophenyl)-5-phenylbenzoxazole (200 mg, 0.6 mmol) in THF (10 ml). After 4 h the reaction was concentrated. The residue was triturated with methanol and filtered to give the subtitle compound (216 mg, 90%). $^1$H NMR (CDCl$_3$) δ 8.69(d, 1H), 8.03(dd, 1H), 7.95(d, 1H), 7.65–7.58(m, 4H), 7.48(m, 2H), 7.34(t, 1H), 7.22(d, 1H), 3.89(t, 4H), 3.21(t, 4H).

b) 2-(3-Amino-4-morpholinyl)-5-phenylbenzoxazole

Prepared by the method of Example 40b), from 2-(3-nitro-4-morpholinyl)-5-phenylbenzoxazole (100 mg, 0.25 mmol) the subtitle compound was obtained (69 mg, 74%). $^1$H NMR (CDCl$_3$) δ 7.94(d, 1H), 7.70–7.54(m, 6H), 7.48(m, 2H), 7.38(t, 1H), 7.11(d, 1H), 3.90(t, 4H), 3.03(t, 4H).

c) 2-[2-(4-Morpholinyl)-5-(5-phenylbenzoxazol-2-yl)phenyl]-1,3-dioxo-2,3-dihydro-1H-isoindole-5-carboxylic acid, acetic acid salt c) 2-[4-Ethylamino-3-(5-phenylbenzoxazol-2-yl)phenyl]-1,3-dioxo-2,3-dihydro-1H-isoindole-5-carboxylic acid

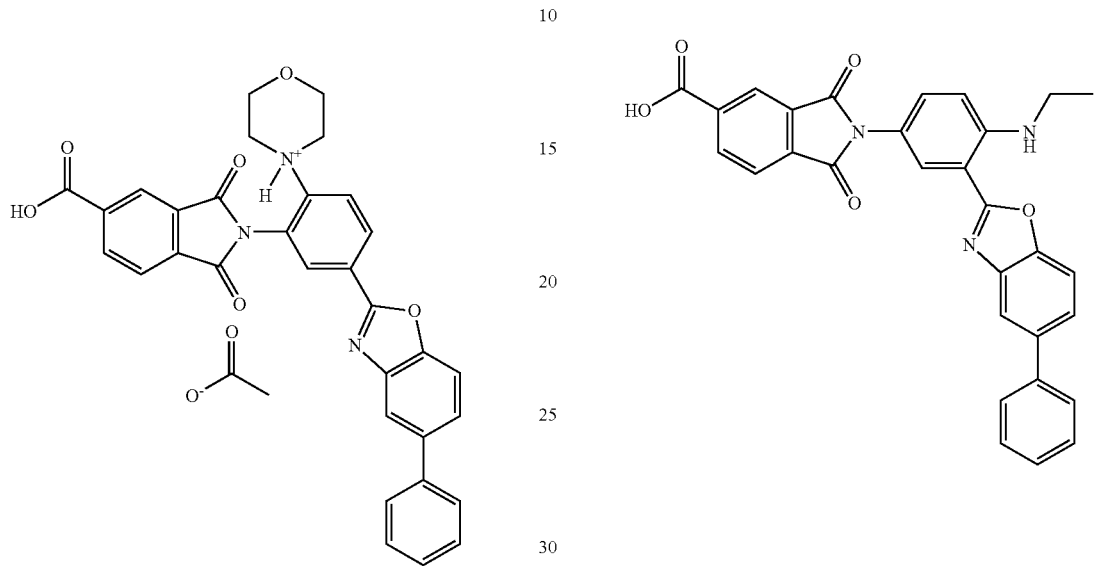

Prepared by the method of Example 15f), from 2-(3-amino-4-morpholinyl)-5-phenylbenzoxazole (47 mg, 0.12 mmol) and 1,2,4-benzenetricarboxylic anhydride (24 mg, 0.12 mmol) the title compound was obtained (20 mg, 29%). $^1$H NMR (DMSO) δ 8.46(dd, 1H), 8.36(d, 1H), 8.28(m, 2H), 8.14(d, 1H), 8.02(d, 1H), 7.72(m, 3H), 7.50(m, 2H), 7.39(t, 1H), 3.48(t, 4H), 2.93(t, 4H), 1.91(s, 3H). MS 544.0 m/z (M–H)$^-$.

Prepared by the method of Example 1b), from 2-(5-amino-2-ethylaminophenyl)-5-phenylbenzoxazole (158 mg, 0.48 mmol) and 1,2,4-benzenetricarboxylic anhydride (92 mg, 0.48 mmol) the title compound was obtained (154 mg, 64%). $^1$H NMR (DMSO) δ 8.42(m, 2H), 8.31(s, 1H), 8.14(d, 1H), 8.07(m, 2H), 7.83(d, 1H), 7.74(m, 3H), 7.50(m, 3H), 7.39(t, 1H), 7.04(d, 1H), 3.48(q, 2H), 1.39(t, 3H). MS 504 m/z (M+H)$^+$.

Example 55

2-[4-Ethylamino-3-(5-phenylbenzoxazol-2-yl)phenyl]-1,3-dioxo-2,3-dihydro-1H-isoindole-5-carboxylic acid a) 2-(5-Nitro-2-ethylaminophenyl)-5-phenylbenzoxazole Prepared by the method of Example 54a), from 2-(2-fluoro-5-nitrophenyl)-5-phenylbenzoxazole (200 mg, 0.60 mmol), and ethylamine (3 ml) the subtitle compound was obtained (217 mg, 100%). MS 360 m/z (M+H)$^+$.

b) 2-(5-Amino-2-ethylaminophenyl)-5-phenylbenzoxazole

Prepared by the method of Example 15e), from 2-(5-nitro-2-ethylaminophenyl)-5-phenylbenzoxazole (217 mg, 0.60 mmol) the subtitle compound was obtained (158 mg, 80%). The product was used directly in the next step without purification.

Example 56

2-[4-Propylamino-3-(5-phenylbenzoxazol-2-y)phenyl]-1,3-dioxo-2,3-dihydro-1H-isoindole-5-carboxylic acid a) 2-(5-Nitro-2-propylaminophenyl)-5-phenylbenzoxazole Prepared by the method of Example 54a), from 2-(2-fluoro-5-nitro)-5-phenylbenzoxazole (200 mg, 0.60 mmol), and propylamine (3 ml) the subtitle compound was obtained (228 mg, 100%). MS 374 m/z (M+H)$^+$.

b) 2-(5-Amino-2-propylaminophenyl)-5-phenylbenzoxazole

Prepared by the method of Example 15e), from 2-(5-nitro-2-propylaminophenyl)-5-phenylbenzoxazole (228 mg, 0.61 mmol) the subtitle compound was obtained (161 mg, 77%). The product was used directly in the next step without purification.

c) 2-[4-Propylamino-3-(5-phenylbenzoxazol-2-yl)phenyl]-1,3-dioxo-2,3-dihydro-1H-isoindole-5-carboxylic acid c) 2-[4-(2-Methoxyethylamino)-3-(5-phenylbenzoxazol-2-yl)phenyl]-1,3-dioxo-2,3-dihydro-1H-isoindole-5-carboxylic acid

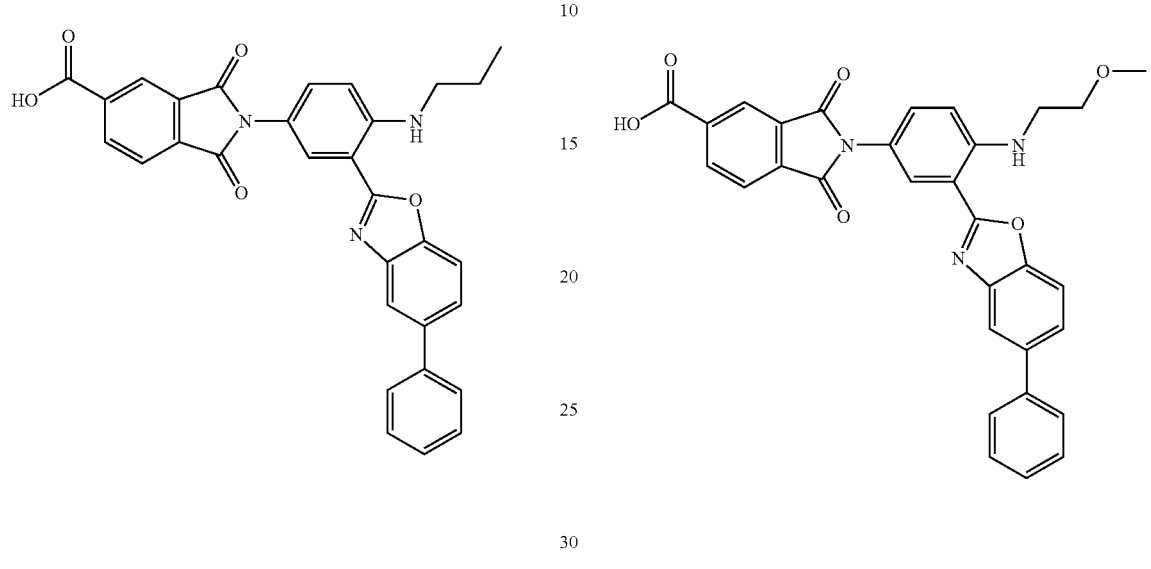

Prepared by the method of Example 1b), from 2-(5-amino-2-propylaminophenyl)-5-phenylbenzoxazole (161 mg, 0.47 mmol) and 1,2,4-benzenetricarboxylic anhydride (90 mg, 0.47 mmol) the title compound was obtained (174 mg, 72%). $^1$H NMR (DMSO) δ 8.51(t, 1H), 8.42(dd, 1H), 8.31(s, 1H), 8.15(d, 1H), 8.08(m, 2H), 7.77(m, 4H), 7.50(m, 3H), 7.39(t, 1H), 7.03(d, 1H), 3.40(q, 2H), 1.68(m, 2H), 1.34(t, 3H). MS 518 m/z $(M+H)^+$.

Prepared by the method of Example 1b), from 2-(5-amino-2-(2-methoxyethylamino)phenyl)-5-phenylbenzoxazole (131 mg, 0.36 mmol) and 1,2,4-benzenetricarboxylic anhydride (70 mg, 0.36 mmol) the title compound was obtained (138 mg, 72%). $^1$H NMR (DMSO) δ 8.61(t, 1H), 8.42(dd, 1H), 8.31(s, 1H), 8.13(d, 1H), 8.08(m, 2H), 7.83(d, 1H), 7.53(m, 3H), 7.50(m, 3H), 7.41(t, 1H), 7.08(d, 1H), 3.69(m, 2H), 3.59(m, 2H), 3.35(s, 3H). MS 534 m/z $(M+H)^+$.

Example 57

2-[4-(2-Methoxyethylamino)-3-(5-phenylbenzoxazol-2-yl)phenyl]-1,3-dioxo-2,3-dihydro-1H-isoindole-5-carboxylic acid a) 2-(5-Nitro-2-(2-methoxyethylamino)phenyl)-5-phenylbenzoxazole Prepared by the method of Example 54a), from 2-(2-fluoro-5-nitrophenyl)-5-phenylbenzoxazole (200 mg, 0.60 mmol), and 2-methoxyethylamine (3 ml) the subtitle compound was obtained (216 mg, 93%). MS 390 m/z $(M+H)^+$.

b) 2-(5-Amino-2-(2-methoxyethylamino)phenyl)-5-phenylbenzoxazole

Prepared by the method of Example 15e), from 2-(5-nitro-2-(2-methoxyethylamino)phenyl)-5-phenylbenzoxazole (216 mg, 0.55 mmol) the subtitle compound was obtained (131 mg, 67%). The product was used directly in the next step without purification.

Example 58

2-[4-Morpholinyl-3-(5-phenylbenzoxazol-2-yl)phenyl]-1,3-dioxo-2,3-dihydro-1H-isoindole-5-carboxylic acid a) 2-(5-Nitro-2-(4-morpholinyl)phenyl)-5-phenylbenzoxazole Prepared by the method of Example 54a), from 2-(2-fluoro-5-nitrophenyl)-5-phenylbenzoxazole (200 mg, 0.60 mmol), and morpholine (3 ml) the subtitle compound was obtained (274 mg, 100%). MS 402 m/z $(M+H)^+$.

b) 2-(5-Amino-2-(4-morpholinyl)phenyl)-5-phenylbenzoxazole

Prepared by the method of Example 15e), from 2-(5-nitro-2-(4-morpholinyl)phenyl)-5-phenylbenzoxazole (274 mg, 0.68 mmol) the subtitle compound was obtained (175 mg, 69%). The product was used directly in the next step without purification.

c) 2-[4-Morpholinyl-3-(5-phenylbenzoxazol-2-yl)phenyl]-1,3-dioxo-2,3-dihydro-1H-isoindole-5-carboxylic acid c) 2-[4-Butylamino-3-(5-phenylbenzoxazol-2-yl)phenyl]-1,3-dioxo-2,3-dihydro-1H-isoindole-5-carboxylic acid

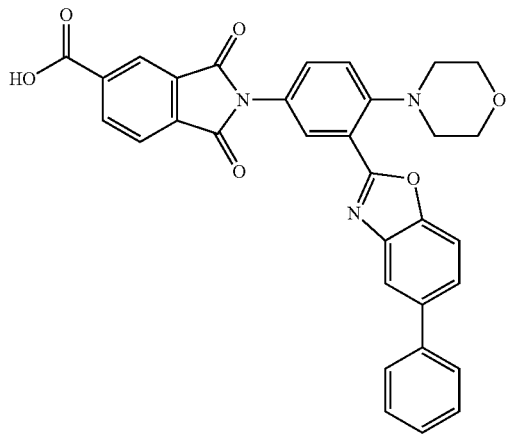

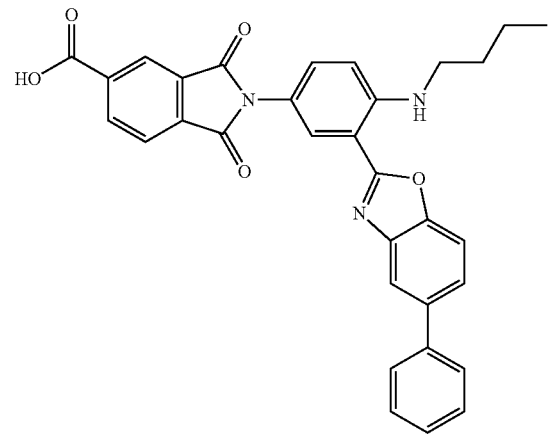

Prepared by the method of Example 1b), from 2-(5-amino-2-(4-morpholinyl)phenyl)-5-phenylbenzoxazole (175 mg, 0.47 mmol) and 1,2,4-benzenetricarboxylic anhydride (90 mg, 0.47 mmol) the title compound was obtained (136 mg, 53%). $^1$H NMR (DMSO) δ 8.43(dd, 1H), 8.32(s, 1H), 8.18(d, 1H), 8.09(m, 2H), 7.90(d, 1H), 7.75(m, 3H), 7.65(dd, 1H), 7.50(t, 2H), 7.38(m, 2H), 3.80(m, 4H), 3.05 (m, 4H). MS 546 m/z (M+H)$^+$.

Prepared by the method of Example 1b), from 2-(5-amino-2-butylaminophenyl)-5-phenylbenzoxazole (409 mg, 1.14 mmol) and 1,2,4-benzenetricarboxylic anhydride (219 mg, 1.14 mmol) the title compound was obtained (390 mg, 64%). $^1$H NMR (DMSO) δ 8.71(t, 1H), 8.65(dd, 1H), 8.36(d, 1H), 8.29(m, 2H), 8.08(d, 1H), 8.00(d, 2H), 7.93(dd, 1H), 7.73(m, 3H) 7.62(t, 1H), 7.27(d, 1H), 3.60(m, 2H), 1.97(q, 2H), 1.74(m, 2H), 1.22(t, 3H) MS 532 m/z (M+H)$^+$.

Example 59

2-[4-Butylamino-3-(5-phenylbenzoxazol-2-yl)phenyl]-1,3-dioxo-2,3-dihydro-1H-isoindole-5-carboxylic acid a) 2-(5-Nitro-2-butylaminophenyl)-5-phenylbenzoxazole Prepared by the method of Example 54a), from 2-(2-fluoro-5-nitrophenyl)-5-phenylbenzoxazole (200 mg, 0.60 mmol), and butylamine (2 ml) the subtitle compound was obtained (563 mg, 100%). MS 388 m/z (M+H)$^+$.

b) 2-(5-Amino-2-butylaminophenyl)-5-phenylbenzoxazole

Prepared by the method of Example 15e), from 2-(5-nitro-2-butylaminophenyl)-5-phenylbenzoxazole (563 mg, 1.50 mmol) the subtitle compound was obtained (409 mg, 76%). MS 358 m/z (M+H)$^+$.

Example 60

2-[4-Hexylamino-3-(5-phenylbenzoxazol-2-yl)phenyl]-1,3-dioxo-2,3-dihydro-1H-isoindole-5-carboxylic acid a) 2-(5-Nitro-2-hexylaminophenyl)-5-phenylbenzoxazole Prepared by the method of Example 54a), from 2-(2-fluoro-5-nitrophenyl)-5-phenylbenzoxazole (200 mg, 0.60 mmol), and hexylamine (2 ml) the subtitle compound was obtained (298 mg, 100%). MS 416 m/z (M+H)$^+$.

b) 2-(5-Amino-2-hexylaminophenyl)-5-phenylbenzoxazole

Prepared by the method of Example 15e), from 2-(5-nitro-2-hexylaminophenyl)-5-phenylbenzoxazole (289 mg, 0.69 mmol) the subtitle compound was obtained (237 mg, 89%). MS 386 m/z c) 2-[4-Hexylamino-3-(5-phenylbenzoxazol-2-yl)phenyl]-1,3-dioxo-2,3-dihydro-1H-isoindole-5-carboxylic acid

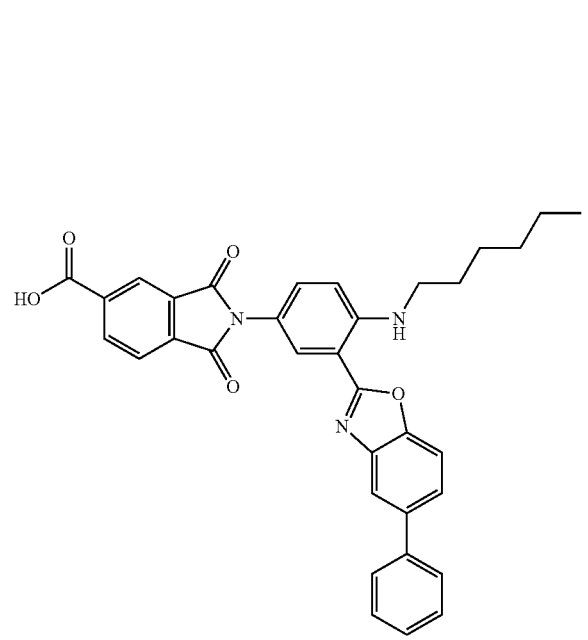

Prepared by the method of Example 1b), from 2-(5-amino-2-hexylaminophenyl)-5-phenylbenzoxazole (237 mg, 0.61 mmol) and 1,2,4-benzenetricarboxylic anhydride (117 mg, 0.61 mmol) the title compound was obtained (129 mg, 38%). $^1$H NMR (DMSO) δ 8.46(m, 2H), 8.30(m, 1H), 8.08(m, 2H), 7.80(m, 4H), 7.49(m, 3H), 7.40(m, 1H), 7.02 (m, 1H), 3.40(m, 2H), 1.75(m, 2H), 1.41(m, 6H), 0.91(m, 3H). MS 560 m/z (M+H)$^+$.

Example 61

2-[4-Pentylamino-3-(5-phenylbenzoxazol-2-yl)phenyl]-1,3-dioxo-2,3-dihydro-1H-isoindole-5-carboxylic acid a) 2-(5-Nitro-2-pentylaminophenyl)-5-phenylbenzoxazole Prepared by the method of Example 54a), from 2-(2-fluoro-5-nitrophenyl)-5-phenylbenzoxazole (200 mg, 0.60 mmol), and pentylamine (2 ml) the subtitle compound was obtained (289 mg, 100%). MS 402 m/z (M+H)$^+$.

b) 2-(5-Amino-2-pentylaminophenyl)-5-phenylbenzoxazole

Prepared by the method of Example 15e), from 2-(5-nitro-2-pentylaminophenyl)-5-phenylbenzoxazole (289 mg, 0.72 mmol) the subtitle compound was obtained (239 mg, 90%). MS 372 m/z (M+H)$^+$.

c) 2-[4-Pentylamino-3-(5-phenylbenzoxazol-2-yl)phenyl]-1,3-dioxo-2,3-dihydro-1H-isoindole-5-carboxylic acid

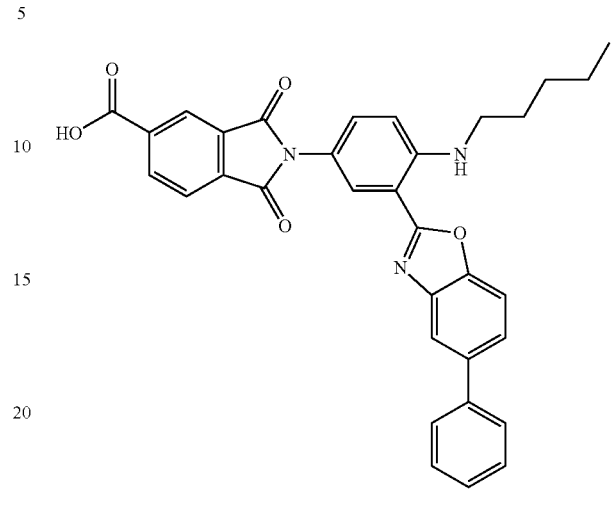

Prepared by the method of Example 1b), from 2-(5-amino-2-pentylaminophenyl)-5-phenylbenzoxazole (239 mg, 0.64 mmol) and 1,2,4-benzenetricarboxylic anhydride (123 mg, 0.64 mmol) the title compound was obtained (114 mg, 33%). $^1$H NMR (DMSO) δ 8.48(t, 1H), 8.43(dd, 1H), 8.30(s, 1H), 8.14(d, 1H), 8.07(m, 2H), 7.83(d, 1H), 7.74(m, 3H), 7.48(m, 3H), 7.39(t, 1H), 7.02(d, 1H), 3.50(m, 2H), 1.75(q, 2H), 1.43(m, 4H), 0.95(t, 3H). MS 546 m/z (M+H)$^+$.

Example 62

2-(3-Benzoxazol-2-yl-4-propylaminophenyl)-1,3-dioxo-2,3-dihydro-1H-isoindole-5-carboxylic acid a) 2-Fluoro-5-nitrobenzoylchloride Prepared by then method of Example 15a), from 2-fluoro-5-nitrobenzoic acid (2.0 g, 11.0 mmol) and oxalyl chloride (2.89 ml, 33.0 mmol) the subtitle compound was obtained. The product was used directly in the next step without purification.

b) N-Phenyl-2-fluoro-5-nitrobenzamide

Prepared by the method of Example 15b), from 2-fluoro-5-nitrobenzoylchloride (2.23 g, 11.0 mmol) and 2-aminophenol (1.20 g, 11.0 mmol) the subtitle compound was obtained (2.89 g, 91%). $^1$H NMR (DMSO) δ 10.00(s, 1H), 9.75(d, 1H), 8.62(m, 1H), 8.46(m, 1H), 7.96(d, 1H), 7.67(t, 1H), 7.03(t, 1H), 6.94(d, 1H), 6.85(t, 1H).

c) 2-(3-Nitro-6-fluorophenyl)benzoxazole

Prepared by the method of Example 15c), from N-phenyl-2-fluoro-5-nitrobenzamide (2.89 g, 10.4 mmol) and p-toluenesulfonic acid monohydrate (3.80 g, 20.0 mmol) the subtitle compound was obtained (2.41 g, 90%). $^1$H NMR (DMSO) δ 8.95(m, 1H), 8.52(m, 1H), 7.90(m, 2H), 7.81(t, 1H), 7.50(m, 2H).

d) 2-(3-Nitro-6-propylamino)benzoxazole

Prepared by the method of Example 54a), from 2-(3-nitro-6-fluorophenyl)benzoxazole (500 mg, 1.93 mmol) and propylamine (228 µL, 3.87 mmol) the subtitle compound was obtained (500 mg, 87%). $^1$H NMR (DMSO) δ 9.21(t, 1H), 8.81(d, 1H), 8.20(dd, 1H), 7.83(m, 2H), 7.46(m, 2H), 7.03 (d, 1H), 3.44(q, 2H), 1.74(m, 2H), 1.04(t, 3H).

e) 2-(3-Amino-6-propylamino)benzoxazole

Prepared by the method of Example 15e), from 2-(3-nitro-6-propylaminophenyl)benzoxazole (500 mg, 1.68 mmol) the subtitle compound was prepared (375 mg, 83%). $^1$H NMR (DMSO) δ 7.73(m, 2H), 7.59(t, 1H), 7.39–7.33(m, 3H), 6.82(dd, 1H), 6.69(d, 1H), 4.59(bs, 2H), 3.20(q, 2H), 1.67 (m, 2H), 1.01(t, 3H).

f) 2-(3-Benzoxazol-2-yl-4-propylaminophenyl)-1,3-dioxo-2,3-dihydro-1H-isoindole-5-carboxylic acid

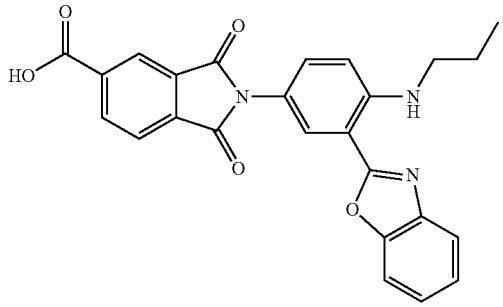

Prepared by the method of Example 15f), from 2-(3-amino-6-propylamino)benzoxazole (100 mg, 0.37 mmol) and 1,2,4-benzenetricarboxylic anhydride (79 mg, 0.41 mmol) the title compound was obtained (89 mg, 54%). $^1$H NMR (DMSO) δ 8.48(m, 2H), 8.30(s, 1H), 8.11(d, 1H), 8.06(d, 1H), 7.83–7.74(m, 2H), 7.49–7.40(m, 3H), 7.03(d, 1H), 3.37(q, 2H), 1.75(m, 2H), 1.06(t, 3H). MS 440.2 m/z (M–H)⁻.

Example 63

2-(3-Naphtho[2,3-d]oxazol-2-yl-4-propylaminophenyl)-1,3-dioxo-2,3-dihydro-1H-isoindole-5-carboxylic acid a) 2-(3-Nitro-6-fluorophenyl)naphthol Prepared by the method of Example 15a), from 3-amino-2-naphthol (781 mg, 4.9 mmol) and 2-fluoro-5-nitrobenzoyl chloride (1.00 g, 5.0 mmol) the subtitle compound was obtained. The product was used directly in the next step without purification.

b) 2-(3-Nitro-6-fluorophenyl)naphth[2,3-d]oxazole

Prepared by the method of Example 15b), from 2-(3-nitro-6-fluorophenyl)naphthol (800 mg, 2.8 mmol) and p-toluenesulfonic acid monohydrate (1.17 g, 6.16 mmol) the subtitle compound was obtained (403 mg, 53%). MS m/z 309.2 (M+H)⁺.

c) 2-(3-Nitro-6-propylaminophenyl)naphth[2,3-d]oxazole

Prepared by the method of Example 54a), from 2-(3-nitro-6-fluorophenyl)naphth[2,3-d]oxazole (277 mg, 0.9 mmol) and propylamine (400 µL, 5.0 mmol) the subtitle compound was obtained (250 mg, 80%). $^1$H NMR (DMSO) δ 9.37(t, 1H), 8.90(d, 1H), 8.38(s, 1H), 8.33(s, 1H), 8.26(dd, 1H), 8.11(m, 2H), 7.56(m, 1H), 7.11(d, 1H), 3.50(q, 2H), 1.76(m, 2H), 1.09(t, 3H).

d) 2-(3-Amino-6-propylaminophenyl)naphth[2,3-d]oxazole

Prepared by the method of Example 15e), 2-(3-nitro-6-propylaminophenyl)naphth[2,3-d]oxazole (250 mg, 0.7 mmol) the subtitle compound was obtained (188 mg, 85%). MS 315.1 (M–H)⁻.

e) 2-(3-Naphtho[2,3-d]oxazol-2-yl-4-propylaminophenyl)-1,3-dioxo-2,3-dihydro-1H-isoindole-5-carboxylic acid

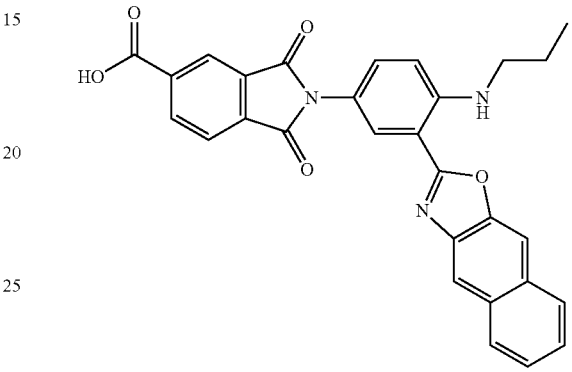

Prepared by the method of Example 15f), from 2-(3-amino-6-propylaminophenyl)naphth[2,3-d]oxazole (100 mg, 0.32 mmol) and 1,2,4-benzenetricarboxylic anhydride (67 mg, 0.35 mmol) the title compound was obtained (97 mg, 62%). $^1$H NMR (DMSO) δ 8.61(t, 1H), 8.42(dd, 1H), 8.32(m, 2H), 8.19(m, 2H), 8.11–8.05(m, 3H), 7.51(m, 3H), 7.05(d, 1H), 3.39(q, 2H), 1.79(m, 2H), 1.10(t, 3H). MS 490.0 m/z (M–H)⁻.

Example 64

2-[3-(5-Chlorobenzoxazol-2-yl)-4-propylaminophenyl]-1,3-dioxo-2,3-dihydro-1H-isoindole-5-carboxylic acid a) N-(2-Hydroxy-5-chlorophenyl)-2-fluoro-5-nitrobenzamide Prepared by the method of Example 15a), from 2-amino-4-chlorophenol (705 mg, 4.9 mmol) and 2-fluoro-5-nitrobenzoyl chloride (1.00 g, 5.0 mmol) the subtitle compound was obtained. The product was used directly in the next step without purification.

b) 2-(3-Nitro-6-fluorophenyl)-5-chlorobenzoxazole

Prepared by the method of Example 15b), from N-(2-hydroxy-5-chlorophenyl)-2-fluoro-5-nitrobenzamide (800 mg, 2.6 mmol) and p-toluenesulfonic acid monohydrate (1.17 g, 6.16 mmol) the subtitle compound was obtained (403 mg, 53%). MS m/z 291.9 (M+H)⁺.

c) 2-(3-Nitro-6-propylaminophenyl)-5-chlorobenzoxazole

Prepared by the method of Example 54a), from 2-(3-nitro-6-fluorophenyl)-5-chlorobenzoxazole (263 mg, 0.9 mmol) and propylamine (400 µL, 5.0 mmol) the subtitle compound was obtained (296 mg, 99%). $^1$H NMR (DMSO) δ 9.33(t, 1H), 9.02(s, 1H), 8.44(dd, 1H), 8.16–8.11(m, 2H), 7.75(dd, 1H), 7.29(d, 1H), 3.67(q, 2H), 1.97(m, 2H), 1.28(t, 3H).

d) 2-(3-Amino-6-propylaminophenyl)-5-chlorobenzoxazole

Prepared by the method of Example 15e), from 2-(3-nitro-6-propylaminophenyl)-5-chlorobenzoxazole (250 mg, 0.75 mmol) the subtitle compound was obtained (203 mg, 90%). MS m/z 299.0 (M−H)⁻.

e) 2-[3-(5-Chlorobenzoxazol-2-yl)-4-propylaminophenyl]-1,3-dioxo-2,3-dihydro-1H-isoindole-5-carboxylic acid

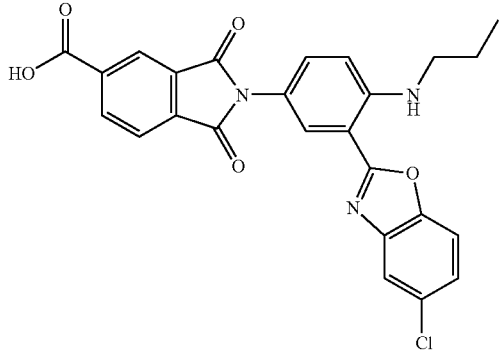

Prepared by the method of Example 15f), from 2-(3-amino-6-propylaminophenyl)-5-chlorobenzoxazole (100 mg, 0.33 mmol) and 1,2,4-benzenetricarboxylic anhydride (69 mg, 0.36 mmol) the title compound was obtained (92 mg, 58%). ¹H NMR (DMSO) δ 8.41(dd, 1H), 8.37(t, 1H), 8.09–8.05(m, 2H), 7.92(d, 1H), 7.79(d, 1H), 7.47(m, 2H), 7.03(d, 1H), 3.34(m, 2H), 1.74(m, 2H), 1.05(t, 3H). MS m/z 474.0 (M−H)⁻.

Example 65

2-[3-(6-Methylbenzoxazol-2-yl)-4-propylaminophenyl]-1,3-dioxo-2,3-dihydro-1H-isoindole-5-carboxylic acid a) N-(2-Hydroxy-4-methylphenyl)-2-fluoro-5-nitrobenzamide Prepared by the method of Example 15a), from 2-amino-5-methylphenol (605 mg, 4.9 mmol) and 2-fluoro-5-nitrobenzoyl chloride (1.00 g, 5.0 mmol) the subtitle compound was obtained. The product was used directly in the next step without purification.

b) 2-(3-Nitro-6-fluorophenyl)-6-methylbenzoxazole

Prepared by the method of Example 15b), from N-(2-hydroxy-4-methylphenyl)-2-fluoro-5-nitrobenzamide (300 mg, 2.8 mmol) and p-toluenesulfonic acid monohydrate (1.17 g, 6.16 mmol) the subtitle compound was obtained (403 mg, 53%). MS m/z 273.2 (M+H)⁺.

c) 2-(3-Nitro-6-propylaminophenyl)-6-methylbenzoxazole

Prepared by the method of Example 54a), from 2-(3-nitro-6-fluorophenyl)-6-methylbenzoxazole (250 mg, 0.9 mmol) and propylamine (400 µL, 5.0 mmol) the subtitle compound was obtained (262 mg, 94%). ¹H NMR (DMSO) δ 9.21(t, 1H), 8.78(d, 1H), 8.19(dd, 1H), 7.70–7.66(m, 2H), 7.25(d, 1H), 7.03(d, 1H), 3.43(q, 2H), 2.47(s, 3H), 1.73(m, 2H), 1.01(t, 3H).

d) 2-(3-Amino-6-propylaminophenyl)-6-methylbenzoxazole

Prepared by the method of Example 15e), from 2-(3-nitro-6-propylaminophenyl)-6-methylbenzoxazole (250 mg, 0.8 mmol) the subtitle compound was obtained (205 mg, 91%). MS m/z 279.1 (M−H)⁻. The product was used directly in the next step without purification.

e) 2-[3-(6-Methylbenzoxazol-2-yl)-4-propylaminophenyl]-1,3-dioxo-2,3-dihydro-1H-isoindole-5-carboxylic acid

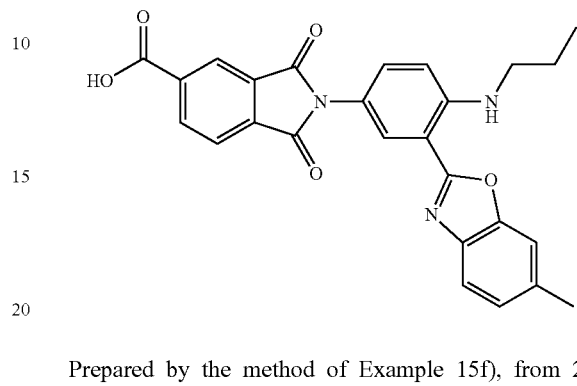

Prepared by the method of Example 15f), from 2-(3-amino-6-propylaminophenyl)-6-methylbenzoxazole (100 mg, 0.33 mmol) and 1,2,4-benzenetricarboxylic anhydride (73 mg, 0.38 mmol) the title compound was obtained (87 mg, 58%). ¹H NMR (DMSO) δ 8.47–8.40(m, 2H), 8.30(s, 1H), 8.08–8.06(m, 2H), 7.68(d, 1H), 7.56(s, 1H), 7.44(dd, 1H), 7.23(d, 1H), 7.01(d, 1H), 3.34(m, 2H), 2.46(s, 3H), 1.74(m, 2H), 1.05(t, 3H). MS 454.1 m/z (M−H)⁻.

Example 66

2-[3-(6-Fluorobenzoxazol-2-yl)-4-propylaminophenyl]-1,3-dioxo-2,3-dihydro-1H-isoindole-5-carboxylic acid a) N-(2-Hydroxy-4-fluorophenyl)-2-fluoro-5-nitrobenzamide Prepared by the method of Example 15a), from 2-amino-5-fluorophenol (508 mg, 4.0 mmol) and 2-fluoro-5-nitrobenzoyl chloride (814 g, 4.0 mmol) the subtitle compound was obtained. The product was used directly in the next step without purification.

b) 2-(3-Nitro-6-fluorophenyl)-6-fluorobenzoxazole

Prepared by the method of Example 15b), from N-(2-hydroxy-4-fluoro)-2-fluoro-5-nitrobenzamide (1.18 g, 4.0 mmol) and p-toluenesulfonic acid monohydrate (1.67 g, 8.8 mmol) the subtitle compound was obtained (675 mg, 61%). MS m/z 277.1 (M+H)⁺.

c) 2-(3-Nitro-6-propylaminophenyl)-6-fluorobenzoxazole

Prepared by the method of Example 54a), from 2-(3-nitro-6-fluorophenyl)-6-fluorobenzoxazole (552 mg, 2.0 mmol) and propylamine (492 µL, 6.0 mmol) the subtitle compound was obtained. The product was used directly in the next step without purification.

d) 2-(3-Amino-6-propylaminophenyl)-6-fluorobenzoxazole

Prepared by the method of Example 15e), from 2-(3-nitro-6-propylaminophenyl)-6-fluorobenzoxazole (205 mg, 0.65 mmol) the subtitle compound was obtained (178 mg, 96%). MS 286.3 m/z (M+H)⁺.

e) 2-[3-(6-Fluorobenzoxazol-2-yl)-4-propylaminophenyl]-1,3-dioxo-2,3-dihydro-1H-isoindole-5-carboxylic acid

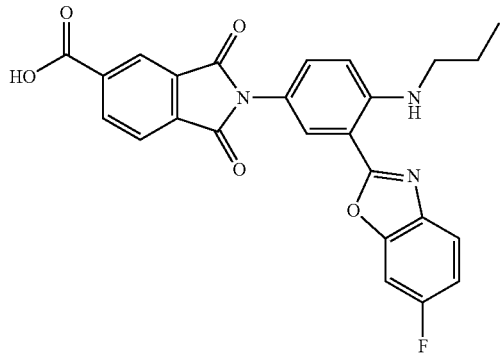

Prepared by the method of Example 15f), from 2-(3-amino-6-propylaminophenyl)-6-fluorobenzoxazole (71 mg, 0.25 mmol) and 1,2,4-benzenetricarboxylic anhydride (54 mg, 0.28 mmol) the title compound was obtained (84 mg, 73%). $^1$H NMR (DMSO) δ 8.41(dd, 1H), 8.36(t, 1H), 8.30(s, 1H), 8.07(m, 2H), 7.84(m, 1H), 7.77(dd, 1H), 7.46(dd, 1H), 7.29(m, 1H), 7.03(d, 1H), 3.34(m, 2H), 1.74(m, 2H), 1.05(t, 3H). MS 458.1 m/z (M−H)$^-$.

Example 67

2-[3-(5-Bromobenzoxazol-2-yl)-4-propylaminophenyl]-1,3-dioxo-2,3-dihydro-1H-isoindole-5-carboxylic acid a) N-(2-Hydroxy-5-bromophenyl)-2-fluoro-5-nitrobenzamide Prepared by the method of Example 15a), from 2-amino-4-bromophenol (752 mg, 4.0 mmol) and 2-fluoro-5-nitrobenzoyl chloride (814 g, 4.0 mmol) the subtitle compound was obtained. The product was used directly in the next step without purification.

b) 2-(3-Nitro-6-fluorophenyl)-5-bromobenzoxazole

Prepared by the method of Example 15b), from N-(2-hydroxy-5-bromophenyl)-2-fluoro-5-nitrobenzamide (1.42 g, 4.0 mmol) and p-toluenesulfonic acid monohydrate (1.67 g, 8.8 mmol) the subtitle compound was obtained (654 mg, 48%). MS 339.0 m/z (M+H)$^+$.

c) 2-(3-Nitro-6-propylaminophenyl)-5-bromobenzoxazole

Prepared by the method of Example 54a), from 2-(3-nitro-6-fluorophenyl)-5-bromobenzoxazole (576 mg, 2.0 mmol) and propylamine (492 μL, 6.0 mmol) the subtitle compound was obtained. The product was used directly in the next step without purification.

d) 2-(3-Amino-6-propylaminophenyl)-5-bromobenzoxazole

Prepared by the method of Example 15e), from 2-(3-nitro-6-propylaminophenyl)-5-bromobenzoxazole (244 mg, 0.65 mmol) the subtitle compound was obtained (217 mg, 96%). MS 346.2 & 348.2 m/z (M+H)$^+$.

e) 2-[3-(5-Bromobenzoxazol-2-yl)-4-propylaminophenyl]-1,3-dioxo-2,3-dihydro-1H-isoindole-5-carboxylic acid

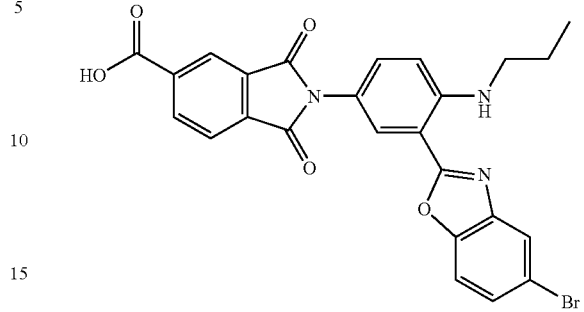

Prepared by the method of Example 15f), from 2-(3-amino-6-propylaminophenyl)-5-bromobenzoxazole (87 mg, 0.25 mmol) and 1,2,4-benzenetricarboxylic anhydride (54 mg, 0.28 mmol) the title compound was obtained (77 mg, 59%). $^1$H NMR (DMSO) δ 8.41(dd, 1H), 8.37(t, 1H), 8.30(s, 1H), 8.09–8.05(m, 3H), 7.74(d, 1H), 7,57(dd, 1H), 7.48(dd, 1H), 7.03(d, 1H), 3.34(m, 2H), 1.74(m, 2H), 1.05(t, 3H). MS 518.0 m/z (M−H)$^-$.

Example 68

2-[3-(5-Methoxybenzoxazol-2-yl)-4-propylaminophenyl]-1,3-dioxo-2,3-dihydro-1H-isoindole-5-carboxylic acid a) N-(2-Hydroxy-5-methoxyphenyl)-2-fluoro-5-nitrobenzamide Prepared by the method of Example 15a), from 2-amino-4-methoxyphenol (557 mg, 4.0 mmol) and 2-fluoro-5-nitrobenzoyl chloride (814 mg, 4.0 mmol) the subtitle compound was obtained. The product was used directly in the next step without purification.

b) 2-(3-Nitro-6-fluorophenyl)-5-methoxybenzoxazole

Prepared by the method of Example 15b), from N-(2-hydroxy-5-methoxyphenyl)-2-fluoro-5-nitro benzamide (1.23 g, 4.0 mmol) and p-toluenesulfonic acid monohydrate (1.67 g, 8.8 mmol) the subtitle compound was obtained (700 mg, 53%). MS 289.1 m/z (M+H)$^+$.

c) 2-(3-Nitro-6-propylaminophenyl)-5-methoxybenzoxazole

Prepared by the method of Example 54a), from 2-(3-nitro-6-fluorophenyl)-5-methoxybenzoxazole (674 mg, 2.0 mmol) and propylamine (492 μL, 6.0 mmol) the subtitle compound was obtained. The product was used directly in the next step without purification.

d) 2-(3-Amino-6-propylaminophenyl)-5-methoxybenzoxazole

Prepared by the method of Example 15e), from 2-(3-nitro-6-propylaminophenyl)-5-methoxybenzoxazole (213 mg, 0.65 mmol) the subtitle compound was obtained (178 mg, 92%). MS 298.3 m/z (M+H)$^+$.

e) 2-[3-(5-Methoxybenzoxazol-2-yl)-4-propylaminophenyl]-1,3-dioxo-2,3-dihydro-1H-isoindole-5-carboxylic acid

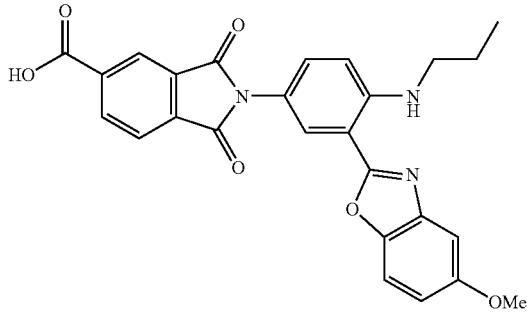

Prepared by the method of Example 15f), from 2-(3-amino-6-propylaminophenyl)-5-methoxybenzoxazole (74 mg, 0.25 mmol) and 1,2,4-benzenetricarboxylic anhydride (54 mg, 0.28 mmol) the title compound was obtained (68 mg, 58%). $^1$H NMR (DMSO) δ 8.46(t, 1H), 8.41(dd, 1H), 8.22(s, 1H), 8.07(m, 2H), 7.64(d, 1H), 7.45(dd, 1H), 7.37(d, 1H), 7.00(m, 2H), 3.84(s, 3H), 3.34(m, 2H), 1.75(m, 2H), 1.06(t, 3H). MS 470.1 m/z (M–H)$^-$.

Example 69

2-[3-(5,7-Dichlorobenzoxazol-2-yl)-4-propylaminophenyl]-1,3-dioxo-2,3-dihydro-1H-isoindole-5-carboxylic acid a) N-(2-Hydroxy-3,5-dichlorophenyl)-2-fluoro-5-nitrobenzamide Prepared by the method of Example 15a), from 2-amino-4,6-dichlorophenol (409 mg, 2.3 mmol) and 2-fluoro-5-nitrobenzoyl chloride (468 mg, 2.3 mmol) the subtitle compound was obtained. The product was used directly in the next step without purification.

b) 2-(3-Nitro-6-fluorophenyl)-5,7-dichlorobenzoxazole

Prepared by the method of Example 15b), from N-(2-hydroxy-3,5-dichlorophenyl)-2-fluoro-5-nitrobenzamide (798 g, 2.3 mmol) and p-toluenesulfonic acid monohydrate (961 g, 5.1 mmol) the subtitle compound was obtained (597 mg, 79%). $^1$H NMR (DMSO) δ 9.00(t, 1H), 8.78(s, 1H), 8.24(dd, 1H), 7.97(s, 1H), 7.77(s, 1H), 7.09(d, 1H), 3.46(q, 2H), 1.73(m, 2H), 1.04(t, 3H).

c) 2-(3-Nitro-6-propylaminophenyl)-5,7-dichlorobenzoxazole

Prepared by the method of Example 54a), from 2-(3-nitro-6-fluorophenyl)-5,7-dichlorobenzoxazole (250 mg, 0.8 mmol) and propylamine (328 μL, 4.0 mmol) the subtitle compound was obtained. The product was used directly in the next step without purification.

d) 2-(3-Amino-6-propylaminophenyl)-5,7-dichlorobenzoxazole

Prepared by the method of Example 15e), from 2-(3-nitro-6-propylaminophenyl)-5,7-dichlorobenzoxazole (150 mg, 0.4 mmol) the subtitle compound was obtained. The product was used directly in the next step without purification.

e) 2-[3-(5,7-Dichlorobenzoxazol-2-yl)-4-propylaminophenyl]-3-dioxo-2,3-dihydro-1H-isoindole-5-carboxylic acid

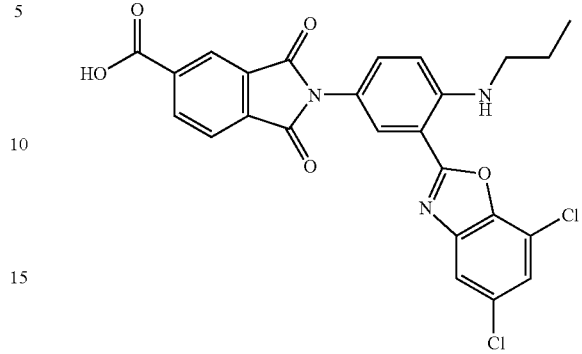

Prepared by the method of Example 15f), from 2-(3-amino-6-propylaminophenyl)-5,7-dichlorobenzoxazole (134 mg, 0.4 mmol) and 1,2,4-benzenetricarboxylic anhydride (96 mg, 0.5 mmol) the title compound was obtained (127 mg, 62%). $^1$H NMR (DMSO) δ 8.41(dd, 1H), 8.29(m, 2H), 8.10(d, 1H), 8.06(d, 1H), 7.94(d, 1H), 7.68(d, 1H), 7.49(dd, 1H), 7.05(d, 1H), 3.34(m, 2H), 1.74(m, 2H), 1.05(t, 3H). MS 509.9 m/z (M–H)$^-$.

Example 70

2-[3-(5-Trifluoromethylbenzoxazol-2-yl)-4-propylaminophenyl]-1,3-dioxo-2,3-dihydro-1H-isoindole-5-carboxylic acid a) N-(2-Hydroxy-5-trifluoromethylphenyl)-2-fluoro-5-nitrobenzamide Prepared by the method of Example 15a), from 2-amino-4-trifluoromethylphenol (407 mg, 2.3 mmol) and 2-fluoro-5-nitrobenzoyl chloride (468 mg, 2.3 mmol) the subtitle compound was obtained. The product was used directly in the next step without purification.

b) 2-(3-Nitro-6-fluorophenyl)-5-trifluoromethylbenzoxazole

Prepared by the method of Example 15b), from N-(2-hydroxy-5-trifluoromethylphenyl)-2-fluoro-5-nitrobenzamide (667 g, 2.3 mmol) and p-toluenesulfonic acid monohydrate (961 g, 5.1 mmol) the subtitle compound was obtained (349 mg, 56%). $^1$H NMR (DMSO) δ 8.95(m, 1H), 8.56(m, 1H), 8.36(s, 1H), 8.12(d, 1H), 7.84(m, 2H).

c) 2-(3-Nitro-6-propylaminophenyl)-5-trifluoromethylbenzoxazole

Prepared by the method of Example 54a), from 2-(3-nitro-6-fluorophenyl)-5-trifluoromethylbenzoxazole (218 mg, 0.8 mmol) and propylamine (328 μL, 4.0 mmol) the subtitle compound was obtained. The product was used directly in the next step without purification.

d) 2-(3-Amino-6-propylaminophenyl)-5-trifluoromethylbenzoxazole

Prepared by the method of Example 15e), from 2-(3-nitro-6-propylaminophenyl)-5-trifluoromethylbenzoxazole (124 mg, 0.4 mmol) the subtitle compound was obtained. The product was used directly in the next step without purification.

e) 2-[3-(5-Trifluoromethylbenzoxazol-2-yl)-4-propylaminophenyl]-1,3-dioxo-2,3-dihydro-1H-isoindole-5-carboxylic acid

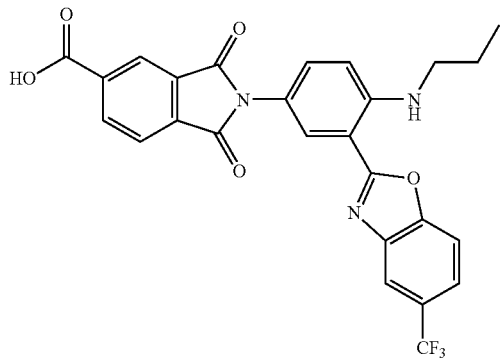

Prepared by the method of Example 15f), from 2-(3-amino-6-propylaminophenyl)-5-trifluoromethylbenzoxazole (113 mg, 0.4 mmol) and 1,2,4-benzenetricarboxylic anhydride (96 mg, 0.5 mmol) the title compound was obtained (120 mg, 59%). $^1$H NMR (DMSO) δ 8.41(m, 2H), 8.30(s, 1H), 8.23(s, 1H), 8.12(d, 1H), 8.07(d, 1H), 7.97(d, 1H), 7.77(d, 1H), 7.49(dd, 1H), 7.04(d, 1H), 3.34(m, 2H) 1.75(m, 2H), 1.06(t, 3H). MS 507.7 m/z (M–H)$^-$.

Example 71

2-[3-(5-Bromo-7-fluorobenzoxazol-2-yl)-4-propylaminophenyl]-1,3-dioxo-2,3-dihydro-1H-isoindole-5-carboxylic acid a) N-(2-Hydroxy-3-fluoro-5-bromophenyl)-2-fluoro-5-nitrobenzamide Prepared by the method of Example 15a), from 2-amino-4-bromo-6-fluorophenol (473 mg, 2.3 mmol) and 2-fluoro-5-nitrobenzoyl chloride (468 mg, 2.3 mmol) the subtitle compound was obtained. The product was used directly in the next step without purification.

b) 2-(3-Nitro-6-fluorophenyl)-5-bromo-7-fluorobenzoxazole

Prepared by the method of Example 15b), from N-(2-hydroxy-3-fluoro-5-bromophenyl)-2-fluoro-5-nitrobenzamide (858 mg, 2.3 mmol) and p-toluenesulfonic acid monohydrate (961 g, 5.1 mmol) the subtitle compound was obtained (475 mg, 58%). $^1$H NMR (DMSO) δ 8.91(m, 1H), 8.57(m, 1H), 8.06(s, 1H), 7.81(m, 3H).

c) 2-(3-Nitro-6-propylaminophenyl)-5-bromo-7-fluorobenzoxazole

Prepared by the method of Example 54a), from 2-(3-nitro-6-fluorophenyl)-5-bromo-7-fluorobenzoxazole (284 mg, 0.8 mmol) and propylamine (328 μL, 4.0 mmol) the subtitle compound was obtained. The product was used directly in the next step without purification.

d) 2-(3-Amino-6-propylaminophenyl)-5-bromo-7-fluorobenzoxazole

Prepared by the method of Example 15e), from 2-(3-nitro-6-propylaminophenyl)-5-bromo-7-fluorobenzoxazole (158 mg, 0.4 mmol) the subtitle compound was obtained. The product was used directly in the next step without purification.

e) 2-[3-(5-Bromo-7-fluorobenzoxazol-2-yl)-4-propylaminophenyl]-1,3-dioxo-2,3-dihydro-1H-isoindole-5-carboxylic acid

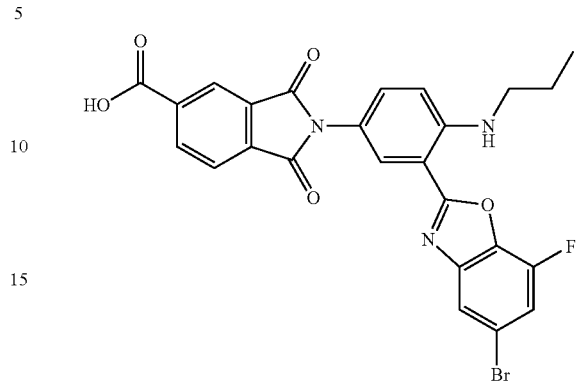

Prepared by the method of Example 15f), from 2-(3-amino-6-propylaminophenyl)-5-trifluoromethylbenzoxazole (146 mg, 0.4 mmol) and 1,2,4-benzenetricarboxylic anhydride (96 mg, 0.5 mmol) the title compound was obtained (127 mg, 59%). $^1$H NMR (DMSO) δ 8.41(d, 1H), 8.28(m, 2H), 8.12(d, 1H), 8.06(d, 1H), 7.94(s, 1H), 7.68(d, 1H), 7.49(d, 1H), 7.05(d, 1H), 3.34(m, 2H), 1.73(m, 2H), 1.04(t, 3H). MS 538.0 m/z (M–H)$^-$.

Example 72

2-[3-(5-Fluorobenzoxazol-2-yl)-4-propylaminophenyl]-1,3-dioxo-2,3-dihydro-1H-isoindole-5-carboxylic acid a) N-(2-Hydroxy-5-fluorophenyl)-2-fluoro-5-nitrobenzamide Prepared by the method of Example 15a), from 2-amino-4-fluorophenol (292 mg, 2.3 mmol) and 2-fluoro-5-nitrobenzoyl chloride (468 mg, 2.3 mmol) the subtitle compound was obtained. The product was used directly in the next step without purification.

b) 2-(3-Nitro-6-fluorophenyl)-5-fluorobenzoxazole

Prepared by the method of Example 15b), from N-(2-hydroxy-5-fluorophenyl)-2-fluoro-5-nitrobenzamide (676 mg, 2.3 mmol) and p-toluenesulfonic acid monohydrate (961 g, 5.1 mmol) the subtitle compound was obtained (318 mg, 50%). $^1$H NMR (DMSO) δ 8.94(m, 1H), 8.54(m, 1H), 7.95(m, 1H), 7.81(m, 2H), 7.41(m, 1H).

c) 2-(3-Nitro-6-propylaminophenyl)-5-fluorobenzoxazole

Prepared by the method of Example 54a), from 2-(3-nitro-6-fluorophenyl)-5-fluorobenzoxazole (221 mg, 0.8 mmol) and propylamine (328 μL, 4.0 mmol) the subtitle compound was obtained. The product was used directly in the next step without purification.

d) 2-(3-Amino-6-propylaminophenyl)-5-fluorobenzoxazole

Prepared by the method of Example 15e), from 2-(3-nitro-6-propylaminophenyl)-5-fluorobenzoxazole (126 mg, 0.4 mmol) the subtitle compound was obtained. The product was used directly in the next step.

e) 2-[3-(5-Fluorobenzoxazol-2-yl)-4-propylaminophenyl]-1,3-dioxo-2,3-dihydro-1H-isoindole-5-carboxylic acid

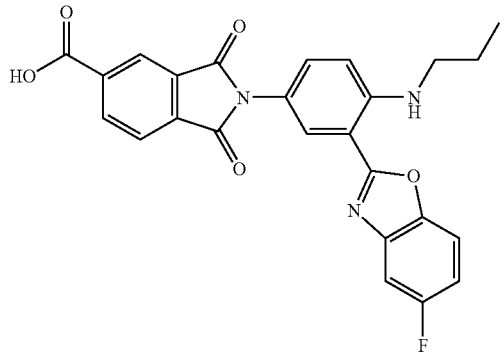

Prepared by the method of Example 15f), from 2-(3-amino-6-propylaminophenyl)-5-fluorobenzoxazole (114 mg, 0.4 mmol) and 1,2,4-benzenetricarboxylic anhydride (96 mg, 0.5 mmol) the title compound was obtained (107 mg, 58%). $^1$H NMR (DMSO) δ 8.40(m, 2H), 8.30(s, 1H), 8.08(m, 2H), 7.79(m, 1H), 7.70(dd, 1H), 7.48(dd, 1H), 7.28(m, 1H), 7.05(d, 1H), 3.34(m, 2H), 1.74(m, 2H), 1.05(t, 3H). MS 457.6 m/z (M–H)⁻.

Example 73

2-[3-(6,7-Difluorobenzoxazol-2-yl)-4-propylaminophenyl]-1,3-dioxo-2,3-dihydro-1H-isoindole-5-carboxylic acid a) N-(2-Hydroxy-3,4-difluorophenyl)-2-fluoro-5-nitrobenzamide Prepared by the method of Example 15a), from 2-amino-5,6-difluorophenol (334 mg, 2.3 mmol) and 2-fluoro-5-nitrobenzoyl chloride (468 mg, 2.3 mmol) the subtitle compound was obtained. The product was used directly in the next step without purification.

b) 2-(3-Nitro-6-fluorophenyl)-6,7-difluorobenzoxazole

Prepared by the method of Example 15b), from N-(2-hydroxy-3,4-difluorophenyl)-2-fluoro-5-nitrobenzamide (718 mg, 2.3 mmol) and p-toluenesulfonic acid monohydrate (961 g, 5.1 mmol) the subtitle compound was obtained (303 mg, 45%). $^1$H NMR (DMSO) δ 8.92(m, 1H), 8.57(m, 1H), 7.85(d, 1H), 7.81(m, 1H), 7.61(m, 1H).

c) 2-(3-Nitro-6-propylaminophenyl)-6,7-difluorobenzoxazole

Prepared by the method of Example 54a), from 2-(3-nitro-6-fluorophenyl)-6,7-difluorobenzoxazole (235 mg, 0.8 mmol) and propylamine (328 μL, 4.0 mmol) the subtitle compound was obtained. The product was used directly in the next step without purification.

d) 2-(3-Amino-6-propylaminophenyl)-6,7-difluorobenzoxazole

Prepared by the method of Example 15e), from 2-(3-nitro-6-propylaminophenyl)-6,7-difluorobenzoxazole (133 mg, 0.4 mmol) the subtitle compound was obtained. The product was used directly in the next step.

e) 2-[3-(6,7-Difluorobenzoxazol-2-yl)-4-propylaminophenyl]-1,3-dioxo-2,3-dihydro-1H-isoindole-5-carboxylic acid

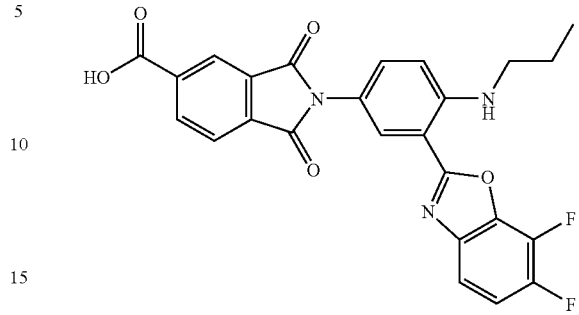

Prepared by the method of Example 15f), from 2-(3-amino-6-propylaminophenyl)-6,7-difluorobenzoxazole (121 mg, 0.4 mmol) and 1,2,4-benzenetricarboxylic anhydride (96 mg, 0.5 mmol) the title compound was obtained (105 mg, 55%). $^1$H NMR (DMSO) δ 8.41(dd, 1H), 8.29(s, 1H), 8.25(t, 1H), 8.14(d, 1H), 8.06(d, 1H), 7.67(m, 1H), 7.50(m, 2H), 7.04(d, 1H), 3.34(m, 2H), 1.74(m, 2H), 1.05(t, 3H). MS 475.7 m/z (M–H)⁻.

Example 74

2-[3-(5-Methylbenzoxazol-2-yl)-4-propylaminophenyl]-1,3-dioxo-2,3-dihydro-1H-isoindole-5-carboxylic acid a) N-(2-Hydroxy-5-methylphenyl)-2-fluoro-5-nitrobenzamide Prepared by the method of Example 15a), from 2-amino-4-methylphenol (283 mg, 2.3 mmol) and 2-fluoro-5-nitrobenzoyl chloride (468 mg, 2.3 mmol) the subtitle compound was obtained. The product was used directly in the next step without purification.

b) 2-(3-Nitro-6-fluorophenyl)-5-methylbenzoxazole

Prepared by the method of Example 15b), from N-(2-hydroxy-5-methylphenyl)-2-fluoro-5-nitrobenzamide (667 mg, 2.3 mmol) and p-toluenesulfonic acid monohydrate (961 g, 5.1 mmol) the subtitle compound was obtained (345 mg, 55%). $^1$H NMR (DMSO) δ 8.92(m, 1H), 8.50(m, 1H), 7.79(t, 1H), 7.67(d, 1H), 7.39(t, 1H), 7.28(d, 1H), 2.60(s, 3H).

c) 2-(3-Nitro-6-propylaminophenyl)-5-methylbenzoxazole

Prepared by the method of Example 54a), from 2-(3-nitro-6-fluorophenyl)-5-methylbenzoxazole (218 mg, 0.8 mmol) and propylamine (328 μL, 4.0 mmol) the subtitle compound was obtained. The product was used directly in the next step without purification.

d) 2-(3-Amino-6-propylaminophenyl)-5-methylbenzoxazole

Prepared by the method of Example 15e), from 2-(3-nitro-6-propylaminophenyl)-5-methylbenzoxazole (124 mg, 0.4 mmol) the subtitle compound was obtained. The product was used directly in the next step.

e) 2-[3-(5-Methylbenzoxazol-2-yl)-4-propylaminophenyl]-1,3-dioxo-2,3-dihydro-1H-isoindole-5-carboxylic acid

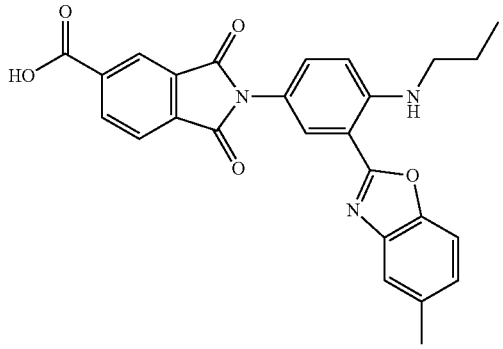

Prepared by the method of Example 15f), from 2-(3-amino-6-propylaminophenyl)-5-methylbenzoxazole (112 mg, 0.4 mmol) and 1,2,4-benzenetricarboxylic anhydride (96 mg, 0.5 mmol) the title compound was obtained (92 mg, 50%). $^1$H NMR (DMSO) δ 8.60(t, 1H), 8.41(d, 1H), 8.29(s, 1H), 8.08(m, 2H), 7.54(d, 1H), 7.45(d, 1H), 7.30(t, 1H), 7.22(d, 1H), 6.99(d, 1H), 3.34(m, 2H), 2.59(s, 3H), 1.79(m, 2H), 1.12(t, 3H). MS 454.1 m/z (M–H)$^-$.

Example 75

2-[3-(4-Methylbenzoxazol-2-yl)-4-propylaminophenyl]-1,3-dioxo-2,3-dihydro-1H-isoindole-5-carboxylic acid a) N-(2-Hydroxy-6-methylphenyl)-2-fluoro-5-nitrobenzamide Prepared by the method of Example 15a), from 2-amino-3-methylphenol (283 mg, 2.3 mmol) and 2-fluoro-5-nitrobenzoyl chloride (468 mg, 2.3 mmol) the subtitle compound was obtained. The product was used directly in the next step without purification.

b) 2-(3-Nitro-6-fluorophenyl)-4-methylbenzoxazole

Prepared by the method of Example 15b), from N-(2-hydroxy-6-methylphenyl)-2-fluoro-5-nitrobenzamide (667 mg, 2.3 mmol) and p-toluenesulfonic acid monohydrate (961 g, 5.1 mmol) the subtitle compound was obtained (327 mg, 52%). $^1$H NMR (DMSO) δ 8.92(m, 1H), 8.50(m, 1H), 7.82–7.74(m, 2H), 7.70(s, 1H), 7.33(dd, 1H).

c) 2-(3-Nitro-6-propylaminophenyl)-4-methylbenzoxazole

Prepared by the method of Example 54a), from 2-(3-nitro-6-fluorophenyl)-4-methylbenzoxazole (218 mg, 0.8 mmol) and propylamine (328 µL, 4.0 mmol) the subtitle compound was obtained. The product was used directly in the next step without purification.

d) 2-(3-Amino-6-propylaminophenyl)-4-methylbenzoxazole

Prepared by the method of Example 15e), from 2-(3-nitro-6-propylaminophenyl)-4-methylbenzoxazole (124 mg, 0.4 mmol) the subtitle compound was obtained. The product was used directly in the next step.

e) 2-[3-(4-Methylbenzoxazol-2-yl)-4-propylaminophenyl]-1,3-dioxo-2,3-dihydro-1H-isoindole-5-carboxylic acid

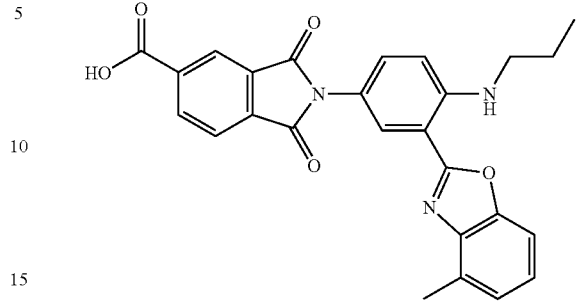

Prepared by the method of Example 15f), from 2-(3-amino-6-propylaminophenyl)-4-methylbenzoxazole (112 mg, 0.4 mmol) and 1,2,4-benzenetricarboxylic anhydride (96 mg, 0.5 mmol) the title compound was obtained (110 mg, 60%). $^1$H NMR (DMSO) δ 8.46(t, 1H), 8.41(dd, 1H), 8.03(s, 1H), 8.06(m, 2H), 7.61(m, 2H), 7.44(dd, 1H), 7.22(d, 1H), 7.00(d, 1H), 3.34(m, 2H), 2.44(s, 3H), 1.74(m, 2H), 1.06(t, 3H). MS 453.9 m/z (M–H)$^-$.

Example 76

2-(3-[6-(2-Tetrahydrofuranylmethylaminocarbonyl)benzoxazol-2-yl]phenyl)-1,3-dioxo-2,3-dihydro-1H-isoindole-5-carboxylic acid a) 4-(3-Nitrobenzamido)-3-hydroxybenzoic acid methyl ester Prepared by the method of Example 15b), from methyl 3-hydroxy-4-aminobenzoate (12.94 g, 77.0 mmol) and 3-nitrobenzoyl chloride (14.29 g, 77.0 mmol) the subtitle compound was obtained (22.45 g, 92%). The product was used directly in the next step without purification.

b) 2-(3-Nitrophenyl)benzoxazole-6-carboxylic acid methyl ester

Prepared from the method of Example 15c), from 4-(3-nitrobenzamido)-3-hydroxybenzoic acid methyl ester (20 g, 63.0 mmol) and p-toluenesulfonic acid monohydrate (26.3 g, 138 mmol) the subtitle compound was obtained (3.05 g, 16%). $^1$H NMR (CDCl$_3$) δ 9.13(t, 1H), 8.62(d, 1H), 8.44(dd, 1H), 8.33(s, 1H), 8.15(dd, 1H), 7.85(d, 1H), 7.77(t, 1H), 4.00(s, 3H).

c) 2-(3-Nitrophenyl)benzoxazole-6-carboxylic acid

A solution of lithium hydroxide (1.78 g, 65.0 mmol) in water (10 ml) was added to a solution of 2-(3-nitrophenyl)benzoxazole-6-carboxylic acid methyl ester (4.0 g, 14.8 mmol) in THF (30 ml). The reaction was heated to 60° C. for 4 h. The cooled reaction mixture was acidified with 2M HCl and the precipitate filtered, washed with water and dried under vacuum to give the subtitle compound (3.47 g, 92%). The product was used directly in the next step without purification.

d) 2-(3-Aminophenyl)benzoxazole-6-carboxylic acid

Prepared from the method of Example 15e), from 2-(3-nitrophenyl)benzoxazole-6-carboxylic acid (3.28 g, 13.0 mmol) the subtitle compound was obtained (2.67 g, 85%). $^1$H NMR (DMSO) δ 8.25(s, 1H), 8.00(dd, 1H), 7.85(d, 1H), 7.46(s, 1H), 7.38(d, 1H), 7.25(t, 1H), 6.82(dt, 1H).

e) 2-[3-(5-Benzyloxycarbonyl-1,3-dioxo-1,3-dihydro-isoindol-2-yl)phenyl]benzoxazole-6-carboxylic acid Prepared by the method of Example 1b), from 2-(3-aminophenyl)benzoxazole-6-carboxylic acid (2.50 g, 9.8 mmol) and 1,2,4-benzenetricarboxylic acid benzyl ester (2.82 g, 10 mmol) the subtitle compound was obtained (2.94 g, 60%). $^1$H NMR (DMSO) δ 8.48(dd, 1H), 8.38(m, 2H), 8.30(m, 2H), 8.15(d, 1H), 8.04(dd, 1H), 7.93(d, 1H), 7.86–7.77(m, 2H), 7.54(m, 2H), 7.48–7.38(m, 3H), 5.45(s, 2H).

f) 2-[3-(6-Chlorocarbonylbenzoxazol-2-yl)phenyl]-1,3-dioxo-2,3-dihydro-1H-isoindole-5-carboxylic acid benzyl ester Prepared by the method of Example 15a), from 2-[3-(5-benzyloxycarbonyl-1,3-dioxo-1,3-dihydro-isoindol-2-yl)phenyl]benzoxazole-6-carboxylic acid (2.50 g, 5.0 mmol) and oxalyl chloride (2.19 ml, 25 mmol) the subtitle compound was obtained. The product was used directly in the next step without purification.

g) 2-(3-[6-(2-Tetrahydrofuranylmethylaminocarbonyl)benzoxazol-2-yl]phenyl)-1,3-dioxo-2,3-dihydro-1H-isoindole-5-carboxylic acid A solution of 2-[3-(6-chlorocarbonylbenzoxazol-2-yl)phenyl]-1,3-dioxo-2,3-dihydro-1H-isoindole-5-carboxylic acid benzyl ester (50 mg, 0.09 mmol) in THF (1 ml) was added to a solution of tetrahydrofurfurylamine (14 mg, 0.14 mmol) in THF (1 ml) containing polymer bound morpholine (2.5 mmol g$^{-1}$, 72 mg). After shaking overnight, polymer bound isocyanate (2.0 mmol g$^{-1}$, 90 mg) was added and the reaction shaken for 4 h. The reaction was filtered and the solvent removed under reduced pressure. The residue was suspended in dioxane and palladium on carbon was added (spatula tip). The reaction vessel was purged with hydrogen and stirred at room temperature overnight. The reaction was filtered through celite and the filtrate concentrated to give the title compound (27 mg, 59%). $^1$H NMR (DMSO) δ 8.74(t, 1H), 8.44(dd, 1H), 8.37(m, 2H), 8.31–8.27(m, 3H), 8.12(d, 1H), 7.97(dd, 1H), 7.90(d, 1H), 7.85–7.76(m, 1H), 4.00(m, 2H), 3.79(m, 1H), 3.65(m, 2H), 1.98–1.77(4H, m). MS 510.2 m/z (M–H)$^-$.

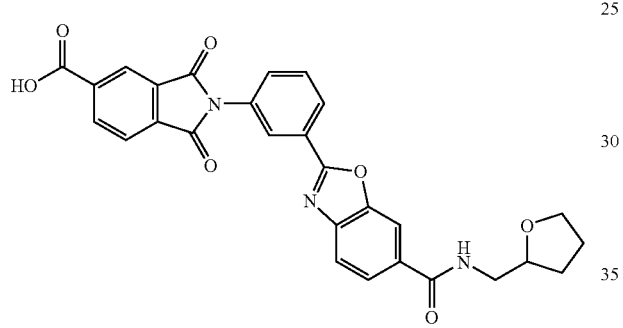

Example 77

2-[3-[6-(4-Piperonylpiperazine-1-carbonyl)benzoxazol-2-yl]phenyl]-1,3-dioxo-2,3-dihydro-1H-isoindole-5-carboxylic acid

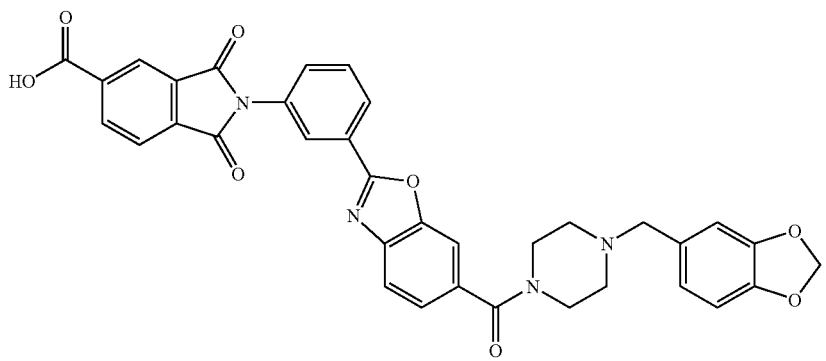

Prepared by the method of Example 76 g), from 2-[3-(6-chlorocarbonylbenzoxazol-2-yl)phenyl]-1,3-dioxo-2,3-dihydro-1H-isoindole-5-carboxylic acid benzyl ester (50 mg, 0.09 mmol) and 1-piperonylpiperazine (31 mg, 0.14 mmol) the title compound was obtained (32 mg, 54%). $^1$H NMR (DMSO) δ 8.33(dd, 1H), 8.25(m, 2H), 8.17(dt, 1H), 8.01(d, 1H), 7.79–7.65(m, 4H), 7.37(d, 1H), 6.77–6.72(m, 2H), 6.64(dd, 1H), 5.88(s, 2H) 3.45(s, 2H), 3.40–3.2(bm, 4H) 2.48–2.22(bm, 4H). MS 629.2 m/z (M–H)$^-$.

Example 78

2-[3-[6-(4-Piperazinoacetophenone-1-carbonyl)benzoxazol-2-yl]phenyl]-1,3-dioxo-2,3-dihydro-1H-isoindole-5-carboxylic acid

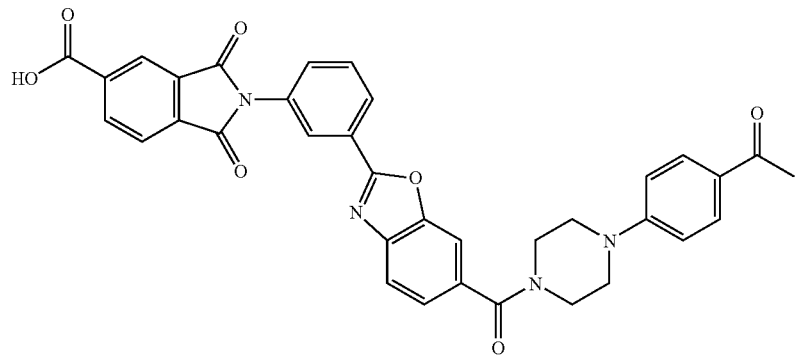

Prepared by the method of Example 76 g), from 2-[3-(6-chlorocarbonylbenzoxazol-2-yl)phenyl]-1,3-dioxo-2,3-dihydro-1H-isoindole-5-carboxylic acid benzyl ester (50 mg, 0.09 mmol) and 4-piperazino acetophenone (31 mg, 0.14 mmol) the title compound was obtained (25 mg, 42%). $^1$H NMR (DMSO) δ 8.73(dd, 1H), 8.64(d, 2H), 8.57(d, 1H), 8.39(d, 1H), 8.24–8.17(m, 2H), 8.12–8.04(m, 3H), 7.97(m, 1H), 7.46(d, 1H), 7.27(d, 1H), 7.18(d, 1H), 3.70–3.45(bm, 8H), 2.73(s, 3H). MS 613.5 m/z (M−H)⁻.

Example 79

2-[3-[6-(3-Trifluoromethylphenyl)piperazine-1-carbonyl]benzoxazol-2-yl]phenyl)-1,3-dioxo-2,3-dihydro-1H-isoindole-5-carboxylic acid

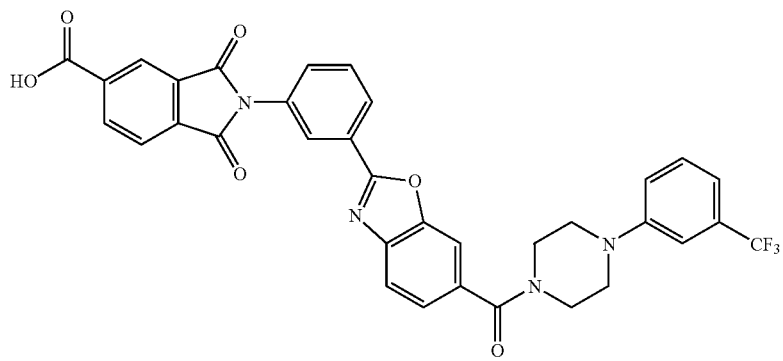

Prepared by the method of Example 76 g), from 2-[3-(6-chlorocarbonylbenzoxazol-2-yl)phenyl]-1,3-dioxo-2,3-dihydro-1H-isoindole-5-carboxylic acid benzyl ester (50 mg, 0.09 mmol) and 1-(3-trifluoromethylphenyl)piperazine (32 mg, 0.14 mmol) the title compound was obtained (33 mg, 57%). $^1$H NMR (DMSO) δ 8.44(dd, 1H), 8.36(m, 2H), 8.30(dt, 1H), 8.12(d, 1H), 7.96–7.91(m, 2H), 7.86–7.77(m, 2H), 7.52(dd, 1H), 7.45(t, 1H), 7.27–7.21(m, 2H), 7.10(d, 1H), 3.90–3.40(bm, 8H). MS 571.0 m/z (M−H)⁻

Example 80

2-[3-[6-(3-Carbamoylpiperidine-1-carbonyl)benzoxazol-2-yl]phenyl]-1,3-dioxo-2,3-dihydro-1H-isoindole-5-carboxylic acid

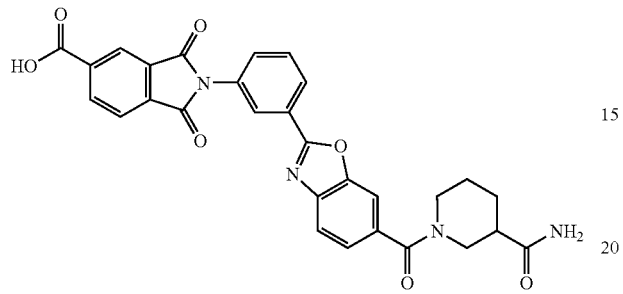

Prepared by the method of Example 76 g), from 2-[3-(6-chlorocarbonylbenzoxazol-2-yl)phenyl]-1,3-dioxo-2,3-dihydro-1H-isoindole-5-carboxylic acid benzyl ester (50 mg, 0.09 mmol) and nipecotamide (18 mg, 0.14 mmol) the title compound was obtained (18 mg, 37%). $^1$H NMR (DMSO) δ 8.44(dd, 1H), 8.36(m, 2H), 8.29(dt, 1H), 7.95–7.76(m, 4H), 7.44(dd, 1H), 4.02(m, 1H), 3.18(bm, 2H), 2.87(bm, 2H), 1.70–1.38(m, 4H). MS 536.8 m/z (M−H)$^-$.

Example 81

2-[3-[6-(4-Methoxybenzylaminocarbonyl)benzoxazol-2-yl]phenyl]-1,3-dioxo-2,3-dihydro-1H-isoindole-5-carboxylic acid

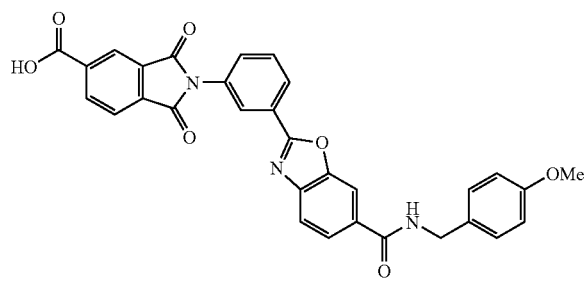

Prepared by the method of Example 76 g), from 2-[3-(6-chlorocarbonylbenzoxazol-2-yl)phenyl]-1,3-dioxo-2,3-dihydro-1H-isoindole-5-carboxylic acid benzyl ester (50 mg, 0.09 mmol) and 4-methoxybenzylamine (19 mg, 0.14 mmol) the title compound was obtained (22 mg, 45%). $^1$H NMR (DMSO) δ 9.20(t, 1H), 8.43(dd, 1H), 8.36(m, 2H), 8.30(m, 2H), 8.09(d, 1H), 7.99(dd, 1H), 7.91(d, 1H), 7.82–7.89(m, 2H), 7.28(d, 2H), 6.89(d, 2H), 4.45(d, 2H), 3.73(s, 3H). MS 545.9 m/z (M−H)$^-$.

Example 82

2-[3-[6-(3,4-Dimethoxybenzylamino)benzoxazol-2-yl]phenyl]-1,3-dioxo-2,3-dihydro-1H-isoindole-5-carboxylic acid

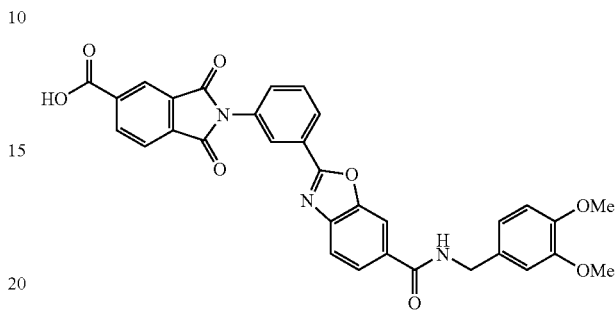

Prepared by the method of Example 76 g), from 2-[3-(6-chlorocarbonylbenzoxazol-2-yl)phenyl]-1,3-dioxo-2,3-dihydro-1H-isoindole-5-carboxylic acid benzyl ester (50 mg, 0.09 mmol) and 3,4-dimethoxybenzylamine (23 mg, 0.14 mmol) the title compound was obtained (17 mg, 33%). $^1$H NMR (DMSO) δ 9.14(t, 1H), 8.44(dd, 1H), 8.36(m, 2H), 8.29(m, 2H), 8.11(d, 1H), 7.99(dd, 1H), 7.91(d, 1H), 7.85–7.76(m, 2H), 6.97(d, 1H), 6.92–6.85(m, 2H), 4.45(d, 2H), 3.73(s, 3H), 3.71(s, 3H). MS 576.2 m/z (M−H)$^-$.

Example 83

2-[3-(5-Carboxy-1,3-dioxo-1,3-dihydroisoindol-2-yl)phenyl]benzoxazole-6-carboxylic acid

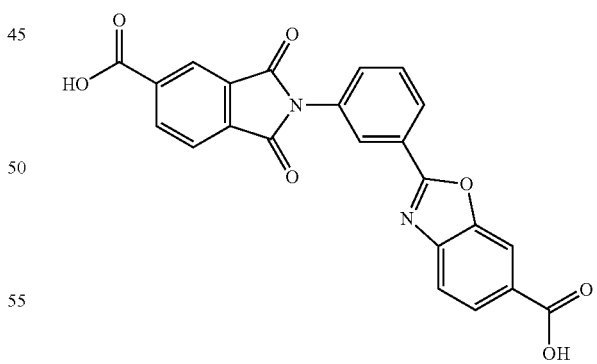

Prepared by the method of Example 1b), from 2-(3-aminophenyl)benzoxazole-6-carboxylic acid (70 mg, 0.27 mmol) and 1,2,4-benzenetricarboxylic anhydride (53 mg, 0.27 mmol) the title compound was obtained (34 mg, 29%). $^1$H NMR (DMSO) δ 8.38(m, 1H), 8.31(m, 2H), 8.06(dd, 1H), 7.92(m, 2H), 7.86(s, 1H), 7.78(m, 3H). MS 429 m/z (M+H)$^+$.

Example 84

2-[3-(5-Carboxy-1,3-dioxo-1,3-dihydroisoindol-2-yl)phenyl]benzoxazole-6-carboxylic acid methyl ester a) 2-(3-Aminophenyl)benzoxazole-6-carboxylic acid methyl ester Prepared by the method of Example 15e), from 2-(3-nitrophenyl)benzoxazole-6-carboxylic acid methyl ester (3.00 g, 10.05 mmol) the subtitle compound was obtained, (1.58 mg, 59%). The product was used directly in the next step without purification.

b) 2-[3-(5-Carboxy-1,3-dioxo-1,3-dihydro-isoindol-2-yl)phenyl]benzoxazole-6-carboxylic acid methyl ester

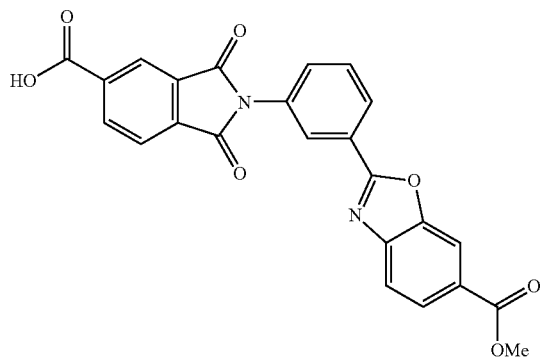

Prepared by the method of Example 1b), from 2-(3-aminophenyl)benzoxazole-6-carboxylic acid methyl ester (100 mg, 0.37 mmol) and 1,2,4-benzenetricarboxylic anhydride (72 mg, 0.37 mmol) the title compound was obtained (148 mg, 90%). $^1$H NMR (DMSO) δ 8.45(dd, 1H), 8.39(m, 1H), 8.32(m, 3H), 8.13(d, 1H), 8.05(dd, 1H), 7.96(d, 1H), 7.80(m, 2H), 3.91(s, 3H). MS 443 m/z (M+H)$^+$.

Example 85

2-[3-(5-Carboxy-1,3-dioxo-1,3-dihydroisoindol-2-yl)phenyl]benzoxazole-7-carboxylic acid a) Methyl 2-hydroxy-3-nitrobenzoate A solution of 3-hydroxy-2-nitrobenzoic acid (10.00 g, 5.46 mmol) in methanolic hydrochloric acid (50 ml) was heated to reflux overnight under an argon atmosphere. The cooled reaction mixture was concentrated to a green solid, which was then partitioned between saturated sodium hydrogen carbonate solution (50 ml) and ethyl acetate (50 ml). The aqueous layer was extracted with ethyl acetate (2×50 ml) and the combined organic layers dried over sodium sulfate and the solvent removed under reduced pressure to give the subtitle compound (885 mg, 81%). $^1$H NMR (DMSO) δ 7.58(t, 1H), 7.47(dd, 1H), 7.40(dd, 1H), 3.89(s, 3H).

b) Methyl 2-hydroxy-3-aminobenzoate

Prepared by the method of Example 15e), from methyl 3-hydroxy-2-nitrobenzoate (875 mg, 4.44 mmol) the subtitle compound was obtained (776 mg, 99%). MS 168.2 m/z (M+H)$^+$.

c) 3-(3-Nitrobenzamido)-2-hydroxybenzoic acid methyl ester

Prepared by the method of Example 15b), from methyl 3-hydroxy-2-aminobenzoate (776 mg, 4.64 mmol), 3-nitrobenzoylchloride (861.4 mg, 4.64 mmol) and triethylamine (939 mg, 9.28 mmol) the subtitle compound was obtained (1.27 g, 87%). MS 317.1 m/z (M+H)$^+$.

d) 2-(3-Nitrophenyl)benzoxazole-7-carboxylic acid methyl ester

Prepared by the method of Example 15c), from 3-(3-nitrobenzamido)-2-hydroxybenzoic acid methyl ester (1.00 mg, 3.16 mmol) and p-toluenesulfonic acid monohydrate (1.26 mg, 6.64 mmol) the subtitle compound was obtained (600 mg, 64%). $^1$H NMR (DMSO) δ 8.95(m, 1H), 8.7(m, 1H), 8.59(dd, 1H), 8.23(d, 1H), 8.05(m, 2H), 7.70(t, 1H).

e) 2-(3-Nitrophenyl)benzoxazole-7-carboxylic acid

Prepared by the method of Example 76c), from 2-(3-nitrophenyl)benzoxazole-7-carboxylic acid methyl ester (600 mg, 2.01 mmol) and lithium hydroxide (240 mg, 10.06 mmol) the subtitle compound was obtained, (442 mg, 77%). The product was used directly in next step without purification.

f) 2-(3-Aminophenyl)benzoxazole-7-carboxylic acid

Prepared by the method of Example 15e), from 2-(3-nitrophenyl)benzoxazole-7-carboxylic acid (400 mg, 1.40 mmol) the subtitle compound was obtained (227 mg, 63%). The product was used directly in the next step without purification.

g) 2-[3-(5-Carboxy-1,3-dioxo-1,3-dihydro-isoindol-2-yl)phenyl]benzoxazole-7-carboxylic acid

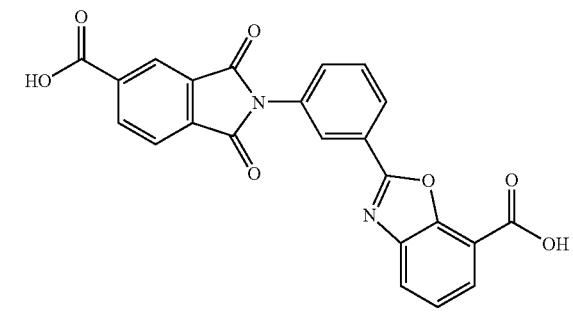

Prepared by the method of Example 1b), from 2-(3-aminophenyl)benzoxazole-7-carboxylic acid (100 mg, 0.39 mmol) and 1,2,4-benzenetricarboxylic anhydride (75 mg, 0.39 mmol) the title compound was obtained, (148 mg, 32%). $^1$H NMR (DMSO) δ 8.50(m, 2H), 8.39(m, 2H), 8.17(m, 2H), 8.01(m, 1H), 7.88(m, 2H), 7.63(t, 1H). MS 429 m/z (M+H)$^+$.

Example 86

2-[3-(5-Benzyloxycarbonyl-1,3-dioxo-1,3-dihydro-isoindol-2-yl)phenyl]benzoxazole-6-carboxylic acid a) 1,2,4-Benzenetricarboxylic anhydride benzyl ester A solution of benzyl alcohol (513 mg, 4.75 mmol) and pyridine (375 mg, 4.75 mmol) in toluene (25 ml) were added dropwise with stirring to a solution of trimellitic anhydride acid chloride (1.00 g, 4.75 mmol) in toluene (25 ml). After addition was complete the reaction was stirred at room temperature for 3 h. The reaction mixture was concentrated to give the subtitle compound as a white solid (1.08 mg, 81%). $^1$H NMR (CDCl$_3$) δ 8.60(s, 1H), 8.51(d, 1H), 8.02(d, 1H), 7.37(m, 5H).

b) 2-[3-(5-Benzyloxycarbonyl-1,3-dioxo-1,3-dihydro-isoindol-2-yl)phenyl]benzoxazole-6-carboxylic acid

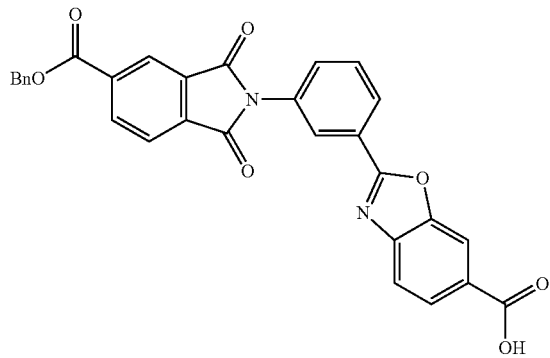

Prepared by the method of Example 1b), from 2-(3-aminophenyl)benzoxazole-6-carboxylic (459 mg, 1.80 mmol) and 1,2,4-benzenetricarboxylic anhydride benzyl ester (509 mg, 1.80 mmol) the title compound was obtained, (312 mg 50%). $^1$H NMR (DMSO) δ 8.40(dd, 1H), 8.29(m, 2H), 8.22(m, 2H), 8.06(d, 1H), 7.95(m, 1H), 7.84(m, 1H), 7.72(m, 2H), 7.45(m, 2H), 7.34(m, 3H), 5.35(s, 2H). MS 517 m/z (M−H)⁻.

Example 87

2-[3-(5-Methyloxycarbonyl-1,3-dioxo-1,3-dihydroisoindol-2-yl)phenyl]benzoxazole-6-carboxylic acid a) 1,2,4-Benzenetricarboxylic anhydride methyl ester Prepared by the method of Example 86a), from trimellitic anhydride acid chloride (200 mg, 0.95 mmol), pyridine (75 mg, 0.95 mmol) and methanol (38 mg, 0.95 mmol) the subtitle compound was obtained as a white solid (143 mg, 73%). The product was used directly in the next step without purification.

b) 2-[3-(5-Methyloxycarbonyl-1,3-dioxo-1,3-dihydroisoindol-2-yl)phenyl]benzoxazole-6-carboxylic acid

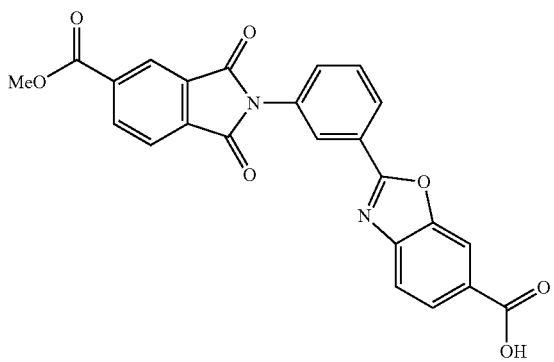

Prepared by the method of Example 1b), from 2-(3-aminophenyl)benzoxazole-6-carboxylic (167 mg, 0.66 mmol) and 1,2,4-benzenetricarboxylic anhydride methyl ester (136 mg, 0.66 mmol) the title compound was obtained (157 mg, 54%). $^1$H NMR (DMSO) δ 8.48(dd, 1H), 8.34(m, 4H), 8.15(d, 1H), 8.04(dd, 1H), 7.86(m, 3H), 3.95(s, 3H). MS 443 m/z (M+H)⁺.

Example 88

2-[5-(5-Bromobenzoxazol-2-yl)-2-methoxyphenyl]-1,3-dioxo-2,3-dihydro-1H-isoindole-5-carboxylic acid a) 2-(3-Amino-4-methoxyphenyl)-5-bromobenzoxazole Prepared by the method of Example 1a), from 3-amino-4-methoxybenzoic acid (1.84 g, 11.0 mmol) and 2-amino-4-bromophenol (2.0 g, 11.0 mmol) the subtitle compound was obtained (2.0 g, 55%). $^1$H NMR (CDCl₃) δ 7.85(t, 1H), 7.64(dd, 1H), 7.58(d, 1H), 7.41(d, 1H), 6.90(d, 1H), 3.95(s, 3H).

b) 2-[5-(5-Bromobenzoxazol-2-yl)-2-methoxyphenyl]-1,3-dioxo-2,3-dihydro-1H-isoindole-5-carboxylic acid

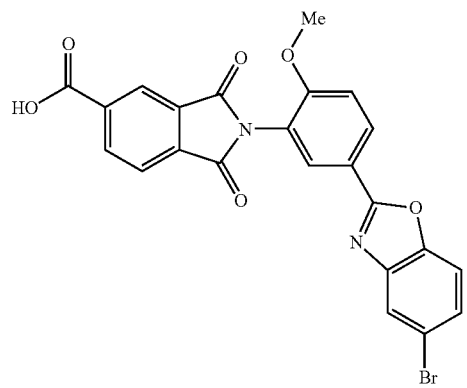

Prepared by the method of Example 1b), from 2-(3-amino-4-methoxyphenyl)-5-bromobenzoxazole (166 mg, 0.5 mmol) and 1,2,4-benzenetricarboxylic anhydride (100 mg, 0.5 mmol) the title compound was obtained (238 mg, 93%). $^1$H NMR (DMSO) δ 8.44(dd, 1H), 8.32(m, 3H), 8.10(d, 1H), 8.02(d, 1H), 7.77(d, 1H), 7.57(dd, 1H), 7.48(d, 1H). MS 490.9 m/z (M−H)⁻.

Example 89

2-[5-(5-Phenylbenzoxazol-2-yl)-2-(3-thienyl)phenyl]-1,3-dioxo-2,3-dihydro-1H-isoindole-5-carboxylic acid a) 2-(3-Nitro-4-(3-thienyl)phenyl)-5-phenylbenzoxazole Prepared by the method of Example 15d), from 2-(3-nitro-4-chlorophenyl)-5-phenylbenzoxazole (177 mg, 0.51 mmol) and thiophene-3-boronic acid (97 mg, 0.76 mmol) the subtitle compound was obtained (150 mg, 74%). $^1$H NMR (DMSO) δ 8.67(d, 1H), 8.48(dd, 1H), 8.12(d, 1H), 7.91(m, 2H), 7.83(m, 1H), 7.79–7.77(m, 4H), 7.51(m, 2H), 7.40(t, 1H), 7.22(dd, 1H).

b) 2-(3-Amino-4-(3-thienyl)phenyl)-5-phenylbenzoxazole

Prepared by the method of Example 39b), from 2-(3-nitro-4-(3-thienyl)phenyl)-5-phenylbenzoxazole (88 mg, 0.22 mmol) the subtitle compound was obtained. The product was used directly in the next step without purification.

c) 2-[5-(5-Phenylbenzoxazol-2-yl)-2-(3-thienyl)phenyl]-1,3-dioxo-2,3-dihydro-1H-isoindole-5-carboxylic acid d) 2-[2-Fluoro-5-(5-phenylbenzoxazol-2-yl)phenyl]-1,3-dioxo-2,3-dihydro-1H-isoindole-5-carboxylic acid

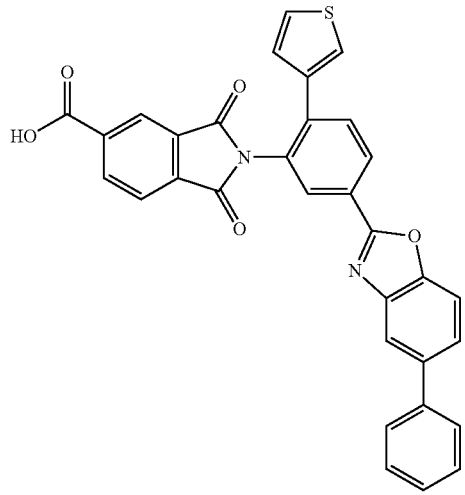

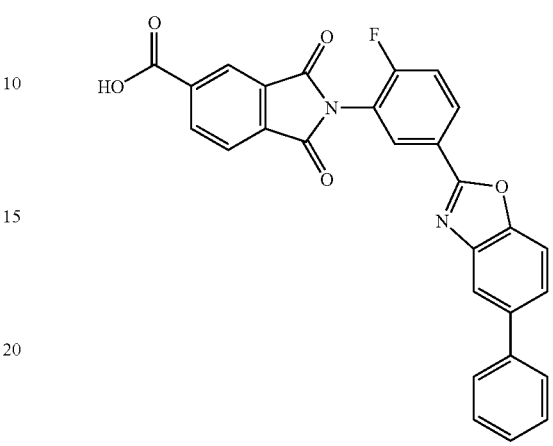

Prepared by the method of Example 15f), from 2-(3-amino-4-(3-thienyl)phenyl)-5-phenylbenzoxazole (61 mg, 0.16 mmol) and 1,2,4-benzenetricarboxylic anhydride (32 mg, 0.16 mmol) the title compound was obtained (66 mg, 75%). $^1$H NMR (DMSO) δ 8.50(d, 1H), 8.41(m, 2H), 8.30(s, 1H), 8.07(m, 2H), 7.90(m, 2H), 7.75(m, 3H), 7.62(m, 1H), 7.55(m, 1H), 7.50(m, 2H), 7.40(t, 1H), 7.11(dd, 1H). MS 540.7 m/z (M−H)$^-$.

Example 90

2-[2-Fluoro-5-(5-phenylbenzoxazol-2-yl)phenyl]-1,3-dioxo-2,3-dihydro-1H-isoindole-5-carboxylic acid a) N-(5-Phenyl-2-hydroxy-5-phenyl)-3-nitro-4-fluorobenzamide Prepared by the method of Example 15b), from 2-amino-4-phenylphenol (8.80 g, 48.0 mmol) and 3-nitro-4-fluorobenzoyl chloride (11.19 g, 55 mmol) the subtitle compound was obtained (15.46 g, 92%). The product was used directly in the next step without purification.

b) 2-(3-Nitro-4-fluoro)-5-phenylbenzoxazole

Prepared by the method of Example 15c), from N-(5-phenyl-2-hydroxyphenyl)-3-nitro-4-fluorobenzamide (15.46 g, 44.0 mmol) and p-toluenesulfonic acid monohydrate (16.74 g, 88 mmol) the subtitle compound was obtained (3.25 g, 23%). $^1$H NMR (DMSO) δ 8.82(dd, 1H), 8.59(m, 1H), 8.11(d, 1H), 7.93–7.73(m, 5H), 7.50(m, 2H), 7.40(t, 1H).

c) 2-(3-Amino-4-fluoro)-5-phenylbenzoxazole

Prepared by the method of Example 15e), from 2-(3-nitro-4-fluoro)-5-phenylbenzoxazole (100 mg, 0.30 mmol) the subtitle compound was obtained (81 mg, 89%). $^1$H NMR (DMSO) δ 7.95(d, 1H), 7.72(dd, 1H), 7.65–7.58(m, 5H), 7.48(m, 2H), 7.38(t, 1H), 7.14(m, 1H).

Prepared by the method of Example 15f), from 2-(3-amino-4-fluoro)-5-phenylbenzoxazole (78 mg, 0.26 mmol) and 1,2,4-benzenetricarboxylic anhydride (49 mg, 0.26 mmol) the title compound was obtained (80 mg, 65%). $^1$H NMR (DMSO) δ 8.54–8.38(m, 4H), 8.16(d, 1H), 8.08(d, 1H), 7.88(d, 1H), 7.80–7.73(m, 4H), 7.50(m, 2H), 7.39(t, 1H). MS 477.3 m/z (M−H)$^-$.

Example 91

2-[2-Chloro-5-(5-phenylbenzoxazol-2-yl)phenyl]-1,3-dioxo-2,3-dihydro-1H-isoindole-5-carboxylic acid a) N-(5-Phenyl-2-hydroxyphenyl)-3-nitro-4-chlorobenzamide Prepared by the method of Example 15b), from 3-nitro-4-chlorobenzoyl chloride (5.28 g, 24.0 mmol) and 4-phenyl-2-aminophenol (3.92 g, 21.0 mmol) the subtitle compound was obtained. The product was used directly in the next step without purification.

b) 2-(3-Nitro-4-chlorophenyl)-5-phenylbenzoxazole

Prepared by the method of Example 15c), from N-(5-phenyl-2-hydroxyphenyl)-3-nitro-4-chlorobenzamide (3.76 g, 10 mmol) and p-toluenesulfonic acid monohydrate (3.80 g, 20 mmol) the subtitle compound was obtained (1.28 g, 40%). MS 351.1 (M+H)$^+$.

c) 2-(3-Amino-4-chlorophenyl-5-phenylbenzoxazole

Prepared by the method of Example 15e), from 2-(3-nitro-4-chlorophenyl)-5-phenylbenzoxazole (240 mg, 0.68 mmol) the subtitle compound was obtained (35 mg, 16%). $^1$H NMR (CDCl$_3$) δ 7.95(s, 1H), 7.70–7.59(m, 6H), 7.48(m, 2H), 7.40(m, 2H).

d) 2-[2-Chloro-5-(5-phenylbenzoxazol-2-yl)phenyl]-1,3-dioxo-2,3-dihydro-1H-isoindole-5-carboxylic acid c) 2-[2-Methoxy-5-[5-(2-benzothiopheneyl)benzoxazol-2-yl]phenyl]-1,3-dioxo-2,3-dihydro-1H-isoindole-5-carboxylic acid

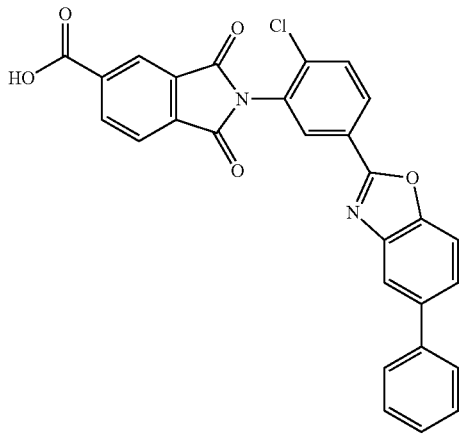

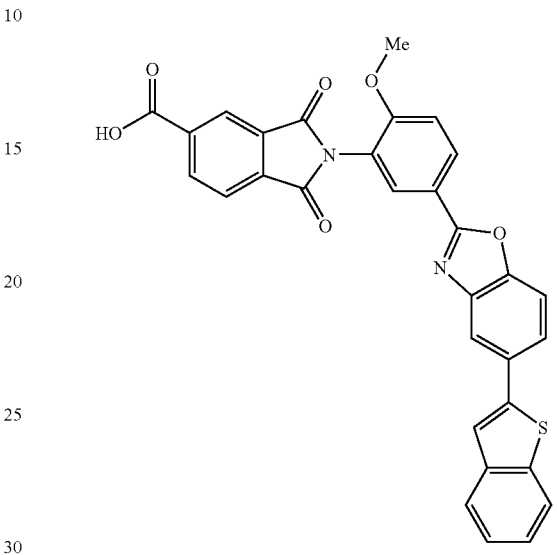

Prepared by the method of Example 15e), from 2-(3-amino-4-chlorophenyl)-5-phenylbenzoxazole (43 mg, 0.13 mmol) and 1,2,4-benzenetricarboxylic acid (26 mg, 0.13 mmol) the title compound was obtained (10 mg, 15%). $^1$H NMR (DMSO) δ 8.58(d, 1H), 8.48(dd, 1H), 8.38(m, 2H), 8.17(d, 1H), 8.08(d, 1H), 7.99(d, 1H), 7.88(d, 1H), 7.76(m, 3H), 7.50(m, 2H), 7.39(t, 1H). MS 492.8 m/z (M–H)$^-$.

Example 92

2-[2-Methoxy-5-[5-(2-benzothiophenyl)benzoxazol-2-yl]phenyl]-1,3-dioxo-2,3-dihydro-1H-isoindole-5-carboxylic acid a) 2-(3-Nitro-4-methoxyphenyl)-5-(2-benzothiophenyl)benzoxazole Prepared by the method of Example 15d), from 2-(3-nitro-4-methoxyphenyl)-5-bromobenzoxazole (200 mg, 0.57 mmol) and benzothiophene-2-boronic acid (153 mg, 0.85 mmol) the subtitle compound was obtained (200 mg, 15%). MS 403.1 m/z (M+H)$^+$.

b) 2-(3-Amino-4-methoxyphenyl)-5-(2-benzothiophenyl)benzoxazole

Prepared by the method of Example 15e), from 2-(3-nitro-4-methoxyphenyl)-5-(2-benzothiophenyl)benzoxazole (200 mg, 0.50 mmol) and palladium on carbon (10%) (10 mg) in dioxane (10 ml), the subtitle compound was obtained.(40 mg, 86%). MS 373.2 m/z (M+H)$^+$.

Prepared by the method of Example 15f), from 2-(3-amino-4-methoxyphenyl-5-(2-benzothiophenyl)benzoxazole (120 mg, 0.32 mmol) and 1,2,4-benzenetricarboxylic anhydride (62 mg, 0.32 mmol) the title compound was obtained. (41 mg, 23%). $^1$H NMR (DMSO) δ 13.82(s, 1H), 8.46(dd, 1H), 8.38(d, 1H), 8.35(m, 2H), 8.18(d, 1H), 8.13(d, 1H), 8.00(d, 1H), 7.96(s, 1H), 7.85(m, 3H), 7.50(d, 1H), 7.40(m, 2H), 3.90(s, 3H). MS 547.2 m/z (M+H)$^+$.

Example 93

2-[2-Methoxy-5-[5-(3-methyl-4-chlorophenyl)benzoxazol-2-yl]phenyl]-1,3-dioxo-2,3-dihydro-1H-isoindole-5-carboxylic acid a) 2-(3-Nitro-4-methoxyphenyl)-5-(3-methyl-4-chlorophenyl)benzoxazole Prepared by the method of Example 15d), from 2-(3-nitro-4-methoxyphenyl)-5-bromobenzoxazole (200 mg, 0.57 mmol) and 4-chloro-3-methylphenylboronic acid (145 mg, 0.85 mmol) the subtitle compound was obtained (85 mg, 25%). MS 395 m/z (M+H)$^+$.

b) 2-(3-Amino-4-methoxyphenyl)-5-(3-methyl-4-chlorophenyl)benzoxazole

Prepared by the method of Example 15e), from 2-(3-nitro-4-methoxyphenyl)-5-(3-methyl-4-chlorophenyl)benzoxazole (85 mg, 0.21 mmol) the subtitle compound was obtained (79 mg, 100%). MS 365 m/z (M+H)$^+$.

c) 2-[2-Methoxy-5-[5-(3-methyl-4-chlorophenyl)benzoxazol-2-yl]phenyl]-1,3-dioxo-2,3-dihydro-1H-isoindole-5-carboxylic acid c) 2-[2-Methoxy-5-[5-(4-fluoro-3-formylphenyl)benzoxazol-2-yl]phenyl]-1,3-dioxo-2,3-dihydro-1H-isoindole-5-carboxylic acid

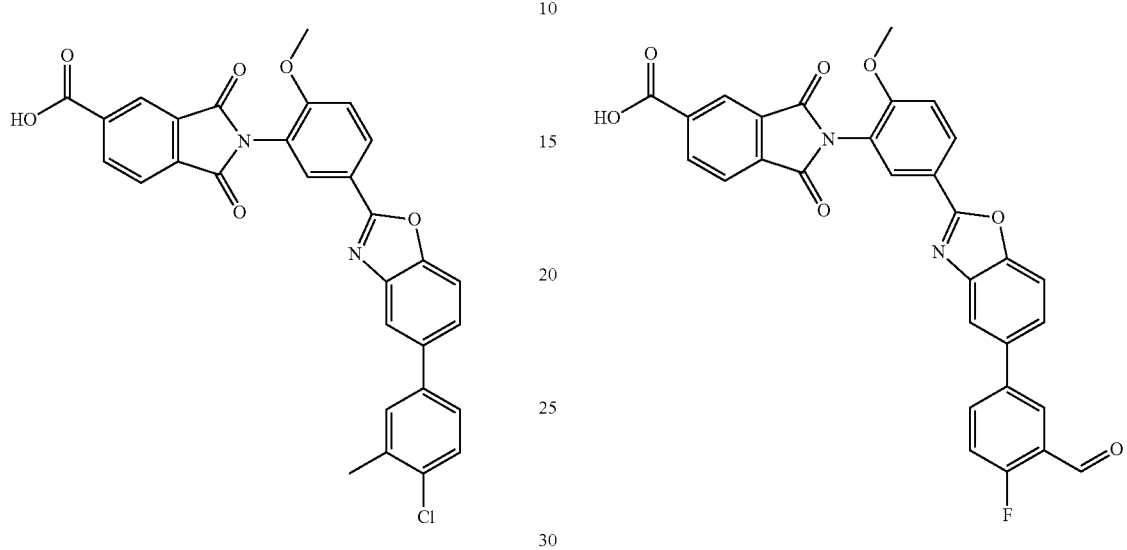

Prepared by the method of Example 1b), from 2-(3-amino-4-methoxyphenyl)-5-(3-methyl-4-chlorophenyl)benzoxazole (79 mg, 0.22 mmol) and 1,2,4-benzenetricarboxylic anhydride (42 mg, 0.22 mmol) the title compound was obtained (22 mg, 19%). $^1$H NMR (DMSO) δ 8.55(dd, 1H), 8.44(m, 3H), 8.22(d, 1H), 8.14(m, 1H), 7.90(m, 3H), 7.65 (m, 3H), 4.00(s, 3H), 2.45(s, 3H). MS 527 m/z (M+H)$^+$.

Prepared by the method of Example 1b), from 2-(3-amino-4-methoxyphenyl)-5-(4-fluoro-3-formylbenzene) benzoxazole (62 mg, 0.17 mmol) and 1,2,4-benzenetricarboxylic anhydride (62 mg, 0.17 mmol) the title compound was obtained (48 mg, 53%). $^1$H NMR (DMSO) δ 10.40(s, 1H), 8.53(dd, 1H), 8.45(m, 3H), 8.22(m, 4H), 7.95(d, 1H), 7.82(dd, 1H), 7.60(m, 2H), 3.95(s, 3H). MS 537 m/z (M+H)$^+$.

Example 94

2-[2-Methoxy-5-[5-(4-fluoro-3-formylphenyl)benzoxazol-2-yl]phenyl]-1,3-dioxo-2,3-dihydro-1H-isoindole-5-carboxylic acid Example 95

2-[2-Methoxy-5-[5-(3,4-difluorophenyl)benzoxazol-2-yl]phenyl]-1,3-dioxo-2,3-dihydro-1H-isoindole-5-carboxylic acid a) 2-(3-Nitro-4-methoxyphenyl)-5-(4-fluoro-3-formylphenyl)benzoxazole Prepared by the method of Example 15d), from 2-(3-nitro-4-methoxyphenyl)-5-bromobenzoxazole (200 mg, 0.57 mmol) and 4-fluoro-3-formylphenylboronic acid (143 mg, 0.85 mmol) the subtitle compound was obtained (146 mg, 44%). MS 393 m/z (M+H)$^+$.

a) 2-(3-Nitro-4-methoxyphenyl)-5-(3,4-difluorophenyl)benzoxazole

Prepared by the method of Example 15d), from 2-(3-nitro-4-methoxyphenyl)-5-bromobenzoxazole (200 mg, 0.57 mmol) and 3,4-difluorophenylboronic acid (134 mg, 0.85 mmol) the subtitle compound was obtained (68 mg, 21%). MS 383 m/z (M+H)$^+$.

b) 2-(3-Amino-4-methoxyphenyl)-5-(4-fluoro-3-formylphenyl)benzoxazole

Prepared by the method of Example 15e), from 2-(3-nitro-4-methoxyphenyl)-5-(4-fluoro-3-formylbenzene)benzoxazole (146 mg, 0.37 mmol) the subtitle compound was obtained (62 mg, 46%). MS 363 m/z (M+H)$^+$.

b) 2-(3-Amino-4-methoxyphenyl)-5-(3,4-difluorophenyl)benzoxazole

Prepared by the method of Example 15e), from 2-(3-nitro-4-methoxyphenyl)-5-(3,4-difluorophenyl)benzoxazole (68 mg, 0.18 mmol) the subtitle compound was obtained (63 mg, 100%). MS 353 m/z (M+H)$^+$.

c) 2-[2-Methoxy-5-[5-(3,4-difluorophenyl)benzoxazol-2-yl]phenyl]-1,3-dioxo-2,3-dihydro-1H-isoindole-5-carboxylic acid

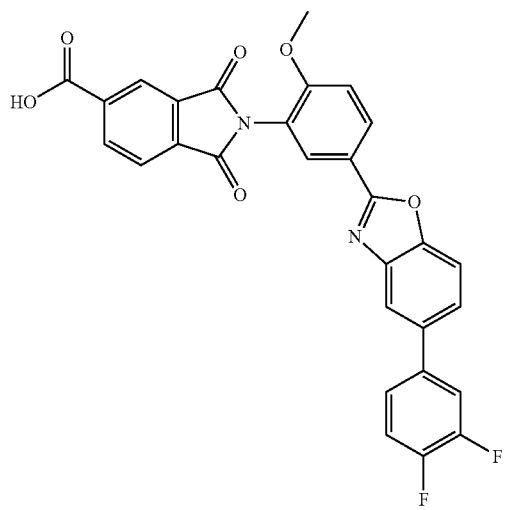

Prepared by the method of Example 1b), from 2-(3-amino-4-methoxyphenyl)-5-(3,4-difluorophenyl)benzoxazole (63 mg, 0.18 mmol) and 1,2,4-benzenetricarboxylic anhydride (35 mg, 0.18 mmol) the title compound was obtained (25 mg, 27%). $^1$H NMR (DMSO) δ 8.53(dd, 1H), 8.42(m, 3H), 8.18(m, 2H), 7.94(m, 2H), 7.79(dd, 1H), 7.60(m, 3H), 3.95(s, 3H). MS 527 m/z (M+H)$^+$.

Example 96

2-[2-Methoxy-5-[5-(4-ethylsulfonylphenyl)benzoxazol-2-yl]phenyl]-1,3-dioxo-2,3-dihydro-1H-isoindole-5-carboxylic acid a) 2-(3-Nitro-4-methoxyphenyl)-5-(4-ethylsulfonylphenyl)benzoxazole Prepared by the method of Example 15d), from 2-(3-nitro-4-methoxyphenyl)-5-bromobenzoxazole (400 mg, 1.15 mmol) and 4-(ethylsulfonyl)phenylboronic acid (214 mg, 1.75 mmol) the subtitle compound was obtained (88 mg, 12%). MS 439 m/z (M+H)$^+$.

b) 2-(3-Amino-4-methoxyphenyl)-5-(4-ethylsulfonylphenyl)benzoxazole

Prepared by the method of Example 15e), from 2-(3-nitro-4-methoxyphenyl)-5-(4-ethylsulfonyphenyl)benzoxazole (88 mg, 0.20 mmol) the subtitle compound was obtained (63 mg, 78%). MS 409 m/z (M+H)$^+$.

c) 2-[2-Methoxy-5-[5-(4-ethylsulfonylphenyl)benzoxazol-2-yl]phenyl]-1,3-dioxo-2,3-dihydro-1H-isoindole-5-carboxylic acid

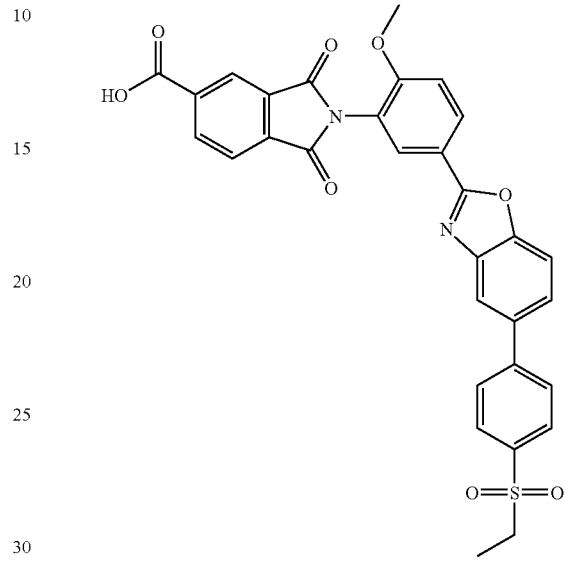

Prepared by the method of Example 1b), from 2-(3-amino-4-methoxyphenyl)-5-(4-ethylsulfonylphenyl)benzoxazole (63 mg, 0.15 mmol) and 1,2,4-benzenetricarboxylic anhydride (29 mg, 0.15 mmol) the title compound was obtained (34 mg, 39%). $^1$H NMR (DMSO) δ 8.57(dd, 1H), 8.57(m, 4H), 8.30(d, 1H) 8.10(m, 4H), 8.03(d, 1H), 7.92(dd, 1H), 7.61(d, 1H), 4.00(s, 3H), 3.45(q, 2H), 1.25(t, 3H). MS 583 m/z (M+H)$^+$.

Example 97

2-[2-Methoxy-5-[5-(4-N,N-dimethylaminophenyl)benzoxazol-2-yl]phenyl]-1,3-dioxo-2,3-dihydro-1H-isoindole-5-carboxylic acid a) 2-(3-Nitro-4-methoxyphenyl)-5-(4-N,N-dimethylaminophenyl)benzoxazole Prepared by the method of Example 15d), from 2-(3-nitro-4-methoxyphenyl)-5-bromobenzoxazole (400 mg, 1.15 mmol) and 4-(N,N-dimethylamino)phenylboronic acid (285 mg, 1.75 mmol) the subtitle compound was obtained (114 mg, 17%). MS 390 m/z (M+H)$^+$.

b) 2-(3-Amino-4-methoxyphenyl)-5-(4-N,N-dimethylaminophenyl)benzoxazole

Prepared by the method of Example 15e), from 2-(3-nitro-4-methoxyphenyl)-5-(4-N,N-dimethylaminophenyl)benzoxazole (144 mg, 0.30 mmol) the subtitle compound was obtained (79 mg, 76%). MS 360 m/z (M+H)$^+$.

c) 2-[2-Methoxy-5-[5-(4-N,N-dimethylaminophenyl)benzoxazol-2-yl]phenyl]-1,3-dioxo-2,3-dihydro-1H-isoindole-5-carboxylic acid

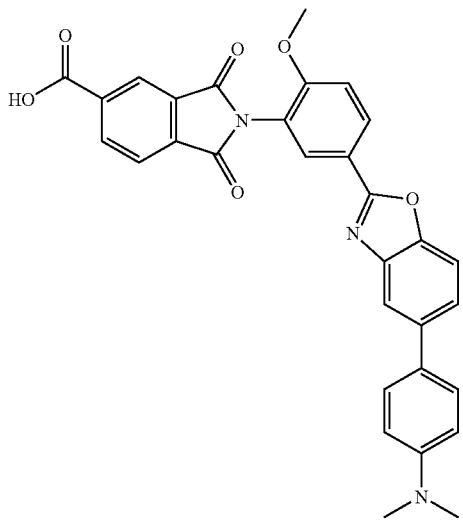

Prepared by the method of Example 1b), from 2-(3-amino-4-methoxyphenyl)-5-(4-N,N-dimethylaminophenyl)benzoxazole (79 mg, 0.22 mmol) and 1,2,4-benzenetricarboxylic anhydride (42 mg, 0.22 mmol) the title compound was obtained (52 mg, 44%). $^1$H NMR (DMSO) δ 8.46(d, 1H), 8.40(m, 3H), 8.20(d, 1H), 7.98(s, 1H), 7.82(d, 1H), 7.65(m, 3H), 7.55(d, 1H), 6.89(d, 2H), 3.95(s, 3H), 3.00(s, 6H). MS 534 m/z $(M+H)^+$.

Example 98

2-[2-Methoxy-5-[5-(2,3-dichlorophenyl)benzoxazol-2-yl]phenyl]-1,3-dioxo-2,3-dihydro-1H-isoindole-5-carboxylic acid a) 2-(3-Nitro-4-methoxyphenyl)-5-(2,3-dichlorophenyl)benzoxazole Prepared by the method of Example 15d), from 2-(3-nitro-4-methoxyphenyl)-5-bromobenzoxazole (400 mg, 1.15 mmol) and 2,3-dichlorophenylboronic acid (329 mg, 1.72 mmol) the subtitle compound was obtained (288 mg, 60%). MS 415 m/z $(M+H)^+$.

b) 2-(3-Amino-4-methoxyphenyl)-5-(2,3-dichlorophenyl)benzoxazole

Prepared by the method of Example 15e), from 2-(3-nitro-4-methoxyphenyl)-5-(2,3-dichlorophenyl)benzoxazole (288 mg, 0.70 mmol) the subtitle compound was obtained (238 mg, 82%). The product was used directly in the next step without purification.

c) 2-[2-Methoxy-5-[5-(2,3-dichlorophenyl)benzoxazol-2-yl]phenyl]-1,3-dioxo-2,3-dihydro-1H-isoindole-5-carboxylic acid

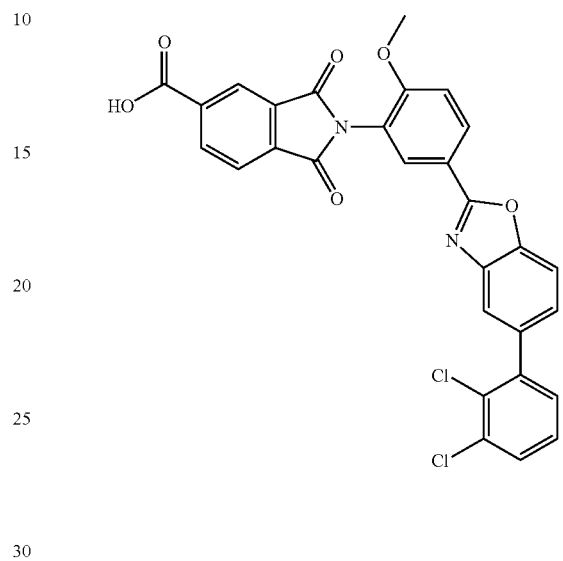

Prepared by the method of Example 1b), from 2-(3-amino-4-methoxyphenyl)-5-(2,3-dichlorophenyl)benzoxazole (238 mg, 0.60 mmol) and 1,2,4-benzenetricarboxylic anhydride (119 mg, 0.60 mmol) the title compound was obtained (191 mg, 57%). $^1$H NMR (DMSO) δ 8.46(dd, 1H), 8.35(m, 3H), 8.13(d, 1H), 7.84(m, 2H), 7.70(m, 1H), 7.47 (m, 4H), 3.87(s, 3H). MS 560 m/z $(M+H)^+$.

Example 99

2-[4-Methoxy-5-[5-(2-benzothiophenyl)benzoxazol-2-yl]phenyl]-1,3-dioxo-2,3-dihydro-1H-isoindole-5-carboxylic acid a) 2-(3-Nitro-6-Methoxyphenyl)-5-(2-benzothiophenyl)benzoxazole Prepared by the method of Example 15d), from 2-(3-nitro-6-methoxyphenyl)-5-bromobenzoxazole (400 mg, 1.14 mmol) and benzothiophene-2-boronic acid (306 mg, 1.71 mmol) the subtitle compound was obtained (569 mg, 123%). The product was used directly in the next step without purification.

b) 2-(3-Amino-6-methoxyphenyl)-5-(2-benzothiophenyl)benzoxazole

Prepared by the method of Example 15e), from 2-(3-nitro-6-methoxyphenyl)-5-(2-benzothiophenyl)benzoxazole (485 mg, 1.37 mmol) the subtitle compound was obtained (420 mg, 82%). MS 373.2 m/z $(M+H)^+$.

c) 2-[4-Methoxy-5-[5-(2-benzothiophenyl)benzoxazol-2-yl]phenyl]-1,3-dioxo-2,3-dihydro-1H-isoindole-5-carboxylic acid

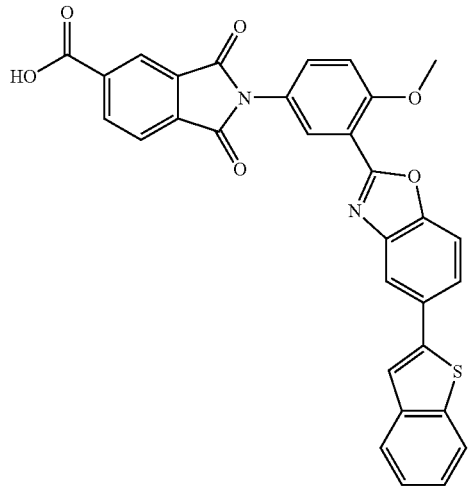

Prepared by the method of Example 15f), from 2-(3-amino-6-methoxyphenyl)-5-(2-benzothiophenyl)benzoxazole (140 mg, 0.38 mmol) and 1,2,4-benzenetricarboxylic anhydride (72 mg, 0.38 mmol) the title compound was obtained (100 mg, 22%). $^1$H NMR (DMSO) δ 13.79(s, 1H), 8.44(dd, 1H), 8.34(s, 1H), 8.22(m, 2H), 8.11(d, 1H), 8.01(d, 1H), 7.97(s, 1H), 7.92(d, 1H), 7.87(m, 2H), 7.73(dd, 1H), 7.48(d, 1H), 7.40(m, 2H), 4.04(s, 3H). MS 547.0 m/z (M+H)$^+$.

Example 100

2-[4-Methoxy-5-[5-(4-chlorophenyl)benzoxazol-2-yl]phenyl]-1,3-dioxo-2,3-dihydro-1H-isoindole-5-carboxylic acid a) 2-(3-Nitro-6-methoxyphenyl)-5-(4-chlorophenyl)benzoxazole Prepared by the method of Example 15d), from 2-(3-nitro-6-methoxyphenyl)-5-bromobenzoxazole (400 mg, 1.14 mmol) and 4-chlorophenylboronic acid (269 mg, 1.71 mmol) the subtitle compound was obtained (323 mg, 74%). The product was used directly in the next step without purification.

b) 2-(3-Amino-6-methoxyphenyl)-5-(4-chlorophenyl)benzoxazole

Prepared by the method of Example 15e), from 2-(3-nitro-6-methoxyphenyl)-5-(4-chlorophenyl)benzoxazole (310 mg, 0.93 mmol) the subtitle compound was obtained (225 mg, 69%). MS 351.2 m/z (M+H)$^+$.

c) 2-[4-Methoxy-5-[5-(4-chlorophenyl)benzoxazol-2-yl]phenyl]-1,3-dioxo-2,3-dihydro-1H-isoindole-5-carboxylic acid

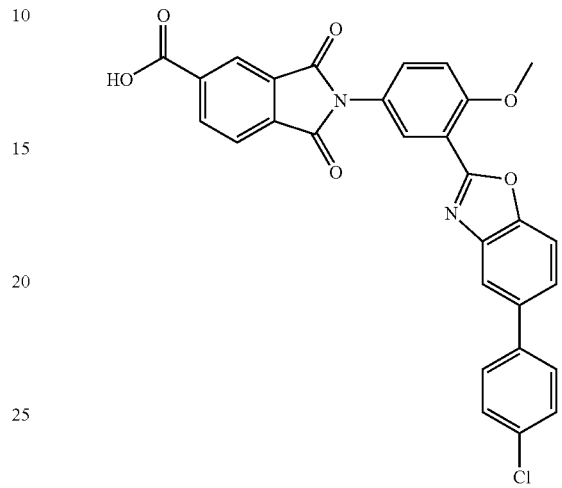

Prepared by the method of Example 15f), from 2-(3-amino-6-methoxyphenyl)-5-(4-chlorophenyl)benzoxazole (75 mg, 0.21 mmol) and 1,2,4-benzenetricarboxylic anhydride (41 mg, 0.21 mmol) the title compound was obtained (105 mg, 45%). $^1$H NMR (DMSO) δ 13.72(s, 1H), 8.42(dd, 1H), 8.32(s, 1H), 8.20(d, 1H), 8.09(m, 2H), 7.87(d, 1H), 7.78(d, 2H), 7.72(m, 2H), 7.54(d, 2H), 7.48(d, 1H), 4.04(s, 3H). MS 525.3 m/z (M+H)$^+$.

Example 101

2-[4-Methoxy-5-[5-(3-chloro-4-fluorophenyl)benzoxazol-2-yl]phenyl]-1,3-dioxo-2,3-dihydro-1H-isoindole-5-carboxylic acid a) 2-(3-Nitro-6-methoxyphenyl)-5-(3-chloro-4-fluorophenyl)benzoxazole Prepared by the method of Example 15d), from 2-(3-nitro-6-methoxyphenyl)-5-bromobenzoxazole (400 mg, 1.14 mmol) and 3-chloro-4-fluorophenylboronic acid (299 mg, 1.71 mmol) the subtitle compound was obtained (277 mg, 47%). The product was used directly in the next step without purification b) 2-(3-Amino-6-methoxyphenyl)-5-(3-chloro,4-fluoro)phenylbenzoxazole Prepared by the method of Example 15e), from 2-(3-nitro-6-methoxyphenyl)-5-(3-chloro-4-fluorophenyl)benzoxazole (277 mg, 0.81 mmol) the subtitle compound was obtained (180 mg, 60%). MS 369.2 m/z (M+H)$^+$.

c) 2-[4-Methoxy-5-[5-(3-chloro-4-fluorophenyl)benzoxazol-2-yl]phenyl]-1,3-dioxo-2,3-dihydro-1H-isoindole-5-carboxylic acid c) 2-[4-Methoxy-5-[5-(4-trifluoromethylphenyl)benzoxazol-2-yl]phenyl]-1,3-dioxo-2,3-dihydro-1H-isoindole-5-carboxylic acid

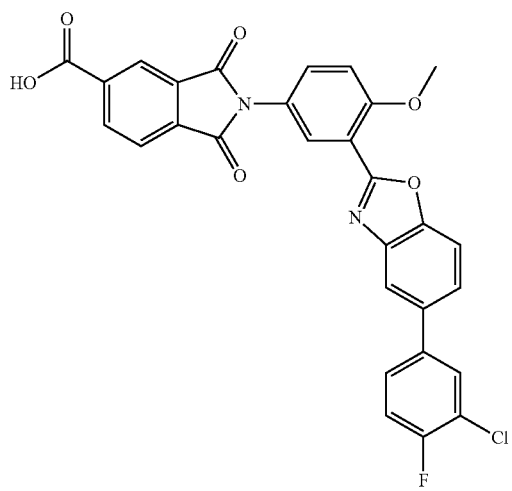

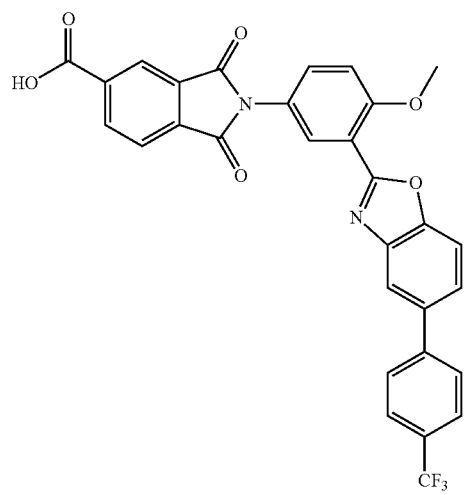

Prepared by the method of Example 15f), from 2-(3-amino-6-methoxyphenyl)-5-(3-chloro-4-fluorophenyl)benzoxazole (60 mg, 0.16 mmol) and 1,2,4-benzenetricarboxylic anhydride (31 mg, 0.16 mmol) the title compound was obtained (75 mg, 86%). $^1$H NMR (DMSO) δ 13.80(s, 1H), 8.43(d, 1H), 8.32(s, 1H), 8.21(d, 1H), 8.15(s, 1H), 8.10(d, 1H), 7.99(dd, 1H), 7.88(d, 1H), 7.75(m, 3H), 7.53(t, 1H), 7.47(d, 1H), 4.03(s, 3H). MS 542.6 m/z (M+H)$^+$.

Prepared by the method of Example 15f), from 2-(3-amino-6-methoxyphenyl)-5-(4-trifluoromethylphenyl)benzoxazole (90 mg, 0.23 mmol) and 1,2,4-benzenetricarboxylic anhydride (45 mg, 0.23 mmol) the title compound was obtained (102 mg, 79%). $^1$H NMR (DMSO) δ 13.74(s, 1H), 8.43(d, 1H), 8.33(s, 1H), 8.22(d, 1H), 8.20(d, 1H), 8.10(d, 1H), 7.99(d, 2H), 7.93(d, 1H), 7.83(m, 3H), 7.72(dd, 1H), 7.48(d, 1H), 4.03(s, 3H). MS 559.3 m/z (M+H)$^+$.

Example 102

2-[4-Methoxy-5-[5-(4-trifluoromethylphenyl)benzoxazol-2-yl]phenyl]-1,3-dioxo-2,3-dihydro-1H-isoindole-5-carboxylic acid a) 2-(3-Nitro-6-methoxyphenyl)-5-(4-trifluoromethylphenyl)benzoxazole Prepared by the method of Example 15d), from 2-(3-nitro-methoxyphenyl)-5-bromobenzoxazole (400 mg, 1.14 mmol) and 4-trifluoromethylphenylboronic acid (326 mg, 1.71 mmol) the subtitle compound was obtained (312 mg, 52%). The product was used directly in the next step without purification b) 2-(3-Amino-6-methoxyphenyl)-5-(4-trifluoromethylphenyl)benzoxazole Prepared by the method of 15e), from 2-(3-nitro-6-methoxyphenyl)-5-(4-trifluoromethylphenyl)benzoxazole (312 mg, 0.88 mmol) the subtitle compound was obtained (270 mg, 80%). MS 385.2 m/z (M+H)$^+$.

Example 103

2-[4-Methoxy-5-[5-(2-benzofuranyl)benzoxazol-2-yl]phenyl]-1,3-dioxo-2,3-dihydro-1H-isoindole-5-carboxylic acid a) 2-(3-Nitro-6-methoxyphenyl)-5-(2-benzofuranyl)benzoxazole Prepared by the method of Example 15d), from 2-(3-nitro-6-methoxyphenyl)-5-bromobenzoxazole (400 mg, 1.14 mmol) and 2-benzofuranboronic acid (278 mg, 1.71 mmol) the subtitle compound was obtained (342 mg, 61%). The product was used directly in the next step without purification b) 2-(3-Amino-6-methoxyphenyl)-5-(2-benzofuranyl)benzoxazole Prepared by the method of Example 15e), from 2-(3-nitro-6-methoxyphenyl)-5-(2-benzofuranyl)benzoxazole (342 mg, 1.05 mmol) the subtitle compound was obtained (315 mg, 91%). MS 357.2 m/z (M+H)$^+$.

c) 2-[4-Methoxy-5-[5-(2-benzofuranyl)benzoxazol-2-yl]phenyl]-1,3-dioxo-2,3-dihydro-1H-isoindole-5-carboxylic acid

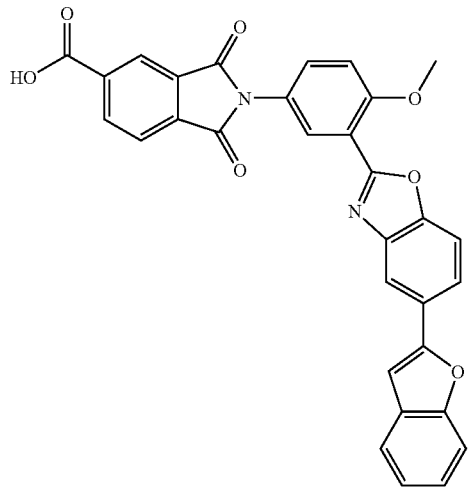

Prepared by the method of Example 15f), from 2-(3-amino-6-methoxyphenyl)-5-(2-benzofuranyl)benzoxazole (105 mg, 0.29 mmol) and 1,2,4-benzenetricarboxylic anhydride (57 mg, 0.29 mmol) the title compound was obtained (98 mg, 63%). $^1$H NMR (DMSO) δ 13.74(s, 1H), 8.43(dd, 1H), 8.32(d, 2H), 8.21(d, 1H), 8.10(d, 1H), 8.02(dd, 1H), 7.92(d, 1H), 7.72(dd, 1H), 7.67(t, 2H), 7.54(s, 1H), 7.47(d, 1H), 7.31(m, 2H), 4.03(s, 3H). MS 531.2 m/z (M+H)$^+$.

Example 104

2-[4-Methoxy-5-[5-(3,5-difluorophenyl)benzoxazol-2-yl]phenyl]-1,3-dioxo-2,3-dihydro-1H-isoindole-5-carboxylic acid a) 2-(3-Nitro-6-methoxyphenyl)-5-(3-difluorophenyl)benzoxazole Prepared by the method of Example 15d), from 2-(3-nitro-6-methoxyphenyl)-5-bromobenzoxazole (400 mg, 1.14 mmol) and 3,5-difluorophenylboronic acid (326 mg, 1.71 mmol) the subtitle compound was obtained (271 mg, 28%). The product was used directly in the next step without purification.

b) 2-(3-Amino-6-methoxyphenyl)-5-(3,5-difluorophenyl)benzoxazole

Prepared by the method of Example 15e), from 2-(3-nitro-6-methoxyphenyl)-5-(3,5-difluorophenyl)benzoxazole (271 mg, 0.84 mmol), the subtitle compound was obtained (210 mg, 67%). MS 353.2 m/z (M+H)$^+$.

c) 2-[4-Methoxy-5-[5-(3,5-difluorophenyl)benzoxazol-2-yl]phenyl]-1,3-dioxo-2,3-dihydro-1H-isoindole-5-carboxylic acid

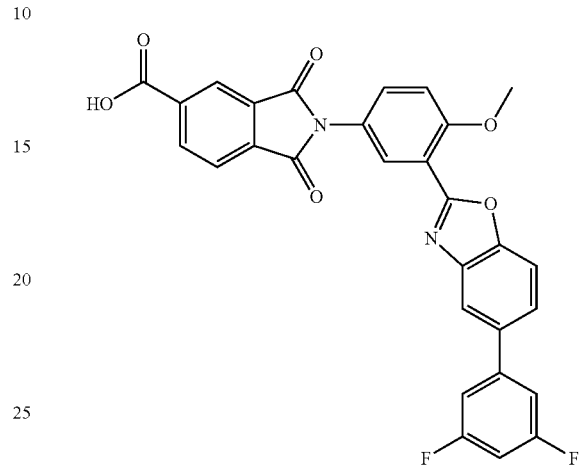

Prepared by the method of Example 15f), from 2-(3-amino-6-methoxyphenyl)-5-(3,5-difluorophenyl)benzoxazole (70 mg, 0.20 mmol) and 1,2,4-benzenetricarboxylic anhydride (38 mg, 0.20 mmol) the title compound was obtained (72 mg, 68%). $^1$H NMR (DMSO) δ 13.79(s, 1H), 8.42(dd, 1H), 8.33(s, 1H), 8.23(d, 1H), 8.21(d, 1H), 8.10(d, 1H), 7.90(d, 1H), 7.83(dd, 1H), 7.72(dd, 1H), 7.56(m, 2H), 7.48(d, 1H), 7.26(m, 1H), 4.03(s, 3H). MS 527.3 m/z (M+H)$^+$.

Example 105

2-[4-Methoxy-5-[5-(3,4-methylenedioxyphenyl)benzoxazol-2-yl]phenyl]-1,3-dioxo-2,3-dihydro-1H-isoindole-5-carboxylic acid a) 2-(3-Nitro-6-methoxyphenyl)-5-(3,4-methylenedioxyphenyl)benzoxazole Prepared by the method of Example 15d), from 2-(3-nitro-6-methoxyphenyl)-5-bromobenzoxazole (400 mg, 1.14 mmol) and 3,4-methylenedioxyphenylboronic acid (285 mg, 1.71 mmol) the subtitle compound was obtained (270 mg, 48%). The product was used directly in the next step without purification.

b) 2-(3-Amino-6-methoxyphenyl)-5-(3,4-methylenedioxyphenyl)benzoxazole

Prepared by the method of Example 15e), from 2-(3-nitro-6-methoxyphenyl)-5-(3,4-methylenedioxyphenyl)benzoxazole (270 mg, 0.82 mmol) the subtitle compound was obtained (150 mg, 51%). MS 361.2 m/z (M+H)$^+$.

c) 2-[4-Methoxy-5-[5-(3,4-methylenedioxyphenyl)benzoxazol-2-yl]phenyl]-1,3-dioxo-2,3-dihydro1H-isoindole-5-carboxylic acid

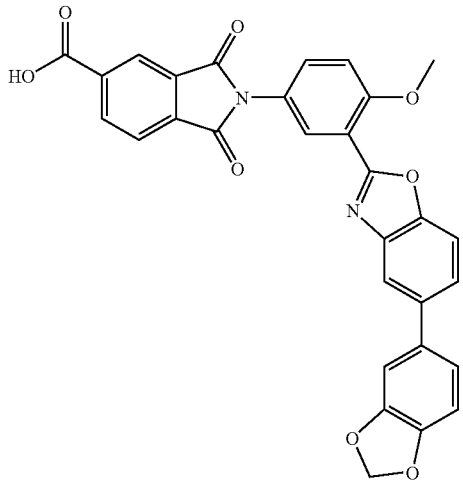

Prepared by the method of Example 15f), from 2-(3-amino-6-methoxyphenyl)-5-(3,4-methylenedioxyphenyl)benzoxazole (50 mg, 0.14 mmol) and 1,2,4-benzenetricarboxylic anhydride (27 mg, 0.14 mmol) the title compound was obtained (72 mg, 92%). $^1$H NMR (DMSO) δ 13.85(s, 1H), 8.44(dd, 1H), 8.33(s, 1H), 8.21(d, 1H), 8.11(d, 1H), 8.02(d, 1H), 7.83(d, 1H), 7.71(dd, 1H), 7.66(dd, 1H), 7.47(d, 1H), 7.35(d, 1H), 7.22(dd, 1H), 7.03(d, 1H), 6.08(s, 2H), 4.03(s, 3H). MS 535.1 m/z (M+H)$^+$.

Example 106

2-[4-Methoxy-5-[5-(3-methoxy)phenylbenzoxazol-2-yl]phenyl]-1,3-dioxo-2,3-dihydro-1H-isoindole-5-carboxylic acid a) 2-(3-Nitro-6-methoxyphenyl)-5-(3-methoxyphenyl)benzoxazole Prepared by the method of Example 15d), from 2-(3-nitro-6-methoxyphenyl)-5-bromobenzoxazole (400 mg, 1.14 mmol) and 3-methoxyphenylboronic acid (261 mg, 1.71 mmol) the subtitle compound was obtained (280 mg, 51%). The product was used directly in the next step without purification.

b) 2-(3-Amino-6-methoxyphenyl)-5-(3-methoxyphenyl)benzoxazole

Prepared by the method of Example 15e), from 2-(3-nitro-6-methoxyphenyl)-5-(3-methoxyphenyl)benzoxazole (280 mg, 0.89 mmol) the subtitle compound was obtained (150 mg, 49%). MS 347.3 m/z (M+H)$^+$.

c) 2-[4-Methoxy-5-[5-(3-methoxyphenyl)benzoxazol-2-yl]phenyl]-1,3-dioxo-2,3-dihydro-1H-isoindole-5-carboxylic acid

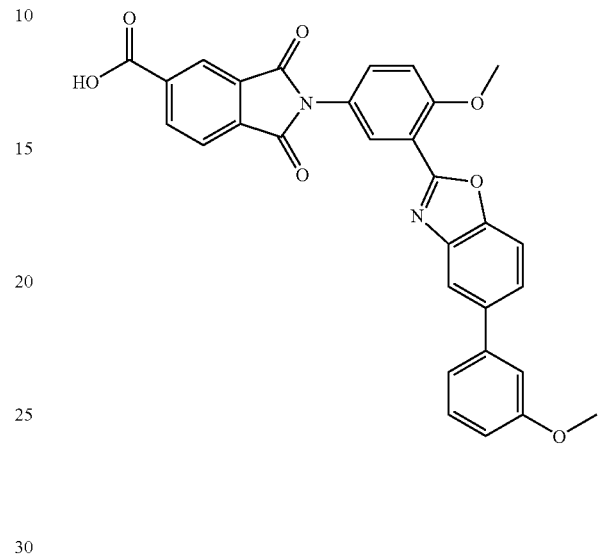

Prepared by the method of Example 15f), from 2-(3-amino-6-methoxyphenyl)-5-(3-methoxyphenyl)benzoxazole (50 mg, 0.14 mmol) and 1,2,4-benzenetricarboxylic anhydride (28 mg, 0.14 mmol) the title compound was obtained (52 mg, 71%). $^1$H NMR (DMSO) δ 8.43(d, 1H), 8.33(s, 1H), 8.22(d, 1H), 8.10(m, 2H), 7.87(d, 1H), 7.74(m, 2H), 7.48(d, 1H), 7.41(t, 1H), 7.30(m, 2H), 6.96(dd, 1H), 4.04(s, 3H), 3.85(s, 3H). MS 521.3 m/z (M+H)$^+$.

Example 107

2-[4-Methoxy-5-[5-(4-methylphenyl)benzoxazol-2-yl]phenyl]-1,3-dioxo-2,3-dihydro-1H-isoindole-5-carboxylic acid a) 2-(3-Nitro-6-methoxyphenyl)-5-(4-methylphenyl)benzoxazole Prepared by the method of Example 15d), from 2-(3-nitro-6-methoxyphenyl)-5-bromobenzoxazole (400 mg, 1.14 mmol) and 4-methylphenylboronic acid (234 mg, 1.71 mmol) the subtitle compound was obtained (273 mg, 53%). The product was used directly in the next step without purification.

b) 2-(3-Amino-6-methoxyphenyl)-5-(4-methylphenyl)benzoxazole

Prepared by the method of Example 15e), from 2-(3-nitro-6-methoxyphenyl)-5-(4-methylphenyl)benzoxazole (273 mg, 0.92 mmol) the subtitle compound was obtained (225 mg, 74%). MS 331.3 m/z (M+H)$^+$.

c) 2-[4-Methoxy-5-[5-(4-methylphenyl)benzoxazol-2-yl]phenyl]-1,3-dioxo-2,3-dihydro-1H-isoindole-5-carboxylic acid

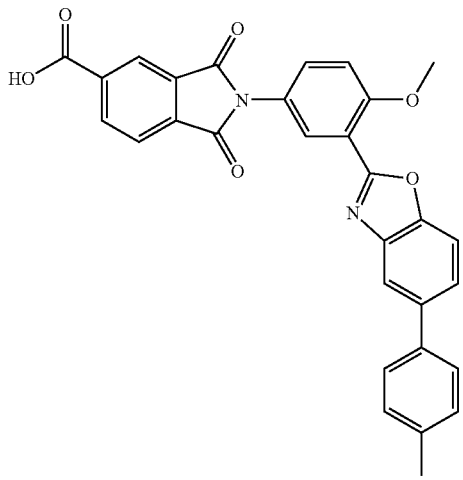

Prepared by the method of Example 15f), from 2-(3-amino-6-methoxyphenyl)-5-(4-methylphenyl)benzoxazole (75 mg, 0.23 mmol) and 1,2,4-benzenetricarboxylic anhydride (44 mg, 0.23 mmol) the title compound was obtained (78 mg, 67%). $^1$H NMR (DMSO) δ 8.43(dd, 1H), 8.33(s, 1H), 8.21(d, 1H), 8.10(d, 1H), 8.04(d, 1H), 7.85(d, 1H), 7.71(m, 2H), 7.63(d, 2H), 7.46(d, 1H), 7.30(d, 2H), 4.03(s, 3H), 2.36(s, 3H). MS 505.1 m/z (M+H)$^+$.

Example 108

2-[4-Propylamino-3-[5-(2-benzofuranyl)benzoxazol-2-yl]phenyl]-1,3-dioxo-2,3-dihydro-1H-isoindole-5-carboxylic acid a) 2-(2-Fluoro-5-nitrophenyl)-5-(2-benzofuranyl)benzoxazole Prepared by the method of Example 15d), from 2-(2-fluoro-5-nitrophenyl)-5-bromobenzoxazole (1.00 g, 3.0 mmol) and benzofuran-2-boronic acid (728 mg, 4.50 mmol) the subtitle compound was obtained (208 mg, 18%). The product was used directly in the next step without purification.

b) 2-(2-Propylamino-5-nitrophenyl)-5-(2-benzofuranyl)benzoxazole

Prepared by the method of Example 54a), from 2-(2-fluoro-5-nitrophenyl)-5-(2-benzofuranyl)benzoxazole (200 mg, 0.53 mmol), and propylamine (3 ml) the subtitle compound was obtained (199 mg, 91%). The product was used directly in the next step without purification.

c) 2-(2-Propylamino-5-aminophenyl)-5-(2-benzofuranyl)benzoxazole

Prepared by the method of Example 47b), from 2-(2-propylamino-5-nitrophenyl)-5-(2-benzofuranyl)benzoxazole (190 mg, 0.46 mmol) and zinc (300 mg, 4.6 mmol) the subtitle compound was obtained (150 mg, 85%). The product was used directly in the next step without purification.

d) 2-[4-Propylamino-3-[5-(2-benzofuranyl)benzoxazol-2-yl]phenyl]-1,3-dioxo-2,3-dihydro-1H-isoindole-5-carboxylic acid

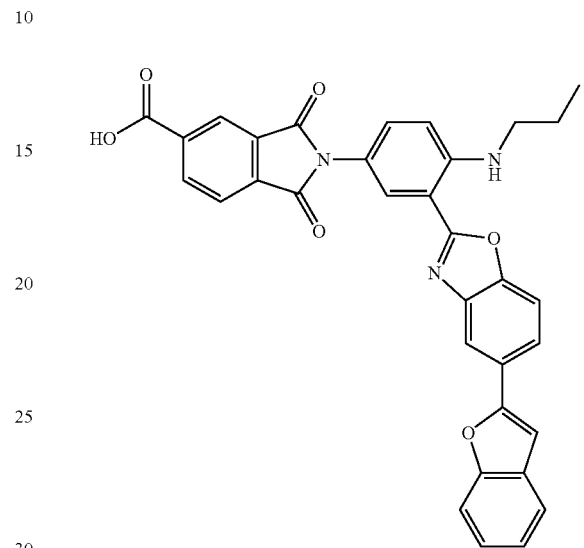

Prepared by the method of Example 1b), from 2-(2-propylamino-5-aminophenyl)-5-(2-benzofuranyl)benzoxazole (50 mg, 0.13 mmol) and 1,2,4-benzenetricarboxylic anhydride (30 mg, 0.13 mmol) the title compound was obtained (40 mg, 55%). $^1$H NMR (DMSO) δ 8.53(t, 1H), 8.46(dd, 1H), 8.37(d, 2H), 8.18(d, 1H), 8.12(d, 1H), 8.05(dd, 1H), 7.93(d, 1H), 7.72(m, 2H), 7.60(s, 1H), 7.54(dd, 1H), 7.36(m, 2H), 7.10(d, 1H), 3.44(m, 2H), 1.84(m, 2H), 1.15(t, 3H). MS 556 m/z (M−H)$^−$.

Example 109

2-[4-Propylamino-5-[5-(3,4-methylenedioxyphenyl)benzoxazol-2-yl]phenyl]-1,3-dioxo-2,3-dihydro-1H-isoindole-5-carboxylic acid a) 2-(3-Nitro-6-propylaminophenyl)-5-(3,4-methylenedioxyphenyl)benzoxazole Prepared by the method of Example 15d), from 2-(3-nitro-6-propylaminophenyl)-5-bromobenzoxazole (400 mg, 1.59 mmol) and 3,4-methylenedioxyphenylboronic acid (264 mg, 1.59 mmol) the subtitle compound was obtained (337 mg, 51%). The product was used directly in the next step without purification.

b) 2-(3-Amino-6-propylaminophenyl)-5-(methylenedioxy)phenylbenzoxazole

Prepared by the method of Example 47b), from 2-(3-nitro-6-propylaminophenyl)-5-(3,4-methylenedioxyphenyl)benzoxazole (337 mg, 0.81 mmol) and zinc (530 mg, 8.1 mmol) the subtitle compound was obtained (313 mg, 100%). MS 388.3 m/z (M+H)$^+$.

c) 2-[4-Propylamino-5-[5-(3,4-methylenedioxyphenyl)benzoxazol-2-yl]phenyl]-1,3-dioxo-2,3-dihydro-1H-isoindole-5-carboxylic acid c) 2-[4-Propylamino-5-[5-(2-benzothiophenyl)phenylbenzoxazol-2-yl]phenyl]dioxo-2,3-dihydro-1H-isoindole-5-carboxylic acid

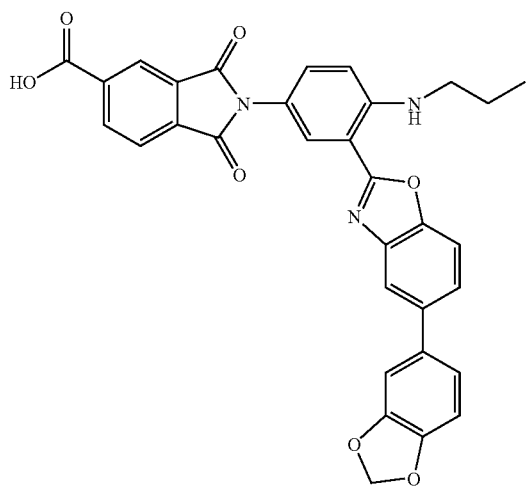

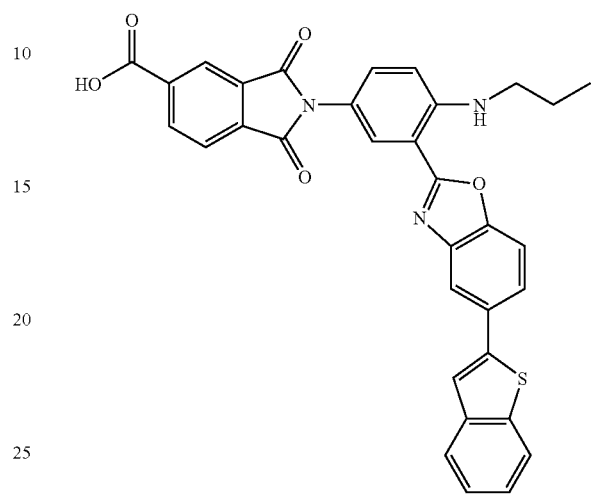

Prepared by the method of Example 15f), from 2-(3-amino-6-propylaminophenyl)-5-(3,4-methylenedioxyphenyl)benzoxazole (157 mg, 0.40 mmol) and 1,2,4-benzenetricarboxylic anhydride (76 mg, 0.40 mmol) the title compound was obtained (82 mg, 36%). $^1$H NMR (DMSO) δ 13.78(s, 1H), 8.49(t, 1H), 8.42(dd, 1H), 8.30(s, 1H), 8.12(d, 1H), 8.07(d, 1H), 8.00(d, 1H), 7.78(d, 1H), 7.64(dd, 1H), 7.47(dd, 1H), 7.35(d, 1H), 7.24(dd, 1H), 7.04(d, 1H), 7.01(d, 1H), 6.08(s, 2H), 3.35(m, 2H), 1.76(m, 2H), 1.07(t, 3H). MS 562.2 m/z (M+H)$^+$.

Prepared by the method of Example 15f), from 2-(3-amino-6-propylaminophenyl)-5-(2-benzothiophenyl)benzoxazole (180 mg, 0.45 mmol) and 1,2,4-benzenetricarboxylic anhydride (86 mg, 0.45 mmol) the title compound was obtained (100 mg, 39%). $^1$H NMR (DMSO) δ 8.48(t, 1H), 8.40(dd, 1H), 8.30(s, 1H), 8.21(s, 1H), 8.12(d, 1H), 8.04(d, 1H), 8.00(m, 2H), 7.85(m, 3H), 7.48(dd, 1H), 7.39(m, 2H), 7.04(d, 1H), 3.38(m, 2H), 1.77(m, 2H), 1.08(t, 3H). MS 574.2 m/z (M+H)$^+$.

Example 110

2-[4-Propylamino-5-[5-(2-benzothiophenyl)benzoxazol-2-yl]phenyl]-1,3-dioxo-2,3-dihydro-1H-isoindole-5-carboxylic acid a) 2-(3-Nitro-6-propylaminophenyl)-5-(2-benzothiophenyl)benzoxazole Prepared by the method of Example 15d), from 2-(3-nitro-6-propylaminophenyl)-5-bromobenzoxazole (400 mg, 1.59 mmol) and benzothiophene-2-boronic acid (283 mg, 1.59 mmol) the subtitle compound was obtained (386 mg, 57%). The product was used directly in the next step without purification.

b) 2-(3-Amino-6-propylaminophenyl)-5-(2-benzothiophenyl)benzoxazole

Prepared by the method of Example 47b), from 2-(3-nitro-6-propylaminophenyl)-5-(2-benzothiophenyl)benzoxazole (386 mg, 0.90 mmol) and zinc (589 mg, 9.0 mmol) the subtitle compound was obtained (154 mg, 100%). MS 400.3 m/z (M+H)$^+$.

Example 111

2-[4-Propylamino-5-[5-(3-methyl-4-chlorophenyl)benzoxazol-2-yl]phenyl]-1,3-dioxo-2,3-dihydro-1H-isoindole-5-carboxylic acid a) 2-(3-Nitro-6-propylaminophenyl)-5-(3-methyl-4-chlorophenyl)benzoxazole Prepared by the method of Example 15d), from 2-(3-nitro-6-propylaminophenyl)-5-bromobenzoxazole (400 mg, 1.59 mmol) and 3-methyl-4-chlorophenylboronic acid (271 mg, 1.59 mmol) the subtitle compound was obtained (230 mg, 34%). The product was used directly in the next step without purification.

b) 2-(3-Amino-6-propylaminophenyl)-5-(3-methyl-4-chlorophenyl)benzoxazole

Prepared by the method of Example 47b), from 2-(3-nitro-6-propylaminophenyl)-5-(3-methyl-4-chlorophenyl)benzoxazole (230 mg, 0.48 mmol) and zinc (314 mg, 4.8 mmol) the subtitle compound was obtained (187 mg, 100%). MS 392.3 m/z (M+H)$^+$.

c) 2-[4-Propylamino-5-[5-(3-methyl-4-chlorophenyl)benzoxazol-2-yl]phenyl]-1,3-dioxo-2,3-dihydro-1H-isoindole-5-carboxylic acid

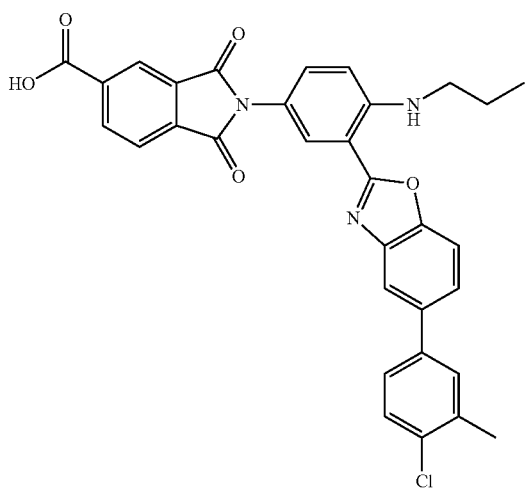

Prepared by the method of Example 15f), from 2-(3-amino-6-propylaminophenyl)-5-(3-methyl-4-chlorophenyl)benzoxazole (94 mg, 0.24 mmol) and 1,2,4-benzenetricarboxylic anhydride (45.6 mg, 0.24 mmol) in acetic acid (10 ml) the title compound was obtained (109 mg, 81%). $^1$H NMR (DMSO) δ 13.79(s, 1H), 8.49(t, 1H), 8.42(dd, 1H), 8.31(s, 1H), 8.12(d, 1H), 8.07(m, 2H), 7.83(d, 1H), 7.80(d, 1H), 7.71(dd, 1H), 7.61(dd, 1H), 7.48(m, 2H), 7.03(d, 1H), 3.38(m, 2H), 2.42(s, 3H), 1.76(m, 2H), 1.08(t, 3H). MS 566.2 m/z (M+H)$^+$.

Example 112

2-[4-Propylamino-5-[5-(4-chlorophenyl)benzoxazol-2-yl]phenyl]-1,3-dioxo-2,3-dihydro-1H-isoindole-5-carboxylic acid a) 2-(3-Nitro-6-propylaminophenyl)-5-(4-chlorophenyl)benzoxazole Prepared by the method of Example 15d), from 2-(3-nitro-6-propylaminophenyl)-5-bromobenzoxazole (400 mg, 1.59 mmol) and 4-chlorophenylboronic acid (258 mg, 1.65 mmol) the subtitle compound was obtained (284 mg, 64%). MS 408.2 m/z (M+H)$^+$.

b) 2-(3-Amino-6-propylaminophenyl)-5-(4-chlorophenyl)benzoxazole

Prepared by the method of Example 47b), from 2-(3-nitro-6-propylaminophenyl)-5-(4-chlorophenyl)benzoxazole (284 mg, 0.70 mmol) and zinc (455 mg, 7.0 mmol) the subtitle compound was obtained (264 mg, 99%). The product was used directly in the next step without purification c) 2-[4-Propylamino-5-[5-(4-chloro)phenylbenzoxazol-2-yl]phenyl]-1,3-dioxo-2,3-dihydro-1H-isoindole-5-carboxylic acid

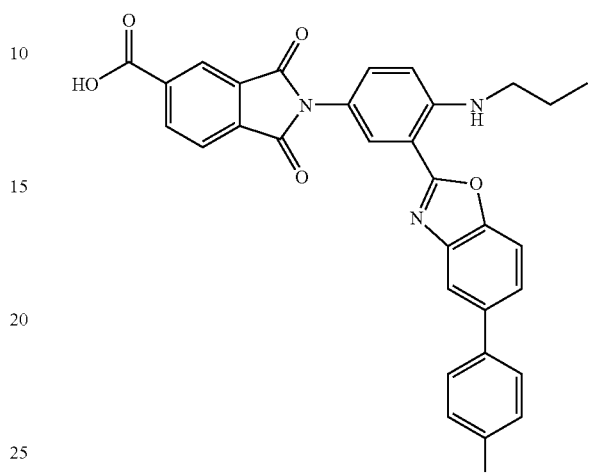

Prepared by the method of Example 15f), from 2-(3-amino-6-propylaminophenyl)-5-(4-chlorophenyl)benzoxazole (136 mg, 0.36 mmol) and 1,2,4-benzenetricarboxylic anhydride (68 mg, 0.36 mmol) in acetic acid (10 ml) the title compound was obtained (104 mg, 52%). $^1$H NMR (DMSO) δ 13.78(s, 1H), 8.49(t, 1H), 8.42(dd, 1H), 8.31(s, 1H), 8.12(d, 1H), 8.08(m, 2H), 7.81(m, 3H), 7.71(dd, 1H), 7.54 (d, 2H), 7.48(dd, 1H), 7.05(d, 1H), 3.35(m, 2H), 1.77(m, 2H), 1.08(t, 3H). MS 552.2 m/z (M+H)$^+$.

Example 113

2-[4-Propylamino-5-[5-(3-chloro-4-fluoro)phenylbenzoxazol-2-yl]phenyl]-1,3-dioxo-2,3-dihydro-1H-isoindole-5-carboxylic acid a) 2-(3-Nitro-6-propylaminophenyl)-5-(3-chloro-4-fluoro)phenylbenzoxazole Prepared by the method of Example 15d), from 2-(3-nitro-6-propylaminophenyl)-5-bromobenzoxazole (360 mg, 0.96 mmol) and 3-chloro-4-fluorophenylboronic acid (250 mg, 1.40 mmol) the subtitle compound was obtained (408 mg, 99%). MS 426.2 m/z(M+H)$^+$.

b) 2-(3-Amino-6-propylaminophenyl)-5-(3-chloro-4-fluoro)phenylbenzoxazole

Prepared by the method of Example 47b), from 2-(3-nitro-6-propylaminophenyl)-5-(3-chloro-4-fluorophenyl)benzoxazole (408 mg, 0.96 mmol) and zinc (627 mg, 9.6 mmol) the subtitle compound was obtained (175 mg, 46%). The product was used directly in the next step without purification.

c) 2-[4-Propylamino-5-[5-(3-chloro-4-fluoro)phenylbenzoxazol-2-yl]phenyl]-1,3-dioxo-2,3-dihydro-1H-isoindole-5-carboxylic acid

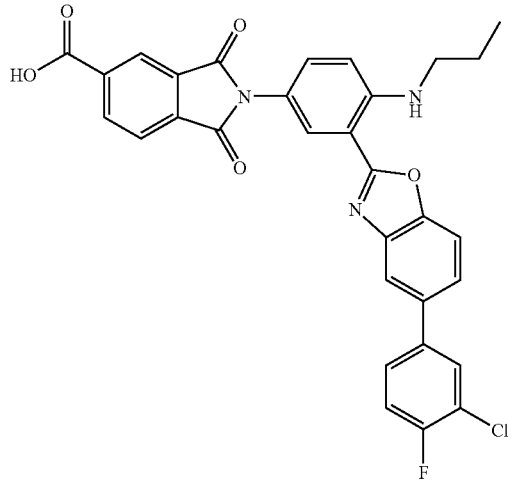

Prepared by the method of Example 15f), from 2-(3-amino-6-propylaminophenyl)-5-(3-chloro-4-fluorophenyl)benzoxazole (70 mg, 0.18 mmol) and 1,2,4-benzenetricarboxylic anhydride (34 mg, 0.18 mmol) the title compound was obtained (60 mg, 59%). $^1$H NMR (DMSO) δ 13.78(s, 1H), 8.48(t, 1H), 8.42(dd, 1H), 8.30(s, 1H), 8.11(m, 2H), 8.07(d, 1H), 8.01(dd, 1H), 7.83(d, 1H), 7.78(m, 1H), 7.72(dd, 1H), 7.50(m, 2H), 7.04(d, 1H), 3.39(m, 2H), 1.76(m, 2H), 1.07(t, 3H). MS 570.1 m/z (M+H)$^+$.

Example 114

2-[4-Propylamino-5-[5-(3,5-difluoro)phenylbenzoxazol-2-yl]phenyl]-1,3-dioxo-2,3-dihydro-1H-isoindole-5-carboxylic acid a) 2-(3-Nitro-6-propylaminophenyl)-5-(3,5-difluoro)phenylbenzoxazole Prepared by the method of Example 15d), from 2-(3-nitro-6-propylaminophenyl)-5-bromobenzoxazole (360 mg, 0.96 mmol) and 3,5-difluorophenylboronic acid (226 mg, 1.40 mmol) the subtitle compound was obtained (309 mg, 78%). MS 410.2 m/z(M+H)$^+$.

b) 2-(3-Amino-6-propylaminophenyl)-5-(3,5-difluoro)phenylbenzoxazole

Prepared by the method of Example 47b), from 2-(3-nitro-6-propylaminophenyl)-5-(3,5-difluorophenyl)benzoxazole (309 mg, 0.76 mmol) and zinc (497 mg, 7.6 mmol) the subtitle compound was obtained (227 mg, 79%). The product was used directly in the next step without purification.

c) 2-[Propylamino-5-[5-(3,5-difluoro)phenylbenzoxazol-2-yl]phenyl]-1,3-dioxo-2,3-dihydro-1H-isoindole-5-carboxylic acid

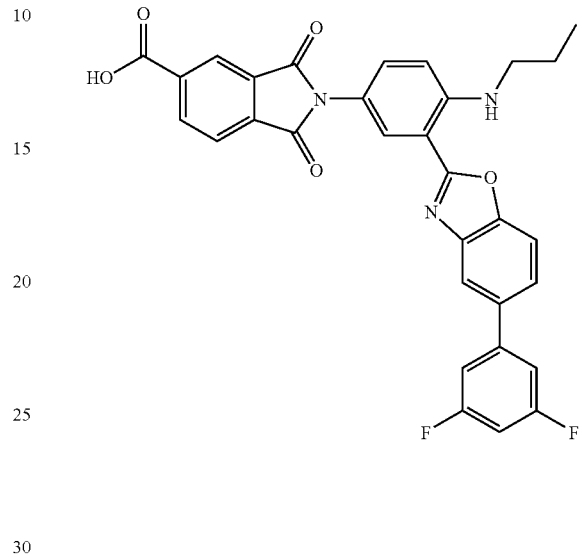

Prepared by the method of Example 15f), from 2-(3-amino-6-propylaminophenyl)-5-(3,5-difluorophenyl)benzoxazole (90 mg, 0.24 mmol) and 1,2,4-benzenetricarboxylic anhydride (45 mg, 0.24 mmol) the title compound was obtained. (80 mg, 61%). $^1$H NMR (DMSO) δ 13.77(s, 1H), 8.47(t, 1H), 8.41(dd, 1H), 8.30(s, 1H), 8.20(d, 1H), 8.11(d, 1H), 8.07(d, 1H), 7.84(d, 1H), 7.79(dd, 1H), 7.58(m, 2H), 7.47(dd, 1H), 7.24(m, 1H), 7.03(d, 1H), 3.38(m, 2H), 1.76(m, 2H), 1.08(t, 3H). MS 554.1 m/z (M+H)$^+$.

Example 115

2-[4-Propylamino-5-[5-(4-fluorophenyl)benzoxazol-2-yl]phenyl]-1,3-dioxo-2,3-dihydro-1H-isoindole-5-carboxylic acid a) 2-(3-Nitro-6-propylaminophenyl)-5-(4-fluoro)phenylbenzoxazole Prepared by the method of Example 15d), from 2-(3-nitro-6-propylaminophenyl)-5-bromobenzoxazole (360 mg, 0.96 mmol) and 4-fluorophenylboronic acid (201 mg, 1.40 mmol) the subtitle compound was obtained (184 mg, 49%). MS 392.3 m/z (M+H)$^+$.

b) 2-(3-Amino-6-propylaminophenyl)-5-(4-fluoro)phenylbenzoxazole

Prepared by the method of Example 47b), from 2-(3-nitro-6-propylaminophenyl)-5-(4-fluorophenyl)benzoxazole (184 mg, 0.47 mmol) and zinc (307 mg, 4.7 mmol) the subtitle compound was obtained (108 mg, 63%). The product was used directly in the next step without purification.

c) 2-[4-Propylamino-5-[5-(4-fluorophenyl)benzoxazol-2-yl]phenyl]-1,3-dioxo-2,3-dihydro-1H-isoindole-5-carboxylic acid c) 2-[4-Propylamino-5-[5-(4-trifluoromethoxy)phenylbenzoxazol-2-yl]phenyl]-1,3-dioxo-2,3-dihydro-1H-isoindole-5-carboxylic acid

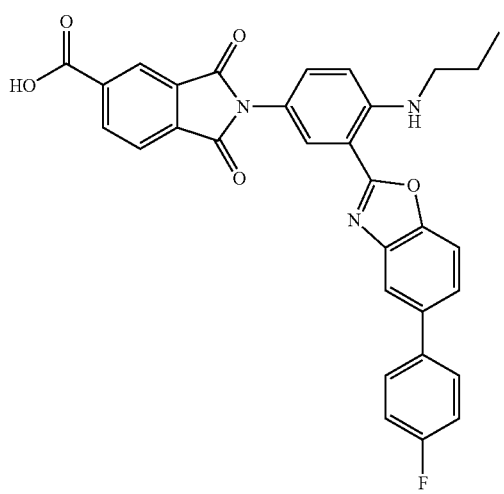

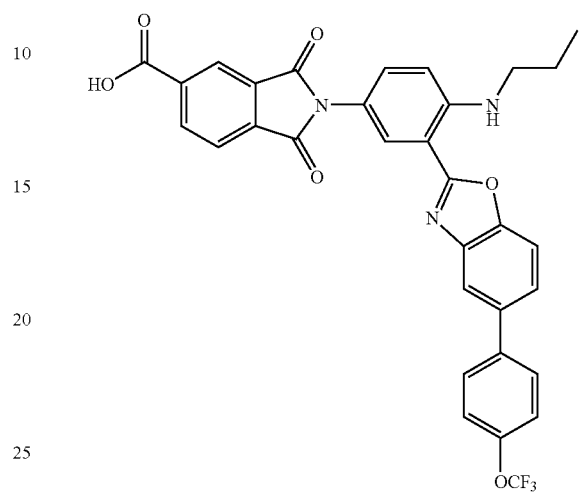

Prepared by the method of Example 15f), from 2-(3-amino-6-propylaminophenyl)-5-(4-fluorophenyl)benzoxazole (108 mg, 0.30 mmol) and 1,2,4-benzenetricarboxylic anhydride (57 mg, 0.30 mmol) the title compound was obtained. (74 mg, 46%). $^1$H NMR (DMSO) δ 13.63(s, 1H), 8.49(t, 1H), 8.42(dd, 1H), 8.31(s, 1H), 8.12(d, 1H), 8.08(m, 2H), 7.81(m, 3H), 7.68(dd, 1H), 7.47(dd, 1H), 7.32(t, 2H), 7.03(d, 1H), 3.34(m, 2H), 1.76(m, 2H), 1.07(t, 3H). MS 536.2 m/z (M+H)$^+$.

Example 116

2-[4-Propylamino-5-[5-(4-trifluoromethoxy)phenylbenzoxazol-2-yl]phenyl]-1,3-dioxo-2,3-dihydro-1H-isoindole-5-carboxylic acid a) 2-(3-Nitro-6-propylaminophenyl)-5-(4-trifluoromethoxy)phenylbenzoxazole Prepared by the method of Example 15d), from 2-(3-nitro-6-propylaminophenyl)-5-bromobenzoxazole (360 mg, 0.96 mmol) and 4-trifluoromethoxyphenylboronic acid (297 mg, 1.40 mmol) the subtitle compound was obtained (249 mg, 57%). MS 458.3 m/z (M+H)$^+$.

b) 2-(3-Amino-6-propylaminophenyl)-5-(4-trifluoromethoxy)phenylbenzoxazole

Prepared by the method of Example 47b), from 2-(3-nitro-6-propylaminophenyl)-5-(4-trifluoromethoxyphenyl)benzoxazole (249 mg, 0.55 mmol) and zinc (360 mg, 5.5 mmol) the subtitle compound was obtained (166 mg, 71%). The product was used directly in the next step without purification.

Prepared by the method of Example 15f), from 2-(3-amino-6-propylaminophenyl)-5-(4-trifluoromethoxyphenyl)benzoxazole (83 mg, 0.19 mmol) and 1,2,4-benzenetricarboxylic anhydride (36 mg, 0.19 mmol) the title compound was obtained (23 mg, 21%). $^1$H NMR (DMSO) δ 13.81(s, 1H), 8.49(t, 1H), 8.42(dd, 1H), 8.31(s, 1H), 8.13(m, 2H), 8.06(d, 1H), 7.90(d, 2H), 7.84(d, 1H), 7.72(dd, 1H), 7.48(d, 3H), 7.04(d, 1H), 3.34(m, 2H), 1.76(m, 2H), 1.07(t, 3H). MS 602.1 m/z (M+H)$^+$.

Example 117

2-[4-Propylamino-5-[5-(4-trifluoromethyl)phenylbenzoxazol-2-yl]phenyl]-1,3-dioxo-2,3-dihydro-1H-isoindole-5-carboxylic acid a) 2-(3-Nitro-6-propylaminophenyl)-5-(4-trifluoromethyl)phenylbenzoxazole Prepared by the method of Example 15d), from 2-(3-nitro-6-propylaminophenyl)-5-bromobenzoxazole (180 mg, 0.48 mmol) and 4-trifluoromethylphenylboronic acid (137 mg, 0.72 mmol) the subtitle compound was obtained (126 mg, 59%). MS 442.3 m/z (M+H)$^+$.

b) 2-(3-Amino-6-propylaminophenyl)-5-(4-trifluoromethyl)phenylbenzoxazole

Prepared by the method of Example 47b), from 2-(3-nitro-6-propylaminophenyl)-5-(4-trifluoromethylphenyl)benzoxazole (126 mg, 0.29 mmol) and zinc (189 mg, 2.9 mmol), the subtitle compound was obtained (68 mg, 57%). The product was used directly in the next step without purification.

c) 2-[4-Propylamino-5-[5-(4-trifluoromethyl)phenylbenzoxazol-2-yl]phenyl]-1,3-dioxo-2,3-dihydro-1H-isoindole-5-carboxylic acid

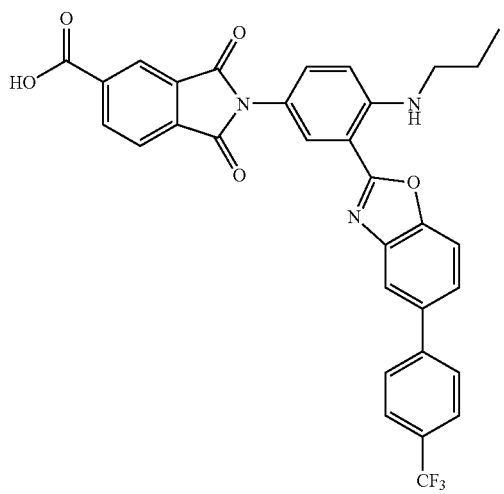

Prepared by the method of Example 15f), from 2-(3-amino-6-propylaminophenyl)-5-(4-trifluoromethylphenyl)benzoxazole (116 mg, 0.28 mmol) and 1,2,4-benzenetricarboxylic anhydride (53 mg, 0.28 mmol) in acetic acid (10 ml) the title compound was obtained (83 mg, 51%). $^1$H NMR (DMSO) δ 13.78(s, 1H), 8.49(t, 1H), 8.42(dd, 1H), 8.31(s, 1H), 8.13(m, 2H), 8.07(d, 1H), 7.84(m, 2H), 7.74(dd, 2H), 7.49(m, 3H), 7.04(d, 1H), 3.37(m, 2H), 1.76(m, 2H), 1.08(t, 3H). MS 586.2 m/z (M+H)$^+$.

Example 118

2-[4-Propylamino-5-[5-(3-chloro)phenylbenzoxazol-2-yl]phenyl-]-1,3-dioxo-2,3-dihydro-1H-isoindole-5-carboxylic acid a) 2-(3-Nitro-6-propylaminophenyl)-5-(3-chloro)phenylbenzoxazole Prepared by the method of Example 15d), from 2-(3-nitro-6-propylaminophenyl)-5-bromobenzoxazole (360 mg, 0.96 mmol) and 3-chlorophenylboronic acid (225 mg, 1.40 mmol) the subtitle compound was obtained (390 mg, 99%). MS 408.2 m/z(M+H)$^+$.

b) 2-(3-Amino-6-propylaminophenyl)-5-(3-chloro)phenylbenzoxazole

Prepared by the method of Example 47b), from 2-(3-nitro-6-propylaminophenyl)-5-(3-chlorophenyl)benzoxazole (390 mg, 0.96 mmol) and zinc (627 mg, 9.6 mmol) the subtitle compound was obtained (256 mg, 71%). The product was used directly in the next step without purification.

c) 2-[4-Propylamino-5-[5-(3-chloro)phenylbenzoxazol-2-yl]phenyl]-1,3-dioxo-2,3-dihydro-1H-isoindole-5-carboxylic acid

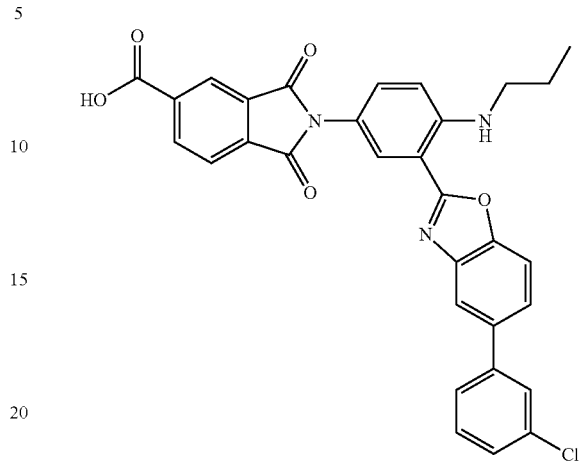

Prepared by the method of Example 15f), from 2-(3-amino-6-propylaminophenyl)-5-(3-chlorophenyl)benzoxazole (80 mg, 0.21 mmol) and 1,2,4-benzenetricarboxylic anhydride (40 mg, 0.21 mmol) in acetic acid (10 ml) the title compound was obtained (42 mg, 37%). $^1$H NMR (DMSO) δ 13.82(s, 1H), 8.49(t, 1H), 8.40(dd, 1H), 8.30(s, 1H), 8.11(d, 1H), 8.06(m, 2H), 7.81(m, 3H), 7.68(dd, 1H), 7.47 (dd, 1H), 7.32(m, 2H), 7.04(d, 1H), 3.37(m, 2H), 1.76(m, 2H), 1.07(t, 3H). MS 552.1 m/z (M+H)$^+$.

Biological Data

Heparanase Assay:

The assay is based upon the specific binding of basic fibroblast growth factor (bFGF) to heparan sulfate. Hence, heparan sulfate concentrations can be detected using bFGF and a horse radish peroxidase-conjugated bFGF antibody. Heparan sulfate will ordinarly adhere to plastic well plate surfaces. Following cleavage of high molecular weight heparan sulfate by heparanase, the smaller material generated will no longer adhere to the surface of a well plate. Thus, upon addition to the plate of bFGF, heparanase activity can be followed as a reduction in bFGF binding.

Nunc Maxisorp 96-well plates are coated for 16 h at room temperature with 100 μl/well 0.04 mg/ml heparan sulfate in PBS. The wells are then aspirated and blocked for 1 h with 200 μl/well 1% BSA-PBS. Following five washes with 0.01% BSA, 0.05% Tween20 PBS (wash buffer), 100 μl of recombinant human basic FGF (90 ng/ml in 0.1% BSA/PBS) is added per well and the plate is incubated at room temperature for 1 h.

After a further five washes with the wash buffer, 10 μl of test compound (in 10% DMSO) and 90 μl of human heparanase (Vlodavsky I et al., (1999) Nat. Med. 5, 793–802) in 100 mM Sodium acetate, 5 mM CaCl$_2$, pH 5.5 are added to each well and the plate incubated for 2 h at 37° C. The human heparanase used is expressed in insect cells. The wells are washed again with wash buffer and 100 μl of bFGF antibody-horse radish peroxidase conjugate is added. The plate is then incubated at room temperature for 1 h and subsequently washed five times with wash buffer. 100 μl of TMB peroxidase substrate is added and the colour allowed to develop for 10 min. The reaction is stopped with 50 μl 1M H$_2$SO$_4$ and the colour intensity is read at 450 nm on a plate reader.

Angiogenesis Assay

A commercial angiogenesis assay for analysing the angiogenic or anti-angiogenic properties of test compounds (AngioKit catalogue no. ZHA-1000, TCS CellWorks Ltd, Buckingham, U.K) was used. In this assay, human endothelial cells were co-cultured with other human cells in a specifically designed medium. The endothelial cells initially form small islands within the culture matrix. They subsequently proliferate and then enter a migratory phase during which they move through the matrix to form threadlike tubule structures. These gradually join up (by 12–14 days) to form networks of anatomising tubules which closely resemble a capillary bed structure. These tubules stain positive for von Willebrand's Factor, Platelet Endothelial Cell Adhesion Molecule-1 (PECAM-1 or CD31) and Intercellular Adhesion Molecule-2 (ICAM-2).

The assay is supplied as growing cultures at the earliest stage of tubule formation in a 24 well plate format It is designed so that test compounds and conditioned media can be added to the cultures within individual wells. The resulting effect on tubule formation can then be monitored. Positive and negative test agents are provided in the kit, e.g. Vascular Endothelial Growth Factor (VEGF) and sumarin. All reagents were included as part of the kit and the assay was performed according to the protocol supplied by TCS CellWorks Ltd. Briefly, on day 1, fresh growth medium, medium plus control agent or medium plus test compound was added to the cells and the cultures were incubated at 37° C., 5% $CO_2$. Test compounds were dissolved in DMSO and the final concentration of DMSO in the medium did not exceed 0.1% (v/v). The specified medium was changed at days 4, 7 and 9 and the cells were monitored for growth. On day 11, the cells were washed with Dulbecco's Phosphate-Buffered Saline (PBS) and fixed using 70% ethanol (−20° C.) for 30 min at room temperature. After fixing, the cells were washed and treated with blocking buffer, 1% BSA in PBS. The cells were stained for PECAM-1 on the same day, following standard immunohistochemistry procedures well known to those skilled in the art, using mouse anti-human CD31 as the primary antibody and a goat anti-mouse IgG alkaline phosphate conjugate. Tubule formation was quantitatively assessed by measuring PECAM-1 positive staining using the image analysis program "Matrox inspector" to evaluate the percentage tubule staining relative to an untreated control.

| Compound | Inhibition of Heparanase ($IC_{50}$, µM) | Inhibition of angiogenesis ($IC_{50}$, µM) |
|---|---|---|
| Example 1 | 5.0 | 40.0 |
| Example 2 | 0.7 | 5.0 |
| Example 9 | 3.0 | 1.0 |
| Example 15 | 0.5 | 1.0 |
| Example 27 | 0.4 | 15.0 |
| Example 65 | 0.8 | 5.0 |
| Example 66 | 0.8 | 2.0 |
| Example 71 | 0.5 | 0.5 |
| Example 92 | 0.4 | 0.2 |
| Example 97 | 0.8 | 2.0 |
| Example 104 | 0.9 | 0.75 |
| Example 105 | 0.2 | 3.0 |
| Example 108 | 0.5 | 2.0 |
| Example 110 | 0.6 | 5.0 |
| Example 112 | 0.2 | 2.0 |
| Example 115 | 0.5 | 0.25 |
| Example 116 | 0.8 | 0.1 |

The invention claimed is:
1. A compound of formula (I) or a pharmaceutically acceptable salt or prodrug thereof:

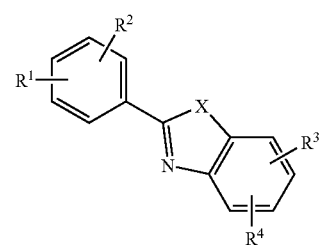

wherein
X is O or S;
$R^1$ is a phthalimide carboxylic acid group of formula (II):

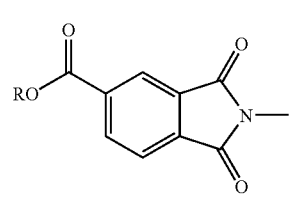

R is hydrogen, $C_1$–$C_6$ alkyl, aryl or $C_1$–$C_3$ alkylaryl;
$R^2$ is hydrogen, halogen, $C_1$–$C_6$ alkyl, $OR^5$, a 5-membered heteroaryl ring, or $NR^5R^5$;
$R^3$ and $R^4$ are independently hydrogen, halogen, $C_1$–$C_6$ alkyl optionally substituted by hydroxy or $C_1$–$C_3$ alkoxy, $CF_3$, $OCF_3$, $OR^{10}$, $COR^6$, $NHCOR^7$, $NHSO_2R^9$, CN, $S(O)_pR^9$, phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^6$, CN, CHO, $OCHF_2$, $NR^7R^8$, $NHCOR^7$, $NHSO_2R^9$, $S(O)_pR^9$ and methylenedioxo, or a 5- to 10-membered heteroaryl ring which is optionally substituted by $C_1$–$C_6$ alkyl;
or $R^3$ and $R^4$ together form a fused phenyl ring or a —O—$(CH_2)_x$—O— group, wherein x is 1 or 2;
$R^5$ is independently hydrogen, $C_3$–$C_6$ alkenyl, $C_3$–$C_6$ alkynyl, or $C_1$–$C_6$ alkyl optionally substituted by hydroxy, $C_1$–$C_3$ alkoxy, $NR^7R^8$, phenyl or a 5- or 6-membered heteroaryl ring, wherein phenyl is optionally substituted by one or more substituents selected from halogen, $CF_3$, $OCF_3$, CHO, $OR^{10}$, $COR^{10}$, $R^{10}$, CN and methylenedioxo and wherein the heteroaryl ring is optionally substituted by $C_1$–$C_6$ alkyl;
or $R^5$ and $R^5$, together with the nitrogen atom to which they are attached, form a 5- or 6-membered ring which optionally contains an additional heteroatom selected from O, S, and $NR^{10}$;
$R^6$ is $C_1$–$C_6$ alkyl, $OR^5$, $NR^7R^8$ or phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^{10}$, CN, CHO, $OCHF_2$, $NR^7R^8$, $NHCOR^7$, $NHSO_2R^9$, $S(O)_pR^9$ and methylenedioxo;
$R^7$ and $R^8$ are independently hydrogen, phenyl, a 5- to 10-membered heterocyclic ring, $C_1$–$C_6$ alkoxy, or $C_1$–$C_6$ alkyl optionally substituted by phenyl or a 5- to 10-membered heterocyclic ring, wherein in each case, the phenyl is optionally substituted by one or more substituents selected from halogen, $CF_3$, $OCF_3$, CHO, $OR^{10}$, $COR^{10}$, $R^{10}$, CN and methylenedioxo and the heterocyclic ring is optionally substituted by $C_1–C_6$ alkyl;

or $R^7$ and $R^8$ together with the nitrogen to which they are attached form a 5- or 6-membered heterocyclic ring which is optionally substituted by $CONR^{10}R^{10}$ and optionally contains an additional heteroatom selected from O, S and $NR^{11}$;

$R^9$ is $C_1–C_6$ alkyl or phenyl optionally substituted by one or more substituents selected from halogen, $CF_3$, $OCF_3$, CHO, $OR^{10}$, $COR^{10}$, $R^{10}$, CN and methylenedioxo;

$R^{10}$ is hydrogen, $C_3–C_6$ alkenyl, $C_3–C_6$ alkynyl, or $C_1–C_6$ alkyl optionally substituted by hydroxy or $C_1–C_3$ alkoxy;

$R^{11}$ is hydrogen, phenyl or $C_1–C_3$ alkyl optionally substituted by phenyl, wherein in each case the phenyl is optionally substituted by one or more substituents selected from halogen, $CF_3$, $OCF_3$, CHO, $OR^{10}$, $COR^{10}$, $R^{10}$, CN and methylenedioxo; and p is 0, 1 or 2;

provided that the compound is not 2-[4-(5-carboxy-1,3-dihydro-1,3-dioxo-2H-isoindol-2-yl)phenyl]-6-benzothiazolecarboxylic acid.

2. A compound according to claim 1 wherein X is O.

3. A compound according to claim 1 wherein $R^1$ is meta to the benzoxazole or benzothiazole group.

4. A compound according to claim 1 wherein $R^2$ is hydrogen, $OR^5$ or $NR^5R^5$.

5. A compound according to claim 1 wherein $R^3$ is hydrogen or halogen.

6. A compound according to claim 1 wherein $R^4$ is hydrogen, halogen, $C_1–C_6$ alkyl optionally substituted by hydroxy or $C_1–C_3$ alkoxy, $CF_3$, $OCF_3$, $OR^{10}$, $COR^6$, phenyl optionally substituted by one or more substituents selected from halogen, $C_1–C_6$ alkyl optionally substituted by hydroxy or $C_1–C_3$ alkoxy, $CF_3$, $OCF_3$, $OR^5$, $COR^6$, CN, CHO, $OCHF_2$ and $NR^7R^8$, or a 5- to 10-membered heteroaryl ring which is optionally substituted by $C_1–C_6$ alkyl; or $R^3$ and $R^4$ together form a fused phenyl ring.

7. A compound according to claim 6 wherein $R^4$ is $COR^6$, phenyl optionally substituted by one or more substituents selected from halogen, $C_1–C_6$ alkyl optionally substituted by hydroxy or $C_1–C_3$ alkoxy, $CF_3$, $OCF_3$, $OR^5$, $COR^6$, CN, CHO, $OCHF_2$ and $NR^7R^8$, or a 5- to 10-membered heteroaryl ring which is optionally substituted by $C_1–C_6$ alkyl.

8. A compound according to claim 1 wherein each $R^5$ is, independently, hydrogen, $C_3–C_6$ alkenyl, $C_3–C_6$ alkynyl, or $C_1–C_6$ alkyl optionally substituted by hydroxy, $C_1–C_3$ alkoxy or a 5- or 6-membered heteroaryl ring, wherein the heteroaryl ring is optionally substituted by $C_1–C_6$ alkyl.

9. A compound according to claim 1 wherein $R^6$ is $C_1–C_6$ alkyl, $OR^5$ or $NR^7R^8$.

10. A compound according to claim 9 wherein $R^6$ is $OR^5$ or $NR^7R^8$.

11. A compound according to claim 1 wherein $R^7$ and $R^8$ are independently hydrogen, or $C_1–C_6$ alkyl optionally substituted by phenyl or a 5- to 10-membered heterocyclic ring, wherein the phenyl is optionally substituted by one or more substituents selected from halogen, $CF_3$, $OCF_3$, CHO, $OR^{10}$, $COR^{10}$, $R^{10}$, CN and methylenedioxo and the heterocyclic ring is optionally substituted by $C_1–C_6$ alkyl; or $R^7$ and $R^8$ together with the nitrogen to which they are attached form a 5- or 6-membered heterocyclic ring which is optionally substituted by $CONH_2$ and optionally contains an additional heteroatom selected from O, S and $NR^{11}$.

12. A compound according to claim 1 wherein $R^9$ is $C_1–C_6$ alkyl.

13. A compound which is

2-[3-(Benzoxazol-2-yl)phenyl]-2,3-dihydro-1,3-dioxo-1H-isoindole-5-carboxylic acid;

2-[3-(Naphth[2,3-d]oxazol-2-yl)phenyl]-2,3-dihydro-1,3-dioxo-1H-isoindole-5-carboxylic acid;

2-[3-(6-Methylbenzoxazol-2-yl)phenyl]-2,3-dihydro-1,3-dioxo-1H-isoindole-5-carboxylic acid;

2-[3-(5-Chlorobenzoxazol-2-yl)phenyl]-2,3-dihydro-1,3-dioxo-1H-isoindole-5-carboxylic acid;

2-[3-(5-Phenylbenzoxazol-2-yl)phenyl]-2,3-dihydro-1,3-dioxo-1H-isoindole-5-carboxylic acid;

2-[2-Methoxy-5-(naphth[2,3-d]oxazol-2-yl)phenyl]-2,3-dihydro-1,3-dioxo-1H-isoindole-5-carboxylic acid;

2-[2-Methoxy-5-(6-methylbenzoxazol-2-yl)phenyl]-2,3-dihydro-1,3-dioxo-1H-isoindole-5-carboxylic acid;

2-[2-Methoxy-5-(5-chlorobenzoxazolyl)phenyl]-2,3-dihydro-1,3-dioxo-1H-isoindole-5-carboxylic acid;

2-[2-Methoxy-5-(5-phenylbenzoxazol-2-yl)phenyl]-1,3-dioxo-2,3-dihydro-1H-isoindole-5-carboxylic acid;

2-[2-Methoxy-5-(benzoxazol-2-yl)phenyl]-2,3-dihydro-1,3-dioxo-1H-isoindole-5-carboxylic acid;

2-[2-Chloro-(5-chlorobenzoxazol-2-yl)phenyl]-2,3-dihydro-1,3-dioxo-1H-isoindole-5-carboxylic acid;

2-[4-Chloro-(5-phenylbenzoxazol-2-yl)phenyl]-2,3-dihydro-1,3-dioxo-1H-isoindole-5-carboxylic acid;

2-[2-Methyl-5-(5-phenylbenzoxazol-2-yl)phenyl]-2,3-dihydro-1,3-dioxo-1H-isoindole-5-carboxylic acid;

2-[2-Methyl-5-(benzoxazol-2-yl)phenyl]-2,3-dihydro-1,3-dioxo-1H-isoindole-5-carboxylic acid;

2-[2-Methoxy-5-[5-(benzofuran-2-yl)benzoxazol-2-yl]phenyl]-1,3-dioxo-2,3-dihydro-1H-isoindole-5-carboxylic acid;

2-[2-Methoxy-5-[5-(3-acetyl)phenylbenzoxazol-2yl]phenyl]-1,3-dioxo-2,3-dihydro-1H-isoindole-5-carboxylic acid;

2-[2-Methoxy-5-[5-(3,4-methylenedioxyphenyl)benzoxazol-2-yl]phenyl]-1,3-dioxo-2,3-dihydro-1H-isoindole-5-carboxylic acid;

2-[2-Methoxy-5-[5-(4-chlorophenyl)benzoxazol-2-yl]phenyl]-1,3-dioxo-2,3-dihydro-1H-isoindole-5-carboxylic acid;

2-[2-Methoxy-5-[5-(3,4-dimethoxy)phenylbenzoxazol-2-yl]phenyl]-1,3-dioxo-2,3-dihydro-1H-isoindole-5-carboxylic acid;

2-[2-Methoxy-5-[5-(2-methoxy)phenylbenzoxazol-2-yl]phenyl]-1,3-dioxo-2,3-dihydro-1H-isoindole-5-carboxylic acid;

2-[2-Methoxy-5-[5-(3,4-dichloro)phenylbenzoxazol-2-yl]phenyl]-1,3-dioxo-2,3-dihydro-1H-isoindole-5-carboxylic acid;

2-[2-Methoxy-5-[5-(3-chloro-4-fluoro)phenylbenzoxazol-2-yl]phenyl]-1,3-dioxo-2,3-dihydro-1H-isoindole-5-carboxylic acid;

2-[2-Methoxy-5-[5-(4-trifluoromethyl)phenylbenzoxazol-2-yl]phenyl]-1,3-dioxo-2,3-dihydro-1H-isoindole-5-carboxylic acid;

2-[2-Methoxy-5-[5-[4-(1-hydroxyethyl)]phenylbenzoxazol-2-yl]phenyl]-1,3-dioxo-2,3-dihydro-1H-isoindole-5-carboxylic acid;

2-[2-Methoxy-5-[5-(4-methyl)phenylbenzoxazol-2-yl]phenyl]-1,3-dioxo-2,3-dihydro-1H-isoindole-5-carboxylic acid;

2-[2-Methoxy-5-[5-[(5-methyl)thiophen-2-yl]benzoxazol-2-yl]phenyl]-1,3-dioxo-2,3-dihydro-1H-isoindole-5-carboxylic acid;
2-[2-Methoxy-5-[5-(4-methoxy)phenylbenzoxazol-2-yl]phenyl]-1,3-dioxo-2,3-dihydro-1H-isoindole-5-carboxylic acid;
2-[2-Methoxy-5-[5-(3-cyano)phenylbenzoxazol-2-yl]phenyl]-1,3-dioxo-2,3-dihydro-1H-isoindole-5-carboxylic acid;
2-[2-Methoxy-5-[5-(3-methyl)phenylbenzoxazol-2-yl]phenyl]-1,3-dioxo-2,3-dihydro-1H-isoindole-5-carboxylic acid;
2-[2-Methoxy-5-[5-(3-methoxy)phenylbenzoxazol-2-yl]phenyl]-1,3-dioxo-2,3-dihydro-1H-isoindole-5-carboxylic acid;
2-[2-Methoxy-5-[5-(3-fluoro)phenylbenzoxazol-2-yl]phenyl]-1,3-dioxo-2,3-dihydro-1H-isoindole-5-carboxylic acid;
2-[2-Methoxy-5-[5-(3-chloro)phenylbenzoxazol-2-yl]phenyl]-1,3-dioxo-2,3-dihydro-1H-isoindole-5-carboxylic acid;
2-[2-Methoxy-5-[5-(4-fluoro)phenylbenzoxazol-2-yl]phenyl]-1,3-dioxo-2,3-dihydro-1H-isoindole-5-carboxylic acid;
2-[2-Methoxy-5-[5-(2,4-difluoro)phenylbenzoxazol-2-yl]phenyl]-1,3-dioxo-2,3-dihydro-1H-isoindole-5-carboxylic acid;
2-[2-Methoxy-5-[5-(3,5-difluoro)phenylbenzoxazol-2-yl]phenyl]-1,3-dioxo-2,3-dihydro-1H-isoindole-5-carboxylic acid;
2-[2-Methoxy-5-[5-(4-trifluoromethoxy)phenylbenzoxazol-2-yl]phenyl]-1,3-dioxo-2,3-dihydro-1H-isoindole-5-carboxylic acid;
2-[2-Methoxy-5-[5-(4-trifluoromethoxy)phenylbenzoxazol-2-yl]phenyl]-1,3-dioxo-2,3-dihydro-1H-isoindole-5-carboxylic acid;
2-[2-Methoxy-5-[5-(2,4-dichloro)phenylbenzoxazol-2-yl]phenyl]-1,3-dioxo-2,3-dihydro-1H-isoindole-5-carboxylic acid;
2-[2-Propargyloxy-5-(5-phenylbenzoxazol-2-yl)phenyl]-1,3-dioxo-2,3-dihydro-1H-isoindole-5-carboxylic acid;
2-[2-Ethoxy-5-(5-phenylbenzoxazol-2-yl)phenyl]-1,3-dioxo-2,3-dihydro-1H-isoindole-5-carboxylic acid;
2-[2-(2-Methoxyethylamino)-5-(5-phenylbenzoxazol-2-yl)phenyl]-1,3-dioxo-2,3-dihydro-1H-isoindole-5-carboxylic acid;
2-[4-Methoxy-5-(5-phenylbenzoxazol-2-yl)phenyl]-1,3-dioxo-2,3-dihydro-1H-isoindole-5-carboxylic acid;
2-[4-Ethoxy-3-(5-phenylbenzoxazol-2-yl)phenyl]-1,3-dioxo-2,3-dihydro-1H-isoindole-5-carboxylic acid;
2-[4-(2-Methoxyethoxy)-3-(5-phenylbenzoxazol-2-yl)phenyl]-1,3-dioxo-2,3-dihydro-1H-isoindole-5-carboxylic acid;
2-[4-Butoxy-3-(5-phenylbenzoxazol-2-yl)phenyl]-1,3-dioxo-2,3-dihydro-1H-isoindole-5-carboxylic acid;
2-[4-Isopropoxy-3-(5-phenylbenzoxazol-2-yl)phenyl]-1,3-dioxo-2,3-dihydro-1H-isoindole-5-carboxylic acid;
2-[4-Allyloxy-3-(5-phenylbenzoxazol-2-yl)phenyl]-1,3-dioxo-2,3-dihydro-1H-isoindole-5-carboxylic acid;
2-[4-Hydroxy-3-(5-phenylbenzoxazol-2-yl)phenyl]-1,3-dioxo-2,3-dihydro-1H-isoindole-5-carboxylic acid;
2-[4-Propoxy-5-(5-phenylbenzoxazol-2-yl)phenyl]-1,3-dioxo-2,3-dihydro-1H-isoindole-5-carboxylic acid;
2-[2-(3-Furanylmethoxy)-5-(5-phenylbenzoxazol-2-yl)phenyl]-1,3-dioxo-2,3-dihydro-1H-isoindole-5-carboxylic acid;
2-[2-(2-Methoxyethoxy)-5-(5-phenylbenzoxazol-2-yl)phenyl]-1,3-dioxo-2,3-dihydro-1H-isoindole-5-carboxylic acid;
2-[5-(5-Phenylbenzoxazol-2-yl)-2-(3-tetrahydrofuranylmethoxy)phenyl]-1,3-dioxo-2,3-dihydro-1H-isoindole-5-carboxylic acid;
2-[5-(5-Phenylbenzoxazol-2-yl)-2-(3-thiophenylmethoxy)phenyl]-1,3-dioxo-2,3-dihydro-1H-isoindole-5-carboxylic acid;
2-[2-(4-Morpholinyl)-5-(5-phenylbenzoxazol-2-yl)phenyl]-1,3-dioxo-2,3-dihydro-1H-isoindole-5-carboxylic acid, acetic acid salt;
2-[4-Ethylamino-3-(5-phenylbenzoxazol-2-yl)phenyl]-1,3-dioxo-2,3-dihydro-1H-isoindole-5-carboxylic acid;
2-[4-Propylamino-3-(5-phenylbenzoxazol-2-yl)phenyl]-1,3-dioxo-2,3-dihydro-1H-isoindole-5-carboxylic acid;
2-[4-(2-Methoxyethylamino)-3-(5-phenylbenzoxazol-2-yl)phenyl]-1,3-dioxo-2,3-dihydro-1H-isoindole-5-carboxylic acid;
2-[4-Morpholinyl-3-(5-phenylbenzoxazol-2-yl)phenyl]-1,3-dioxo-2,3-dihydro-1H-isoindole-5-carboxylic acid;
2-[4-Butylamino-3-(5-phenylbenzoxazol-2-yl)phenyl]-1,3-dioxo-2,3-dihydro-1H-isoindole-5-carboxylic acid;
2-[4-Hexylamino-3-(5-phenylbenzoxazol-2-yl)phenyl]-1,3-dioxo-2,3-dihydro-1H-isoindole-5-carboxylic acid;
2-[4-Pentylamino-3-(5-phenylbenzoxazol-2-yl)phenyl]-1,3-dioxo-2,3-dihydro-1H-isoindole-5-carboxylic acid;
2-(3-Benzoxazol-2-yl-4-propylaminophenyl)-1,3-dioxo-2,3-dihydro-1H-isoindole-5-carboxylic acid;
2-(3-Naphtho[2,3-d]oxazol-2-yl-4-propylaminophenyl)-1,3-dioxo-2,3-dihydro-1H-isoindole-5-carboxylic acid;
2-[3-(5-Chlorobenzoxazol-2-yl)-4-propylaminophenyl]-1,3-dioxo-2,3-dihydro-1H-isoindole-5-carboxylic acid;
2-[3-(6-Methylbenzoxazol-2-yl)-4-propylaminophenyl]-1,3-dioxo-2,3-dihydro-1H-isoindole-5-carboxylic acid;
2-[3-(6-Fluorobenzoxazol-2-yl)-4-propylaminophenyl]-1,3-dioxo-2,3-dihydro-1H-isoindole-5-carboxylic acid;
2-[3-(5-Bromobenzoxazol-2-yl)-4-propylaminophenyl]-1,3-dioxo-2,3-dihydro-1H-isoindole-5-carboxylic acid;
2-[3-(5-Methoxybenzoxazol-2-yl)-4-propylaminophenyl]-1,3-dioxo-2,3-dihydro-1H-isoindole-5-carboxylic acid;
2-[3-(5,7-Dichlorobenzoxazol-2-yl)-4-propylaminophenyl]-1,3-dioxo-2,3-dihydro-1H-isoindole-5-carboxylic acid;
2-[3-(5-Trifluoromethylbenzoxazol-2-yl)-4-propylaminophenyl]-1,3-dioxo-2,3-dihydro-1H-isoindole-5-carboxylic acid;
2-[3-(5-Bromo-7-fluorobenzoxazol-2-yl)-4-propylaminophenyl]-1,3-dioxo-2,3-dihydro-1H-isoindole-5-carboxylic acid;
2-[3-(5-Fluorobenzoxazol-2-yl)-4-propylaminophenyl]-1,3-dioxo-2,3-dihydro-1H-isoindole-5-carboxylic acid;
2-[3-(6,7-Difluorobenzoxazol-2-yl)-4-propylaminophenyl]-1,3-dioxo-2,3-dihydro-1H-isoindole-5-carboxylic acid;
2-[3-(5-Methylbenzoxazol-2-yl)-4-propylaminophenyl]-1,3-dioxo-2,3-dihydro-1H-isoindole-5-carboxylic acid;
2-[3-(4-Methylbenzoxazol-2-yl)-4-propylaminophenyl]-1,3-dioxo-2,3-dihydro-1H-isoindole-5-carboxylic acid;
2-(3-[6-(2-Tetrahydrofuranylmethylaminocarbonyl)benzoxazol-2-yl]phenyl)-1,3-dioxo-2,3-dihydro-1H-isoindole-5-carboxylic acid;
2-[3-[6-(4-Piperonylpiperazine-1-carbonyl)benzoxazol-2-yl]phenyl]-1,3-dioxo-2,3-dihydro-1H-isoindole-5-carboxylic acid;

2-[3-[6-(4-Piperazinoacetophenone-1-carbonyl)benzoxazol-2-yl]phenyl]-1,3-dioxo-2,3-dihydro-1H-isoindole-5-carboxylic acid;
2-[3-[6-(3-Trifluoromethylphenyl)piperazine-1-carbonyl]benzoxazol-2-yl]phenyl)-1,3-dioxo-2,3-dihydro-1H-isoindole-5-carboxylic acid;
2-[3-[6-(3-Carbamoylpiperidine-1-carbonyl)benzoxazol-2-yl]phenyl]-1,3-dioxo-2,3-dihydro-1H-isoindole-5-carboxylic acid;
2-[3-[6-(4-Methoxybenzylaminocarbonyl)benzoxazol-2-yl]phenyl]-1,3-dioxo-2,3-dihydro-1H-isoindole-5-carboxylic acid;
2-[3-[6-(3,4-Dimethoxybenzylaminocarbonyl)benzoxazol-2-yl]phenyl]-1,3-dioxo-2,3-dihydro-1H-isoindole-5-carboxylic acid;
2-[3-(5-Carboxy-1,3-dioxo-1,3-dihydroisoindol-2-yl)phenyl]benzoxazole-6-carboxylic acid;
2-[3-(5-Carboxy-1,3-dioxo-1,3-dihydroisoindol-2-yl)phenyl]benzoxazole-6-carboxylic acid methyl ester;
2-[3-(5-Carboxy-1,3-dioxo-1,3-dihydroisoindol-2-yl)phenyl]benzoxazole-7-carboxylic acid;
2-[3-(5-Benzyloxycarbonyl-1,3-dioxo-1,3-dihydro-isoindol-2-yl)phenyl]benzoxazole-6-carboxylic acid;
2-[3-(5-Methyloxycarbonyl-1,3-dioxo-1,3-dihydroisoindol-2-yl)phenyl]benzoxazole-6-carboxylic acid;
2-[5-(5-Bromobenzoxazol-2-yl)-2-methoxyphenyl]-1,3-dioxo-2,3-dihydro-1H-isoindole-5-carboxylic acid;
2-[5-(5-Phenylbenzoxazol-2-yl)-2-(3-thienyl)phenyl]-1,3-dioxo-2,3-dihydro-1H-isoindole-5-carboxylic acid;
2-[2-Fluoro-5-(5-phenylbenzoxazol-2-yl)phenyl]-1,3-dioxo-2,3-dihydro-1H-isoindole-5-carboxylic acid;
2-[2-Chloro-5-(5-phenylbenzoxazol-2-yl)phenyl]-1,3-dioxo-2,3-dihydro-1H-isoindole-5-carboxylic acid;
2-[2-Methoxy-5-[5-(2-benzothiophenyl)benzoxazol-2-yl]phenyl]-1,3-dioxo-2,3-dihydro-1H-isoindole-5-carboxylic acid;
2-[2-Methoxy-5-[5-(3-methyl-4-chlorophenyl)benzoxazol-2-yl]phenyl]-1,3-dioxo-2,3-dihydro-1H-isoindole-5-carboxylic acid;
2-[2-Methoxy-5-[5-(4-fluoro-3-formylphenyl)benzoxazol-2-yl]phenyl]-1,3-dioxo-2,3-dihydro-1H-isoindole-5-carboxylic acid;
2-[2-Methoxy-5-[5-(3,4-difluorophenyl)benzoxazol-2-yl]phenyl]-1,3-dioxo-2,3-dihydro-1H-isoindole-5-carboxylic acid;
2-[2-Methoxy-5-[5-(4-ethylsulfonylphenyl)benzoxazol-2-yl]phenyl]-1,3-dioxo-2,3-dihydro-1H-isoindole-5-carboxylic acid;
2-[2-Methoxy-5-[5-(4-N,N-dimethylaminophenyl)benzoxazol-2-yl]phenyl]-1,3-dioxo-2,3-dihydro-1H-isoindole-5-carboxylic acid;
2-[2-Methoxy-5-[5-(2,3-dichlorophenyl)benzoxazol-2-yl]phenyl]-1,3-dioxo-2,3-dihydro-1H-isoindole-5-carboxylic acid;
2-[4-Methoxy-5-[5-(2-benzothiophenyl)benzoxazol-2-yl]phenyl]-1,3-dioxo-2,3-dihydro-1H-isoindole-5-carboxylic acid;
2-[4-Methoxy-5-[5-(4-chlorophenyl)benzoxazol-2-yl]phenyl]-1,3-dioxo-2,3-dihydro-1H-isoindole-5-carboxylic acid;
2-[4-Methoxy-5-[5-(3-chloro-4-fluoro)phenyl]benzoxazol-2-yl]phenyl]-1,3-dioxo-2,3-dihydro-1H-isoindole-5-carboxylic acid;
2-[4-Methoxy-5-[5-(4-trifluoromethylphenyl)benzoxazol-2-yl]phenyl]-1,3-dioxo-2,3-dihydro-1H-isoindole-5-carboxylic acid;

2-[4-Methoxy-5-[5-(2-benzofuranyl)benzoxazol-2-yl]phenyl]-1,3-dioxo-2,3-dihydro-1H-isoindole-5-carboxylic acid;
2-[4-Methoxy-5-[5-(3,5-difluorophenyl)benzoxazol-2-yl]phenyl]-1,3-dioxo-2,3-dihydro-1H-isoindole-5-carboxylic acid;
2-[4-Methoxy-5-[5-(3,4-methylenedioxyphenyl)benzoxazol-2-yl]phenyl]-1,3-dioxo-2,3-dihydro-1H-isoindole-5-carboxylic acid;
2-[4-Methoxy-5-[5-(3-methoxy)phenylbenzoxazol-2-yl]phenyl]-1,3-dioxo-2,3-dihydro-1H-isoindole-5-carboxylic acid;
2-[4-Methoxy-5-[5-(4-methylphenyl)benzoxazol-2-yl]phenyl]-1,3-dioxo-2,3-dihydro-1H-isoindole-5-carboxylic acid;
2-[4-Propylamino-3-[5-(2-benzofuranyl)benzoxazol-2-yl]phenyl]-1,3-dioxo-2,3-dihydro-1H-isoindole-5-carboxylic acid;
2-[4-Propylamino-5-[5-(3,4-methylenedioxyphenyl)benzoxazol-2-yl]phenyl]-1,3-dioxo-2,3-dihydro-1H-isoindole-5-carboxylic acid;
2-[4-Propylamino-5-[5-(2-benzothiophenyl)benzoxazol-2-yl]phenyl]-1,3-dioxo-2,3-dihydro-1H-isoindole-5-carboxylic acid;
2-[4-Propylamino-5-[5-(3-methyl-4-chlorophenyl)benzoxazol-2-yl]phenyl]-1,3-dioxo-2,3-dihydro-1H-isoindole-5-carboxylic acid;
2-[4-Propylamino-5-[5-(4-chlorophenyl)benzoxazol-2-yl]phenyl]-1,3-dioxo-2,3-dihydro-1H-isoindole-5-carboxylic acid;
2-[4-Propylamino-5-[5-(3-chloro-4-fluoro)phenylbenzoxazol-2-yl]phenyl]-1,3-dioxo-2,3-dihydro-1H-isoindole-5-carboxylic acid;
2-[4-Propylamino-5-[5-(3,5-difluoro)phenylbenzoxazol-2-yl]phenyl]-1,3-dioxo-2,3-dihydro-1H-isoindole-5-carboxylic acid;
2-[4-Propylamino-5-[5-(4-fluorophenyl)benzoxazol-2-yl]phenyl]-1,3-dioxo-2,3-dihydro-1H-isoindole-5-carboxylic acid;
2-[4-Propylamino-5-[5-(4-trifluoromethoxy)phenylbenzoxazol-2-yl]phenyl]-1,3-dioxo-2,3-dihydro-1H-isoindole-5-carboxylic acid;
2-[4-Propylamino-5-[5-(4-trifluoromethyl)phenylbenzoxazol-2-yl]phenyl]-1,3-dioxo-2,3-dihydro-1H-isoindole-5-carboxylic acid;
2-[4-Propylamino-5-[5-(3-chloro)phenylbenzoxazol-2-yl]phenyl]-1,3-dioxo-2,3-dihydro-1H-isoindole-5-carboxylic acid;

or a pharmaceutically acceptable salt or prodrug thereof.

14. A process for the preparation of a compound according to claim 1 which comprises:

a) heating a compound of formula (III):

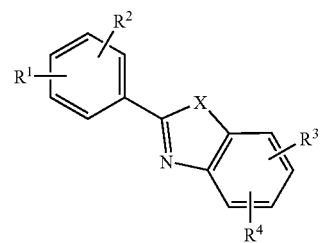

(III)

wherein R¹ is NH₂ or a protected derivative thereof with a compound of formula (IV):

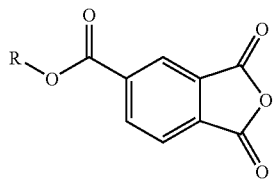

(IV)

in a suitable acidic medium, or b) heating a compound of formula (III) with a compound of formula (IV) with an organic base in a suitable solvent, followed by heating in a suitable acidic medium.

15. A pharmaceutical composition comprising a compound of formula (I) or a pharmaceutically acceptable salt or prodrug thereof:

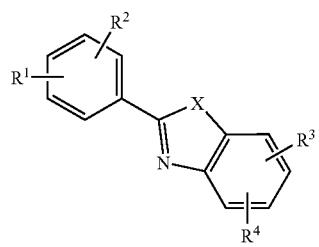

(I)

wherein
X is O or S;
R¹ is a phthalimide carboxylic acid group of formula (II):

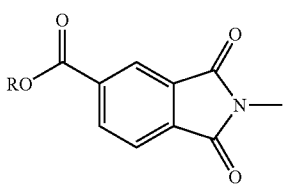

(II)

R is hydrogen, $C_1$–$C_6$ alkyl, aryl or $C_1$–$C_3$ alkylaryl;
R² is hydrogen, halogen, $C_1$–$C_6$ alkyl, $OR^5$, a 5-membered heteroaryl ring, or $NR^5R^5$;
R³ and R⁴ are independently hydrogen, halogen, $C_1$–$C_6$ alkyl optionally substituted by hydroxy or $C_1$–$C_3$ alkoxy, $CF_3$, $OCF_3$, $OR^{10}$, $COR^6$, $NHCOR^7$, $NHSO_2R^9$, $CN$, $S(O)_pR^9$, phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^6$, $CN$, $CHO$, $OCHF_2$, $NR^7R^8$, $NHCOR^7$, $NHSO_2R^9$, $S(O)_pR^9$ and methylenedioxo, or a 5- to 10-membered heteroaryl ring which is optionally substituted by $C_1$–$C_6$ alkyl;
or R³ and R⁴ together form a fused phenyl ring or a —O—(CH₂)ₓ—O— group, wherein x is 1 or 2;
R⁵ is independently hydrogen, $C_3$–$C_6$ alkenyl, $C_3$–$C_6$ alkynyl, or $C_1$–$C_6$ alkyl optionally substituted by hydroxy, $C_1$–$C_3$ alkoxy, $NR^7R^8$, phenyl or a 5- or 6-membered heteroaryl ring, wherein phenyl is optionally substituted by one or more substituents selected from halogen, $CF_3$, $OCF_3$, $CHO$, $OR^{10}$, $COR^{10}$, $R^{10}$, $CN$ and methylenedioxo and wherein the heteroaryl ring is optionally substituted by $C_1$–$C_6$ alkyl;
or R⁵ and R⁵, together with the nitrogen atom to which they are attached, form a 5- or 6-membered ring which optionally contains an additional heteroatom selected from O, S, and $NR^{10}$;
R⁶ is $C_1$–$C_6$ alkyl, $OR^5$, $NR^7R^8$ or phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^{10}$, $CN$, $CHO$, $OCHF_2$, $NR^7R^8$, $NHCOR^7$, $NHSO_2R^9$, $S(O)_pR^9$ and methylenedioxo;
R⁷ and R⁸ are independently hydrogen, phenyl, a 5- to 10-membered heterocyclic ring, $C_1$–$C_6$ alkoxy, or $C_1$–$C_6$ alkyl optionally substituted by phenyl or a 5- to 10-membered heterocyclic ring, wherein in each case, the phenyl is optionally substituted by one or more substituents selected from halogen, $CF_3$, $OCF_3$, $CHO$, $OR^{10}$, $COR^{10}$, $R^{10}$, $CN$ and methylenedioxo and the heterocyclic ring is optionally substituted by $C_1$–$C_6$ alkyl;
or R⁷ and R⁸ together with the nitrogen to which they are attached form a 5- or 6-membered heterocyclic ring which is optionally substituted by $CONR^{10}R^{10}$ and optionally contains an additional heteroatom selected from O, S and $NR^{11}$;
R⁹ is $C_1$–$C_6$ alkyl or phenyl optionally substituted by one or more substituents selected from halogen, $CF_3$, $OCF_3$, $CHO$, $R^{10}$, $COR^{10}$, $R^{10}$, $CN$ and methylenedioxo;
R¹⁰ is hydrogen, $C_3$–$C_6$ alkenyl, $C_3$–$C_6$ alkynyl, or $C_1$–$C_6$ alkyl optionally substituted by hydroxy or $C_1$–$C_3$ alkoxy;
R¹¹ is hydrogen, phenyl or $C_1$–$C_3$ alkyl optionally substituted by phenyl, wherein in each case the phenyl is optionally substituted by one or more substituents selected from halogen, $CF_3$, $OCF_3$, $CHO$, $OR^{10}$, $COR^{10}$, $R^{10}$, $CN$ and methylenedioxo; and
p is 0, 1 or 2,
and a pharmaceutically acceptable carrier, excipient and/or diluent.

16. A method for the treatment of melanoma comprising administering to a patient suffering from melanoma a pharmaceutically effective amount of a compound of formula I or a pharmaceutically acceptable salt or prodrug thereof:

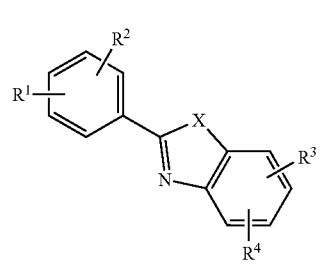

(I)

wherein
X is O or S;

$R^1$ is a phthalimide carboxylic acid group of formula (II):

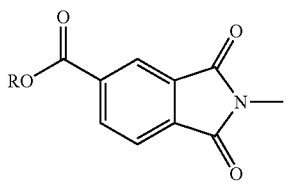

(II)

R is hydrogen, $C_1$–$C_6$ alkyl, aryl or $C_1$–$C_3$ alkylaryl;

$R^2$ is hydrogen, halogen, $C_1$–$C_6$ alkyl, $OR^5$, a 5-membered heteroaryl ring, or $NR^5R^5$;

$R^3$ and $R^4$ are independently hydrogen, halogen, $C_1$–$C_6$ alkyl optionally substituted by hydroxy or $C_1$–$C_3$ alkoxy, $CF_3$, $OCF_3$, $OR^{10}$, $COR^6$, $NHCOR^7$, $NHSO_2R^9$, CN, $S(O)_pR^9$, phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^6$, CN, CHO, $OCHF_2$, $NR^7R^8$, $NHCOR^7$, $NHSO_2R^9$, $S(O)_pR^9$ and methylenedioxo, or a 5- to 10-membered heteroaryl ring which is optionally substituted by $C_1$–$C_6$ alkyl;

or $R^3$ and $R^4$ together form a fused phenyl ring or a —O—$(CH_2)_x$—O— group, wherein x is 1 or 2;

$R^5$ is independently hydrogen, $C_3$–$C_6$ alkenyl, $C_3$–$C_6$ alkynyl, or $C_1$–$C_6$ alkyl optionally substituted by hydroxy, $C_1$–$C_3$ alkoxy, $NR^7R^8$, phenyl or a 5- or 6-membered heteroaryl ring, wherein phenyl is optionally substituted by one or more substituents selected from halogen, $CF_3$, $OCF_3$, CHO, $OR^{10}$, $COR^{10}$, $R^{10}$, CN and methylenedioxo and wherein the heteroaryl ring is optionally substituted by $C_1$–$C_6$ alkyl;

or $R^5$ and $R^5$, together with the nitrogen atom to which they are attached, form a 5- or 6-membered ring which optionally contains an additional heteroatom selected from O, S, and $NR^{10}$;

$R^6$ is $C_1$–$C_6$ alkyl, $OR^5$, $NR^7R^8$ or phenyl optionally substituted by one or more substituents selected from halogen, $C_1$–$C_6$ alkyl optionally substituted by hydroxy or $C_1$–$C_3$ alkoxy, $CF_3$, $OCF_3$, $OR^5$, $COR^{10}$, CN, CHO, $OCHF_2$, $NR^7R^8$, $NHCOR^7$, $NHSO_2R^9$, $S(O)_pR^9$ and methylenedioxo;

$R^7$ and $R^8$ are independently hydrogen, phenyl, a 5- to 10-membered heterocyclic ring, $C_1$–$C_6$ alkoxy, or $C_1$–$C_6$ alkyl optionally substituted by phenyl or a 5- to 10-membered heterocyclic ring, wherein in each case, the phenyl is optionally substituted by one or more substituents selected from halogen, $CF_3$, $OCF_3$, CHO, $OR^{10}$, $COR^{10}$, $R^{10}$, CN and methylenedioxo and the heterocyclic ring is optionally substituted by $C_1$–$C_6$ alkyl;

or $R^7$ and $R^8$ together with the nitrogen to which they are attached form a 5- or 6-membered heterocyclic ring which is optionally substituted by $CONR^{10}R^{10}$ and optionally contains an additional heteroatom selected from O, S and $NR^{11}$;

$R^9$ is $C_1$–$C_6$ alkyl or phenyl optionally substituted by one or more substituents selected from halogen, $CF_3$, $OCF_3$, CHO, $OR^{10}$, $COR^{10}$, $R^{10}$, CN and methylenedioxo;

$R^{10}$ is hydrogen, $C_3$–$C_6$ alkenyl, $C_3$–$C_6$ alkynyl, or $C_1$–$C_6$ alkyl optionally substituted by hydroxy or $C_1$–$C_3$ alkoxy;

$R^{11}$ is hydrogen, phenyl or $C_1$–$C_3$ alkyl optionally substituted by phenyl, wherein in each case the phenyl is optionally substituted by one or more substituents selected from halogen, $CF_3$, $OCF_3$, CHO, $OR^{10}$, $COR^{10}$, $R^{10}$, CN and methylenedioxo; and p is 0, 1 or 2.

* * * * *